United States Patent
Qiao et al.

(10) Patent No.: US 12,281,205 B2
(45) Date of Patent: Apr. 22, 2025

(54) MODIFIED ANTIBACTERIAL COMPOSITIONS AND METHODS

(71) Applicant: The University of Melbourne, Melbourne (AU)

(72) Inventors: Greg GuangHua Qiao, Melbourne (AU); Neil Martin O'Brien-Simpson, Melbourne (AU); Shu Jie Lam, Melbourne (AU); Anton Richard Blencowe, Melbourne (AU); Eric Charles Reynolds, Melbourne (AU)

(73) Assignee: The University of Melbourne, Melbourne (AU)

( * ) Notice: Subject to any disclaimer, the term of this patent is extended or adjusted under 35 U.S.C. 154(b) by 746 days.

(21) Appl. No.: 16/343,218

(22) PCT Filed: Nov. 2, 2017

(86) PCT No.: PCT/AU2017/051207
§ 371 (c)(1),
(2) Date: Apr. 18, 2019

(87) PCT Pub. No.: WO2018/081862
PCT Pub. Date: May 11, 2018

(65) Prior Publication Data
US 2020/0123328 A1    Apr. 23, 2020

(30) Foreign Application Priority Data
Nov. 2, 2016   (WO) ............... PCT/AU2016/051037

(51) Int. Cl.
*A61K 9/00*   (2006.01)
*A61P 31/04*  (2006.01)
(Continued)

(52) U.S. Cl.
CPC ............ *C08G 83/003* (2013.01); *A61P 31/04* (2018.01); *C08G 69/10* (2013.01); *C08G 73/028* (2013.01)

(58) Field of Classification Search
CPC .................................................. C08G 83/003
See application file for complete search history.

(56) References Cited

U.S. PATENT DOCUMENTS

2019/0247459 A1   8/2019  Qiao et al.

FOREIGN PATENT DOCUMENTS

| WO | WO 2000/015240 | 3/2000 |
| WO | WO 2014/165923 | 10/2014 |
| WO | WO 2015/144928 | 10/2015 |

OTHER PUBLICATIONS

Gao et al., "Synthesis and Mechanism Insight of a Peptide-Grafted Hyperbranched Polymer Nanosheet with Weak Positive Charges but Excellent Intrinsically Antibacterial Efficacy," Biomacromolecules, Jun. 13, 2016;17:2080-6.
(Continued)

*Primary Examiner* — Paul W Dickinson
(74) *Attorney, Agent, or Firm* — Fish & Richardson P.C.

(57) ABSTRACT

This invention relates to antibacterial compounds and compositions thereof. The invention also relates to the use of the compounds and compositions in methods of treating bacterial infections, particularly those bacterial infections including bacteria that exhibit antibiotic resistance. More specifically, the present invention provides a star shaped peptide polymer comprising a multifunctional core with a plurality of terminal arms extending therefrom, wherein the terminal arms are statistical or random peptide copolymers of at least a cationic amino acid residue and a hydrophobic amino acid residue.

27 Claims, 80 Drawing Sheets

(51) Int. Cl.
*C08G 69/10* (2006.01)
*C08G 73/02* (2006.01)
*C08G 83/00* (2006.01)

(56) References Cited

OTHER PUBLICATIONS

Lam et al., "Combating multidrug-resistant Gram-negative bacteria with structurally nanoengineered antimicrobial peptide polymers," Nat Microbiol., Sep. 12, 2016;1(11):16162.
Lam et al., "SNAPPing Gram-negative bacteria with star-shaped polypeptides," Abstracts of Papers, 250th ACS National Meeting & Exposition, Boston, MA, U.S., Aug. 16-20, 2015, pmse-370.
Stach et al., "Combining topology and sequence design for the discovery of potent antimicrobial peptide dendrimers against multidrug-resistant Pseudomonas aeruginosa," Angew Chem Int Ed Engl., Nov. 17, 2014;53:12827-31.
Stach et al., "Membrane disrupting antimicrobial peptide dendrimers with multiple amino termini," Med. Chem. Commun., 2012;3:86-89.
International Search Report and Written Opinion for App. No. PCT/AU2017/051207, mailed Dec. 18, 2017, 8 pages.
Chen et al., "The outer membrane protein LptO is essential for the O-deacylation of LPS and the co-ordinated secretion and attachment of A-LPS and CTD proteins in Porphyromonas gingivalis," Molecular Microbiology, Mar. 2011, 79(5):1380-401.
GenBank Accession No. AB011549, "*Escherichia coli* O157:H7 str. Sakai plasmid pO157 DNA, complete sequence," dated Jul. 26, 2016, 34 pages.
GenBank Accession No. AF074613, "*Escherichia coli* O157:H7 str. EDL933 plasmid pO157, complete sequence," dated Jul. 26, 2016, 47 pages.
GenBank Accession No. AJ007716, "*Escherichia coli* plasmid pO157, espP natural mutant with inserted IS1203," 4 pages.
GenBank Accession No. X97542, "*E.coli* 8.6 kb DNA from plasmid p0157," dated Jul. 24, 2016, 4 pages.
GenBank Accession No. Y11275, "*E.coli* 7.4 kb DNA from plasmid pO157," Jul. 26, 2016, 4 pages.
Hegreness et al., "Accelerated evolution of resistance in multidrug environments," Proceedings of the National Academy of Sciences, Sep. 16, 2008, 105(37):13977-81.
Morones-Ramirez et al., "Silver enhances antibiotic activity against gram-negative bacteria," Science Translational Medicine, Jun. 19, 2013, 5(190):190ra81-.
Pankey et al., "Clinical relevance of bacteriostatic versus bactericidal mechanisms of action in the treatment of Gram-positive bacterial infections," Clinical Infectious Diseases, Mar. 15, 2004. 38(6):864-70.
PCT International Preliminary Report on Patentability in International Appln. No. PCT/AU2017/051207, dated May 7, 2019, 6 pages.
PCT International Preliminary Report on Patentability in International Appln. No. PCT/AU2017/051206, dated May 7, 2019, 8 pages.
PCT International Search Report and Written Opinion for App. No. PCT/AU2017/051207, mailed Dec. 18, 2017, 8 pages.
Sani et al., "Maculatin 1.1 disrupts *Staphylococcus aureus* lipid membranes via a pore mechanism," Antimicrobial Agents and Chemotherapy, Aug. 1, 2013, 57(8):3593-600.
Stach et al., "Membrame disrupting antimicrobial peptide dendrimers with multiple amino termini," Med. Chem. Commun., 2012;3:86-89.
Fishbain and Peleg, "Treatment of *Acinetobacter* infections," Clinical Infectious Diseases, Jul. 1, 2010, 51(1):79-84.

Figure 13
a
S16
Diameter = 7.8 ± 1.2 nm
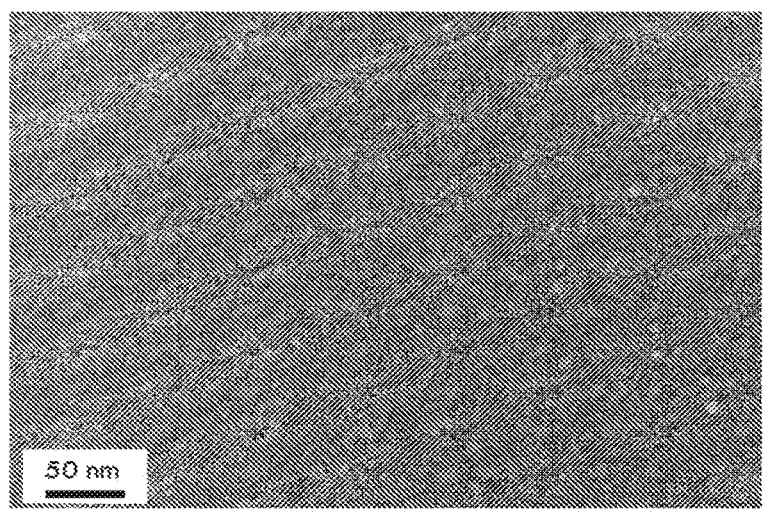
b
S32
Diameter = 7.5 ± 1.6 nm
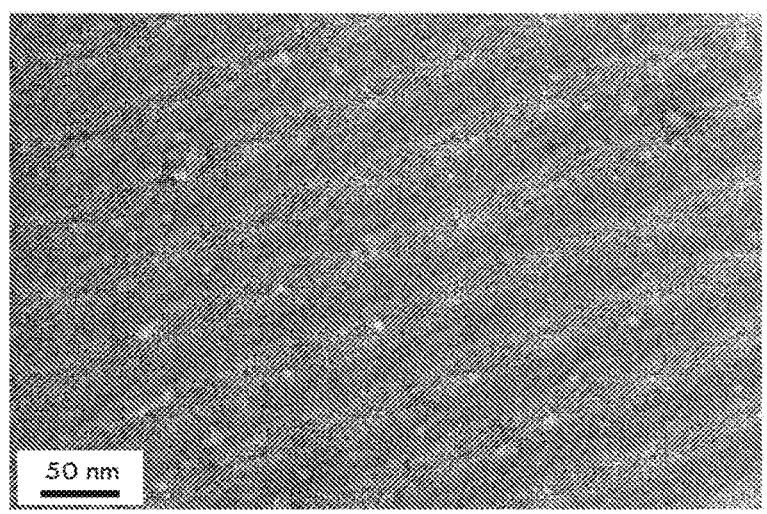

Figure 22
a – Bacteria counts in blood
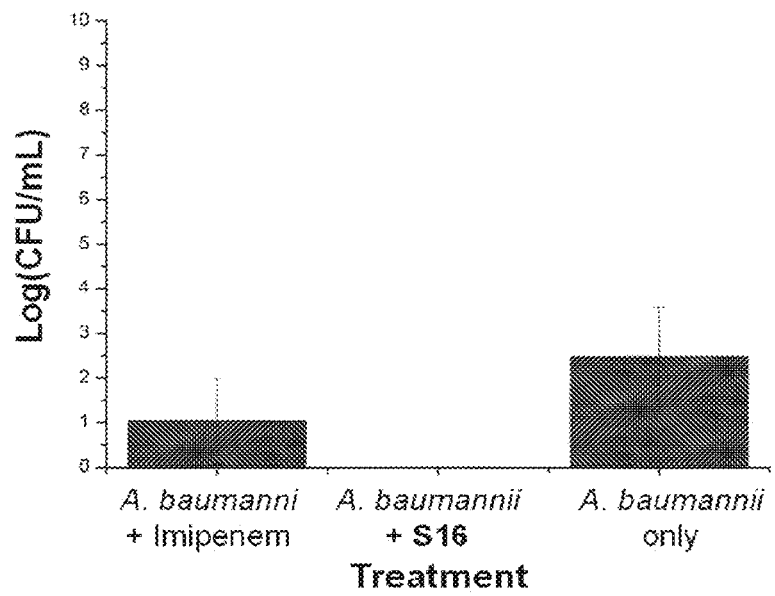
b – Bacteria counts in spleen
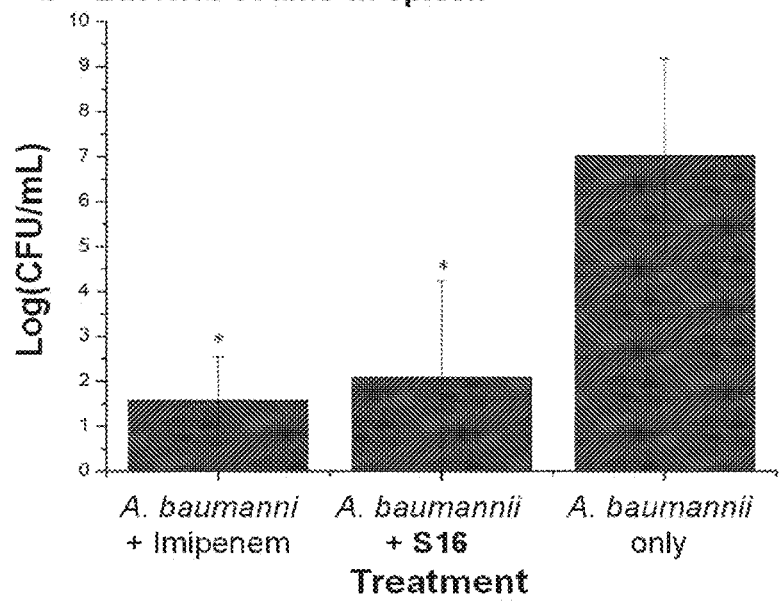

Figure 23
a – Bacteria counts in blood
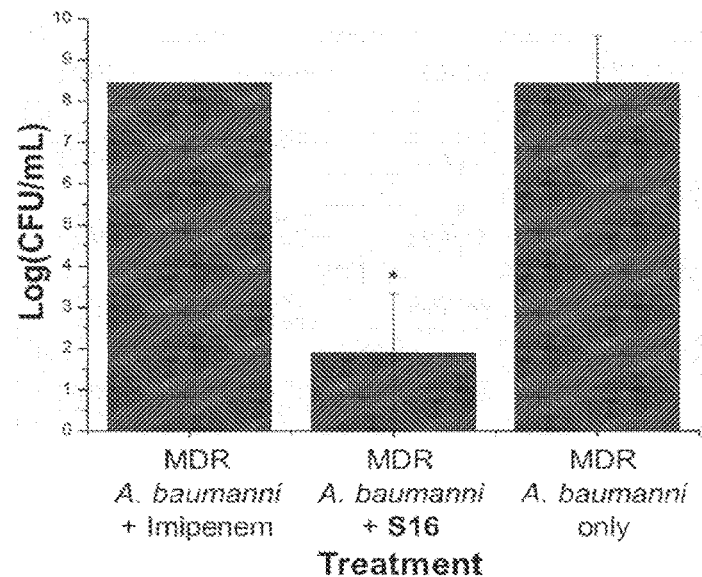
b – Bacteria counts in spleen
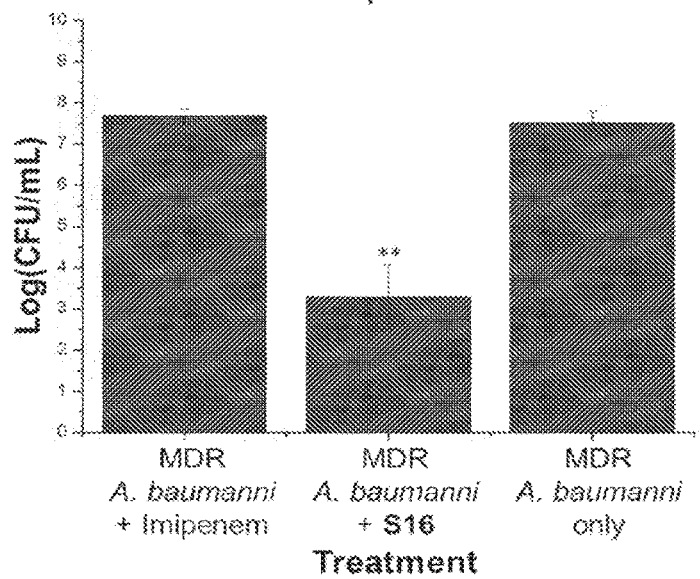

Figure 29
a – *E. coli* + LPS (1000 µg/mL)
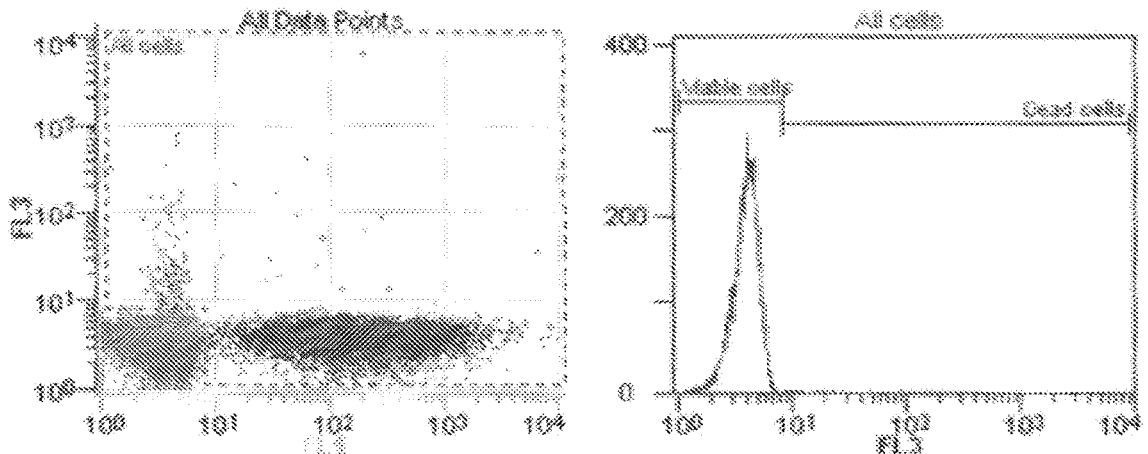
b – *E. coli* + S16 (4 µg/mL)
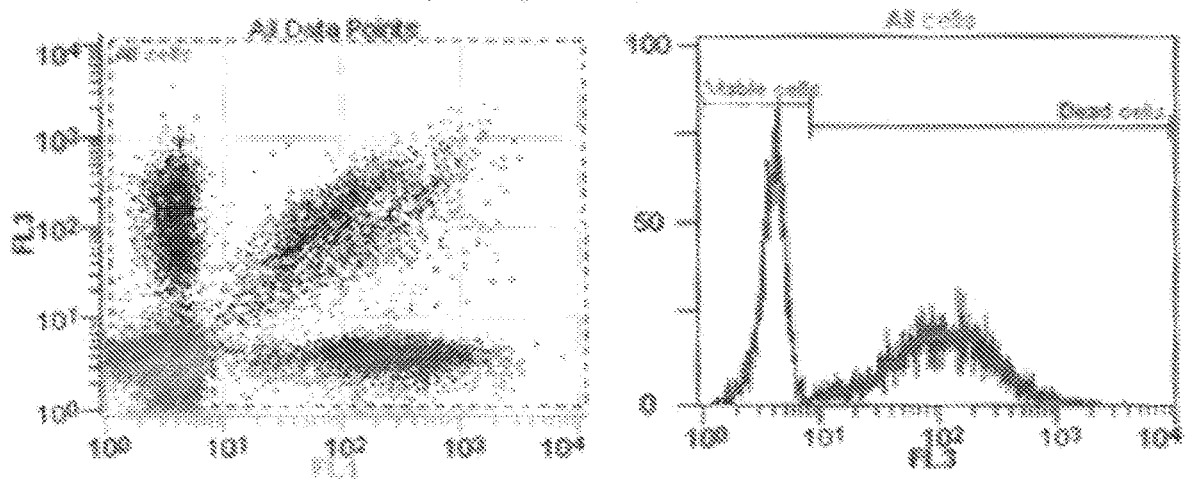
c – *E. coli* + LPS (1000 µg/mL) + S16 (4 µg/mL)
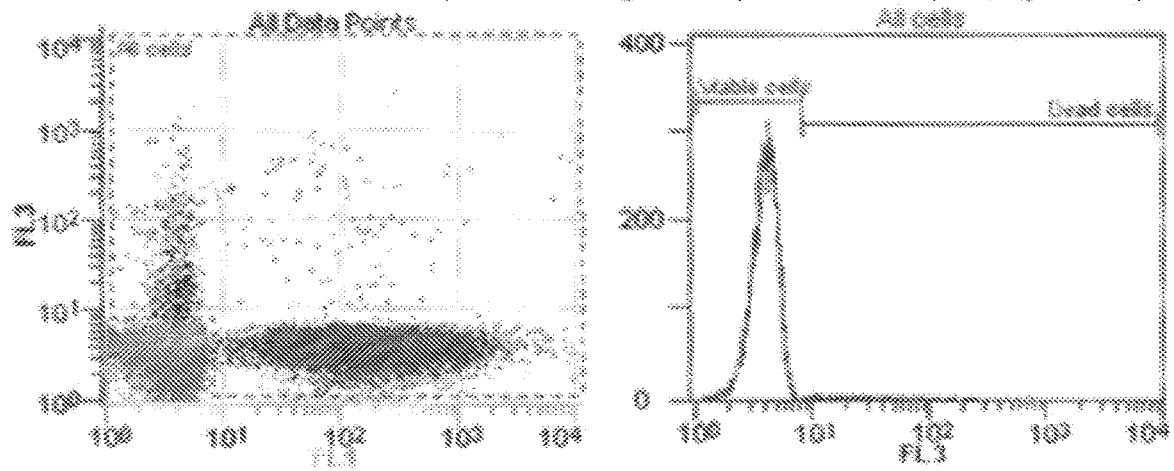

Figure 29 continued...
d – *E. coli* + LPS (500 µg/mL) + S16 (4 µg/mL)
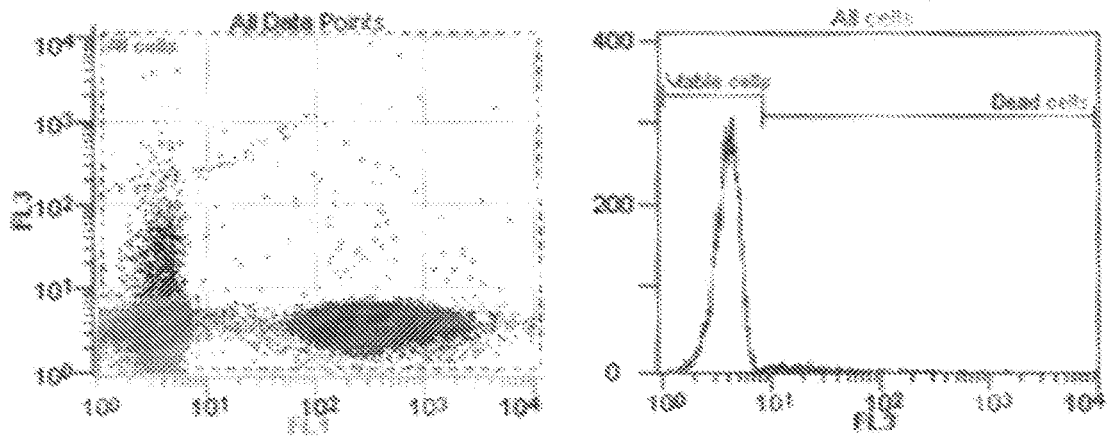
e – *E. coli* + LPS (250 µg/mL) + S16 (4 µg/mL)
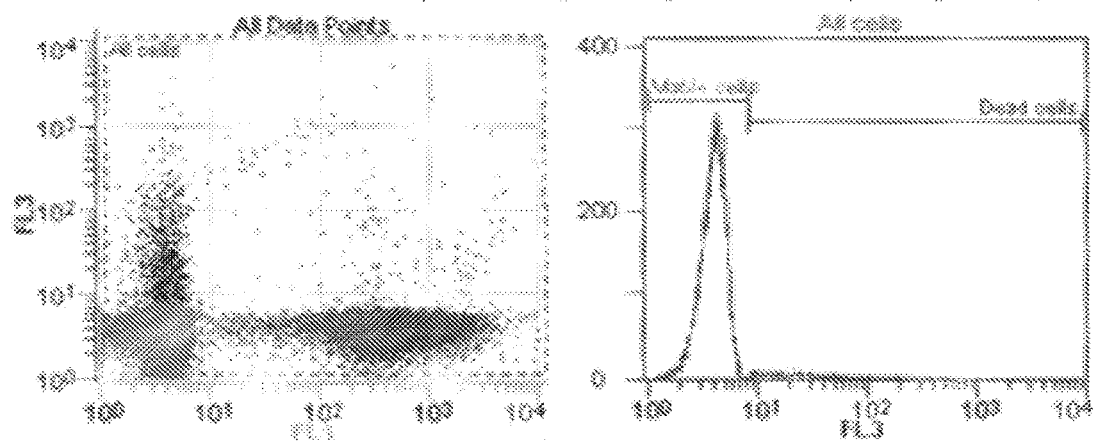
f – *E. coli* + LPS (125 µg/mL) + S16 (4 µg/mL)
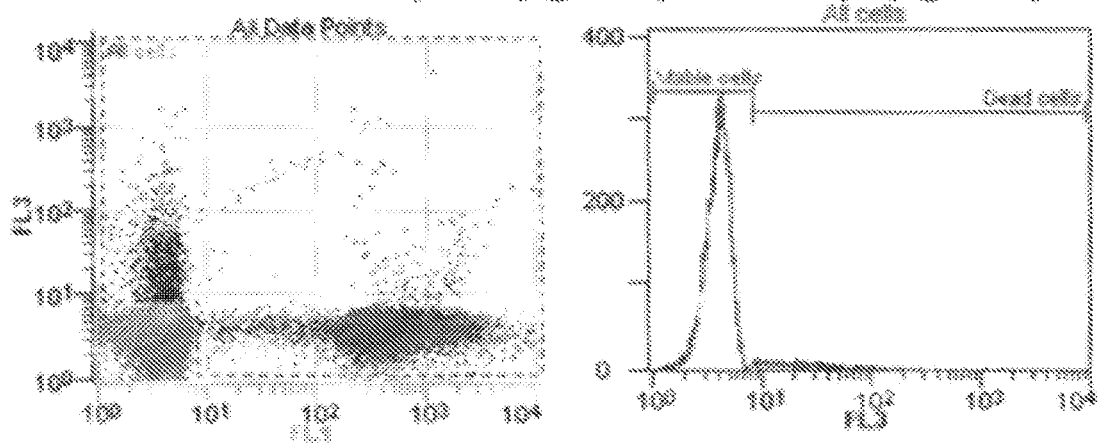

Figure 29 continued...
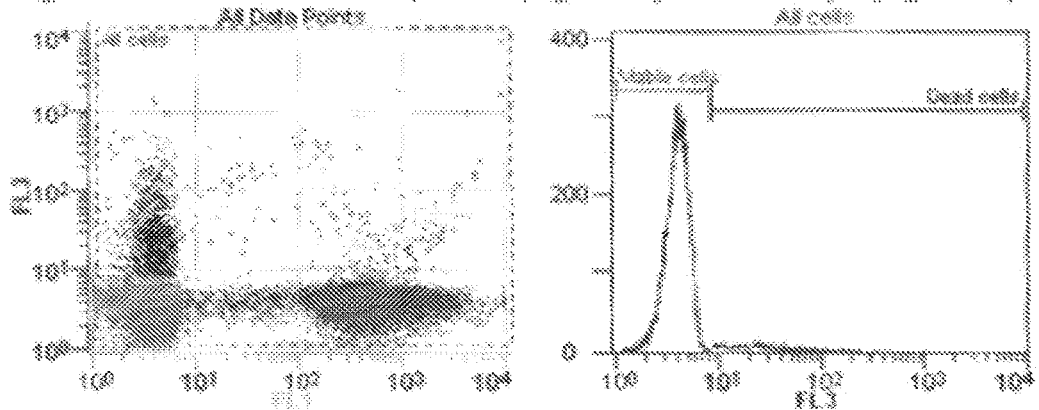
g – E. coli + LPS (62.5 µg/mL) + S16 (4 µg/mL)
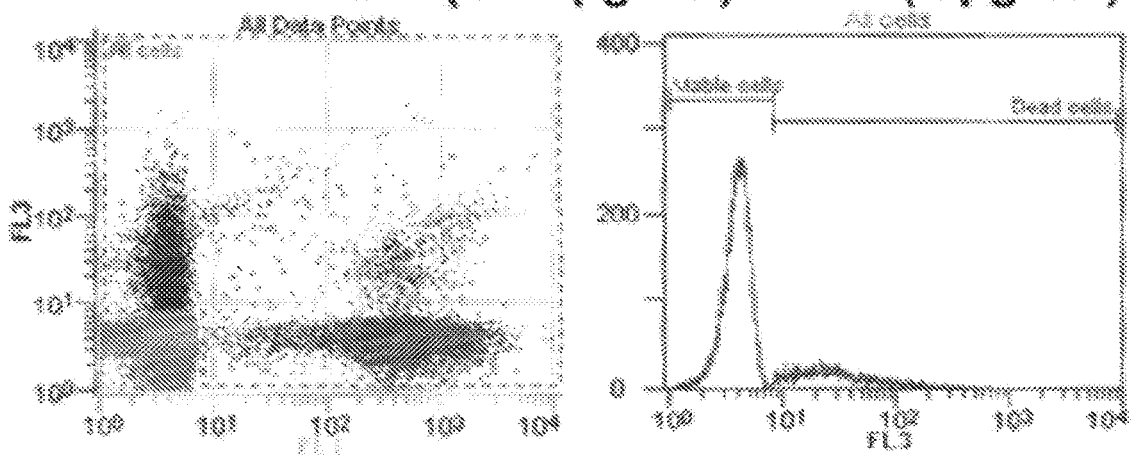
h – E. coli + LPS (31.3 µg/mL) + S16 (4 µg/mL)
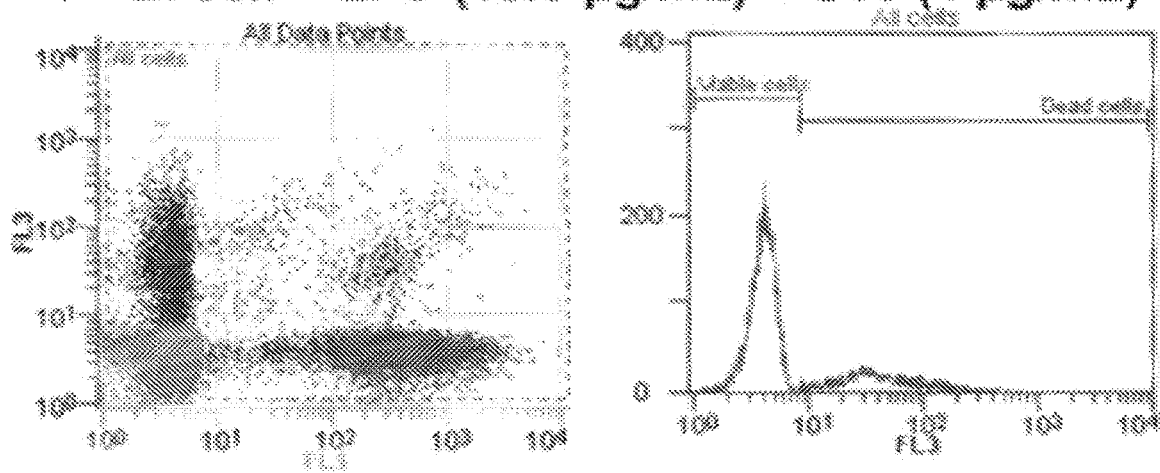
i – E. coli + LPS (15.6 µg/mL) + S16 (4 µg/mL)

Figure 29 continued.
j – *E. coli* + LPS (8.3 µg/mL) + S16 (4 µg/mL)
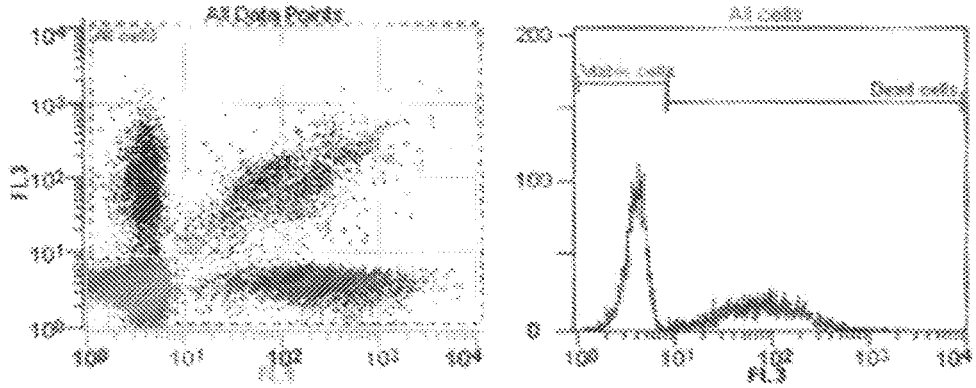
k – *E. coli* + LPS (3.9 µg/mL) + S16 (4 µg/mL)
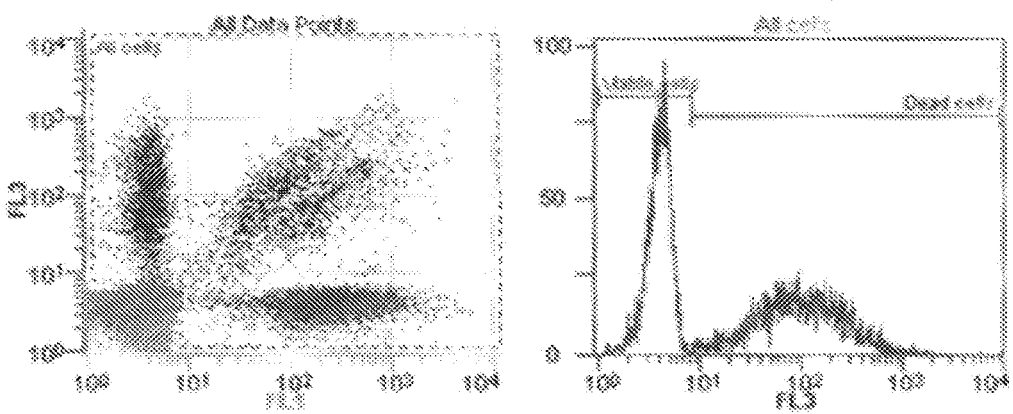
l – *E. coli* + LPS (2.0 µg/mL) + S16 (4 µg/mL)
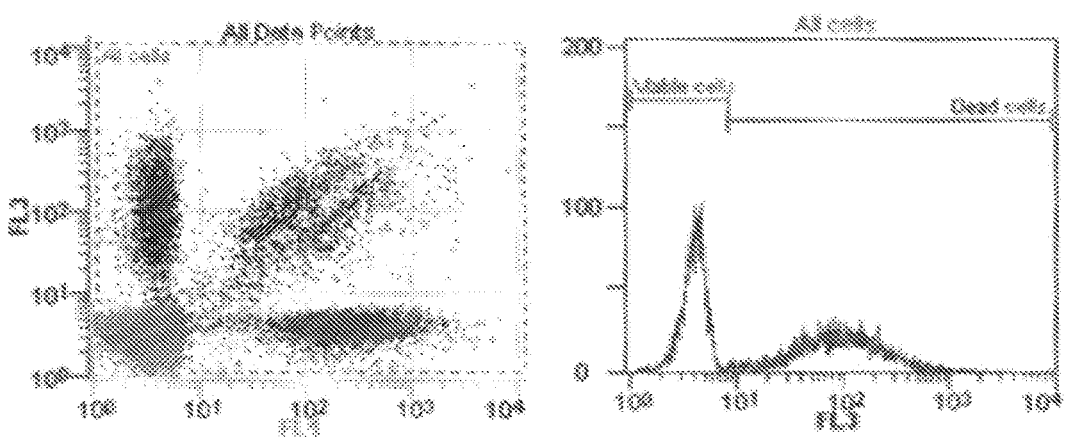

Figure 52
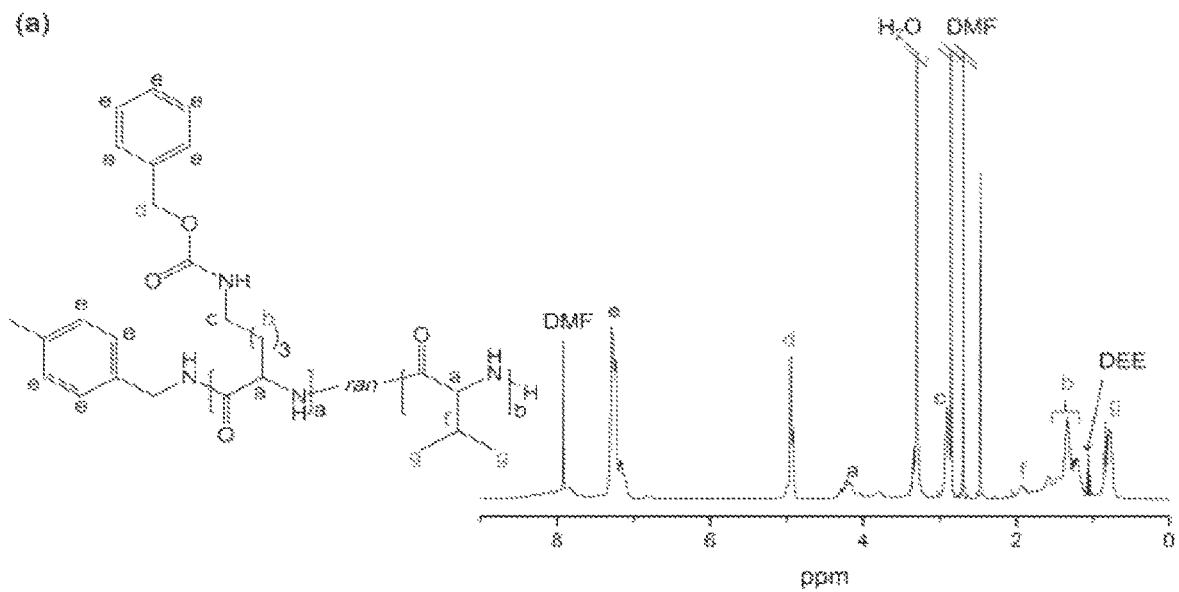
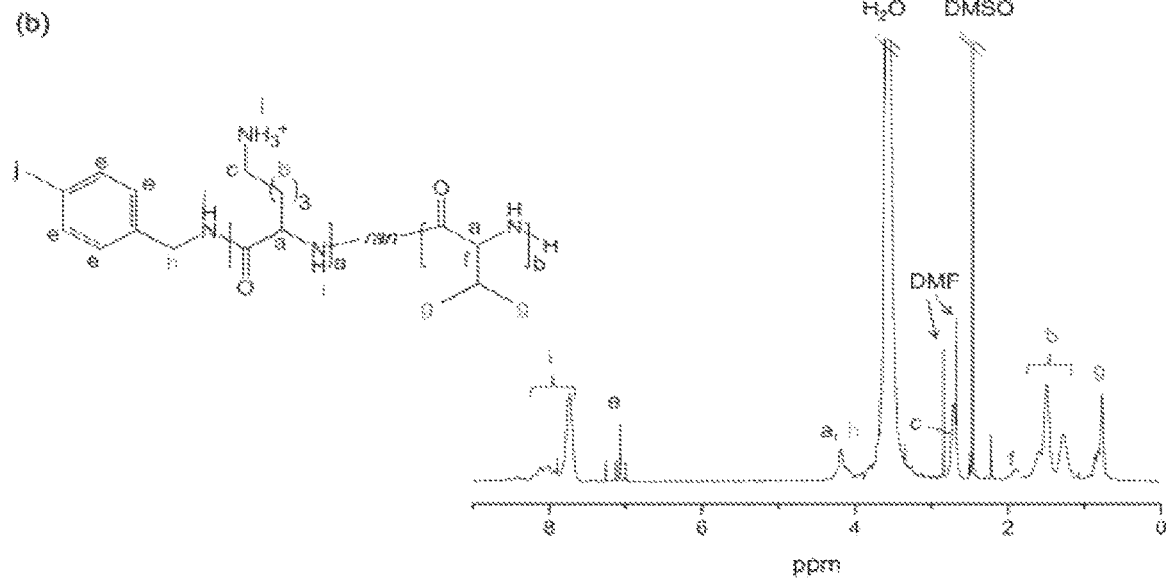

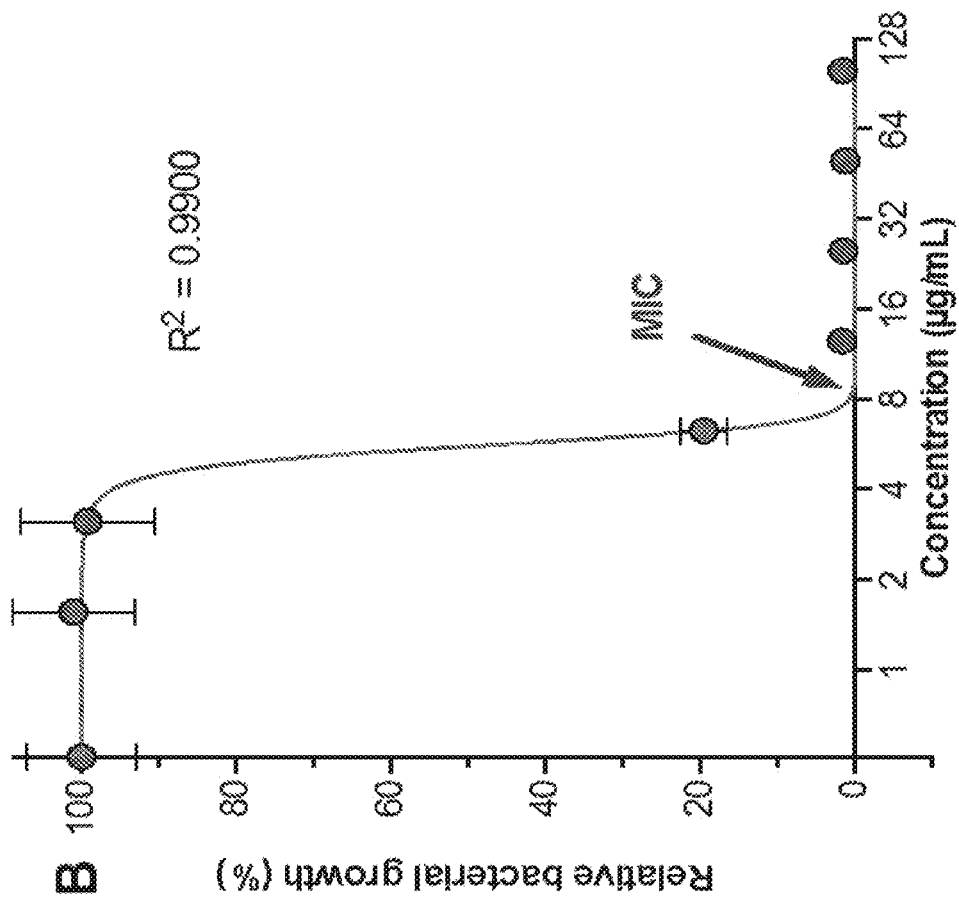
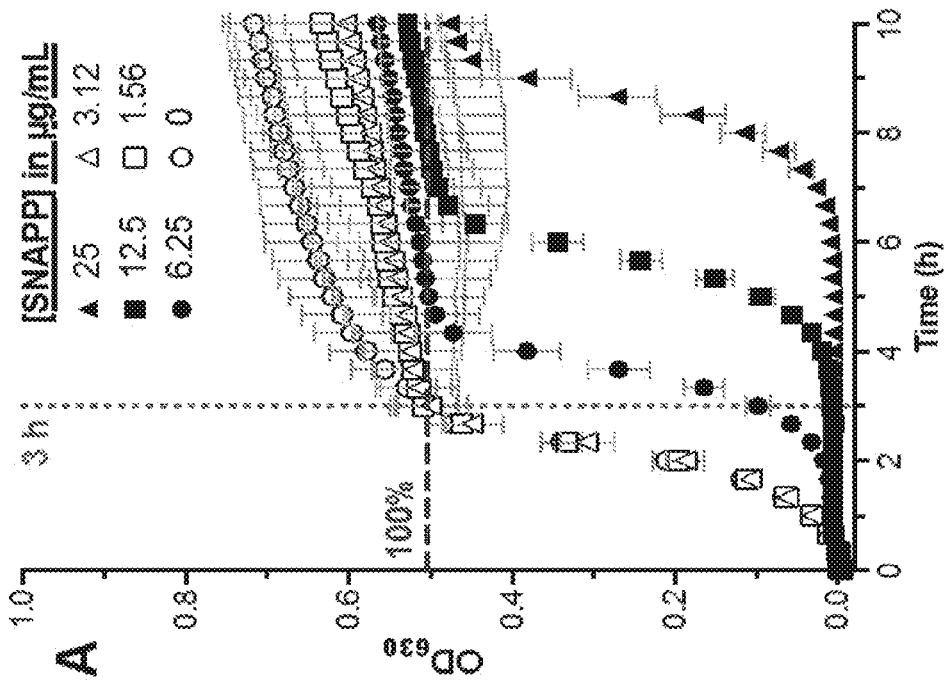
Figure 70

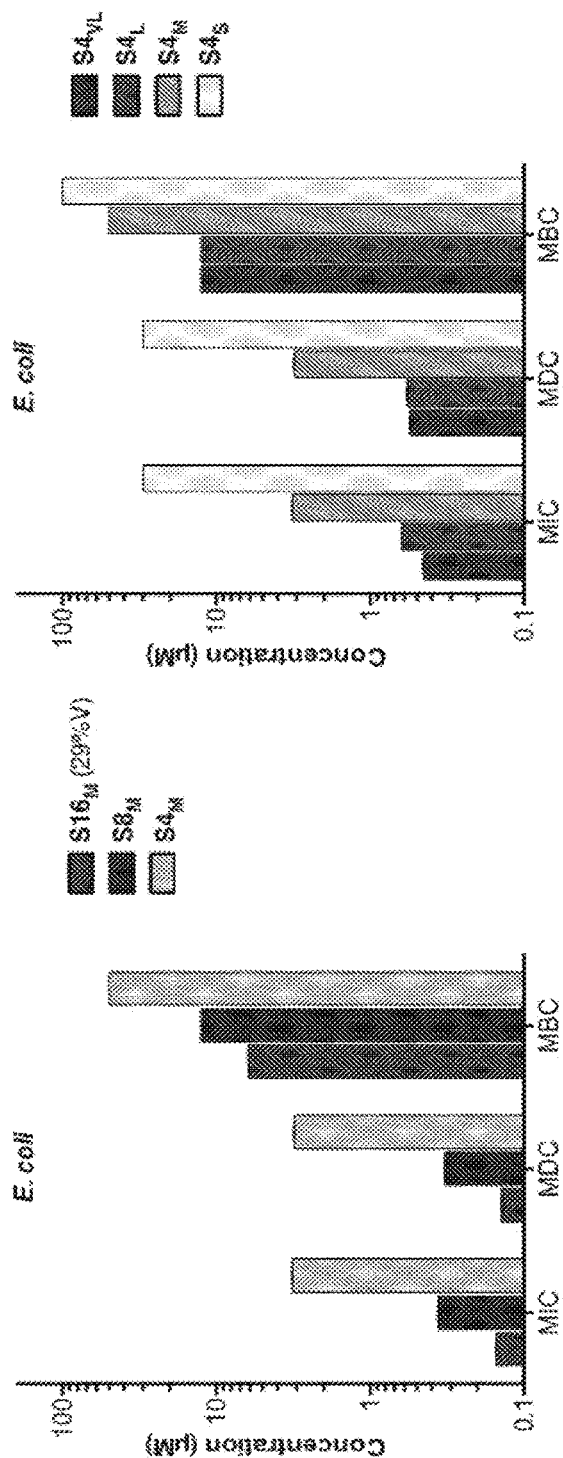
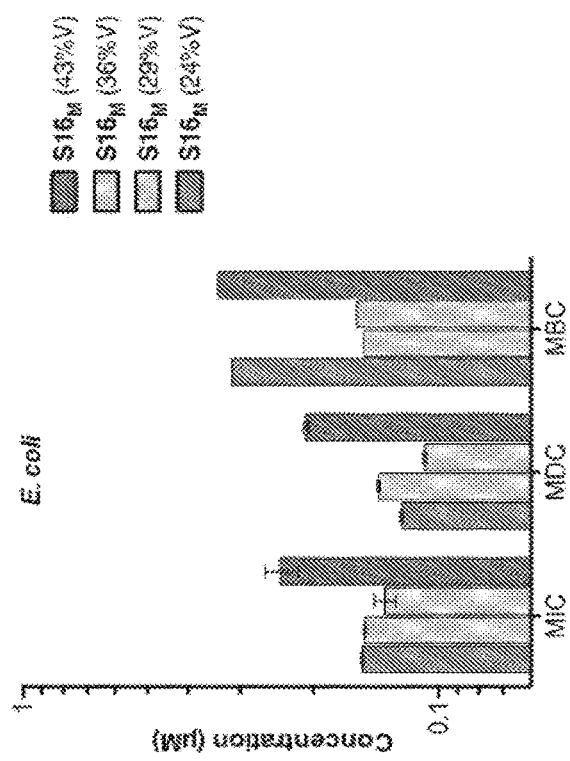
Figure 73

//MODIFIED ANTIBACTERIAL COMPOSITIONS AND METHODS

CROSS REFERENCE TO RELATED APPLICATION(S)

This application claims priority to PCT/AU2016/051037, the entire contents of which is herein incorporated by reference in its entirety.

FIELD OF THE INVENTION

This invention relates to antibacterial compounds and compositions thereof. The invention also relates to the use of the compounds and compositions in methods of treating bacterial infections, particularly those bacterial infections including bacteria that exhibit antibiotic resistance.

BACKGROUND OF THE INVENTION

A group of pathogens responsible for the majority of hospital-acquired infections—commonly referred to as the "ESKAPE" pathogens—have been named as one of the biggest threats to health as a result of their multidrug resistance. Although the Gram-positive bacteria in the ESKAPE group, including the methicillin-resistant *S. aureus*, have rightly drawn attention over the past decade, infections caused by the Gram-negative microbes have been recently recognized as a more critical healthcare issue. Despite the fact that many Gram-negative bacteria have acquired antibiotic resistance, the pipeline for the development of new antimicrobials that target Gram-negative bacteria remains empty. The dearth of drug candidates against Gram-negative bacteria is attributed to the fact that they might be harder to kill compared to Gram-positive bacteria, largely due to the presence of an outer membrane (OM). The outer membrane of Gram-negative bacteria may also contribute to the difficulty in treating infections caused by these pathogens by acting as an efficient permeability barrier, because the narrow porin channels limit the penetration of hydrophilic solutes and the low fluidity of the lipopolysaccharide leaflet decelerates the inward diffusion of lipophilic solutes. In addition, drug efflux pumps, sometimes with unusually broad specificity, act as another factor to increase the general intrinsic resistance of Gram-negative bacteria. When their expression levels are increased, either in a response to an environmental or genetic change, they often result in significant resistance to a wide variety of antimicrobial agents.

Antimicrobial peptides (AMPs) have been widely regarded as a promising solution to combat MDR bacteria. Unlike conventional antibiotics that act on specific intracellular targets, AMPs interact with microbial membranes through electrostatic interactions and physically damage the bacterial morphology. The nature of this antimicrobial mechanism renders bacteria less likely to develop resistance against AMPs. However, AMPs have had limited success in clinical settings, primarily due to their high toxicity towards mammalian cells.

The frequency of antimicrobial resistance in Gram-negative bacterial pathogens, and its association with serious infectious diseases has increased significantly over the past years. This has resulted in significant morbidity and mortality, as well as an increased economic burden on the healthcare system.

Treatment of Gram-negative infections is currently limited by both the agents available and the bacterial resistance to those agents. In this regard, as clinical treatment options have become severely limited, there is a growing medical need for the development of novel antibacterial agents. One such way to combat the continued spread of antibacterial resistance is to develop new antibacterials, particularly those with either a novel mechanism of action and/or containing new pharmacophoric groups.

Additionally, there is an unmet medical need to develop antibacterials where there are presently limited agents or in infections where the pathogens are difficult to treat. Such pathogens may include *Pseudomonas aeruginosa* and *Acinetobacter baumannii*.

As such, there is a need for new or improved compounds that treat infections caused by Gram-negative and/or Gram-positive bacteria, particularly those bacteria that exhibit resistance to antibiotics.

SUMMARY OF THE INVENTION

In one aspect the present invention provides a star shaped peptide polymer comprising a multifunctional core with a plurality of terminal arms extending therefrom, wherein the terminal arms are statistical or random peptide copolymers of at least a cationic amino acid residue and a hydrophobic amino acid residue.

These star shaped peptide polymers are also referred to throughout this specification as star nanoparticles, and as 'Structurally Nanoengineered Antimicrobial Peptide Polymers' (SNAPPs).

In an embodiment, the terminal arms are statistical or random peptide copolymers of the cationic amino acid residue and the hydrophobic amino acid residue.

In an embodiment, the multifunctional core is a dendrimer.

In an embodiment the dendrimer comprises a dendrimer centre with a plurality of dendron arms extending therefrom, the dendron arms having a plurality of branches formed from repeat units, each branch terminated with a terminal unit having a terminal moiety; and wherein the plurality of terminal arms are each covalently bonded to terminal moieties of the dendrimer.

In an embodiment the terminal moiety is a secondary amine with one terminal arm covalently bonded thereto.

In an embodiment, the copolymer has a molar ratio of cationic amino acid residue to hydrophobic amino acid residue of from about 1.5:1 to about 3.5:1, and more preferably from about 1.8:1 to about 3:1. The molar ratio may be any one described herein, including in Tables 2, 13, 14 and 24.

In an embodiment the cationic amino acid residue is a lysine residue (such as an L-lysine residue), and the hydrophobic amino acid residue is a valine residue (such as a D-valine, an L-valine, or DL-valine residues).

In an embodiment, the copolymer exhibits a degree of polymerisation of at least 5 and up to 50. In one form the degree of polymerisation is at least 8, in another form at least 10, in still another form at least 12, in yet another form at least 15, and in yet another form at least 20. Additionally, or alternatively, it is preferred that the degree of polymerisation is up to 45, more preferably up to 40.

In an embodiment, the degree of polymerisation is from about 5 to 35, and most preferably about 10 to about 30.

In one embodiment, the degree of copolymerisation is about 5, is about 10 to about 15, is 12 or 15, is about 20, is 18, is at least 25, or is at least 26 or 29.

In an embodiment, the dendrimer centre is a diamine core. Preferably the diamine core is of the form $R^1{}_2N$—$(C_2\text{-}C_6$ alkyl)-NR$^1_2$, where each R$^1$ represents a covalent bond to a separate dendron arm. More preferably, the diamine core is of the form R$^1_2$N—(C$_2$-C$_3$ alkyl)-NR$^1_2$. Most preferably, the diamine core is of the form R$^1_2$N—(C$_2$H$_4$)—NR$^1_2$.

In an embodiment, the repeat unit is an amidoamine, such as of the form R$^A$[C$_2$H$_4$C(=O)NH$_2$C$_2$H$_4$N]R$^B$R$^C$ where R$^A$ is a single covalent bond to either the dendrimer centre (in which case R$^A$ is an R$^1$) or R$^A$ is a bond to a preceding repeat unit that is closer to the dendrimer centre (in which case R$^A$ is an R$^B$ or R$^C$ on the preceding repeat unit); R$^B$ and R$^C$ represent a single bond to a following repeat unit (in which case R$^B$ is an R$^A$ on the following repeat unit) or, where there are no following repeat units R$^B$ represents a single bond to the terminal arm, and R$^C$ represents a hydrogen atom.

There is no particular size limit on the dendrimer, for example, the dendrimer may be any generation of dendrimer. However, it is preferred that the dendrimer is a generation 0 to generation 5 dendrimer. More preferably, the dendrimer is a generation 0, 1, 2 or 3 dendrimer.

In an embodiment, the star shaped peptide polymer includes a number of terminal arms of from at least 3 and up to 256 terminal arms. Preferably the number of terminal arms is from at least 4 and up to 64. More preferably, the number of terminal arms is 4 to 32.

In an embodiment, the star shaped peptide polymer includes a number of terminal arms selected from the group consisting of: 4 terminal arms, 8 terminal arms, 16 terminal arms, 32 terminal arms, 64 terminal arms, 128 terminal arms, and 256 terminal arms. Preferably, the star shaped peptide polymer includes a number of terminal arms selected from the group consisting of: 4 terminal arms, 8 terminal arms, 16 terminal arms, 32 terminal arms.

In an embodiment, the statistical or random peptide copolymer exhibits an α-helix secondary structure. The presence of an α-helix secondary structure may be ascertained by circular dichroism (CD) spectroscopy. Where an α-helix secondary structure is present, the CD spectrum exhibits a characteristic band or bands in the far UV range (at wavelengths of 190 nm to 250 nm). In particular, a first negative band or trough is observable at a wavelength of between about 205 nm and about 210 nm, and a second negative band or trough is observable at a wavelength of between about 220 nm and about 225 nm. The presence of an α-helix secondary structure may also exhibit a positive band or peak at a wavelength between about 190 nm and 200 nm. The α-helix secondary structure is typically induced when the star shaped peptide polymer is exposed to a hydrophobic cell membrane. Thus, exposure of the star shaped peptide polymer to a hydrophobic environment that mimics that of the hydrophobic cell membrane can induce the α-helix secondary structure in the statistical or random peptide copolymer. In the present case, it is preferred that the statistical or random peptide copolymer exhibits the α-helix secondary structure when exposed to around 80% v/v trifluoroethanol (TFE), and such α-helix secondary structure is detectable using CD spectroscopy.

In an embodiment, the dendrimer is a PAMAM (Poly (amidoamine)) dendrimer. It is preferred that the PAMAM dendrimer. The number of branches that the PAMAM dendrimer has will depend on the number of repeat subunits that the dendrimer has. This may also be referred to as the "generation" of the PAMAM dendrimer. Those skilled in the art will appreciate that the PAMAM dendrimer may be continually grown outward through a series of two reactions (e.g. (i) Michael addition of an amino terminated surface onto methyl acrylate, resulting in an ester-terminated outer layer, and (ii) coupling this with ethylene diamine to achieve a new amino-terminated surface).

However, it is preferred that the PAMAM dendrimer is a generation 1 to generation 5 PAMAM dendrimer, and preferably a generation 0, 1, 2 or 3 PAMAM dendrimer. For the avoidance of doubt, a generation 0 PAMAM dendrimer has 4 branches terminating in 4 terminal moieties, a generation 1 PAMAM dendrimer has 8 branches terminating in 8 terminal moieties, a generation 2 PAMAM dendrimer has 16 branches terminating in 16 terminal moieties, a generation 3 PAMAM dendrimer has 32 branches terminating in 32 terminal moieties, and so on.

In an embodiment, the star shaped peptide polymer is selected from:

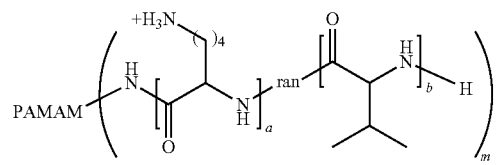

Where m is $2^n$ and n is a number between 2 and 8. Preferably n is 2, 3, 4 or 5, and m is 4, 8, 16 or 32 accordingly. In this context, 'm' represents the total number of statistical or random peptide copolymers extending from the branches, and thus represents the total number of branches. 'a' and 'b' represent the number of repeat units of lysine and valine in the peptide copolymer respectively.

In embodiments where n is 2, 3, 4 or 5, and m is 4, 8, 16 or 32 accordingly, it is preferred that the copolymer exhibits a degree of polymerisation of at least 5 and up to 50; preferably, at least 8 and up to 45; and more preferably at least 10 and up to 40.

In another aspect the present invention provides a star shaped peptide polymer of the invention prepared by a process comprising the steps of: forming a reaction solution comprising: a solvent, the multifunctional core, and either: (i) the statistical or random peptide copolymer, or (ii) a cationic peptide monomer and a hydrophobic peptide monomer; and agitating the solution for a period of time to form the star shaped peptide polymer. In an embodiment, the multifunctional core is the dendrimer.

In an embodiment, the solvent is a non-aqueous solution. The non-aqueous solvent may be a polar non-aqueous solvent and/or a water miscible solvent. Preferably, the solvent is an organic solvent. While a range of different solvents may be employed, the most preferred solvent is dimethylformamide (DMF), such as anhydrous DMF.

In an embodiment, the step of agitating the solution is conducted under an inert atmosphere. The term "inert atmosphere" is intended to refer to a gaseous mixture that contains little or no oxygen (preferably no oxygen) and primarily consists of gases or gases that are non-reactive within the context of this method. Suitable gases include nitrogen, argon, helium, carbon dioxide, and mixtures thereof. However, it is preferred that the inert atmosphere comprises argon gas. More preferably the inert atmosphere consists of argon gas.

In an embodiment, the step of agitating the solution includes agitating the solution at ambient temperature.

In an embodiment, the method includes forming a reaction solution comprising: a solvent, the multifunctional core, and a cationic peptide monomer and a hydrophobic peptide monomer. In this embodiment, it is preferred that the step of agitating the solution includes agitating the solution at a temperature of from greater than 0° C. and up to 10° C. Preferably, the temperature is from greater than 0° C. and up to 8° C. More preferably, the temperature is from greater than 0° C. and up to 6° C. Even more preferably, the temperature is from greater than 0° C. and up to 5° C. Most preferably, the temperature is from greater than 0° C. and up to 4° C.

In an embodiment, the solution is agitated for a period of at least 2 hours, preferably at least 6 hours, more preferably at least 12 hours, even more preferably at least 18 hours, most preferably at least 24 hours. The duration of the reaction is important for forming terminal arms of the desired composition and/or number of repeating units. Shorter reaction times result in shorter statistical or random peptide copolymer terminal arms. It is preferred that the solution is agitated for a period of up to 30 hours, more preferably up to 26 hours, and most preferably up to 24 hours.

In an embodiment where the reaction solution comprises the cationic peptide monomer and the hydrophobic peptide monomer, the step of forming the reaction solution includes adding the cationic peptide monomer and the hydrophobic peptide monomer to the solvent at substantially the same time. In this context, the term "substantially the same time" is intended to cover the situation where the cationic peptide monomer and the hydrophobic peptide monomer are added simultaneously, or where the cationic peptide monomer and the hydrophobic peptide monomer are added sequentially. Where the cationic peptide monomer and the hydrophobic peptide monomer are added sequentially, it is preferred that this is within a time period of 10 minutes, and more preferably within a time period of 5 minutes.

The cationic peptide monomer may be a cationic amino acid or a cationic amino acid derivative that is polymerisable to form the cationic amino acid residue. Similarly, the hydrophobic peptide monomer may be a hydrophobic amino acid or a hydrophobic amino acid derivative that is polymerisable to form the hydrophobic amino acid residue. It is preferred that the cationic amino acid derivative and the hydrophobic amino acid derivative are in the form of amino acid N-carboxyanhydrides. In one form of the invention, the cationic peptide monomer is lysine or a lysine N-carboxyanhydride, and the hydrophobic peptide monomer is valine or a valine N-carboxyanhydride.

In an embodiment, the cationic peptide monomer includes a cationic moiety that is protected with a protecting group, such as with a Fluorenylmethyloxycarbonyl (FMOC) protecting group, a carboxybenzyl (Cbz) protecting group, or a tert-Butyloxycarbonyl (BOC) protecting group. In a preferred form, where the cationic peptide monomer is lysine or a lysine derivative, a pendant amine group is protected with a protecting group. In instances where a protecting group is present, the method may further include the step of removing the protecting group from the peptide copolymer. The protecting group may be removed by using techniques disclosed herein or techniques known to those skilled in the art.

In an embodiment, the process further includes precipitating the star shaped peptide polymer into a second solvent phase comprising a second solvent within which the star shaped peptide polymer is not soluble. Preferably, the solvent is a polar solvent, and the second solvent is a non-polar solvent. Diethyl ether is a suitable non-polar solvent.

The process may include any one or more steps as described in the Examples.

In another aspect the present invention provides a method of treating a bacterial infection in a subject, the method comprising administering to the subject an effective amount of a star shaped peptide polymer of the invention, thereby treating the bacterial infection in the subject.

In another aspect present invention provides a method of treating a bacterial infection comprising antibiotic resistant bacteria in a subject, the method comprising administering to the subject an effective amount of a star shaped peptide polymer of the invention, thereby treating the bacterial infection comprising antibiotic resistant bacteria in the subject.

The bacteria may exhibit resistance to any one or more of the antibiotics described herein. For example, the bacteria may exhibit resistance to any one or more of Amikacin, Ampicillin, Amoxicillin/Clavulanic Acid, Aztreonam, Cefazolin, Cefepime, Cefoxitin, Ceftazidime, Ceftriaxone, Ciprofloxacin, Gentamicin, Meropenem, Nalidixic Acid, Nitrofurantoin, Norfloxacin, Piperacillin/Tazobactam, Ticarcillin/Clavulanic Aid, Tobramycin, Trimethoprim, Trimethoprim/Sulfamethoxazole, Imipenem and Colistin Sulfate.

Preferably, the bacteria exhibits resistance to colistin and/or aztreonam. The colistin may be colistin sulfate or colistimethate sodium. Preferably, the bacteria that exhibits resistance to colistin sulfate is any bacteria described herein known or identified as exhibiting resistance. Preferably, the bacteria that exhibits resistance to colistin sulfate is a bacteria other than *A. baumannii* FADDI-AB156.

In any aspect of a method or use of the invention the *A. baumannii* present in the infection may exhibit resistance to treatment of any one or more of Amoxicillin/Clavulanic Acid, Ampicillin, Cefazolin, Cefepime, Cefoxitin, Ceftazidime, Ceftriaxone, Ciprofloxacin, Gentamicin, Meropenem, Nalidixic Acid, Nitrofurantoin, Norfloxacin, Piperacillin/Tazobactam, Ticarcillin/Clavulanic Aid, Tobramycin, Trimethoprim, Trimethoprim/Sulfamethoxazole, Imipenem and Colistin Sulfate. The *P. aeruginosa* present in the infection may exhibit resistance to treatment of any one or more of Ampicillin, Aztreonam, Ceftazidime, Gentamicin, Piperacillin, Ticarcillin, Tobramycin and Colistin Sulfate.

In another aspect the present invention provides a method of treating a condition associated with, or caused by, a bacterial infection in a subject, the method comprising administering to the subject an effective amount of a star shaped peptide polymer of the invention, thereby treating the condition associated with, or caused by, a bacterial infection in the subject. A condition associated with, or caused by, a bacterial infection may be any condition described herein. In one embodiment, the condition is an oral disease such as chronic periodontitis or oral infection.

In another aspect the present invention provides a method of treating an acute bacterial infection in a subject, the method comprising administering to the subject an effective amount of a star shaped peptide polymer of the invention, thereby treating the acute bacterial infection.

In another aspect, the present invention provides a method of treating a subject with a blood borne bacterial infection, the method comprising administering to the subject an effective amount of a star shaped peptide polymer of the invention sufficient to reduce the level of bacteria in the blood and spleen, thereby treating a subject with a blood borne bacterial infection.

In another aspect the present invention provide a method of treating a subject with a bacterial infection of the spleen, the method comprising administering to the subject an effective amount of a star shaped peptide polymer of the invention to the subject, thereby treating the subject the bacterial infection of the spleen. The subject may be identified as having a bacterial infection of the spleen by presenting with an enlarged spleen.

In another aspect the present invention provides a method of treating a bacterial infection in a subject, the method comprising administering to a subject an effective amount of a star shaped peptide polymer of the invention for period of 4, 5, 6, 7, 8, 9, 10, 11, 12, 13, or 14 days, whereby reduction in bacterial level observed on the last day of treatment is the same or similar as the reduction on the first day of treatment, thereby treating a bacterial infection in a subject.

In another aspect the present invention provides a method of treating a bacterial infection in a subject at risk of, or diagnosed with, toxic shock, the method comprising administering to the subject an effective amount of a star shaped peptide polymer of the invention, thereby treating the bacterial infection in the subject and minimising the risk of toxic shock.

In any aspect of the present invention, the subject may have been previously administered an antibiotic with the intention of treating the bacterial infection, however the bacterial infection still persisted. For example, the subject having the bacterial infection may have been administered any one or more of the following antibiotics that did not treat the bacterial infection:

(1) Macrolides or ketolides such as erythromycin, azithromycin, clarithromycin and telithromycin;
(2) Beta (β)-lactams such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefinetazole, cefotaxime, ceftizoxime, ceftriaxone, cefoperazone, ceftazidime, cefixime, cefpodoxime, ceftibuten, cefdinir, cefpirome, cefepime, aztreonam, imipenem, meropenem, ertapenem, doripenem, ceftobiprole, and ceftaroline;
(3) Quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, garenoxacin, gemifloxacin and pazufloxacin;
(4) Antibacterial sulfonanmides and antibacterial sulphanilamides, including para-aminobenzoic acid, sulfadiazine, sulfisoxazole, sulfamethoxazole and sulfathalidine;
(5) Aminoglycosides such as streptomycin, neomycin, kanamycin, paromycin, gentamicin, tobramycin, amikacin, netilmicin, spectinomycin, sisomicin, dibekacin and isepamicin;
(6) Tetracyclines such as tetracycline, chlortetracycline, demeclocycline, minocycline, oxytetracycline, methacycline, tigecycline, doxycycline;
(7) Rifamycins such as rifampicin (also called rifampin), rifapentine, rifabutin, bezoxazinorifamycin and rifaximin;
(8) Lincosamides such as lincomycin and clindamycin,
(9) Glycopeptides such as telavancin, vancomycin and teicoplanin or lipopeptides such as daptomycin;
(10) Streptogramins such as quinupristin and dalfopristin;
(11) Oxazolidinones such as linezolid;
(12) Polymyxin, colistin and colymycin; and
(13) Trimethoprim and bacitracin.

More preferably, the subject having the bacterial infection may have been administered any one of more of the following antibiotics that did not treat the bacterial infection: Amikacin, Ampicillin, Amoxicillin/Clavulanic Acid, Aztreonam, Cefazolin, Cefepime, Cefoxitin, Ceftazidime, Ceftriaxone, Ciprofloxacin, Gentamicin, Meropenem, Nalidixic Acid, Nitrofurantoin, Norfloxacin, Piperacillin/Tazobactam, Ticarcillin/Clavulanic Aid, Tobramycin, Trimethoprim, Trimethoprim/Sulfamethoxazole, Imipenem and Colistin Sulfate In any aspect of the present invention, the bacteria may be Gram-positive or Gram-negative bacteria. Preferably, the bacteria are Gram-negative.

In any aspect of a method or use of the invention, the star shaped peptide polymer or composition of the invention may be administered to allow the star shaped peptide polymer or composition to contact the bacteria. Alternatively, the step of administering the star shaped peptide polymer or composition of the invention may be a step of contacting the bacteria with a star shaped peptide polymer or composition of the invention.

In any method or use of the invention described herein, a composition of the invention may be administered systemically or directly to the site of infection.

In another aspect the present invention also provides a pharmaceutical composition comprising, consisting essentially of or consisting of a star shaped peptide polymer of the invention and a carrier, diluent or excipient. Preferably, the carrier, diluent or excipient is pharmaceutically or physiologically relevant. Preferably, the composition further includes a chelating agent. Preferably, the chelating agent chelates divalent cations. Exemplary chelating agents include EDTA, citric acid, DTPA i.e. Diethylenetriamine-N, N,N',N',N''-pentaacetic acid, NTA i.e. N,N-bis(carboxymethyl)glycine, Iminodisuccinic acid (IDS), Polyaspartic acid, Ethylenediamine-N,N'-disuccinic acid (EDDS) and Methylglycinediacetic acid (MGDA).

In another aspect the present invention also provides a pharmaceutical composition comprising a star shaped peptide polymer of the invention and a protein or ion rich carrier, diluent or excipient.

In another aspect the present invention provides a star shaped peptide polymer of the invention for use in the treatment of a bacterial infection in a subject.

In another aspect the present invention provides a star shaped peptide polymer of the invention for use in the treatment of a bacterial infection including antibiotic resistant bacteria in a subject.

In another aspect the present invention provides a star shaped peptide polymer of the invention for use in the treatment of an acute bacterial infection in a subject.

In another aspect the present invention provides a star shaped peptide polymer of the invention for use in the treatment of a bacterial infection of the spleen in a subject.

In another aspect the present invention provides a star shaped peptide polymer of the invention for use in the treatment of a bacterial infection in a subject at risk of toxic shock.

In another aspect the present invention provides a kit or article of manufacture including a star shaped peptide polymer of the invention or pharmaceutical composition of the invention as described herein.

In other embodiments there is provided a kit for use in a therapeutic or prophylactic application mentioned herein, the kit including:
   a container holding a star shaped peptide polymer or pharmaceutical composition of the invention; and
   a label or package insert with instructions for use.

In any method or use of the invention described herein, the bacterial infection may comprise, consisting essentially of or consist of Gram-negative or Gram-positive bacteria. The bacterial infection may include both Gram-negative and Gram-positive bacteria. Typically, the bacterial infection is an infection caused by one or more of Gram-negative bacterium selected from the group consisting of *Acinetobacter baumannii, Acinetobacter haemolyticus, Actinobacillus actinomycetemcomitans, Aeromonas hydrophila, Bacteroides fragilis, Bacteroides thetaiotaomicron, Bacteroides distasonis, Bacteroides ovatus, Bacteroides vulgatus, Bordetella pertussis, Brucella melitensis, Burkholderia cepacia, Burkholderia pseudomallei, Burkholderia mallei, Fusobacterium, Prevotella corporis, Prevotella intermedia, Prevotella endodontalis, Porphyromonas asaccharolytica, Campylobacter jejuni, Campylobacter fetus, Citrobacter freundii, Citrobacter koseri, Edwarsiella tarda, Eikenella corrodens, Enterobacter cloacae, Enterobacter aerogenes, Enterobacter agglomerans, Escherichia coli, Francisella tularensis, Haemophilus influenzae, Haemophilus ducreyi, Helicobacter pylori, Kingella kingae, Klebsiella pneumoniae, Klebsiella oxytoca, Klebsiella rhinoscleromatis, Klebsiella ozaenae, Legionella pneumophila, Moraxella catarrhalis, Morganella morganii, Neisseria gonorrhoeae, Neisseria meningitidis, Pasteurella multocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonas fluorescens, Salmonella typhi, Salmonella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vulnificus, Vibrio alginolyticus, Yersinia enterocolitica, Yersinia pestis, Yersinia pseudotuberculosis, Chlamydia pneumoniae, Chlamydia trachomatis, Rickettsia prowazekii, Coxiella burnetii, Ehrlichia chaffeensis*, and *Bartonella henselae*. More preferably, the bacterial infection is an infection caused by one or more of bacterium selected from the group consisting of *Acinetobacter baumannii, Bordetella pertussis, Burkholderia cepacia, Burkholderia pseudomallei, Burkholderia mallei, Campylobacter jejuni, Campylobacter coli, Enterobacter cloacae, Enterobacter aerogenes, Escherichia coli, Francisella tularensis, Haemophilus influenzae, Haemophilus ducreyi, Helicobacter pylori, Klebsiella pneumoniae, Legionella penumophila, Moraxella catarrhalis, Morganella morganii, Neisseria gonorrhoeae, Neisseria meningitidis, Pasteurella multocida, Proteus mirabilis, Proteus vulgaris, Pseudomonas aeruginosa, Salmonella typhi, Serratia marcescens, Shigella flexneri, Shigella boydii, Shigella sonnei, Shigella dysenteriae, Stenotrophomonas maltophilia, Vibrio cholerae*, and *Chlamydia pneumoniae*. Even more preferably, the bacterial infection is an infection caused by one or more of bacterium selected from the group consisting of *Acinetobacter baumannii, Bordetella pertussis, Burkholderia cepacia, Burkholderia pseudomallei, Burkholderia mallei, Campylobacter jejuni, Campylobacter coli, Enterobacter cloacae, Enterobacter aerogenes, Escherichia coli, Francisella tularensis, Haemophilus influenzae, Haemophilus ducreyi, Helicobacter pylori, Klebsiella pneumoniae, Legionella penumophila, Moraxella catarrhalis, Morganella morganii, Proteus mirabilis, Proteus vulgaris, Pseudomonas aeruginosa, Serratia marcescens*, and *Stenotrophomonas maltophilia*.

Preferably, the bacterial infection may comprise, consisting essentially of *E. coli, P. aeruginosa, K. pneumoniae, A. baumannii*, multi-drug resistant *P. aeruginosa*, or multi-drug resistant *A. baumannii*.

In another aspect, the Gram-negative bacteria may be any one or more of the following implicated in chronic periodontitis: *Porphyromonas gingivalis, Treponema denticola, Tannerella forsythia, Aggregatibacter actinomycetemcomitans, Campylobacter rectus, Prevotella intermedia, Prevotella nigrescens, Fusobacterium nucleatum, Eikenella corrodens* and *Capnocytophaga ochracea*. Therefore, the present invention finds application to treat intra-oral bacterial infection, including antibiotic resistant intra-oral bacteria.

As used herein, except where the context requires otherwise, the term "comprise" and variations of the term, such as "comprising", "comprises" and "comprised", are not intended to exclude further additives, components, integers or steps. As used herein, the terms "including" and "comprising' may be used interchangeably.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 13. a-b, TEM analysis of SNAPPs S16 (a) and S32 (b) in minimal essential media (MEM). The samples were negative-stained and air dried at a sample concentration of 0.5 μg/mL. The images are representative of three independent experiments.

FIG. 22. In vivo efficacy of SNAPP S16 in a mouse peritonitis (*A. baumannii* ATCC 19606-infected) model. a-b, Colony forming units (CFU) of *A. baumannii* (ATCC 19606) found in the blood (a) and spleen (b) of infected mice 24 h after no treatment or treatment with imipenem (40 mg/kg) or S16 (8.3 mg/kg). All data are expressed as mean±standard deviation as indicated by the error bars, based on values obtained from five biological replicates (n=5). *P<0.01, Student's t test, significant difference from the untreated control.

FIG. 23. In vivo efficacy of SNAPP S16 in a mouse peritonitis (MDR *A. baumannii* FADDI-AB156-infected) model. a-b, Colony forming units (CFU) of MDR *A. baumannii* (FADDI-AB156) found in the blood (a) and spleen (b) of infected mice 24 h after no treatment or treatment with imipenem (40 mg/kg) or S16 (8.3 mg/kg). All data are expressed as mean±standard deviation as indicated by the error bars, based on values obtained from four biological replicates (n=4). *P<0.01, **P<0.001, Student's t test, significant difference from the untreated control.

FIG. 29. Flow cytometric analysis of *E. coli* cells in the LPS inhibition assay. a-l, Two-parameter dot plots and histograms obtained from the analysis of samples containing *E. coli* and LPS (a), *E. coli* and S16 (b), and *E. coli*, S16 and varying concentrations of LPS (2 to 1000 µg/mL) (c-l). The concentration of S16 used was fixed at 4 µg/mL (0.09 µM, i.e., $MBC_{50}$ in MEM). Samples were incubated at 37° C. for 90 min prior to analysis. On the two-parameter dot plots, the x-axis represents fluorescent channel 1 (FL-1), which measures the fluorescent emission of SYTO® 9. The y-axis represents fluorescent channel 2 (FL-2), which measures the fluorescent emission of PI. All data are representative of three independent experiments.

FIG. 33*a*: S16 resulted in only a marginal release of the 4 kDa or 70 kDa dextrans from the LUVs, which was in stark contrast to the release of dextrans induced by the pore-forming AMP, maculatin 1.1. FIG. 33*b*: S16 induced a 50% chloride ion efflux ($EC_{50}$) at a concentration of ca. 2.7 µg/mL (corresponding to a lipid to S16 molar ratio of 4798±431:1) which was similar to the $EC_{50}$ of maculatin 1.1 (ca. 1.7 µg/mL at a lipid to peptide molar ratio of 381±46:1).

FIG. 52: 1H NMR spectra (d6-DMSO) of (a) linear Cbz-protected polymer LRZ and (b) deprotected polymer LR.

FIG. 70: Growth curves of $E.$ $coli$ in the presence and absence of different $S4_{VL}$ concentrations (A). Relative $OD_{630}$ at 3 h of these samples compared to the control (0 µg/mL, '100%') fitted to an exponential function, whose X value at Y=0.1% was established as the MIC (B). n=10; Data points represent the mean value±one standard deviation.

FIG. 73: Antimicrobial concentrations (MIC/MDC/MBC) of different SNAPPs against $E.$ $coli$.

DETAILED DESCRIPTION OF THE EMBODIMENTS

Figure 1:
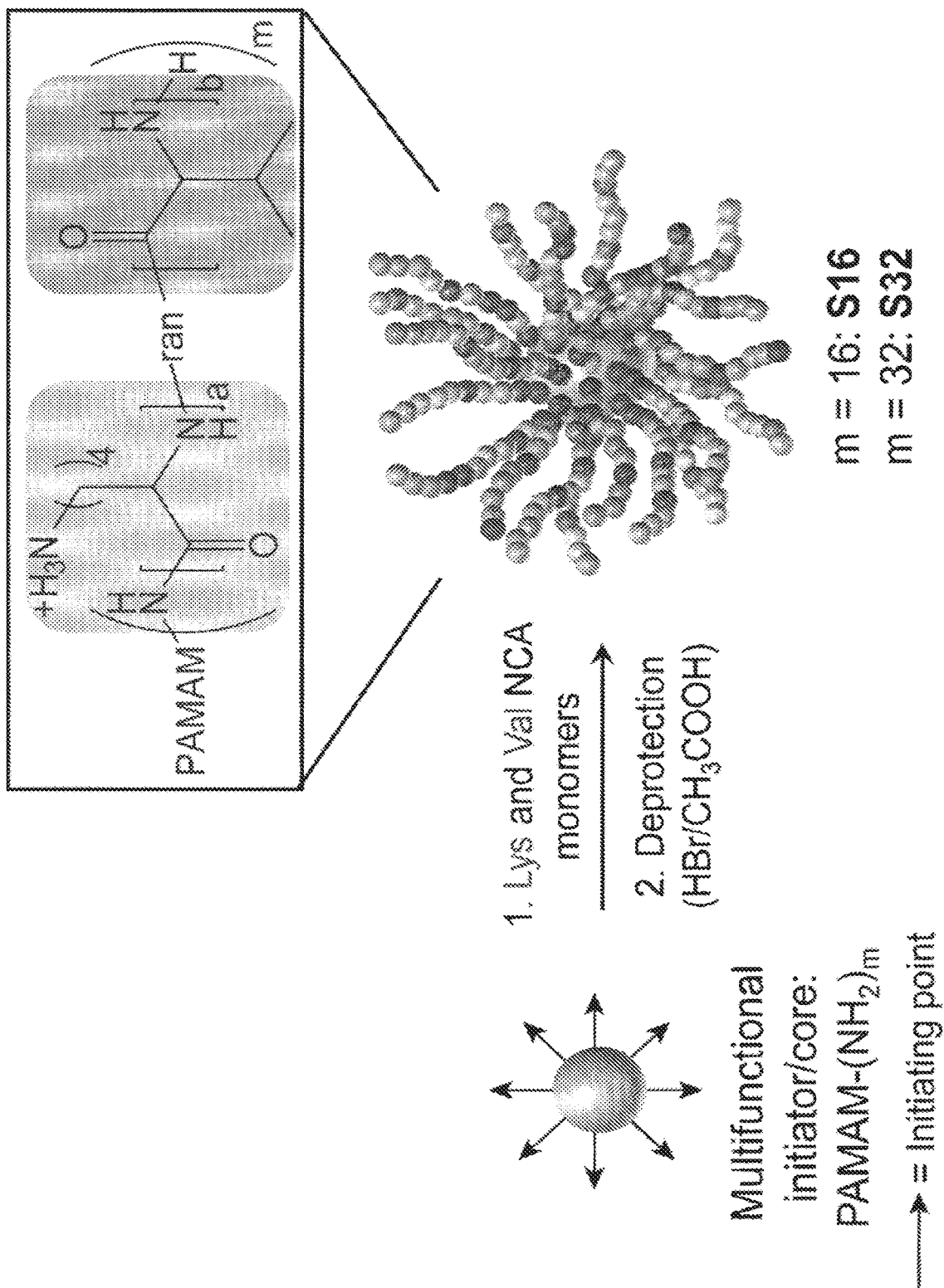
FIG. 1. Synthesis of SNAPPs. Synthesis of SNAPPs via ring-opening polymerization (ROP) of lysine and valine N-carboxyanhydrides (NCAs) was initiated from the terminal amines of poly(amido amine) (PAMAM) dendrimers. Second (G2) and third (G3) generation PAMAM dendrimers (see FIG. 7 for structure of the former) with 16 and 32 peripheral primary amines were used to prepare 16- and 32-arm SNAPPs, respectively. Note that the number of initiating points on the figure does not reflect the actual number which is 16 or 32. The number of repeat units for lysine and valine are a and b, respectively. The lysine-to-valine ratios (i.e., a:b) are provided in Table 2.

It will be understood that the invention disclosed and defined in this specification extends to all alternative combinations of two or more of the individual features mentioned or evident from the text or drawings. All of these different combinations constitute various alternative aspects of the invention.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention.

The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

The present invention is based on the discovery of star-shaped peptide polymer nanoparticles consisting of lysine and valine residues, synthesized via NCA-ROP, as a new class of antimicrobial agents. These star nanoparticles are referred to herein as 'Structurally Nanoengineered Antimicrobial Peptide Polymers' (SNAPPs) and are star shaped peptide polymer of the invention. Unlike existing self-assembled antimicrobial macromolecules that will dissociate to unimers below their critical micelle concentration, star shaped peptide polymer of the invention are stable unimolecular architectures up to infinite dilution. The inventors demonstrated that star shaped peptide polymer of the invention exhibit superior antibacterial activity against a range of clinically-important Gram-negative and Gram-positive bacteria, possess high therapeutic indices, and display selectivity towards pathogens over mammalian cells. The inventors also showed that star shaped peptide polymer of the invention can combat antibiotic resistant bacteria and without being bound by any theory or mode of action have a multi-modal antimicrobial mechanism involving disruption of the integrity of the OM, cytoplasmic membrane (CM) disruption, unregulated ion efflux/influx, and induction of apoptotic-like death (ALD), which potentially accounts for the superior performance of star shaped peptide polymer of the invention and differs from that typically reported for most AMPs.

Star shaped peptide polymers of the invention are generally described as comprising a multifunctional core with a plurality of terminal arms extending therefrom, wherein the terminal arms are statistical or random peptide copolymers of at least a cationic amino acid residue and a hydrophobic amino acid residue. The multifunctional core, may for example be a dendrimer. The dendrimer comprises a dendrimer centre, a plurality of dendron arms having a plurality of branches formed from repeat units and terminate with a terminal unit having a terminal moiety. The star shaped peptide polymer, may in certain embodiments, have a multifunctional core that is based on this dendrimer structure, wherein a statistical or random peptide copolymer (of at least a cationic amino acid residue and a hydrophobic amino acid residue) is covalently bonded to the terminal moieties of the dendrimer.

In this context, the term dendrimer centre is intended to refer to the molecule at the center of the dendrimer that gives rise to the final structure of the dendrimer. In the context of dendrimers formed via divergent synthesis techniques, the dendron centre is is effectively an "initiator" molecule which contains functional groups capable of acting as the initial active sites for forming the dendrimer. By way of example, in the context of a PAMAM based dendrimer, the dendrimer centre is based on an ethylene diamine initiator. Once the dendrimer has formed, each of the primary amine groups originally on the ethylene diamine molecule have been reacted with, and covalently bound to two dendron arms. Thus, the resultant dendrimer centre has the form of an ethylene diamine molecule wherein each amine group is a tertiary amine, such as of the form $R_2N(CH_2)_2NR_2$.

The term "dendron arms" is intended to refer to the branched groups that are covalently bound to the dendrimer centre. The number of dendron arms is dependent on the number of functional groups capable of acting as the initial active sites on the dendrimer centre. PAMAM has a core formed from an ethylene diamine initiator, and as such provides four active sites to which the dendron arms may be bound.

The dendron arms have a plurality of branches formed from repeat units and terminate with a terminal unity having a terminal moiety. It will be appreciated that the terms "terminal unit(s)" and the "terminal moiety" or "terminal moieties" relate to the dendrimer structure itself and are not intended to designate terminal groups of the star shaped peptide polymer. As is clear from the above, the star shaped peptide polymer further includes terminal arms (being statistical or random peptide copolymers of at least a cationic amino acid residue and a hydrophobic amino acid residue) which in one or more embodiments are covalently bound to the dendrimer via these terminal moieties on the terminal units of the dendrimer.

A number of different synthetic procedures can be used to generate the dendron arms. Typically, such procedures involve reacting functional groups on the core molecule with a further molecule having a first moiety that allows the nucleophilic addition of that further molecule onto the dendrimer centre (via the functional group on the dendrimer centre) and a second moiety for allowing the nucleophilic addition of two or more additional molecules. Again, in the context of PAMAM, the dendron arms can be formed via step (i) the Michael addition of two methyl acrylates onto each amine group of the ethylene diamine core, resulting in an ester-terminated outer layer, and step (ii) the subsequent coupling of ethylene diamine to ester-terminated outer layer to achieve two new amino-terminated surfaces for each amine surface prior to step (i). Thus, each repetition of reactions (i) and (ii) adds repeat units in a manner which doubles the number of branches in the dendron arms. Each repetition of this sequence of reactions to double the number of branches is referred to as a generation. The process may be repeated until dendron arms of the desired size (re desired number of generations) have been reached. The molecules that form the outer portions of the branches are the terminal units, and these terminal units include a terminal moiety (which in the context of PAMAM is an amine). Thus, in the context of this invention, the terminal moiety refers to the end moiety of the repeat units that form the branches of the dendron arms. Advantageously, another molecule (in particular a statistical or random peptide copolymer) can be conjugated to these terminal moieties.

A statistical or random peptide copolymer is a copolymer formed from at least two different peptide units or amino acid residues. Statistical copolymers are copolymers in which the sequence of monomer residues follows a statistical rule. If the probability of finding a given type monomer residue at a particular point in the chain is equal to the mole fraction of that monomer residue in the chain, then the polymer may be referred to as a random copolymer.

In this context, the "amino acid residues" is intended to refer to discrete amino acid monomers linked by peptide bonds in the copolymer. A cationic amino acid residue is one having a moiety exhibiting a positive charge. An example of this is a lysine residue which includes a protonated sidechain including an $NH^{3+}$ moiety. A hydrophobic amino acid residue is one which includes a non-polar residue, such as valine which has an isopropyl side chain rendering the residue hydrophobic.

Star shaped peptide polymers of the invention exhibit one or more advantages including that bacteria do not, or do not readily, develop resistance and that the star shaped peptide polymers interact with lipopolysaccharide (LPS) such that LPS induced toxic shock is less likely to occur after treatment of the bacterial infection. More specifically, the star shaped peptide polymers dampen the toxic shock arising from treatment of a large bacterial infection as the peptides bind and sequester LPS and in doing so will reduce the huge inflammatory response associated with LPS. Due to the large size of the peptide polymers and how the bacterial membranes are disrupted, mutations of peptides or proteins on the surface of bacteria are less likely to reduce the function of star shaped peptide polymer polymers. Without wishing to be bound by theory, the inventors believe that due to the large size of the peptide polymers and the mechanisms by which bacterial membranes are disrupted, mutations at the surface of bacteria are unlikely to have an adverse impact on the functioning of star shaped peptide polymers.

Subjects suffering from a bacterial infection, or healthy control subjects, may be assessed before and after treatment of a star shaped peptide polymer of the invention, by using any one of, or combination of, numerous different standards or scales employed by a person having ordinary skill in the art. Examples of standards or scales for testing the effectiveness of the methods disclosed herein include assessment of body temperature, body weight, Lab-Score, procalcitonin levels, circulating white blood cell levels, Laboratory Risk Indicator for Necrotizing Fasciitis (LRINEC) score, mucus levels, urea breath test, or levels of bacteria present in a sample taken from a subject (e.g. blood, serum, mucus, skin, stool, urine, sputum, saliva, semen, or biopsy sample).

As used herein, a "subject" refers to an animal, such as a mammalian or an avian species, including a human, an ape, a horse, a cow, a sheep, a goat, a dog, and a cat. The subject may have a bacterial infection, may have been exposed to infectious bacteria, may be at risk for developing a bacterial infection, or may be at greater risk than the general population for developing a bacterial infection. Examples of subjects at greater risk for developing a bacterial infection include patients undergoing treatment for bacterial infections whereby normal gut flora is inhibited by antimicrobial therapy, patients with impaired immune function (e.g., immunoglobulin deficiency, splenic dysfunction, splenectomy, HIV infection, impaired leukocyte function, hemoglobinopathies), the elderly, people with certain malignancies (e.g., multiple myeloma, chronic lympocytic leukemia, lymphoma), people at increased occupational risk (e.g., public services workers, such a fire, water, sanitary, police, medical, and laboratory workers, hospital workers), people in closed populations (e.g., prisons, military, nursing homes) and others that have immunological deficiencies that might enhance their susceptibility to bacterial infection.

A bacterial infection generally refers to:
(1) an elevated level of bacteria in a sample taken from the individual compared to an uninfected control sample;
(2) an increased proportion of one or more types of bacteria in a sample taken from the individual compared to the total level of bacteria in an uninfected control sample;
(3) an increased proportion of bacteria relative to one or more other bacteria species in a sample taken from the individual when compared to an uninfected control sample; or
(4) the presence of a bacteria in a sample compared to an uninfected control sample when that same bacteria is undetectable in the uninfected control.

A subject may be diagnosed as having a bacterial infection by any method described herein or known in the art. A biological sample such as a bodily fluid sample (e.g. blood) or tissue sample or scraping. Then the sample is prepared (various ways) and then cultured on different agar plates with defined media that will classify the microbe. Real time PCR is another method that may be used to identify bacteria in a sample.

An acute bacterial infection refers to an infection in a subject that requires rapid treatment, generally in the range of 15 to 60 minutes, otherwise the infection may progress to endanger the life of the subject. Such acute infections may occur in infants or immunocompromised subjects as described herein.

In one aspect, the terms "infection" and "bacterial infection" refer to an infection caused by Gram-negative bacteria, also referred to as a "Gram-negative infection". In one aspect of this embodiment, the Gram-negative infection is an infection resistant to one or more antibiotics. In one aspect of this embodiment, the Gram-negative infection is a multi-drug resistant infection. In certain embodiments, the Gram-negative bacterium is *Acinetobacter* spp. In certain embodiments, the Gram-negative bacterium is *Acinetobacter* spp., such as *Acinetobacter baumannii*. In certain embodiments, the Gram-negative bacterium is *Burkholderia* spp. In certain embodiments, the Gram-negative bacterium is *Burkholderia pseudomallei*. In certain embodiments, the Gram-negative bacterium is *Pseudomonas aeruginosa*. In certain embodiments, the Gram-negative bacterium is Enterobacteriaceae. In any of these embodiments, the Gram-negative infection arises from a pathogen or pathogen expressing one or more β-lactamase. In any of these embodiments, the Gram-negative infection arises from a pathogen or pathogen expressing one or more Class A, Class C and/or Class D β-lactamase. In any of these embodiments, the Gram-negative infection arises from a pathogen or pathogen expressing one or more Class A β-lactamase. In any of these embodiments, the Gram-negative infection arises from a pathogen or pathogen expressing one or more Class C β-lactamase. In any of these embodiments, the Gram-negative infection arises from a pathogen or pathogen expressing one or more Class D β-lactamase.

An infection caused by "Enterobacteriaceae" refers to any of the Gram-negative bacteria in this family of bacteria which includes, but is not limited to, species such as *Salmonella* spp., *Escherichia coli*, *Yersinia pestis*, *Klebsiella* spp., *Shigella* spp., *Proteus* spp., *Enterobacter* spp., *Serratia* spp., and *Citrobacter* spp. Thus, treatment of a bacterial infection caused by "Enterobacteriaceae" includes any infection caused by any one or more bacteria which is part of this family. In one embodiment, a bacterial infection caused by "Enterobacteriaceae" includes bacterial infections which have at least one *Salmonella* spp. pathogen present. In one embodiment, a bacterial infection caused by "Enterobacteriaceae" includes bacterial infections which have at least one *Escherichia coli* pathogen present. In one embodiment, a bacterial infection caused by "Enterobacteriaceae" includes bacterial infections which have at least one *Yersinia pestis* pathogen present. In one embodiment, a bacterial infection caused by "Enterobacteriaceae" includes bacterial infections which have at least one *Klebsiella* spp. pathogen present. In one embodiment, a bacterial infection caused by "Enterobacteriaceae" includes bacterial infections which have at least one *Shigella* spp. pathogen present. In one embodiment, a bacterial infection caused by "Enterobacteriaceae" includes bacterial infections which have at least one *Proteus* spp. pathogen present. In one embodiment, a bacterial infection caused by "Enterobacteriaceae" includes bacterial infections which have at least one *Enterobacter* spp. pathogen present. In one embodiment, a bacterial infection caused by "Enterobacteriaceae" includes bacterial infections which have at least one *Serratia* spp. pathogen present. In one embodiment, a bacterial infection caused by "Enterobacteriaceae" includes bacterial infections which have at least one *Citrobacter* spp. pathogen present.

In certain embodiments, the terms "infection" and "bacterial infection" refer to a infection caused by Gram-negative bacteria, wherein the Gram-negative bacterium is Enterobacteriaceae which expresses one or more Class A, Class B, Class C and/or Class D β-lactamase. In one aspect of this embodiment, the Gram-negative bacterium is an Enterobacteriaceae which expresses at least one Class B β-lactamase.

In certain embodiments, the Gram-negative bacterium is *Acinetobacter* spp. which expresses one or more β-lactamases. In one embodiment, the Gram-negative bacterium is *Acinetobacter baumannii* which expresses one or more Class A, Class C and/or Class D β-lactamase. In one embodiment, the Gram-negative bacterium is *Acinetobacter baumannii* which expresses one or more Class A β-lactamase. In one embodiment, the Gram-negative bacterium is *Acinetobacter baumannii* which expresses one or more Class C β-lactamase. In one embodiment, the Gram-negative bacterium is *Acinetobacter baumannii* which expresses one or more Class D β-lactamase. In one embodiment, the Gram-negative bacterium is *Acinetobacter baumannii* which expresses TEM-1 or KPC-2.

The term "Gram-negative" is art-recognized as those bacteria that do not retain crystal violet dye in the Gram staining protocol. For example, as used herein, the term "Gram-negative bacteria" describes one or more (i.e., a combination) of the following *Acinetobacter baumannii, Acinetobacter haemolyticus, Actinobacillus actinomycetemcomitans, Aeromonas hydrophila, Bacteroides fragilis, Bacteroides thetaiotaomicron, Bacteroides distasonis, Bacteroides ovatus, Bacteroides vulgatus, Bordetella pertussis, Brucella melitensis, Burkholderia cepacia, Burkholderia pseudomallei, Burkholderia mallei, Fusobacterium, Prevotella corporis, Prevotella intermedia, Prevotella endodontalis, Porphyromonas asaccharolytica, Campylobacter jejuni, Campylobacter coli, Campylobacter fetus, Citrobacter freundii, Citrobacter koseri, Edwardsiella tarda, Eikenella corrodens, Enterobacter cloacae, Enterobacter aerogenes, Enterobacter agglomerans, Escherichia coli, Francisella tularensis, Haemophilus influenzae, Haemophilus ducreyi, Helicobacter pylori, Kingella kingae, Klebsiella pneumoniae, Klebsiella oxytoca, Klebsiella rhinoscleromatis, Klebsiella ozaenae, Legionella penumophila, Moraxella catarrhalis, Morganella morganii, Neisseria gonorrhoeae, Neisseria meningitidis, Pasteurella multocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonas fluorescens, Salmonella typhi, Salmonella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vulnificus, Vibrio alginolyticus, Yersinia enterocolitica, Yersinia pestis, Yersinia pseudotuberculosis, Chlamydophila pneumoniae, Chlamydophila trachomatis, Rickettsia prowazekii, Coxiella burnetii, Ehrlichia chaffeensis,* or *Bartonella henselae*. Moreover, it is expected that the a star shaped peptide polymer or composition of the present invention will be useful in treating one or more bacterial infections.

In another aspect, the Gram-negative bacteria may be any one or more of the following implicated in chronic periodontitis: *Porphyromonas gingivalis, Treponema denticola, Tannerella forsythia, Aggregatibacter actinomycetemcomitans, Campylobacter rectus, Prevotella intermedia, Prevotella nigrescens, Fusobacterium nucleatum, Eikenella corrodens* and *Capnocytophaga ochracea*. Therefore, the present invention finds application to treat intra-oral bacteria infection, including antibiotic resistant intra-oral bacteria.

In another aspect, the terms "infection" and "bacterial infection" refer to an infection caused by Gram-positive bacteria, also referred to as a "Gram-positive infection".

Gram-positive bacteria refer to bacteria that are stained blue or violet by gram staining, and include, for example, *Staphylococcus aureus, Lactobacillus* spp, *Bifidobacteria* and *Scardovia wiggsiae* and the like. Gram-positive bacteria feature of having a thick peptidoglycan layer around a cell membrane and having no outer membrane on a periphery of the cell membrane. Gram-positive bacteria is not limited to Gram-positive cocci or Gram-positive bacilli.

Symptoms of toxic shock or toxic shock syndrome (TSS) vary depending on the underlying cause. TSS resulting from infection with the bacterium *Staphylococcus aureus* typically manifests in otherwise healthy individuals via signs and symptoms including high fever, accompanied by low blood pressure, malaise and confusion, which can rapidly progress to stupor, coma, and multiple organ failure. The characteristic rash, often seen early in the course of illness, resembles a sunburn, and can involve any region of the body including the lips, mouth, eyes, palms and soles. In patients who survive the initial phase of the infection, the rash desquamates, or peels off, after 10-14 days.

In contrast, TSS caused by the bacterium *Streptococcus pyogenes*, or TSLS, typically presents in people with pre-existing skin infections with the bacteria. These individuals often experience severe pain at the site of the skin infection, followed by rapid progression of symptoms as described above for TSS. In contrast to TSS caused by *Staphylococcus*, streptococcal TSS less often involves a sunburn-like rash.

For staphylococcal toxic shock syndrome, the diagnosis is based strictly upon CDC criteria defined in 2011, as follows:
1. Body temperature >38.9° C. (102.02° F.)
2. Systolic blood pressure <90 mmHg
3. Diffuse macular erythroderma
4. Desquamation (especially of the palms and soles) 1-2 weeks after onset
5. Involvement of three or more organ systems:
   Gastrointestinal (vomiting, diarrhoea)
   Muscular: severe myalgia or creatine phosphokinase level at least twice the upper limit of normal
   Mucous membrane hyperaemia (vaginal, oral, conjunctival)
   Kidney failure (serum creatinine >2 times normal)
   Liver inflammation (bilirubin, AST, or ALT>2 times normal)
   Low platelet count (platelet count <100,000/mm$^3$)
   Central nervous system involvement (confusion without any focal neurological findings)
6. Negative results of:
   Blood, throat, and CSF cultures for other bacteria (besides *S. aureus*)

Negative serology for *Rickettsia* infection, leptospirosis, and measles

Cases are classified as confirmed or probable based on the following:

Confirmed: All six of the criteria above are met (unless the patient dies before desquamation can occur); and Probable: Five of the six criteria above are met.

A bacteria may be considered as resistant to a certain antibiotic if the MIC is above its breakpoint. Breakpoint tables are published by the relevant committees and known to the skilled person, for example:

1. European Committee on Antimicrobial Susceptibility http://www.eucast.org/clinical_breakpoints/-Clinical breakpoints-bacteria (v 6.0).
2. Clinical and Laboratory Standards Institute (CLSI) http://clsi.org/m100/

Any clinical or biochemical tests as described herein could be performed to determine whether particular bacteria are resistant to an antibiotic, including Broth microdilution (MIC) and disk diffusion assays.

Bacteria may be considered resistant to an antibiotic or anti-bacterial compound, if no bactericidal effect is observed at up to 5 mg/ml when tested in vitro. Alternatively, bacteria may be deemed resistant to an antibiotic or anti-bacterial compound because no improvement is seen clinically in a patient's condition upon administration of a full regimen of that antibiotic or anti-bacterial compound. Conversely, bacteria are considered to be sensitive to an antibiotic or anti-bacterial compound when bactericidal activity can be detected at therapeutically effective ranges or when an improvement is seen in a patient's condition upon administration of a full regimen of that antibiotic.

An "antibiotic resistant bacteria" or "bacteria that exhibit antibiotic resistance" may exhibit detectable resistance to one or more known antibiotics, including but not limited to:

(1) Macrolides or ketolides such as erythromycin, azithromycin, clarithromycin and telithromycin;

(2) Beta (β)-lactams such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefinetazole, cefotaxime, ceftizoxime, ceftriaxone, cefoperazone, ceftazidime, cefixime, cefpodoxime, ceftibuten, cefdinir, cefpirome, cefepime, aztreonam, imipenem, meropenem, ertapenem, doripenem, ceftobiprole, and ceftaroline;

(3) Quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, garenoxacin, gemifloxacin and pazufloxacin, (4) Antibacterial sulfonanmides and antibacterial sulphanilamides, including para-aminobenzoic acid, sulfadiazine, sulfisoxazole, sulfamethoxazole and sulfathalidine;

(5) Aminoglycosides such as streptomycin, neomycin, kanamycin, paromycin, gentamicin, tobramycin, amikacin, netilmicin, spectinomycin, sisomicin, dibekacin and isepamicin, (6) Tetracyclines such as tetracycline, chlortetracycline, demeclocycline, minocycline, oxytetracycline, methacycline, tigecycline, doxycycline;

(7) Rifamycins such as rifampicin (also called rifampin), rifapentine, rifabutin, bezoxazinorifamycin and rifaximin;

(8) Lincosamides such as lincomycin and clindamycin;

(9) Glycopeptides such as telavancin, vancomycin and teicoplanin or lipopeptides such as daptomycin;

(10) Streptogramins such as quinupristin and daflopristin;

(11) Oxazolidinones such as linezolid;

(12) Polymyxin, colistin and colymycin; and

(13) Trimethoprim and bacitracin.

Non-limiting examples of bacteria exhibiting resistance to aztreonam include examples of staphylococci, *Staphylococcus aureus*, *Staphylococcus hemolyticus*; *Xanthomonas maltophilia*; *Aeromonas hydrophile*; *Citrobacter diversus*; *Enterobacter agglomerans*, *Haemophilus* spp., *Streptococcus pyogenes* and *P. aeruginosa*.

Non-limiting examples of bacteria that exhibit resistance to colistin include *Brucella*, *Burkholderia cepacia*, *Chryseobacterium indologenes*, *Edwardsiella*, *Elizabethkingia meningoseptica*, *Francisella tularensis* spp. Gram-negative cocci, *Helicobacter pylori*, *Moraxella catarrhalis*, *Morganella* spp., *Neisseria gonorrheae* and *Neisseria meningitides*, *Proteus*, *Providencia*, *Serratia*, *Stenotrophomonas maltophila*, *Aeromonas*, *Vibrio*, *Prevotella*, *Fusobacterium*, and *Escherichia coli*.

Exemplary bacteria which can result in an infection and which the present invention finds particular application in the treatment, prevention or prophylaxis of are now described below. Also described in the context of the different types of bacteria are conditions associated with, or caused by, a bacterial infection comprising or consisting of that type of bacteria.

*Escherichia coli* (*E. coli*) is a Gram-negative bacterium that is part of the normal flora of the gastrointestinal tract. There are hundreds of strains of *E. coli*, most of which are harmless and live in the gastrointestinal tract of healthy humans and animals. Currently, there are four recognized classes of enterovirulent *E. coli* (the "EEC group") that cause gastroenteritis in humans. Among these are the enteropathogenic (EPEC) strains and those whose virulence mechanism is related to the excretion of typical *E. coli* enterotoxins. Such strains of *E. coli* can cause various diseases including those associated with infection of the gastrointestinal tract and urinary tract, septicemia, pneumonia, and meningitis. Antibiotics are not effective against some strains and do not necessarily prevent recurrence of infection.

For example, *E. coli* strain 0157:H7 is estimated to cause 10,000 to 20,000 cases of infection in the United States annually (Federal Centers for Disease Control and Prevention). Hemorrhagic colitis is the name of the acute disease caused by *E. coli* O157:H7. Preschool children and the elderly are at the greatest risk of serious complications.

Exemplary sequences for enterovirulent *E. coli* strains include Gen Bank Accession Numbers AB011549, X97542, AF074613, Y11275 and AJ007716.

*Salmonella thyphimurium*, are Gram-negative bacteria which cause various conditions that range clinically from localized gastrointestinal infections, gastroenteritis (diarrhea, abdominal cramps, and fever) to enteric fevers (including typhoid fever) which are serious systemic illnesses. *Salmonella* infection also causes substantial losses of livestock.

Typical of Gram-negative bacilli, the cell wall of *Salmonella* spp. contains a complex lipopolysaccharide (LPS)

structure that is liberated upon lysis of the cell and may function as an endotoxin, which contributes to the virulence of the organism.

Contaminated food is the major mode of transmission for non-typhoidal *Salmonella* infection, due to the fact that *Salmonella* survive in meats and animal products that are not thoroughly cooked. The most common animal sources are chickens, turkeys, pigs, and cows; in addition to numerous other domestic and wild animals. The epidemiology of typhoid fever and other enteric fevers caused by *Salmonella* spp. is associated with water contaminated with human feces.

Vaccines are available for typhoid fever and are partially effective; however, no vaccines are available for non-typhoidal *Salmonella* infection. Non-typhoidal salmonellosis is controlled by hygienic slaughtering practices and thorough cooking and refrigeration of food. Antibiotics are indicated for systemic disease, and Ampicillin has been used with some success. However, in patients under treatment with excessive amounts of antibiotics, patients under treatment with immunosuppressive drugs, following gastric surgery, and in patients with hemolytic anemia, leukemia, lymphoma, or AIDS, *Salmonella* infection remains a medical problem.

*Pseudomonas* spp. are motile, Gram-negative rods which are clinically important because they are resistant to most antibiotics, and are a major cause of hospital acquired (nosocomial) infections. Infection is most common in: immunocompromised individuals, burn victims, individuals on respirators, individuals with indwelling catheters, IV narcotic users and individual with chronic pulmonary disease (e.g., cystic fibrosis). Although infection is rare in healthy individuals, it can occur at many sites and lead to urinary tract infections, sepsis, pneumonia, pharyngitis, and numerous other problems, and treatment often fails with greater significant mortality.

*Pseudomonas aeruginosa* is a Gram-negative, aerobic, rod-shaped bacterium with unipolar motility. An opportunistic human pathogen, *P. aeruginosa* is also an opportunistic pathogen of plants. Like other *Pseudomonas*, *P. aeruginosa* secretes a variety of pigments. Definitive clinical identification of *P. aeruginosa* can include identifying the production of both pyocyanin and fluorescein as well as the organism's ability to grow at 42° C. *P. aeruginosa* is also capable of growth in diesel and jet fuel, for which it is known as a hydrocarbon utilizing microorganism (or "HUM bug"), causing microbial corrosion.

*Vibrio cholerae* is a Gram-negative rod which infects humans and causes cholera, a disease spread by poor sanitation, resulting in contaminated water supplies. *Vibrio cholerae* can colonize the human small intestine, where it produces a toxin that disrupts ion transport across the mucosa, causing diarrhea and water loss. Individuals infected with *Vibrio cholerae* require rehydration either intravenously or orally with a solution containing electrolytes. The illness is generally self-limiting; however, death can occur from dehydration and loss of essential electrolytes. Antibiotics such as tetracycline have been demonstrated to shorten the course of the illness, and oral vaccines are currently under development.

*Neisseria gonorrhoea* is a Gram-negative coccus, which is the causative agent of the common sexually transmitted disease, gonorrhea. *Neisseria gonorrhoea* can vary its surface antigens, preventing development of immunity to reinfection. Nearly 750,000 cases of gonorrhea are reported annually in the United States, with an estimated 750,000 additional unreported cases annually, mostly among teenagers and young adults. Ampicillin, amoxicillin, or some type of penicillin used to be recommended for the treatment of gonorrhea. However, the incidence of penicillin-resistant gonorrhea is increasing, and new antibiotics given by injection, e.g., ceftriaxone or spectinomycin, are now used to treat most gonococcal infections.

*Staphylococcus aureus* is a Gram-positive coccus which normally colonizes the human nose and is sometimes found on the skin. *Staphylococcus* can cause bloodstream infections, pneumonia, and surgical-site infections in the hospital setting (i.e., nosocomial infections). *Staph. aureus* can cause severe food poisoning, and many strains grow in food and produce exotoxins. *Staphylococcus* resistance to common antibiotics, e.g., vancomycin, has emerged in the United States and abroad as a major public health challenge both in community and hospital settings. Recently, a vancomycin-resistant *Staph. aureus* isolate has also been identified in Japan.

*Mycobacterium tuberculosis* is a Gram positive bacterium which is the causative agent of tuberculosis, a sometimes crippling and deadly disease. Tuberculosis is on the rise and globally and the leading cause of death from a single infectious disease (with a current death rate of three million people per year).

It can affect several organs of the human body, including the brain, the kidneys and the bones, however, tuberculosis most commonly affects the lungs.

In the United States, approximately ten million individuals are infected with *Mycobacterium tuberculosis*, as indicated by positive skin tests, with approximately 26,000 new cases of active disease each year. The increase in tuberculosis (TB) cases has been associated with HIV/AIDS, homelessness, drug abuse and immigration of persons with active infections. Current treatment programs for drug-susceptible TB involve taking two or four drugs (e.g., isoniazid, rifampin, pyrazinamide, ethambutol or streptomycin), for a period of from six to nine months, because all of the TB germs cannot be destroyed by a single drug. In addition, the observation of drug-resistant and multiple drug resistant strains of *Mycobacterium tuberculosis* is on the rise.

*Helicobacter pylori* (*H. pylori*) is a micro-aerophilic, Gram-negative, slow-growing, flagellated organism with a spiral or S-shaped morphology which infects the lining of the stomach. *H. pylori* is a human gastric pathogen associated with chronic superficial gastritis, peptic ulcer disease, and chronic atrophic gastritis leading to gastric adenocarcinoma. *H. pylori* is one of the most common chronic bacterial infections in humans and is found in over 90% of patients with active gastritis. Current treatment includes triple drug therapy with bismuth, metronidazole, and either tetracycline or amoxicillin which eradicates *H. pylori* in most cases. Problems with triple therapy include patient compliance, side effects, and metronidazole resistance. Alternate regimens of dual therapy which show promise are amoxicillin plus metronidazole or omeprazole plus amoxicillin.

*Streptococcus pneumoniae* is a Gram-positive coccus and one of the most common causes of bacterial pneumonia as well as middle ear infections (otitis media) and meningitis. Each year in the United States, pneumococcal diseases account for approximately 50,000 cases of bacteremia; 3,000 cases of meningitis; 100,000-135,000 hospitalizations; and 7 million cases of otitis media. Pneumococcal infections cause an estimated 40,000 deaths annually in the United States. Children less than 2 years of age, adults over 65 years of age and persons of any age with underlying medical conditions, including, e.g., congestive heart disease, diabetes, emphysema, liver disease, sickle cell, HIV, and those living in special environments, e.g., nursing homes and long-term care facilities, at highest risk for infection.

Drug-resistant *S. pneumoniae* strains have become common in the United States, with many penicillin-resistant pneumococci also resistant to other antimicrobial drugs, such as erythromycin or trimethoprim-sulfamethoxazole.

*Treponema pallidium* is a spirochete which causes syphilis. *T. pallidum* is exclusively a pathogen which causes syphilis, yaws and non-venereal endemic syphilis or pinta. *Treponema pallidum* cannot be grown in vitro and does replicate in the absence of mammalian cells. The initial infection causes an ulcer at the site of infection; however, the bacteria move throughout the body, damaging many organs over time. In its late stages, untreated syphilis, although not contagious, can cause serious heart abnormalities, mental disorders, blindness, other neurologic problems, and death.

Syphilis is usually treated with penicillin, administered by injection. Other antibiotics are available for patients allergic to penicillin, or who do not respond to the usual doses of penicillin. In all stages of syphilis, proper treatment will cure the disease, but in late syphilis, damage already done to body organs cannot be reversed.

*Chlamydia trachomatis* is the most common bacterial sexually transmitted disease in the United States and it is estimated that 4 million new cases occur each year. The highest rates of infection are in 15 to 19 year olds. *Chlamydia* is a major cause of non-gonococcal urethritis (NGU), cervicitis, bacterial vaginitis, and pelvic inflammatory disease (PID). *Chlamydia* infections may have very mild symptoms or no symptoms at all; however, if left untreated *Chlamydia* infections can lead to serious damage to the reproductive organs, particularly in women. Antibiotics such as azithromycin, erythromycin, ofloxacin, amoxicillin or doxycycline are typically prescribed to treat *Chlamydia* infection.

*Bartonella henselae* Cat Scratch Fever (CSF) or cat scratch disease (CSD), is a disease of humans acquired through exposure to cats, caused by a Gram-negative rod originally named *Rochalimaea henselae*, and currently known as *Bartonella henselae*. Symptoms include fever and swollen lymph nodes and CSF is generally a relatively benign, self-limiting disease in people, however, infection with *Bartonella henselae* can produce distinct clinical symptoms in immunocompromised people, including, acute febrile illness with bacteremia, bacillary angiomatosis, peliosis hepatis, bacillary splenitis, and other chronic disease manifestations such as AIDS encephalopathy.

The disease is treated with antibiotics, such as doxycycline, erythromycin, rifampin, penicillin, gentamycin, ceftriaxone, ciprofloxacin, and azithromycin.

*Haemophilus influenzae* (*H. influenza*) is a family of Gram-negative bacteria; six types of which are known, with most *H. influenza*-related disease caused by type B, or "HIB". Until a vaccine for HIB was developed, HIB was a common causes of otitis media, sinus infections, bronchitis, the most common cause of meningitis, and a frequent culprit in cases of pneumonia, septic arthritis (joint infections), cellulitis (infections of soft tissues), and pericarditis (infections of the membrane surrounding the heart). The *H. influenza* type B bacterium is widespread in humans and usually lives in the throat and nose without causing illness. Unvaccinated children under age 5 are at risk for HIB disease. Meningitis and other serious infections caused by *H. influenza* infection can lead to brain damage or death.

*Shigella dysenteriae* (*Shigella* dys.) is a Gram-negative rod which causes dysentery. In the colon, the bacteria enter mucosal cells and divide within mucosal cells, resulting in an extensive inflammatory response. *Shigella* infection can cause severe diarrhea which may lead to dehydration and can be dangerous for the very young, very old or chronically ill. *Shigella* dys. forms a potent toxin (shiga toxin), which is cytotoxic, enterotoxic, neurotoxic and acts as a inhibitor of protein synthesis. Resistance to antibiotics such as ampicillin and TMP-SMX has developed, however, treatment with newer, more expensive antibiotics such as ciprofloxacin, norfloxacin and enoxacin, remains effective.

*Listeria* is a genus of Gram-positive, motile bacteria found in human and animal feces. *Listeria monocytogenes* causes such diseases as listeriosis, meningoencephalitis and meningitis. This organism is one of the leading causes of death from food-borne pathogens especially in pregnant women, newborns, the elderly, and immunocompromised individuals. It is found in environments such as decaying vegetable matter, sewage, water, and soil, and it can survive extremes of both temperatures and salt concentration making it an extremely dangerous food-born pathogen, especially on food that is not reheated. The bacterium can spread from the site of infection in the intestines to the central nervous system and the fetal-placental unit. Meningitis, gastroenteritis, and septicemia can result from infection. In cattle and sheep, *Listeria* infection causes encephalitis and spontaneous abortion.

*Proteus mirabilis* is an enteric, Gram-negative commensal organism, distantly related to E. coll. It normally colonizes the human urethra, but is an opportunistic pathogen that is the leading cause of urinary tract infections in catheterized individuals. *P. mirabilis* has two exceptional characteristics: 1) it has very rapid motility, which manifests itself as a swarming phenomenon on culture plates; and 2) it produce urease, which gives it the ability to degrade urea and survive in the genitourinary tract.

*Yersinia pestis* is the causative agent of plague (bubonic and pulmonary) a devastating disease which has killed millions worldwide. The organism can be transmitted from rats to humans through the bite of an infected flea or from human-to-human through the air during widespread infection. *Yersinia pestis* is an extremely pathogenic organism that requires very few numbers in order to cause disease, and is often lethal if left untreated. The organism is enteroinvasive, and can survive and propagate in macrophages prior to spreading systemically throughout the host.

*Bacillus anthracis* is also known as anthrax. Humans become infected when they come into contact with a contaminated animal. Anthrax is not transmitted due to person-to-person contact. The three forms of the disease reflect the sites of infection which include cutaneous (skin), pulmonary (lung), and intestinal. Pulmonary and intestinal infections are often fatal if left untreated. Spores are taken up by macrophages and become internalized into phagolysozomes (membranous compartment) whereupon germination initiates. Bacteria are released into the bloodstream once the infected macrophage lyses whereupon they rapidly multiply, spreading throughout the circulatory and lymphatic systems, a process that results in septic shock, respiratory distress and organ failure. The spores of this pathogen have been used as a terror weapon.

*Burkholderia mallei* is a Gram-negative aerobic bacterium that causes Glanders, an infectious disease that occurs primarily in horses, mules, and donkeys. It is rarely associated with human infection and is more commonly seen in domesticated animals. This organism is similar to *B. pseudomallei* and is differentiated by being nonmotile. The pathogen is host-adapted and is not found in the environment outside of its host. Glanders is often fatal if not treated with antibiotics, and transmission can occur through the air, or more commonly when in contact with infected animals. Rapid-onset pneumonia, bacteremia (spread of the organism through the blood), pustules, and death are common outcomes during infection. The virulence mechanisms are not well understood, although a type III secretion system similar to the one from *Salmonella typhimurium* is necessary. No vaccine exists for this potentially dangerous organism which is thought to have potential as a biological terror agent. The genome of this organism carries a large number of insertion sequences as compared to the related *Bukholderia pseudomallei* (below), and a large number of simple sequence repeats that may function in antigenic variation of cell surface proteins.

*Burkholderia pseudomallei* is a Gram-negative bacterium that causes meliodosis in humans and animals. Meliodosis is a disease found in certain parts of Asia, Thailand, and Australia. *B. pseudomallei* is typically a soil organism and has been recovered from rice paddies and moist tropical soil, but as an opportunistic pathogen can cause disease in susceptible individuals such as those that suffer from diabetes mellitus. The organism can exist intracellularly, and causes pneumonia and bacteremia (spread of the bacterium through the bloodstream). The latency period can be extremely long, with infection preceding disease by decades, and treatment can take months of antibiotic use, with relapse a commonly observed phenomenon. Intercellular spread can occur via induction of actin polymerization at one pole of the cell, allowing movement through the cytoplasm and from cell-to-cell. This organism carries a number of small sequence repeats which may promoter antigenic variation, similar to what was found with the *B. mallei* genome.

*Burkholderia cepacia* is a Gram-negative bacterium composed of at least seven different sub-species, including *Burkholderia multivorans, Burkholderia vietnamiensis, Burkholderia stabilis, Burkholderia cenocepacia* and *Burkholderia ambifaria. B. cepacia* is an important human pathogen which most often causes pneumonia in people with underlying lung disease (such as cystic fibrosis or immune problems (such as (chronic granulomatous disease). *B. cepacia* is typically found in water and soil and can survive for prolonged periods in moist environments. Person-to-person spread has been documented; as a result, many hospitals, clinics, and camps for patients with cystic fibrosis have enacted strict isolation precautions *B. cepacia*. Individuals with the bacteria are often treated in a separate area than those without to limit spread. This is because infection with *B. cepacia* can lead to a rapid decline in lung function resulting in death. Diagnosis of *B. cepacia* involves isolation of the bacteria from sputum cultures. Treatment is difficult because *B. cepacia* is naturally resistant to many common antibiotics including aminoglycosides (such as tobramycin) and polymixin B. Treatment typically includes multiple antibiotics and may include ceftazidime, doxycycline, piperacillin, chloramphenicol, and co-trimoxazole.

*Francisella tularensis* was first noticed as the causative agent of a plague-like illness that affected squirrels in Tulare County in California in the early part of the 20th century by Edward Francis. The organism now bears his namesake. The disease is called tularemia and has been noted throughout recorded history. The organism can be transmitted from infected ticks or deerflies to a human, through infected meat, or via aerosol, and thus is a potential bioterrorism agent. It is an aquatic organism, and can be found living inside protozoans, similar to what is observed with *Legionella*. It has a high infectivity rate, and can invade phagocytic and nonphagocytic cells, multiplying rapidly. Once within a macrophage, the organism can escape the phagosome and live in the cytosol.

The invention also finds use in veterinary applications. A healthy microflora in the gastro-intestinal tract of livestock is of vital importance for health and corresponding production of associated food products. As with humans, the gastrointestinal tract of a healthy animal contains numerous types of bacteria (i.e., *E. coli, Pseudomonas aeruginosa* and *Salmonella* spp.), which live in ecological balance with one another. This balance may be disturbed by a change in diet, stress, or in response to antibiotic or other therapeutic treatment, resulting in bacterial diseases in the animals generally caused by bacteria such as *Salmonella, Campylobacter*, Enterococci, Tularemia and E. coll. Bacterial infection in these animals often necessitates therapeutic intervention, which has treatment costs as well-being frequently associated with a decrease in productivity.

As a result, livestock are routinely treated with antibiotics to maintain the balance of flora in the gastrointestinal tract. The disadvantages of this approach are the development of antibiotic resistant bacteria and the carry over of such antibiotics and the resistant bacteria into resulting food products for human consumption.

The term "treat", "treating" or "treatment" as used herein also refers to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection or of one or more symptoms of the bacterial infection, or (iii) reduce the severity of a bacterial infection or of one or more symptoms of the bacterial infections, or (iv) suppress the clinical manifestation of a bacterial infection, or (v) suppress the manifestation of adverse symptoms of the bacterial infections. Further, the terms "treating" and "treatment" may include one or more of, ameliorating a symptom of a bacterial infection in a subject, blocking or ameliorating a recurrence of a symptom of a bacterial infection in a subject, decreasing in severity and/or frequency a symptom of a bacterial infection in a subject, stasis, decreasing, or inhibiting growth of a vegetative form of bacteria in a subject, inhibiting bacterial sporulation in a subject, inhibiting activation of a bacterial spore in a subject, inhibiting germination of a bacterial spore in a subject, and inhibiting outgrowth of a bacterial spore in a subject. Treatment means ameliorating, blocking, reducing, decreasing or inhibiting by about 1% to about 100% versus a subject to which a star shaped peptide polymer or composition of the present invention has not been administered. Preferably, the ameliorating, blocking, reducing, decreasing or inhibiting is 100%, 99%, 98%, 97%, 96%, 95%, 90%, 80%, 70%, 60%, 50%, 40%, 30%, 20%, 10%, 5% or 1% versus a subject to which a star shaped peptide polymer or composition of the present invention has not been administered.

Successful treatment may generally mean improvement in any symptoms associated with or caused by a Gram-positive or Gram-negative bacterial infection for example may refer to an improvement in any of the following: fever, inflammation, swelling, vomiting, fatigue, cramping, coughing, sneezing, respiratory illness, diarrhea, meningitis, headaches, joint pain, body aches, blisters, rashes, nausea, chills, dizziness, drowsiness, sleeplessness, gagging, skin irritation, excessive mucus production (e.g. in the eyes, gastrointestinal tract, sinuses, or respiratory system), ulcers, gastrointestinal discomfort, skin loss, hair loss, necrosis, and organ dysfunction. Improvements in any of these symptoms or in the bacterial infection or conditions described herein can be readily assessed according to standard methods and techniques known in the art. The population of subjects treated by the method of the disease includes subjects suffering from the undesirable condition or disease, as well as subjects at risk for development of the condition or disease.

As used herein, the terms "inhibit", "inhibiting" and "inhibition" have their ordinary and customary meanings, and include one or more of inhibiting growth or a function of bacteria, inhibiting growth of a vegetative form of bacteria, inhibiting a function of a vegetative form of bacteria, inhibiting propagation of bacteria, inhibiting bacterial sporulation, inhibiting activation of a bacterial spore, inhibiting germination of a bacterial spore, and inhibiting outgrowth of a bacterial spore. Such inhibition is an inhibition of about 1% to about 100% of the particular activity versus the activity in a subject to which a star shaped peptide polymer or composition of the present invention has not been administered. Preferably, the inhibition is an inhibition of 100%, 99%, 98%, 97%, 96%, 95%, 90%, 80%, 70%, 60%, 50%, 40%, 30%, 20%, 10%, 5% or 1% of the activity versus a subject to which a star shaped peptide polymer or composition of the present invention has not been administered. As used herein, "spore" refers to both the conventionally used terms "spore" and "endospore."

As used herein, the terms "preventing" and "prevention" have their ordinary and customary meanings, and includes one or more of preventing colonization of bacteria in a subject, preventing an increase in the growth of a population of bacteria in a subject, preventing activation, germination or outgrowth of bacterial spores in a subject, preventing sporulation of bacteria in a subject, preventing development of a disease caused by bacteria in a subject, and preventing symptoms of a disease caused by bacteria in a subject. As used herein, the prevention lasts at least about 0.5, 1, 2, 3, 4, 5, 6, 7, 10, 12, 15, 20, 25, 30, 35, 40 or more days after administration of a star shaped peptide polymer or composition of the present invention.

As used herein, "prophylaxis" includes inhibiting the development of a productive or progressive infection by bacteria in a subject, where the prophylaxis lasts at least about 0.5, 1, 2, 3, 4, 5, 6, 7, 10, 12, 15, 20, 25, 30, 35, 40 or more days after administration of a star shaped peptide polymer or composition of the present invention Inhibition against development of a productive or progressive infection by a bacterial infection means that the severity of a bacterial infection in a subject is reduced by about 1% to about 100% versus a subject to which a star shaped peptide polymer or composition of the present invention has not been administered. Preferably, the reduction in severity is a 100%, 99%, 98%, 97%, 96%, 95%, 90%, 80%, 70%, 60%, 50%, 40%, 30%, 20%, 10%, 5% or 1% reduction in severity. The severity of an infection may be based on the amount of bacteria present in a subject, the length of time that the bacteria can be detected in a subject, and/or the severity of a symptom of a bacterial infection, among other factors.

As used herein, the term "contacting" is meant to broadly refer to bringing a bacterial cell and a star shaped peptide polymer of the present invention into sufficient proximity that the star shaped peptide polymer can exert an effect on the bacterial cell. The star shaped peptide polymer may be transported to the location of the bacterial cell, or the star shaped peptide polymer may be situated in a location to which the bacterial cell travels or is brought into contact. The skilled artisan will understand that the term "contacting" includes physical interaction between a star shaped peptide polymer and a bacterial cell, as well as interactions that do not require physical interaction.

The therapeutically effective amount of any of a star shaped peptide polymer or compositions, and the amounts sufficient to achieve the stated goals of the methods disclosed herein, will vary depending upon the physical characteristics of the subject, the age of the subject, the severity of the subject's symptoms, the identity of the bacteria, the location of the bacterial infection(s), the formulation and the means used to administer the antibacterial agent(s), the number of doses being administered to the subject over the course of treatment, and the method being practiced. The specific doses for a given subject are usually set by the judgment of the attending physician. However, general ranges and some non-limiting specific examples are provided in the following paragraphs.

As used herein administration of a star shaped peptide polymer of the invention and a chelating agent includes either a fixed combination in one dosage unit form, or a kit of parts for the combined administration where a star shaped peptide polymer and chelating agent may be administered independently at the same time or separately within time intervals.

A chelating agent may be administered in combination with a star shaped peptide polymer of present invention wherein the chelating agent is administered prior to, simultaneously, or after a star shaped peptide polymer of the present invention. When simultaneous administration of a star shaped peptide polymer of the invention with a chelating is desired and the route of administration is the same, then a star shaped peptide polymer of the invention may be formulated with the chelating agent into the same dosage form.

The present invention also contemplates the use of more biocompatible chelators (e.g., citric acid), tethering of the chelator to the star shaped peptide polymer through chemical conjugation, on-demand release of the chelator at the infection site, or any combination thereof.

Star shaped peptide polymers and compositions of the invention may be formulated for any appropriate route of administration including, for example, topical (for example, transdermal or ocular), oral, buccal, nasal, vaginal, rectal or parenteral administration. The term parenteral as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. Other routes of administration include intra-oral, intra-sulcular and intra-periodontal pocket. In certain embodiments, compositions in a form suitable for oral use or parenteral use are preferred. Suitable oral forms include, for example, tablets, troches, lozenges, aqueous or oily suspensions, dispersible powders or granules, emulsions, hard or soft capsules, or syrups or elixirs. Within yet other embodiments, compositions provided herein may be formulated as a lyophilizate.

The various dosage units are each preferably provided as a discrete dosage tablet, capsules, lozenge, dragee, gum, or other type of solid formulation. Capsules may encapsulate a powder, liquid, or gel. The solid formulation may be swallowed, or may be of a suckable or chewable type (either frangible or gum-like). The present invention contemplates dosage unit retaining devices other than blister packs; for example, packages such as bottles, tubes, canisters, packets. The dosage units may further include conventional excipients well-known in pharmaceutical formulation practice, such as binding agents, gellants, fillers, tableting lubricants, disintegrants, surfactants, and colorants; and for suckable or chewable formulations.

Compositions intended for oral use may further comprise one or more components such as sweetening agents, flavouring agents, colouring agents and/or preserving agents in order to provide appealing and palatable preparations. Tablets contain the active ingredient in admixture with physiologically acceptable excipients that are suitable for the manufacture of tablets. Such excipients include, for example, inert diluents such as calcium carbonate, sodium carbonate, lactose, calcium phosphate or sodium phosphate, granulating and disintegrating agents such as corn starch or alginic acid, binding agents such as starch, gelatine or acacia, and lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatine capsules wherein the active ingredient is mixed with an inert solid diluent such as calcium carbonate, calcium phosphate or kaolin, or as soft gelatine capsules wherein the active ingredient is mixed with water or an oil medium such as peanut oil, liquid paraffin or olive oil.

Aqueous suspensions contain the active ingredient(s) in admixture with excipients suitable for the manufacture of aqueous suspensions. Such excipients include suspending agents such as sodium carboxymethylcellulose, methylcellulose, hydropropylmethylcellulose, sodium alginate, polyvinylpyrrolidone, gum tragacanth and gum acacia, and dispersing or wetting agents such as naturally-occurring phosphatides (for example, lecithin), condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol mono-oleate, or condensation products of ethylene oxide with partial esters derived from fatty acids and hexitol anhydrides such as polyethylene sorbitan monooleate. Aqueous suspensions may also comprise one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil such as Arachis oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavouring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavouring and colouring agents, may also be present.

Pharmaceutical compositions may also be in the form of oil-in-water emulsions. The oily phase may be a vegetable oil such as olive oil or *Arachis* oil, a mineral oil such as liquid paraffin, or a mixture thereof. Suitable emulsifying agents include naturally-occurring gums such as gum acacia or gum tragacanth, naturally-occurring phosphatides such as soy bean lecithin, and esters or partial esters derived from fatty acids and hexitol, anhydrides such as sorbitan monoleate, and condensation products of partial esters derived from fatty acids and hexitol with ethylene oxide such as polyoxyethylene sorbitan monoleate. An emulsion may also comprise one or more sweetening and/or flavouring agents.

Syrups and elixirs may be formulated with sweetening agents, such as glycerol, propylene glycol, sorbitol or sucrose. Such formulations may also comprise one or more demulcents, preservatives, flavouring agents and/or colouring agents.

Compositions of the invention may be formulated for local or topical administration, such as for topical application to the skin. Formulations for topical administration typically comprise a topical vehicle combined with active agent(s), with or without additional optional components.

Suitable topical vehicles and additional components are well known in the art, and it will be apparent that the choice of a vehicle will depend on the particular physical form and mode of delivery. Topical vehicles include organic solvents such as alcohols (for example, ethanol, iso-propyl alcohol or glycerine), glycols such as butylene, isoprene or propylene glycol, aliphatic alcohols such as lanolin, mixtures of water and organic solvents and mixtures of organic solvents such as alcohol and glycerine, lipid-based materials such as fatty acids, acylglycerols including oils such as mineral oil, and fats of natural or synthetic origin, phosphoglycerides, sphingolipids and waxes, protein-based materials such as collagen and gelatine, silicone-based materials (both nonvolatile and volatile), and hydrocarbon-based materials such as microsponges and polymer matrices.

A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatine-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids, emulsions, sprays and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form. Solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity. Both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels, and often do not contain emulsifiers. Liquid topical products often contain solvents, emulsifiers, moisturizers, emollients, fragrances, dyes/colorants, preservatives and other active ingredients that increase or enhance the efficacy of the final product.

Emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or nonionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylceilulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations.

Preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerine, propylene glycol, and butylene glycol. Suitable emollients include lanolin alcohol, lanolin, lanolin derivatives, cholesterol, petrolatum, isostearyl neopentanoate and mineral oils. Suitable fragrances and colours include, but are not limited to, FD&C Red No. 40 and FD&C Yellow No. 5. Other suitable additional ingredients that may be included in a topical formulation include, but are not limited to, abrasives, absorbents, anticaking agents, antifoaming agents, antistatic agents, astringents (such as witch hazel), alcohol and herbal extracts such as chamomile extract, binders/excipients, buffering agents, chelating agents, film forming agents, conditioning agents, propellants, opacifying agents, pH adjusters and protectants.

Typical modes of delivery for topical compositions include application using the fingers, application using a physical applicator such as a cloth, tissue, swab, stick or brush, spraying including mist, aerosol or foam spraying, dropper application, sprinkling, soaking, and rinsing. Controlled release vehicles can also be used, and compositions may be formulated for transdermal administration (for example, as a transdermal patch).

Pharmaceutical compositions may be formulated as sustained release formulations such as a capsule that creates a slow release of modulator following administration. Such formulations may generally be prepared using well-known technology and administered by, for example, oral, rectal or subcutaneous implantation, or by implantation at the desired target site. Carriers for use within such formulations are biocompatible, and may also be biodegradable. Preferably, the formulation provides a relatively constant level of modulator release. The amount of modulator contained within a sustained release formulation depends upon, for example, the site of implantation, the rate and expected duration of release and the nature of the bacterial infection to be treated or prevented.

In one aspect, multiple doses of a star shaped peptide polymer or pharmaceutical composition may be required to treat an infection. Preferably, there are 2, 3, 4 or more doses, preferably in a 24 hour period. The dose may be about 2, 4, 6, 8 or more mg/kg.

In another aspect the present invention provides a kit or article of manufacture including a star shaped peptide polymer of the invention or pharmaceutical composition of the invention as described herein.

In other embodiments there is provided a kit for use in a therapeutic or prophylactic application mentioned herein, the kit including:
a container holding a star shaped peptide polymer or pharmaceutical composition of the invention; and
a label or package insert with instructions for use.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a star shaped peptide polymer or composition which is effective for treating the condition and may have a sterile access port (for example the container may be an intravenous solution bag or a vial having a stopper pierceable by a hypodermic injection needle). The label or package insert indicates that the star shaped peptide polymer or composition is used for treating a bacterial infection. In one embodiment, the label or package insert includes instructions for use and indicates that the therapeutic or prophylactic composition can be used to treat a bacterial infection described herein.

The kit may comprise (a) a therapeutic or prophylactic composition; and (b) a second container with a second active principle or ingredient contained therein. The kit in this embodiment of the invention may further comprise a package insert indicating the composition and other active principle can be used to treat a disorder or prevent a complication stemming from a bacterial infection described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments the therapeutic composition may be provided in the form of a device, disposable or reusable, including a receptacle for holding the star shaped peptide polymer or therapeutic or prophylactic pharmaceutical composition. In one embodiment, the device is a syringe. The device may hold 1-2 mL of the composition. The therapeutic or prophylactic composition may be provided in the device in a state that is ready for use or in a state requiring mixing or addition of further components.

EXAMPLES

Example 1

Synthesis of L-lysine(Z)-NCA (Lys NCA)

Dried H-Lys(Z)—OH (1.24 g, 4.43 mmol) was added to anhydrous THF (25 mL) in an oven-dried two-necked round bottomed flask under argon. Triphosgene (580 mg, 1.96 mmol) was dissolved in anhydrous THF (5 mL) and added to the H-Lys(Z)—OH suspension. The mixture was heated at 50° C. for 30 min with continuous stirring. The clear solution was allowed to cool to room temperature and added to anhydrous pentane (100 mL). The resulting precipitate was isolated via centrifugation and washed with anhydrous pentane (30 mL×2). The resulting white solid was dried at ambient temperature in vacuo to afford Lys NCA, 0.910 g (81%). $^1$H NMR (400 MHz, $d_6$-DMSO) $\delta_H$ 1.23-1.37 (m, γ-$CH_2$, 2H), 1.37-1.45 (m, δ—$CH_2$, 2H), 1.60-1.80 (m, β-$CH_2$, 2H), 2.94-3.02 (m, ε-$CH_2$, 2H), 4.40-4.43 (m, α-CH, 1H), 5.00 (dd, $C_6H_5CH_2$—, 2H), 6.90 (s, cyclic NH, 1H), 7.30-7.39 (m, $C_6H_5$—, 5H).

Synthesis of DL-valine-NCA (Val NCA)

Dried DL-valine (1.24 g, 4.43 mmol) was dissolved in anhydrous THF (25 mL) in an oven-dried two-necked round bottomed flask under argon. Triphosgene (580 mg, 1.96 mmol) was dissolved in anhydrous THF (5 mL) and added to the DL-val-THF suspension. The mixture was heated at 50° C. for 30 min with continuous stirring. The clear solution was allowed to cool to room temperature and precipitated with anhydrous pentane (100 mL), followed by washing with more anhydrous pentane (30 mL×2). The resulting residue was dried at ambient temperature in vacuo to afford Val NCA, 0.956 mg (85%). $^1$H NMR (400 MHz, $d_6$-DMSO) $\delta_H$ 0.91 (dd, $CH_3$, 6H), 2.00-2.12 (m, CH, 1H), 4.32 (dd, cyclic CH, 1H), 9.06 (s, cyclic NH, 1H).

Synthesis of poly(Z-L-lysine-r-DL-valine)$_{arm}$PAMAM-$(NH_2)_{16,core}$ Star Peptide Polymer S16$_Z$ Lys NCA (1.3 g, 4.19 mmol) and Val NCA (0.3 g, 2.1 mmol) were dissolved in anhydrous DMF (16 mL) and added via syringe to PAMAM-$(NH_2)_{16}$ (dried, 43 mg, 13.1 μmol) dissolved in anhydrous DMF (1 mL). After stirring for 24 h under argon, n-butyl alcohol (1 mL) was added and the mixture was stirred for a further 1 h. Precipitation of the concentrated peptide polymer solution into diethyl ether (3×40 mL), followed by isolation via centrifugation and drying (0.1 mbar), afforded (PZLL-r-PVal)$_{arm}$PAMAM-$(NH_2)_{16,core}$ star peptide polymer S16$_Z$ as an off-white solid, 1.21 g (90%). $^1$H NMR (400 MHz, d6-DMSO) $\delta_H$ 0.67-0.89 (b, $CH_3$, 6H), 1.11-1.77 (b, γ-$CH_2$+δ-$CH_2$+β-$CH_2$, 6H), 1.84-2.00 (b, CH, 1H), 2.78-3.00 (b, ε-$CH_2$, 2H), 4.06-4.40 (b, α-CH, 1H), 4.90-5.00 (b, $C_6H_5CH_2$—, 2H), 7.00-7.44 (b, $C_6H_5$—, 5H), 7.60-8.30 (b, NH, 1H).

Synthesis of poly(Z-L-lysine-r-DL-valine)$_{arm}$PAMAM-$(NH_2)_{32,core}$ Star Peptide Polymer S32$_Z$ Lys NCA (1.3 g, 4.19 mmol) and Val NCA (0.3 g, 2.1 mmol) were dissolved in anhydrous DMF (16 mL) and added via syringe to PAMAM-$(NH_2)_{32}$ (dried, 43 mg, 13.1 μmol) dissolved in anhydrous DMF (1 mL). After stirring for 24 h under argon, n-butyl alcohol (1 mL) was added and the mixture was stirred for a further 1 h. Precipitation of the concentrated peptide polymer solution into diethyl ether (3×40 mL), followed by isolation via centrifugation and drying (0.1 mbar), afforded (PZLL-r-PVal)$_{arm}$PAMAM-$(NH_2)_{32,core}$ star peptide polymer S16$_Z$ as an off-white solid, 1.15 g (85%). $^1$H NMR (400 MHz, $d_6$-DMSO) $\delta_H$ 0.67-0.89 (b, $CH_3$, 6H), 1.11-1.77 (b, γ-$CH_2$+δ-$CH_2$+β-$CH_2$, 6H), 1.84-2.00 (b, CH, 1H), 2.78-3.00 (b, ε-$CH_2$, 2H), 4.06-4.40 (b, α-CH, 1H), 4.90-5.00 (b, $C_6H_5CH_2$—, 2H), 7.00-7.44 (b, $C_6H_5$—, 5H), 7.60-8.30 (b, NH, 1H).

Synthesis of Linear poly(Z-L-lysine-r-DL-valine) Peptide Polymer $L_Z$

Lys NCA (0.5 g, 1.63 mmol) and Val NCA (117 mg, 0.82 mmol) were dissolved in anhydrous DMF (6 mL) and added via syringe to benzylamine (10.3 μL, 81.6 μmol). After stirring for 24 h under argon, n-butyl alcohol (1 mL) was added and the mixture was stirred for a further 1 h. Precipitation of the concentrated peptide polymer solution into diethyl ether (3×40 mL), followed by isolation via centrifugation and drying (0.1 mbar), afforded linear PZLL-r-PVal peptide polymer $L_Z$ as an off-white solid, 420 mg (81%). $^1$H NMR (400 MHz, $d_6$-DMSO) $\delta_H$ 0.67-0.89 (b, $CH_3$, 6H), 1.11-1.77 (b, γ-$CH_2$+δ-$CH_2$+β-$CH_2$, 6H), 1.84-2.00 (b, CH, 1H), 2.78-3.00 (b, ε-$CH_2$, 2H), 4.06-4.40 (b, α-CH, 1H), 4.90-5.00 (b, $C_6H_5CH_2$—, 2H), 7.00-7.44 (b, $C_6H_5$—, 5H), 7.60-8.30 (b, NH, 1H).

General Procedure for Deprotection of Peptide Polymers

The peptide polymer was dissolved in TFA (200 mg/mL) and 33% HBr in acetic acid was then added (20 mL/g peptide polymer). After 24 h stirring at room temperature, the mixture was precipitated into diethyl ether (10 times the volume of the reaction). The precipitate was isolated via centrifugation, redissolved in hydrochloric acid solution (0.2 M, 0.2 mL/mg peptide polymer), and dialyzed against RO water for 4 days. The dialyzed solution was lyophilized to obtain the deprotected SNAPP (e.g., S16 and S32). S16 and S32: $^1$H NMR (400 MHz, $d_6$-DMSO) $\delta_H$ 0.67-0.88 (b, $CH_3$, 6H), 1.05-1.77 (b, γ-$CH_2$+δ-$CH_2$+β-$CH_2$, 6H), 1.84-2.00 (b, CH, 1H), 2.61-2.83 (b, ε-$CH_2$, 2H), 4.00-4.39 (b, α-CH, 1H), 7.60-8.30 (b, NH, 1H). L: $^1$H NMR (400 MHz, $d_6$-DMSO) $\delta_H$ 0.67-0.88 (b, $CH_3$, 6H), 1.05-1.77 (b, γ-$CH_2$+δ-$CH_2$+β-$CH_2$, 6H), 1.84-2.00 (b, CH, 1H), 2.61-2.83 (b, ε-$CH_2$, 2H), 4.00-4.39 (b, α-CH, 1H), 7.00-7.20 (b, $C_6H_4$—, 4H), 7.60-8.30 (b, NH, 1H).

Synthesis of AMPs (Ovispirin, Magainin II and Melittin)

Ovispirin ($NH_2$- KNLRRIIRKIIHIIKKYG-COOH), magainin II ($NH_2$-GIGKFLHSAKKFGKAFVGEIMNS-$CONH_2$) and melittin ($NH_2$-GIGAVLKVLTTGLPAL-ISWIKRKRQQ-$CONH_2$) were chemically synthesized on a CEM Liberty microwave peptide synthesizer (Ai Scientific, Victoria, Australia). The peptide-resins were assembled from Fmoc-Rink-AM SURE™ Resin in the Fmoc/TBu mode of synthesis. For a 0.1 mmol reaction scale, Fmoc-deprotection was performed in two stages by initial treatment with 20% piperidine/0.1 M HOBt/DMF (v/v, 7 ml) under microwave radiation for 30 s (40 W, 40° C.), followed by filtration and a second addition of the above solution (45 W, 75° C., 3 min). The peptide-resins were then rinsed with DMF (4×7 ml). Acylation, where required, was achieved by the addition of a solution containing amino acid (5 eq, relative to reaction scale), HBTU (5 eq) and DIEA (10 eq) in DMF/NMP (7:1, v/v; 4 ml) to the Na-deprotected peptide-resin and the mixture agitated under microwave radiation for 10 min (30 W, 75° C., vessel under external chilled air flow). Dichloromethane (DCM) (5×2 min) was used to rinse the peptide-resins prior to the cleavage step. The peptide was cleaved from the resin support by the addition of TFA/TIPS/thioanisole/phenol/water (90:2.5:2.5:2.5:2.5, % v/v/v/v/v; 5 ml) for 2.5 h, after which the combined cleavage filtrates were evaporated under nitrogen flow and the crude product was isolated by precipitation in cold ether (4×30 ml).

The crude peptide was purified using an Agilent 1200 series liquid chromatograph instrument (Agilent, NSW, Australia) equipped with a UV detector (model G1316A) and a Zorbax 300 SB-C18 reversed phase column (9.4 mm×25 cm). Crude peptide analysis was achieved using a linear acetonitrile gradient in 0.1% TFA at a flow rate of 4 mL/min (linear gradient of 0 to 54% $CH_3CN$ over 15 min). Analysis of the purified peptide was performed using an Esquire HCT electrospray ionization-mass spectrometry system (Bruker Daltronics, NSW, Australia).

Bacterial Cell Culture

Freeze-dried cultures of *Escherichia coli* (*E. coli*, ATCC 25922), *Klebsiella pneumoniae* (*K. pneumoniae*, ATCC 13883), *Acinetobacter baumannii* (*A. baumannii*, ATCC 19606), multi-drug resistant (MDR) *A. baumannii* (FADDI-AB156), MDR *P. aeruginosa* (FADDI-PA067) and *Staphylococcus aureus* (*S. aureus*, ATCC 29213) were grown aerobically and maintained by passage at ambient temperature on horse blood agar (10% v/v defibrinated horse blood, 4.4% w/v Oxoid Blood Agar Base No. 2). *Pseudomonas aeruginosa* (*P. aeruginosa*, ATCC 47085) were cultured in a similar fashion, except at 37° C. Freeze-dried cultures of *Streptococcus mutans* (*S. mutans*, Ingbritt strain) were grown anaerobically and maintained by passage at 37° C. on Todd Hewitt agar (3.6% w/v Oxoid Todd-Hewitt Broth, 1.5% w/v sucrose, 1.5% w/v Bacto™ Agar, 0.8% w/v Oxoid Yeast Extract). For *E. coli*, *K. pneumoniae*, *P. aeruginosa*, MDR *P. aeruginosa*, *A. baumannii*, MDR *A. baumannii* and *S. aureus*, overnight cultures were made from transferring a colony (ca. half a loop) from the agar plates to culture tubes containing sterilized Luria-Bertani broth (LB, 1% w/v Bacto™ Tryptone, 1% w/v NaCl, 0.5% w/v Oxoid Yeast Extract) (20 mL). Bacterial cultures were incubated overnight at 37° C. with aeration and without agitation, with the exception of MDR *P. aeruginosa* which was cultured at 37° C. with aeration and agitation (150 rpm). On the next day, for *E. coli*, *K. pneumoniae*, *P. aeruginosa*, MDR *P. aeruginosa* and *S. aureus*, small aliquots (i.e., 0.5-2 mL) were taken from the culture tubes, further diluted with LB (20 mL), and incubated for 3-4 h at 37° C. with aeration before use. All bacterial cultures were cultured without agitation, with the exception of *P. aeruginosa* and MDR *P. aeruginosa* which were cultured with shaking at 150 rpm. For *A. baumannii*, an aliquot of 0.5 mL was taken from the overnight culture tube, further diluted with LB (200 mL), and incubated overnight at 37° C. with aeration before use. With regards to *S. mutans*, several colonies (ca. half a loop) from the agar plates were transferred to culture tubes containing sterilized Todd Hewitt broth (3.6% w/v Oxoid Todd-Hewitt Broth, 1.5% w/v sucrose, 0.8% w/v Oxoid Yeast Extract) (20 mL). The cultures were incubated overnight at 37° C. in the anaerobic chamber. After 24 h, a small aliquot (i.e., 0.5 mL) was taken from the culture tubes, further diluted with media (ca. 200 mL), and incubated overnight at 37° C. in the anaerobic chamber before use.

Bacterial Cell Counting.

A Cell Lab Quanta SC MPL flow cytometer was used to count the number of bacterial cells prior to use in assays. Cells were diluted with saline using an appropriate dilution factor and incubated with Syto® 9 and PI (i.e., 1 mL cell solution to 1 µL of each dye). Syto® 9 stains the nucleic acids in all cells, while PI stains the nucleic acids in cells with damaged membranes. Using the Cell Lab Quanta SC software, the number of viable cells/mL (Syto® 9-positive, PI-negative) was obtained.

Measurement of Minimum Bactericidal Concentrations (MBC).

Figure 14:
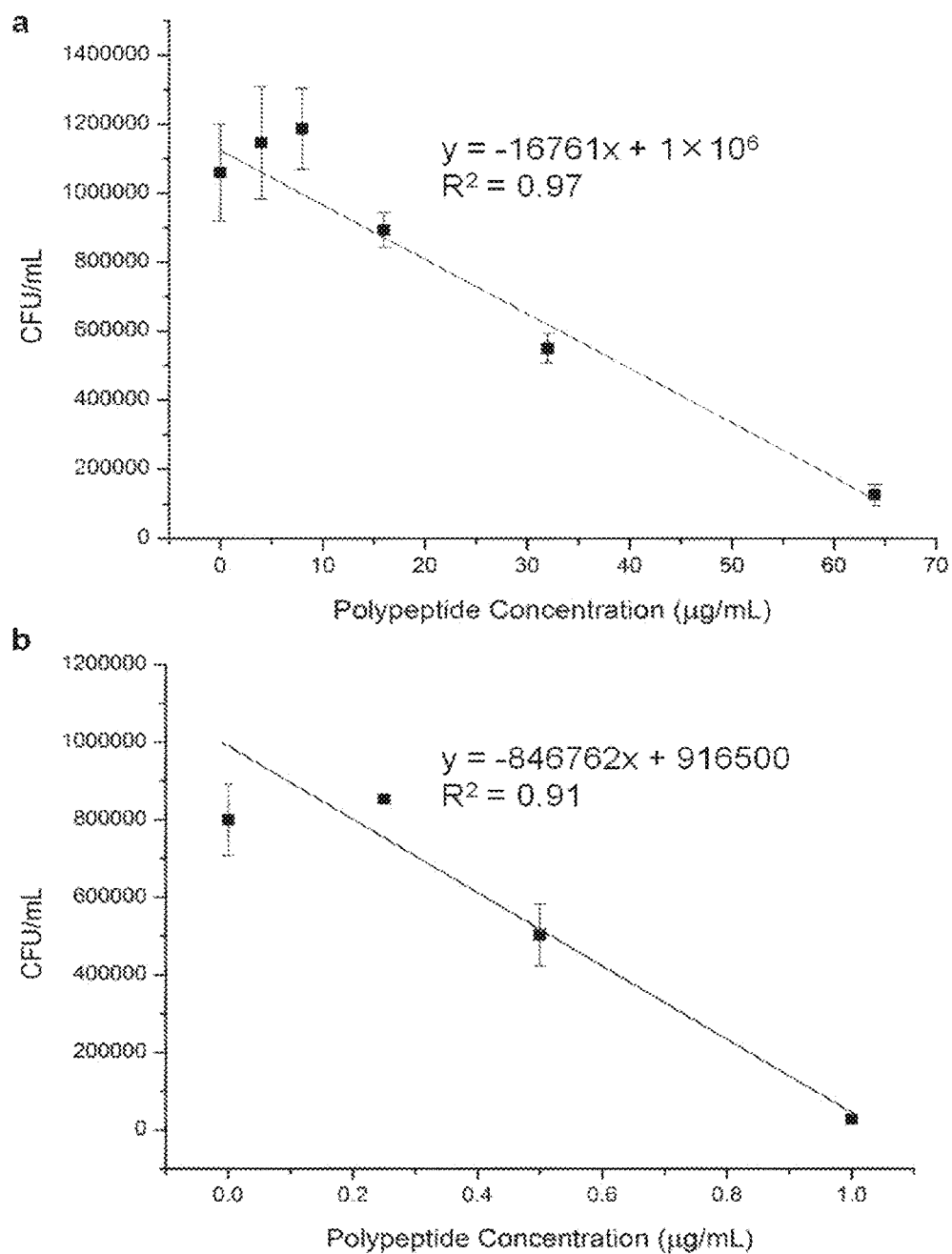
FIG. 14. Method for MBC determination. a-b, Sample concentration-killing curves and linear regression analysis used to determine MBC values. Error bars represent the standard deviation from the mean (n=4). MBC was determined as the concentration at which colony-forming unit (CFU)/mL becomes zero. The examples shown were based on experimental data obtained for S16 against *P. aeruginosa* in Mueller-Hinton broth (MHB) (a) and S32 against multi-drug resistant (MDR) *A. baumannii* in minimal essential medium (MEM) (b). The MBC values calculated were 1.42 μM for (a) and 0.03 μM for (b).

A dilution series of each compound was made by diluting test compound stock in media to a desired range of concentrations and a final volume of 100 µL in each well of a 96-well plate. Bacterial cells (which gave an optical density reading of ~0.7 at 650 nm for *E. coli*, *K. pneumoniae*, *P. aeruginosa*, and *S. aureus*, ~0.5 at 650 nm for *A. baumannii* and ~1.8 at 650 nm for *S. mutans*) were diluted to $2.5 \times 10^6$ cells/mL in media and 100 µL of the bacteria solution was added to each well. The 96-well plate was then incubated at 37° C. for 90 min. For each well, microbial solution was diluted with saline (0.9% NaCl solution) using an appropriate dilution factor and placed on an agar plate (identical to that used for bacteria culture). For *E. coli*, *K. pneumoniae*, *A. baumannii*, and *S. aureus*, the agar plates were incubated overnight at room temperature, and then at 37° C. with aeration for 2 h. For *P. aeruginosa* and *S. mutans*, the agar plates were incubated at 37° C., with the former being incubated overnight with aeration and the latter in an anaerobic chamber for 48 h. The number of colony-forming units (CFU) was counted and expressed as CFU/mL. Positive controls consisting of cells without any treatment were used. Concentration-killing curves were plotted with CFU/mL as a function of compound concentration and linear regression analysis was used to determine the lowest concentration (MBC) at which the CFU/mL becomes zero (FIG. 14). A minimum of two independent experiments (biological replicates) of the assay were conducted and two technical replicates were used in each experiment for each bacterium, compound, and concentration. Data is expressed as mean±standard deviation (SD) of the biological replicates and analysed using student's t-test. Note that for *E. coli*, *K. pneumoniae*, *P. aeruginosa*, and *A. baumannii*, two sets of experiments were performed, either using a nutritionally-rich medium (MHB, 3.8% w/v Oxoid Mueller-Hinton Agar) or a minimal essential medium (MEM, 136.9 mM NaCl, 10.1 mM $Na_2HPO_4$, 2.7 mM KCl, 1.8 mM $KH_2PO_4$, 0.2% w/v D-(+)-glucose). For *S. aureus* and *S. mutans*, the assays were conducted in nutritionally-rich media only, which were Luria-Bertani broth and Todd-Hewitt broth, respectively.

Measurement of Minimum Inhibitory Concentrations (MIC).

The MICs of the PAMAM dendrimers were determined using a broth microdilution method. After the preparation of a dilution series of each compound and the addition of bacterial cells (Note: steps identical to that taken for the measurement of MBC), the optical density readings of each well at 630 nm were measured as a function of time using a microplate reader (Multiskan Ascent, Pathtech Pty. Ltd.). Positive controls containing cells alone were incorporated. Optical density was plotted against polymer concentration and linear regression analysis was used to determine the lowest concentration (MIC) at which the optical density reading becomes zero. A minimum of two independent experiments (biological replicates) of the assay were conducted and two technical replicates were used in each experiment for each bacterium, polymer, and concentration. Data is expressed as mean±standard deviation (SD) of the biological replicates and analysed using student's t-test.

Resistance Studies.

The method used was adapted from Gullberg et al. PLoS Pathog. 7, e1002158 (2011). Overnight cultures of *A. baumannii* cells (ATCC 19606 or FADDI-AB156) in LB broth were obtained from independent colonies grown on horse blood agar. The cells were then serially passaged by 400-fold dilution in 1 mL batch cultures every 24 h for 600 generations (ca. 25 generations of growth per serial passage) in MHB containing 1/10 of the MBC of S16 (for both strains). After every 100 generations of growth, the MBCs of S16 were obtained using cells that were serially passaged in the presence of the antimicrobial agent. As a control, MBCs were also obtained using cells serially passaged in fresh MHB alone.

Hemolysis Assay.

Fresh sheep red blood cells (RBCs) were diluted 1 in 20 in PBS (pH 7.4), pelleted by centrifugation, and washed three times in PBS (1000 g, 10 min). The RBCs were counted using a cell counter (Coulter Particle Counter Z series, Beckman Coulter) and diluted to a final concentration of $2 \times 10^7$ cells/mL. 100 μL aliquots of the RBC solution were seeded into a V-bottomed 96-well plate containing 100 μL of test compound solution of varying concentrations (4-256 μg/mL) and incubated in a humidified atmosphere containing 5% $CO_2$ at 37° C. for 2 h. Following incubation, the 96-well plate was centrifuged (1000 g, 10 min) and aliquots (100 μL) of supernatant were transferred to a flat-bottomed 96-well plate. Hemoglobin release upon lysis of the RBCs was monitored at 405 nm using a microplate reader (PerkinElmer 1420 Multilabel Counter VICTOR$^3$). Positive and negative controls for hemolysis were taken as RBC lysed with 0.5% Triton X-100 (1:1 v/v) and RBC suspension in PBS, respectively. The percentage of hemolysis was calculated using the following formula:

$$\% \text{ Hemolysis} = \left( \frac{A_{405} \text{ test sample} - A_{405} \text{ negative control}}{A_{405} \text{ positive control} - A_{405} \text{ negative control}} \right) \times 100$$

The percentage hemolysis was plotted against peptide polymer concentration and linear regression analysis was used to determine the hemolytic concentration needed to lyse 50% ($HC_{50}$) of RBCs. Two independent runs of the assay were conducted and two replicates were used in each run for each compound and concentration.

Mammalian Cell Culture.

Human embryonic kidney cells (HEK293T) were cultivated in 'complete' RPMI-1640 medium (supplemented with 5% FBS, 1×GlutaMAX™, 1×antibiotic-antimycotic, and 1×MEM non-essential amino acids) in a humidified atmosphere containing 5% $CO_2$ at 37° C. Cells were seeded in a T75 flask (ca. $3 \times 10^6$ cells/ml) and passaged twice a week prior to performing the subsequent cell viability studies. Rat hepatoma cells (H4IIE) were cultivated in DMEM medium (supplemented with 10% FBS, 1×GlutaMAX™, and 1×penicillin-streptomycin) in a humidified atmosphere containing 5% $CO_2$ at 37° C. Cells were seeded in a T75 flask (ca. $3 \times 10^6$ cells/ml) and passaged twice a week prior to performing the subsequent cell viability studies.

Apoptosis/Necrosis Assay.

Adherent HEK293T or H4IIE cells (obtained from the ATCC, and throughout the course of the study were checked for *Mycoplasma* contamination using *Mycoplasma* stain kit, Myc1, Aldrich) were grown to 80% confluence and trypsinized prior to assay. HEK293T and H4IIE cells were chosen for this study as they are standard cell lines used in toxicity studies. Cells were diluted 1:2 with 'complete' medium (RPMI-1640 for HEK293T cells or DMEM for H4IIE cells) and seeded in a 24-well plate (1 mL per well). The cells were incubated at 37° C. in 5% $CO_2$ for 24 h until ca. 95% confluence. The medium was removed. Varying concentrations of test compound (4 to 128 μg/mL) were prepared and 200 μL aliquots of each were added to the cells, after which the cells were incubated at 37° C. in 5% $CO_2$ for 90 min. The cells were then harvested and all well contents were transferred to round-bottomed polypropylene tubes (5 mL). The cells were washed with cold DPBS, then stained with YO-PRO®-1 and PI (0.2 mL from a stock solution, whereby both dyes were diluted 1:1000 in cold DPBS, per well), and incubated on ice for 20 to 30 min. The cells were analyzed by flow cytometry (Cytomics FC 500 MPL System). Standard compensation was performed using single-colour stained cells. Negative controls using untreated cells were included. Two independent runs of the assay were conducted and two replicates were used in each run for each test compound and concentration.

In Vivo Efficacy of SNAPP S16.

All experiments involving animals were performed according to protocols approved by the University of Melbourne Biochemistry and Molecular Biology, Dental Science, Medicine, Microbiology and Immunology, and Surgery Animal Ethics Committee (Project number 1513489). 10 to 14-week-old female C57BL/6 mice (weighing 23.2±1.7 g, animals under 20 g were not used in this study) were used in all in vivo studies with 5 animals per group. Experiments were conducted without randomization or blinded protocol. Using preliminary peritonitis infection data and a power analysis (using SPSS for Windows, version 12), a sample size ≥2 would be needed to detect a large effect size (d=0.8) with 95% power using a t test between means with alpha at 0.01. After 1 week of quarantine, inoculation (t=0) was performed by intraperitoneal injection of 300 μL of $2 \times 10^8$ cells, delivered in MEM, of non-MDR *A. baumannii* (ATCC 19606) or MDR *A. baumannii* (FADDI-AB056) with a 25-gauge syringe. Two groups (n=5 for ATCC 19606 and n=5 for FADDI-AB056) received either SNAPP S16 (8.3 mg/kg per dose in MEM, which corresponds to 1.5× in vitro MBC taking into account the average peritoneal/blood volume of mice) or imipenem (derived from the carbapenem antibiotic family and considered to be the most successful class of antibiotics in evading emerging antimicrobial resistance, 40 mg/kg per dose in MEM) treatment 0.5, 4 and 8 h after introduction of the inoculums. An untreated control group was included. Signs of animal distress were monitored, and mice that did not meet distress-related euthanasia criteria at t<24 h were defined as 'survived'. At t=24 h, all mice were euthanized. Peritoneal washes were performed by injecting 3.0 mL of sterile MEM in the intraperitoneal cavity followed by a massage of the abdomen. Subsequently, the abdomen was opened and 3.0 mL of peritoneal fluid was recovered from the peritoneum for analysis of CFU/mL. Spleen of each mouse was removed and suspended in 5.0 mL MEM in a gentleMACS tube which was then subjected to automatic dissociation (gentleMACS dissociator, Miltenyl Biotec). The peritoneal fluid and supernatant from the dissociation of spleen were serially diluted in saline. A 10-μL portion of each dilution was plated on horse blood agar plates and incubated overnight at 37° C. For mice that were still alive directly before euthanization, blood was also taken from the heart for immediate plating on horse blood agar plates. Colonies were counted and expressed as CFU/mL, and viable bacteria cell counts in the peritoneal cavity (FIG. 2b), blood (FIG. 22a) and spleen (FIG. 22b) were compared with those of the control group at 24 h. The bacterial levels were statistically analyzed using a one-way classification ANOVA and student's t-test (SPSS for Windows, version 12). Data is expressed as mean±standard deviation (SD) of five biological replicates.

Fluorescent Tagging of SNAPP S16 with Alexa Fluor 488.

SNAPP S16 was dissolved in sodium bicarbonate buffer (0.1 M, pH 8.3) (2.5 mg/mL), and Alexa Fluor 488 (AF488) carboxylic acid succinimidyl ester dissolved in DMSO (10 mg/mL) was added (20 µL/mg of peptide polymer) The mixture was stirred for 1 h at room temperature and then passed through a gel separation column (PD MidiTrap G-25) to remove the excess dye. The filtrate was lyophilized to afford the fluorescently tagged derivative, AF488-S16.

Sample Preparation for Imaging with 3D-SIM Super-Resolution Microscopy

Sterilized chambered coverglasses were coated with poly-D-lysine (0.1 mL per well from a 0.1 mg/mL stock solution in DPBS) for 90 min. The excess poly-D-lysine was removed by washing with sterilized MilliQ water (2×0.5 mL) and the coverglasses were left to dry overnight in a sterile environment. E. coli cells ($1.25 \times 10^6$ cells/mL, prepared as per described in the measurement of MBC) were incubated with AF488-S16 (8 to 256 µg/mL) in a 96-well plate at 37° C. for 90 min. The cell suspension was then transferred to Eppendorf tubes (2 mL) and washed with HBSS twice (5000 g, 10 min). FM® 4-64FX dye (0.2 mL from a 5 µg/mL stock solution in HBSS) was added to the cell pellet and the cells were incubated on ice for 10 min with regular mixing. After incubation, the cells were washed with HBSS (5000 g, 10 min), resuspended in HBSS (0.5 mL), and then transferred to the chambered coverglass. Subsequently, the cells were washed in HBSS (800 g, 10 min) then fixed in 2% w/v paraformaldehyde in PBS for 10 min at room temperature. The fixative was removed with HBSS (800 g, 10 min) and HBSS (0.5 mL) was added to each well prior to imaging.

LPS Inhibition Assay.

SNAPP S16 (50 µL) was incubated with LPS from E. coli 0111:84 (50 µL) in MEM in a 96-well plate at 37° C. for 1 h. E. coli cells (which gave an optical density reading of ~0.7 at 650 nm) were diluted to $2.5 \times 10^6$ cells/mL in MEM and 100 µL of the bacteria solution was added to the S16-LPS mixture. The final concentration of S16 was kept at 4 µg/m L, whereas the LPS concentration was varied from 2 to 1000 µg/mL. The 96-well plate was then incubated at 37° C. for 90 min. A 50 µL aliquot was taken from each well, transferred to a second 96-well plate and 100 µL of saline and dye mixture (i.e., saline with 0.1% of SYTO® 9 and 0.1% of PI) was added. Each well in the second 96-well plate was analyzed with a Cell Lab Quanta SC MPL flow cytometer (Beckman Coulter) to determine the % PI-positive cells. Two independent runs of the assay were conducted and two replicates were used in each run for each variation.

Kinetics of Antimicrobial Activity.

SNAPP S16 (at a final concentration of 8 µg/mL) was incubated with E. coli cells (at a final concentration of $1.25 \times 10^6$ cells/mL) in MEM at 37° C. Aliquots were taken at t=0, 15, 30 and 90 min for analysis to determine CFU/mL (refer to procedure for the measurement of MBC) and % of PI-positive cells (via flow cytometry using a Cell Lab Quanta SC MPL flow cytometer (Beckman Coulter)). An untreated control group was also included. Two independent experiments of the assay were conducted and two replicates were used in each experiment for each variation.

Preparation of Large Unilamellar Vesicles (LUVs) for Dye Release (Pore Formation) and Lucigenin (Chloride Ion Transport) Based Assays To represent a model of an E. coli cytoplasmic membrane large unilamellar vesicles (LUVs) consisting of 1-Palmitoyl-2-oleoyl-sn-glycero-3-phosphoethanolamine (POPE) and 1-palmitoyl-2-oleoyl-sn-glycero-3-phosphoglycerol (POPG) at a 7:3 mole ratio, were used to encapsulate 2 mM rhodamine dextran (70 kDa; RD-40) and 2 mM fluorescein dextran (4 kDa; FD-4) in 10 mM Tris and 5 mM NaCl buffer solution (pH 7.3) for the dye release assay or 2 mM lucigenin solution containing NaCl (100 mM), and sodium phosophate salt (10 mM, pH 7.3) for the chloride ion transport assay, using the LUV preparation method we have previously described (Sani, M.-A. et al. Antimicrob. Agents Chemother. 57, 3593-3600 (2013)). The dye release assay was performed as previously described (Sani, M.-A. et al. Antimicrob. Agents Chemother. 57, 3593-3600 (2013)) and the chloride ion transport assay conducted as described by Elie, et al. Org. Biomol. Chem. 11, 923-928 (2013). LUVs were incubated (0.5 h for the dye release experiment or overnight for the chloride ion transport assay) with SNAPP S16 or control AMP maculatin 1.1 at lipid to peptide molar ratios ranging from 50:1 to 10000:1. To afford complete dye release or chloride ion transport, control LUVs were treated with 0.5% v/v Triton X-100. All measurements were made with a Varian Cary Eclipse spectrophotometer (Melbourne, Australia) using a 4-mm path-length quartz microfluorimeter cell (Starna, Hainault, United Kingdom) for the dye release experiment or a FLUOstar Optima plate reader (BMG Labtech, USA) for the chloride ion transport assay. Dye release or chloride ion transport was presented as the percent of fluorescence of RD-70 and FD-4 or lucigenin, respectively, compared to the Triton X-100 control. Data is representative of two independent assays completed in duplicates.

Membrane Potential Assay.

Membrane potential was determined by flow cytometry using a BacLight Bacterial Membrane Potential Kit (Invitrogen). When at low concentrations, the dye $DiOC_2(3)$ exhibits green fluorescence in all bacterial cells. The fluorescence shifts towards red emission as the dye molecules become more concentrated and self-associate in healthy cells that are maintaining a membrane potential. E. coli was inoculated to late exponential phase. Viable cells were then diluted to $2.5 \times 10^6$ cells/mL in PBS and added with variable concentrations (0.5×, 1× and 2×MBC) of SNAPP S16. A fully depolarized control was provided by the addition of the proton ionophore carbonyl cyanide 3-chlorophenylhydrazone (CCCP) at a final concentration of 5 mM to the untreated cells. Prior to a 1 h incubation at 37° C., 30 mM $DiOC_2(3)$ was added to all of the samples. Membrane potential was determined by a Cell Lab Quanta SC MPL flow cytometer (Beckman Coulter) as a ratio of cells that exhibited a red fluorescence (FL-3) to those that displayed a green fluorescence (FL-1). Gates were drawn based on the untreated (polarized) and CCCP-treated (fully depolarized) controls. Data is representative of two independent assays completed in duplicates.

RNA Extraction and Reverse Transcriptase Polymerase Chain Reaction (RT-PCR) Analysis for Programmed Cell Death Pathways.

To determine if the star peptide polymers induced PCD, E. coli cells were incubated with S16 at 1× and 5× the MBC, after which the mRNA levels of recA, lexA and mazEF relative to control genes and untreated E. coli were determined by RT-PCR. Escherichia coli ATCC 25922 was grown overnight at 37° C. in LB broth and used to freshly inoculate LB broth (2% v/v inoculum) and was grown to mid log-phase ($O.D._{600}=0.6$) at 37° C. A 200 µL aliquot of the cell suspension was mixed with 1 µL of Syto9 and 1 µL of PI and counted on the Cell Lab Quanta SC MPL flow cytometer (Beckman Coulter). After counting, cells were collected by centrifugation at 8000 g for 10 min at 4° C., washed twice in MEM and finally resuspended at $2\times10^6$ cells/mL in MEM. A 500 µL aliquot of a stock solution of SNAPP S16 (final concentration of 1×MBC or 5×MBC) was added to 500 µL (final concentration of $1\times10^6$ cells/mL) of E. coli cells. Following incubation (4 h), bacterial cells were collected by centrifugation at 8000 g for 10 min at 4° C. and immediately resuspended in 1 mL RNAprotect Bacteria Reagent (Qiagen).

Total RNA was extracted using the RNAprotect bacterial reagent and RNeasy kit (Qiagen). Cells were collected by centrifugation at 8000 g for 10 min at 4° C. and resuspended in 100 µL TE buffer (10 mM TrisCl, 1 mM EDTA, pH 8.0) containing 1 mg/ml lysozyme. After a 5 min incubation at room temperature, 350 µL of buffer RLT was added and the solution mixed by vortexing. Ethanol (250 µL) was then added and the entire 700 µL was added onto an RNeasy spin column and centrifuged at 16000 g for 1 min. The membrane was washed with 700 µL of buffer RW1 followed by 500 µL of buffer RPE. A final centrifugation at 16000 g for 1 min was performed to dry the membrane. RNase free water (50 µL) was added to the membrane and the RNA was eluted by centrifugation at 16000 g for 1 min. RNA was quantified by absorbance (260 nm/280 nm) using a Nanodrop spectrophotometer (Thermo Scientific).

Extracted RNA was immediately DNase-treated using the TURBO DNA-free kit (Ambion). Briefly, 5 µg of RNA was combined with 2 µL of 10×DNase buffer, 1 µL of DNase and sufficient water to make up a 20 µL reaction volume. The reaction was incubated for 20 min at 37° C., after which a further 1 µL of DNase was added and the reaction incubated for another 20 min at 37° C. Following this second incubation, 2 µL of DNase inactivation reagent was added. After a 5 min incubation at room temperature with occasional mixing, the inactivation reagent was pelleted by centrifugation at 10000 g for 1 min and the supernatant collected.

Reverse transcription was performed using the iScript Reverse Transcription Supermix (Bio-Rad). Briefly, 1 µg (4 µL) of the DNase-treated RNA extract was combined with 4 µL of iScript master mix and 12 µL of RNase free water. The reverse transcription reaction was performed with a 5 min, 25° C. priming step, a 30 min, 42° C. extension step followed by a 5 min, 85° C. inactivation step. A no-reverse transcription reaction was also set up using 1 µg (4 µL) of the DNase treated RNA extraction combined with 16 µL of RNase free water.

RT-PCR was performed using the iTaq Universal SYBR Green Supermix (Bio-Rad). Template cDNA (25 ng, 1 µL) was combined with 0.8 µL of forward primer (5 nM), 0.8 µL of reverse primer (5 nM) and 10 µL of Sybr Green Supermix. Primers used for the RT-PCR; recA (For) AGATCCTC-TACGGCGAAGGT, (rev) CCTGCTTTCTC-GATCAGCTT; lexA (For) GACTTGCTGGCAGTG-CATAA, (rev) TCAGGCGCTTAACGGTAACT; MazEF-1 (For) CTTCGTTGCTCCTCTTGC, (rev) CGTTGGG-GAAATTCACCG; 16SrRNA (For) TGTAGCGGT-GAAATGCGTAGA, (rev) CACCT-GAGCGTCAGTCTTCGT. Thermal cycling was performed using 40 cycles of 95° C. for 15 s, 60° C. for 15 s and 72° C. for 15 s. A positive control of genomic DNA and a no-reverse transcription control were included in each cycling run. Cycling was performed on a Rotor Gene RG-3000A Thermal Cycler running Rotor-Gene V6.1 software (Corbett Research). Analysis of the PCR was performed using the LinRegPCR software version 2015.3. Comparative CT analysis was performed according to the method of Schmittgen and Livak.

ROS Production.

E. coli cells (which gave an optical density reading of ~0.7 at 650 nm) were diluted to $2.5\times10^6$ cells/mL in MEM and 100 µL of the bacteria solution was added to each well containing either MEM (untreated control) or the test compound(s) at the desired concentrations (100 µL). The 96-well plate was then incubated at 37° C. for 90 min. The cells were then stained with the CellROX® Orange Reagent at a final concentration of 750 nM following manufacturer's instructions and were incubated for 1 h at 37° C. The cells were analysed on the Cell Lab Quanta SC MPL flow cytometer (Beckman Coulter) where the fluorescence from the Cell-ROX® Orange Reagent was measured on FL-3. A minimum of two independent experiments of the assay were conducted and two technical replicates were used in each experiment. Data is expressed as mean±standard deviation.

Effect of ALD Inhibition on the Membrane Disruption Ability of SNAPP S16

E. coli cells (which gave an optical density reading of ~0.7 at 650 nm) were diluted to $2.5\times10^6$ cells/mL in MHB, and 5 mL of the bacterial cell solution was added to an equivolume of doxycycline hyclate (to yield a final concentration equivalent to its MIC of 0.5 µg/mL). The mixture was incubated at 37° C. for 4 h and the cells were recovered via centrifugation (3000 g, 10 min) at the end of the incubation period. The recovered cells (100 µL/well) were then incubated at 37° C. for a further 90 min in the absence or presence of SNAPP (at 0.5× and 1×MBC, 100 µL/well) in a 96-well plate. A 50 µL aliquot was taken from each well, transferred to a second 96-well plate and 100 µL of saline and dye mixture (i.e., saline with 0.1% of SYTO® 9 and 0.1% of PI) was added. Each well in the second 96-well plate was analyzed with a Cell Lab Quanta SC MPL flow cytometer (Beckman Coulter) to determine the % PI-positive cells. Two independent runs of the assay were conducted and two replicates were used in each run for each variation.

Cryo-Transmission Electron Microscopy (Cryo-TEM).

Star peptide polymer S16 (35 µg/mL in MHB, 15 and 35 µg/mL in MEM), melittin (64 µg/mL in MHB) or ovispirin (19 µg/mL in MHB) was incubated with E. coli cells ($1.25\times10^6$ cells/mL in MHB or MEM, prepared as per described in the measurement of MBC) at 37° C. for 90 min. After incubation, the cells were pelleted (10000 g, 20 min), washed with pre-filtered PBS and resuspended in the same buffer (ca. 10-30 µL). Subsequent steps were taken based on the protocol previously described (Chen, Y.-Y. et al. Mol. Microbiol. 79, 1380-1401 (2011)).

Statistical Analysis.

Data obtained were determined to be normally distributed. Homogeneity of variances was assessed using the Levene's test (SPSS for Windows, version 12). Statistical analysis was also performed using a one-way classification of ANOVA and student's t-test (two-tailed), where differences were regarded as statistically significant with probability $P<0.05$.

Materials.

H-Lys(Z)—OH (>99%, Fluke), DL-Valine (>99%, Acros Organics), sodium chloride (NaCl, Chem-Supply), potassium chloride (KCl, Chem-Supply), sodium phosphate dibasic ($Na_2HPO_4$, Chem-Supply), potassium phosphate monobasic ($KH_2PO_4$, 99%, Aldrich), TRIS powder (Aldrich), sucrose (Univar), D-(+)-glucose solution (100 g/L, Aldrich), diethyl ether (Chem-Supply), acetonitrile (Univar), generation 2.0 poly(amido amine) dendrimer (G2 PAMAM) (Dendritech), generation 3.0 poly(amido amine) dendrimer (G3 PAMAM) (Dendritech), 4-methylbenzylamine (97%, Aldrich), bis(trichloromethyl)carbonate (triphosgene, 99%, Aldrich), paraformaldehyde (Aldrich), trifluoroacetic acid (TFA) (99%, Aldrich), hydrobromic acid (33% in acetic acid) (Aldrich), pentane (anhyd., >99%, Aldrich), dimethyl sulfoxide (DMSO, Aldrich), N,N-dimethylformamide (DMF, anhyd., Acros Organics), Spectra/Por® molecular porous membrane tubing 8000 MWCO (Spectrum Laboratories, Inc.), poly-D-lysine hydrobromide (70-150 kDa, Aldrich), Hanks' Balanced Salt solution (HBSS, with sodium bicarbonate, without phenol red, Aldrich), penicillin-streptomycin (Aldrich), 1-palmitoyl-2-oleoyl-sn-glycero-3-phosphoethanolamine (POPE, Avanti Polar Lipids), 1-palmitoyl-2-oleoyl-sn-glycero-3-phosphoglycerol (POPG, Avanti Polar Lipids), lucigenin (N,N'-dimethyl-9, 9'-biacridinium dinitrate, Aldrich), fluorescein isothiocyanate-dextran (4 kDa, Aldrich), rhodamine isothiocyanate-dextran (70 kDa, Aldrich), thiourea (>99%, Aldrich), and doxycycline hyclate (>98%, Aldrich) were used as received. THF (99%, Lab Scan) was distilled from sodium benzophenone ketal under argon. Dimetylsulfoxide-$d_6$ (DMSO-$d_6$) (99.9%) was purchased from Cambridge Laboratory Isotopes and used as received. RPMI-1640 medium without L-glutamine (GIBCO Cat. No. 21870), Dulbecco's Modified Eagle Medium (DMEM, GIBCO Cat. No. 11995), fetal bovine serum (FBS, GIBCO Cat. No. 10099), GlutaMAX™ supplement (100×, GIBCO Cat. No. 35050), antibiotic-antimycotic (100×, GIBCO Cat. No. 15240), MEM non-essential amino acids (100×, GIBCO Cat. No. 11140), Dulbecco's Phosphate Buffered Saline (DPBS, GIBCO 14190), 0.05% trypsin-EDTA (1×, GIBCO Cat. No. 25300), Alexa Fluor® 488 carboxylic acid succinimidyl ester, FM® 4-64FX, SYTO® 9 green fluorescent nucleic acid stain, and propidium iodide (PI) were purchased from Invitrogen and used as received. Defibrinated horse and sheep blood were obtained from Commonwealth Serum Laboratories (CSL) Melbourne. Todd-Hewitt Broth (CM0189), Mueller-Hinton Broth (MHB) (CM0405), Blood Agar Base No. 2 (CM0271), and Yeast Extract (LP0021) were purchased from Oxoid. Bacto™ Tryptone, and Bacto™ Agar were purchased from BD Biosciences. Ultra-pure lipopolysaccharide (LPS) from *Escherichia coli* O111:B4 was purchased from Invivogen. Vybrant® Apoptosis Assay Kit #4 (YO-PRO®-1/PI, Invitrogen) was used to perform the apoptosis/necrosis assay. BacLight Bacterial Membrane Potential Kit (Invitrogen) was used to conduct the membrane potential assay. RNeasy Protect Bacteria Mini Kit (Qiagen), TURBO DNA-free kit (Ambion), iScript Reverse Transcription Supermix for RT-qPCR (Bio-Rad Laboratories), and iTaq Universal SYBR Green Supermix (Bio-Rad Laboratories) were used for RNA extraction and reverse transcriptase PCR analysis for programmed cell death pathways. CellROX® Orange Reagent (Invitrogen) was used to perform the reactive oxygen species (ROS) production assay. 96-well cell culture plates were used for cell culture. 8-Well Nunc™ Lab-Tek™ Chambered Coverglass (Thermo Scientific) was used to contain samples for imaging with 3D-SIM.
Instrumentation.

GPC analysis was performed on a Shimadzu liquid chromatography system equipped with a Shimadzu RID-10 refractometer ($\lambda$=633 nm), using three Waters Ultrahydrogel columns in series ((i) 250 Å porosity, 6 µm diameter bead size; (ii) and (iii) linear, 10 µm diameter bead size), operating at 60° C. The eluent was Milli-Q water containing 20% v/v acetonitrile and 0.1% w/v TFA (0.5 mL/min). The molecular weight characteristics of the analytes were determined with reference to a conventional column calibration with narrow molecular weight distribution poly(ethylene glycol) standards (Polymer Standards Service GmbH). All samples for GPC analysis were prepared at a concentration of 10 mg/mL and were filtered through 0.45 µm nylon filters prior to injection. $^1$H NMR spectroscopy was performed at room temperature using a Varian Unity400 (400 MHz) spectrometer with the deuterated solvent as reference and a sample concentration of ca. 10 mg/mL. DLS measurements were performed on a Malvern Zetasizer Nano ZS with a 4.0 mW He—Ne laser (633 nm) at an angle of 173° and a temperature of 25±0.1° C. Initial sample concentrations of 1 mg/mL in either RO water, MEM or MHB were used and serial dilutions were performed until stable spectra were obtained. All sample solutions were filtered using 0.45 µm syringe filters. Bacterial cell sample analysis was performed using a Cell Lab Quanta SC MPL flow cytometer (Beckman Coulter) equipped with a 100 W stabilized mercury arc lamp with wavelengths of 365, 404, and 435 nm, and a 488 nm diode laser. The fluorescence from SYTO® 9 was measured through a 525-nm band-pass filter (Fluorescent Channel 1, FL-1), and the red emission of PI was measured with a 670-nm long pass filter (Fluorescent Channel 3, FL-3). The multiparametric data were analyzed using the Cell Lab Quanta SC software. Super-resolution fluorescence imaging was performed using three dimensional-structured illumination microscopy (3D-SIM) implemented on the DeltaVision OMX V4 Blaze imaging system (Applied Precision, a GE Healthcare Company). Briefly, 488 and 568 nm lasers (for Alexa Fluor® 488 and FM®4-64FX, respectively) were used to provide wide-field illumination and multi-channel images, which were captured on two PCO Edge scientific CMOS cameras (each dedicated to a specific channel) with acquisition rates of up to 400 fps. Data capture used an Olympus PlanApo N 60×1.42 NA oil objective and excitation and emission filter sets of 528/48 for Alexa Fluor® 488 and 609/37 for FM® 4-64FX. The immersion oil 1.514 (GE Healthcare Company) was used. The DeltaVision OMX Master Control Software was used for instrument control. All raw images were reconstructed using SoftWorX 4.0 (Applied Precision). Image analysis was performed using Fiji, a distribution of ImageJ.

Method Used for Calculating MBCs (Molar Concentrations):

The number average molecular weight, $M_n$, obtained from GPC analysis was consistently used in this study to convert mass concentrations to molar concentrations. The reader is referred to Table 2 and Table 8 for the $M_n$ of SNAPPs and their linear analog, respectively.

The following formula was used:

$$\text{Molar concentration}(\mu M) = \frac{\text{Mass concentration }(\mu g/mL)}{M_n(g/mol)} \times 1000$$

The calculation is exemplified as below:
MBC of S16 against *E. coli* in MEM=7.6 µg/mL
$M_n$ of S16=43800 g/mol
Therefore, $$MBC(\mu M) = \frac{7.6\ \mu g/mL}{43800\ g/mol} \times 1000 = 0.17\ \mu M$$

Figure 24:
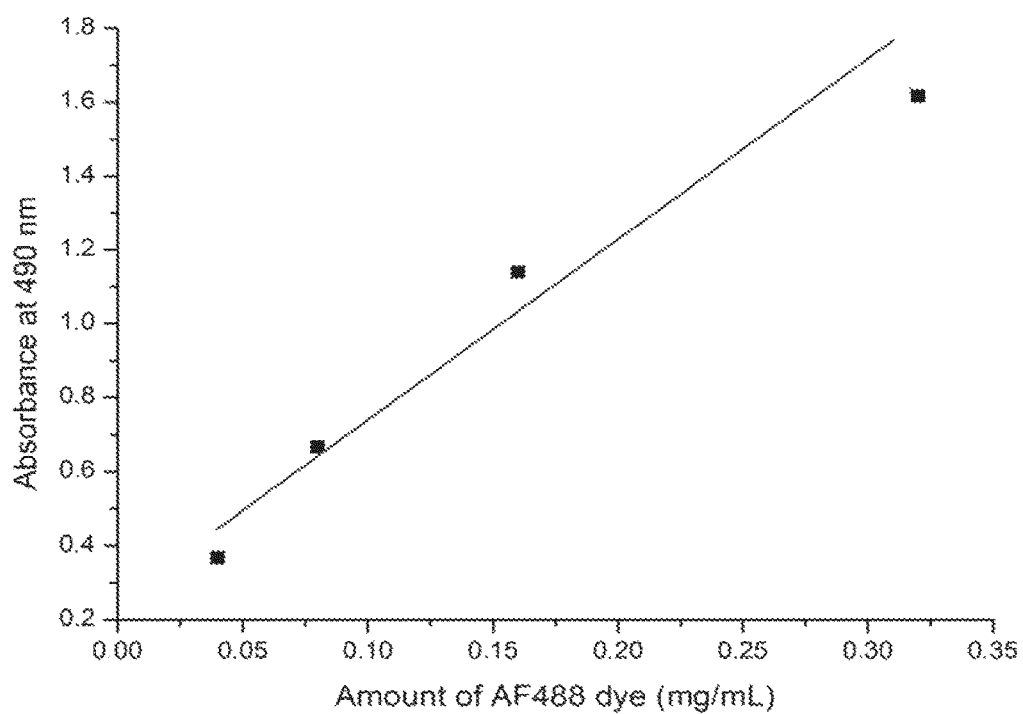
FIG. 24. The calibration curve used to estimate the amount of AF488 dye conjugated based on the absorbance at 490 nm. Sterile water was used to dissolve the AF488 dye. A linear trend line (red) was fitted over the acquired data points (slope=4.333, y-intercept=0.297, $R^2$=0.96). The data are representative of two independent experiments.
Figure 25:
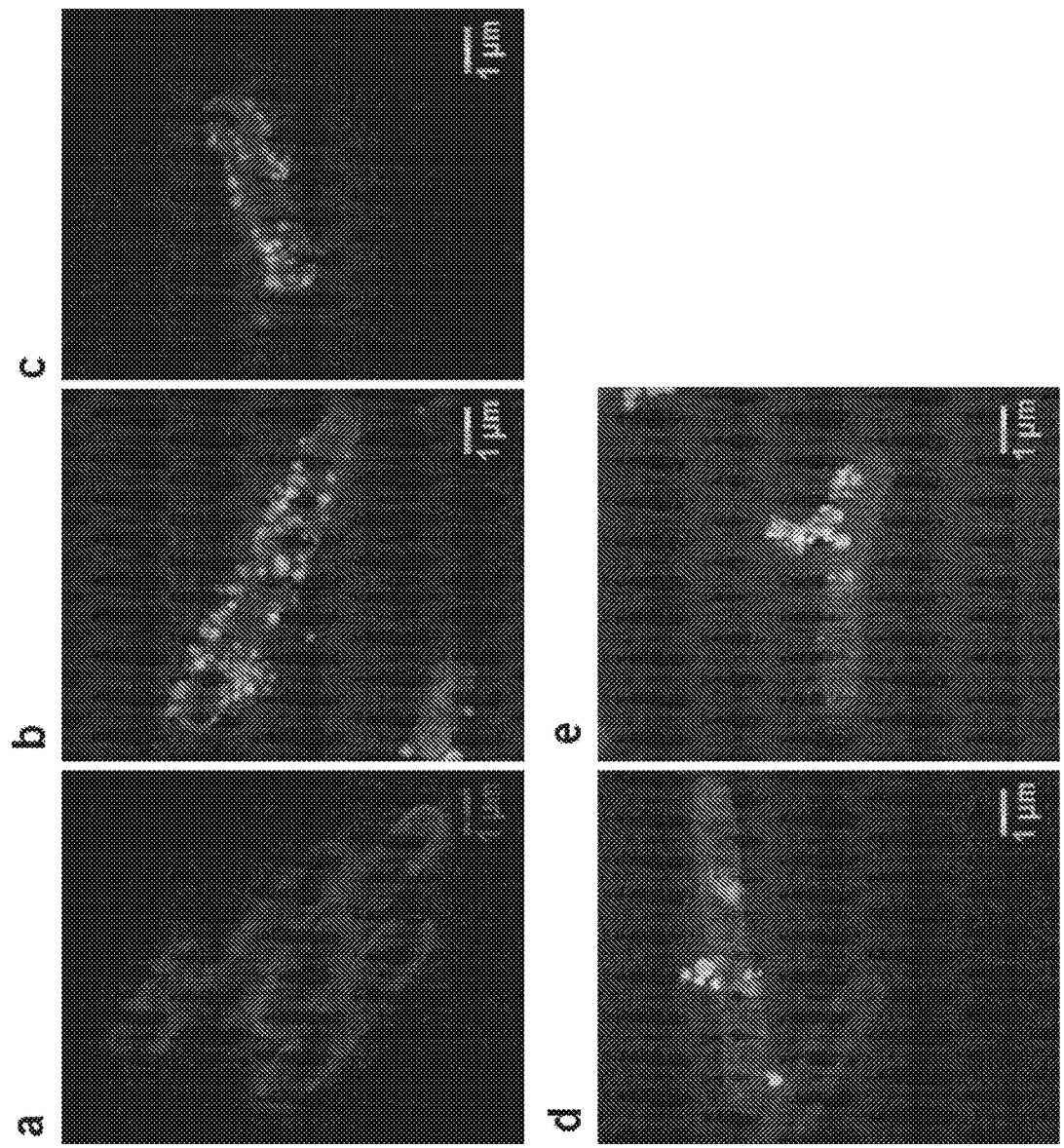
FIG. 25. OMX 3D-SIM images of *E. coli* before and after treatment with AF488-tagged SNAPP S16 in MHB. a, Image of untreated *E. coli*. b-e, Images of *E. coli* incubated with AF488-tagged SNAPP S16 at 2×$MBC_{tagged}$. The *E. coli* cell membrane was stained with FM4-64FX (red) and the star peptide polymer with Alexa Fluor 488 (green) in all images. Note that the MBC used refers to the MBC of the fluorescently tagged star (Table 12). All images are representative of three independent experiments.

Determining the Degree of Labelling (DOL):

A calibration curve (FIG. 24) was constructed to estimate the degree of AF488 conjugation on SNAPP S16. Note that the DOL is calculated based on the assumption that the absorbances of the free and conjugated dye are the same (which might not be the case). In this study, an estimated DOL is sufficient.

The labelled SNAPP (5.2 mg/mL) was found to have an absorbance of 0.78 at 490 nm. This correlates to approximately 0.11 mg/mL of AF488 dye based on the calibration curve. Taking into the account the molarities of the dye and SNAPP in solution, the DOL was found to be approximately 3 dye molecules per SNAPP S16 molecule.

Example 2

Synthesis and Characterization of SNAPPs

Summary

Figure 6:
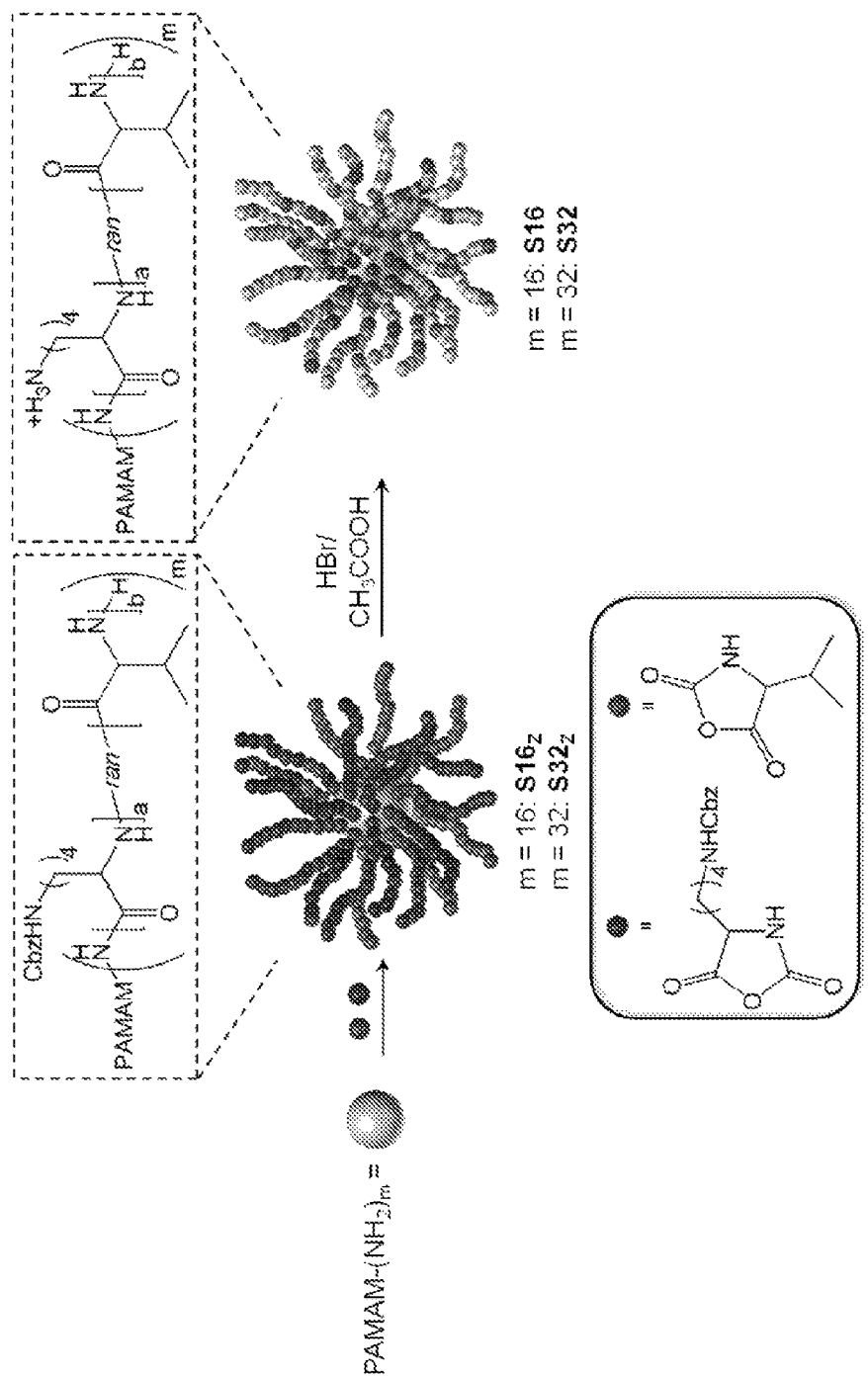
FIG. 6. Synthesis of SNAPPs. Synthesis of SNAPPs via ROP of lysine and valine NCAs was initiated from the terminal amines of PAMAM dendrimers. Second (G2) and third (G3) generation PAMAM dendrimers (see FIG. 7 for structure of the former) with 16 and 32 peripheral primary amines were used to prepare 16- and 32-arm SNAPPs, respectively. The number of repeat units for lysine and valine are a and b, respectively. The lysine-to-valine ratios (i.e., a:b) are provided in Table 2.
Figure 7:
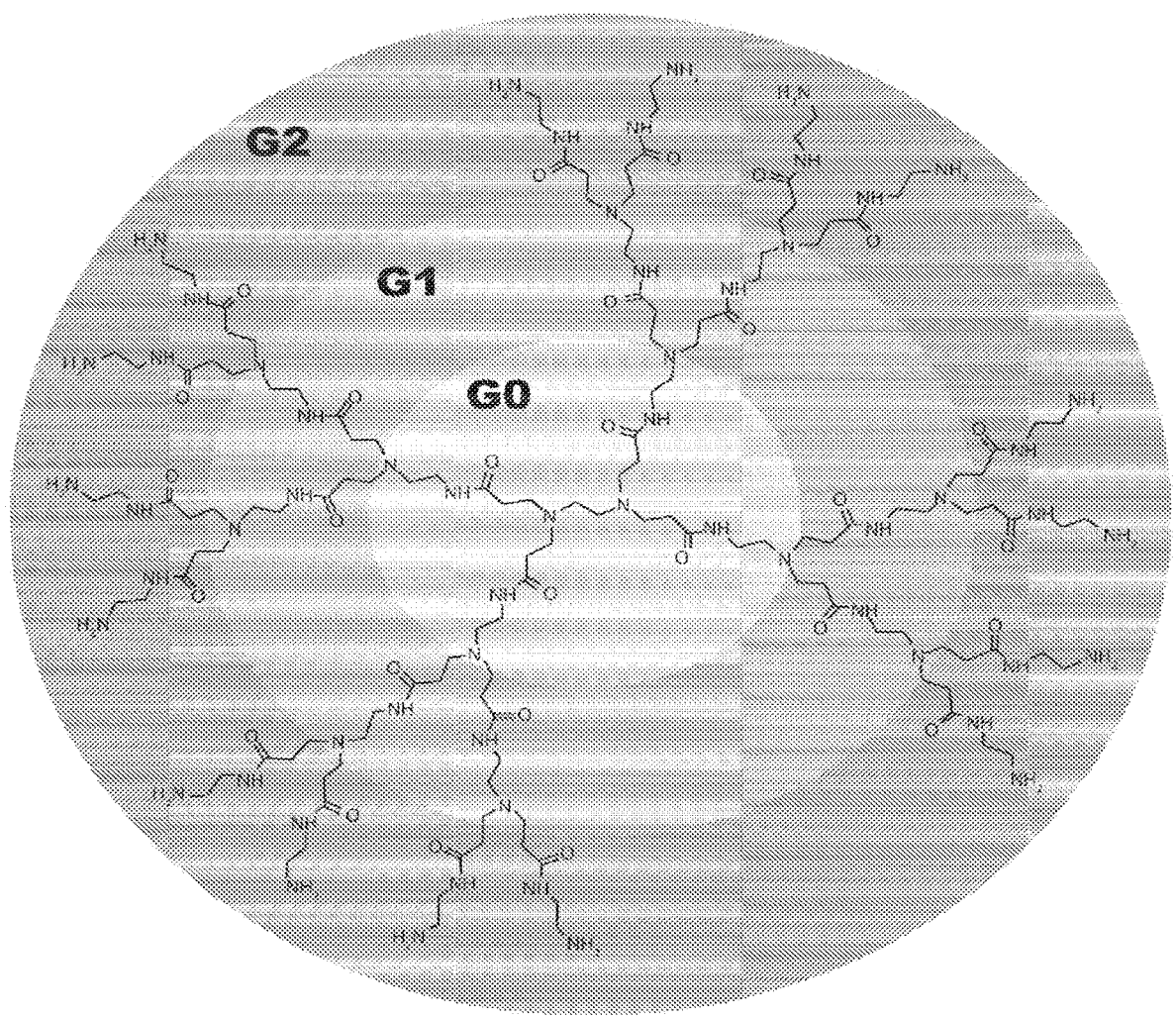
FIG. 7. Structure of a second generation PAMAM dendrimer (G0=generation 0; G1=generation 1; G2=generation 2).
Figure 8:
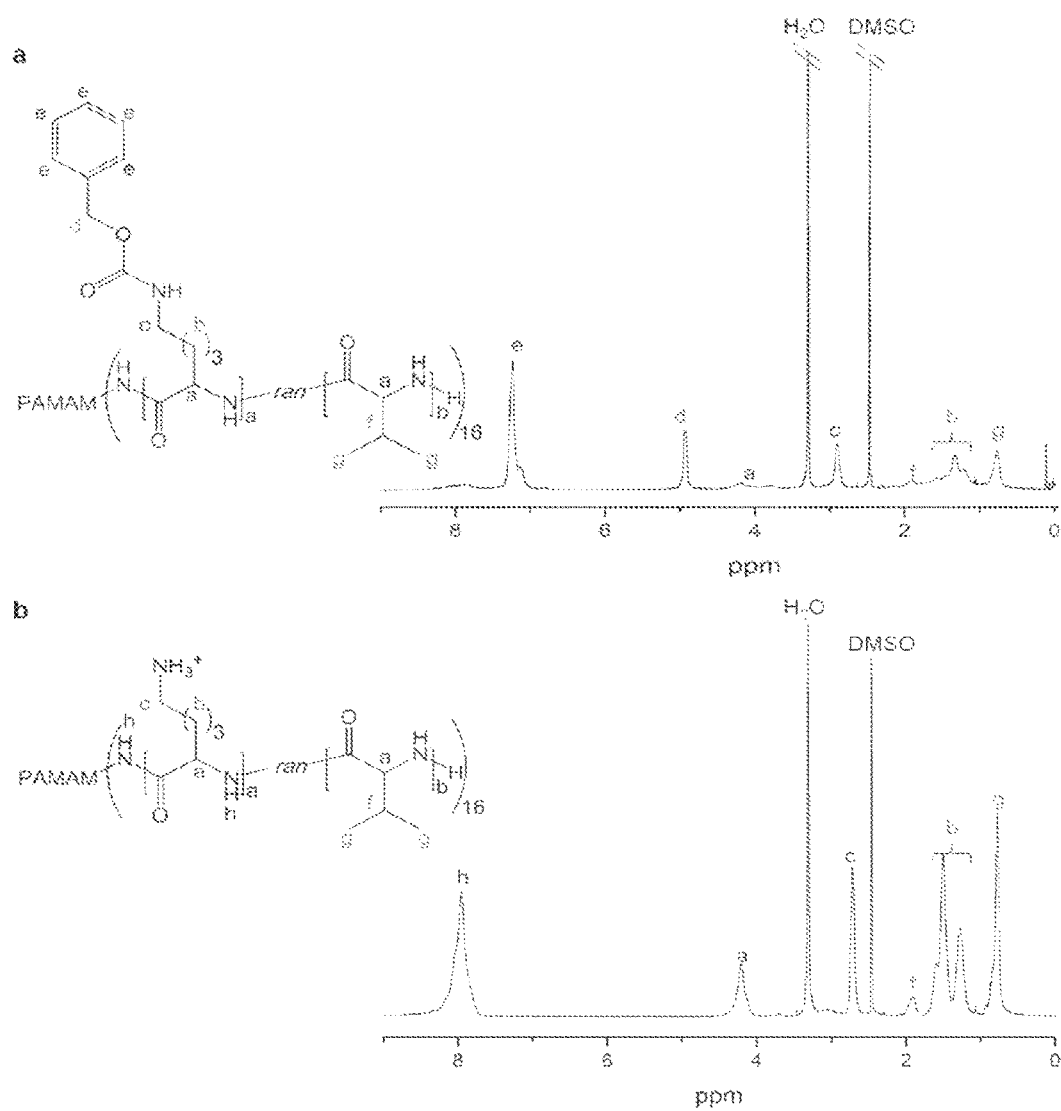
FIG. 8. $^1$H NMR spectra ($d_6$-DMSO) of 16-arm Cbz-protected star peptide polymer $S16_Z$ (a) and deprotected star peptide polymer (SNAPP) S16 (b). The spectra are representative of four independent experiments.
Figure 9:
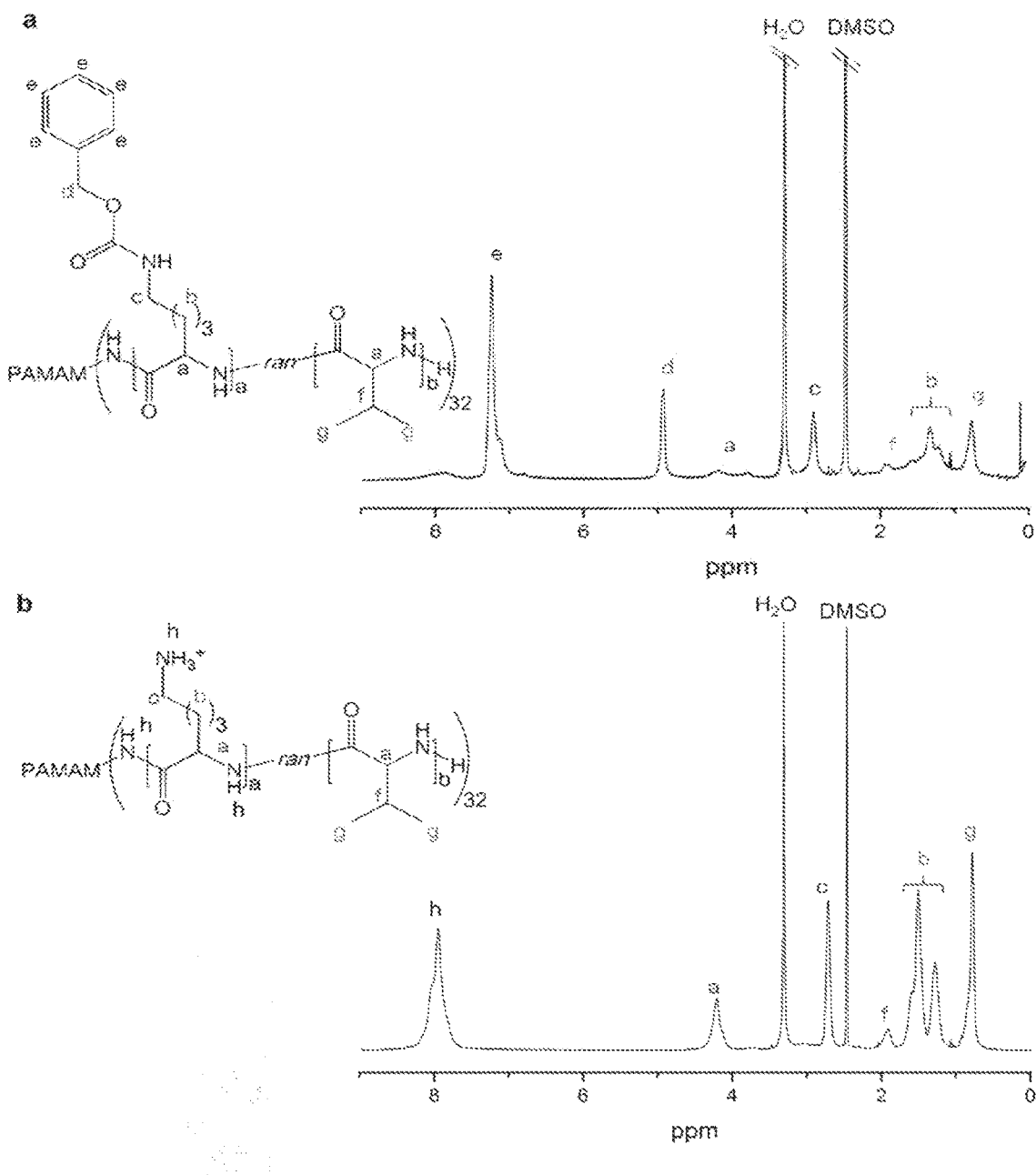
FIG. 9. $^1$H NMR spectra ($d_6$-DMSO) of 32-arm Cbz-protected star peptide polymer $S32_Z$ (a) and deprotected star peptide polymer (SNAPP) S32 (b). The spectra are representative of four independent experiments.
Figure 10:
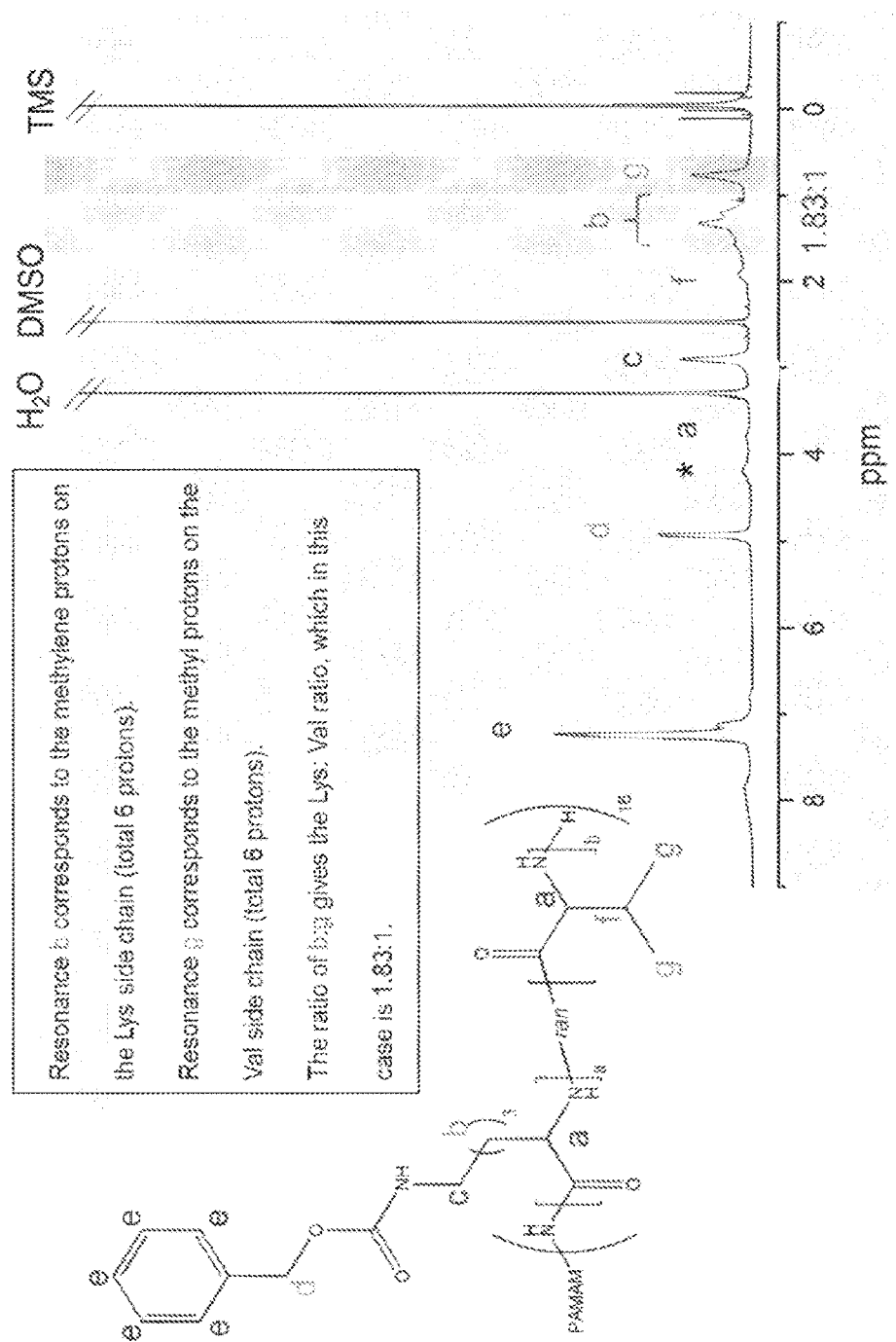
FIG. 10. Integration of $^1$H NMR spectrum ($d_6$-DMSO) of star peptide polymer $S16_Z$ to determine the lysine-to-valine ratio.
Figure 11:
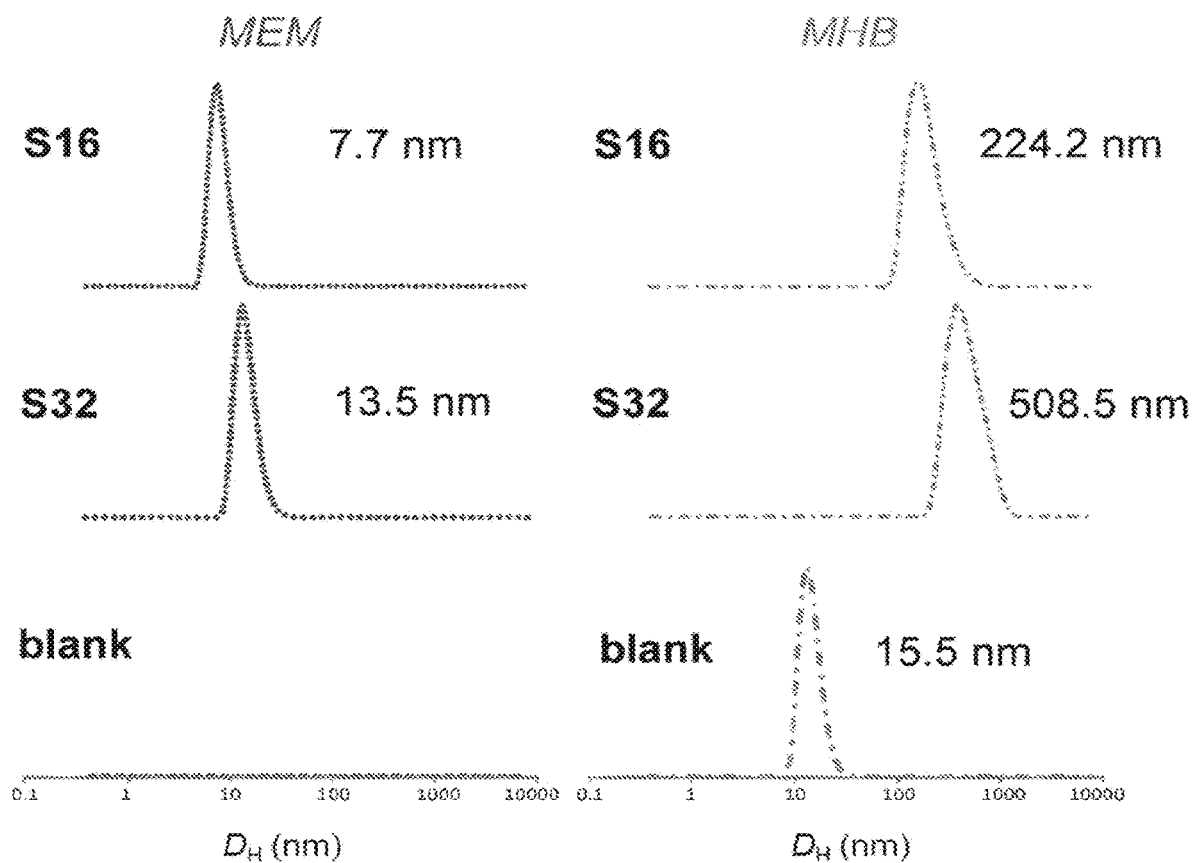
FIG. 11. DLS normalized mass % of SNAPPs as a function of hydrodynamic diameter ($D_H$). The numbers on the DLS distributions show the average $D_H$ of SNAPPs in minimal essential medium (MEM; red dotted lines) and Mueller-Hinton broth (MHB, green dashed lines). The DLS distributions for the 'blank' MEM and MHB are also shown. For each sample, the average $D_H$ was determined as an average of 3 sets containing 15 measurements per set. The data are representative of three independent experiments.
Figure 12:
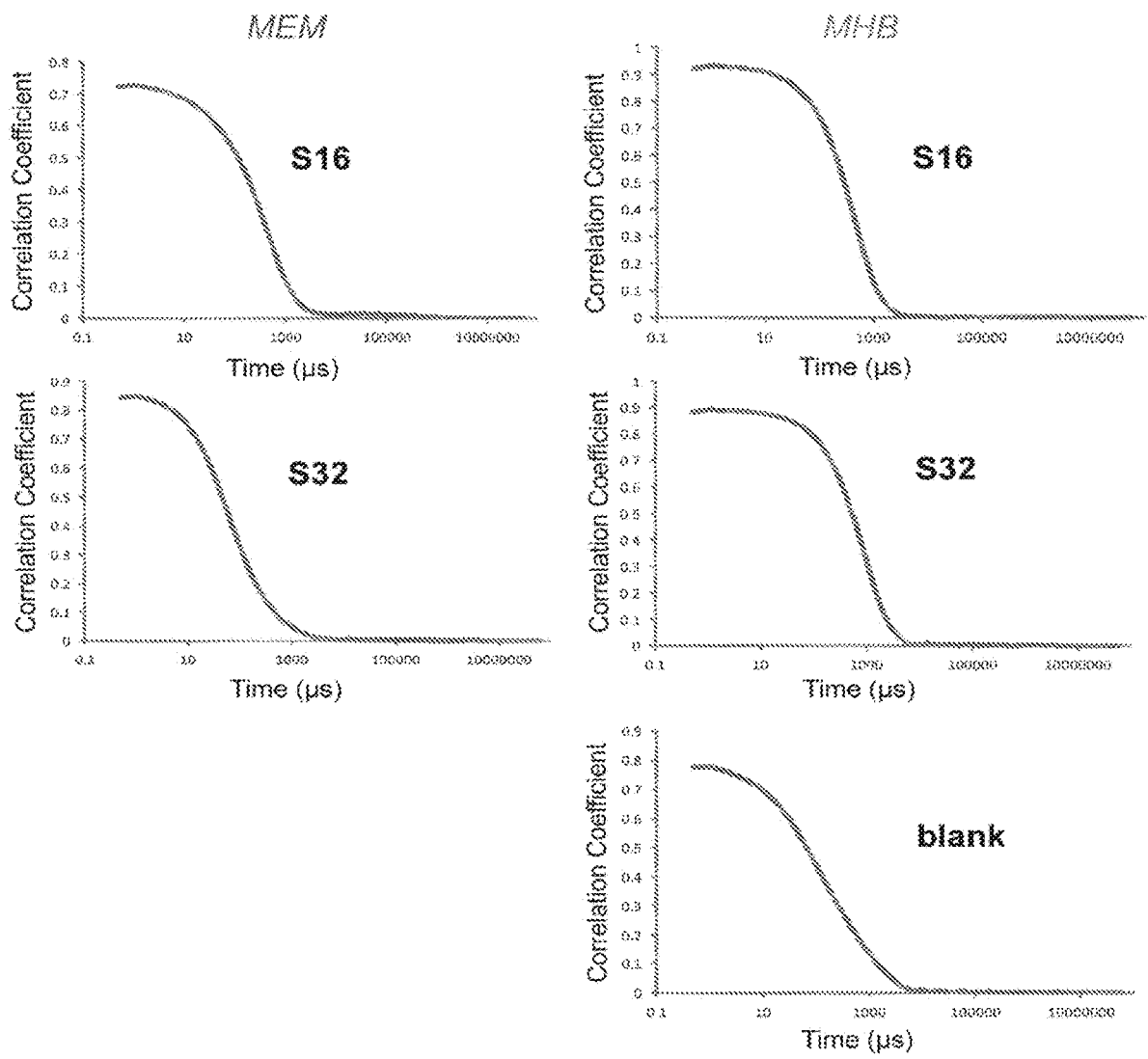
FIG. 12. Intensity autocorrelation curves corresponding to the DLS traces of S16 and S32 in minimal essential medium (MEM) and Mueller-Hinton broth (MHB). The autocorrelation curve that corresponds to the DLS distribution of 'blank' MHB is also provided. The data are representative of three independent experiments.

The synthetic scheme of SNAPPs is provided in FIG. 6. Successful synthesis of SNAPPs was confirmed by $^1$H NMR spectroscopic analysis (FIGS. 8a and 9a), which also allowed calculation of the actual lysine-to-valine ratios to be ~2:1 for both S16$_Z$ and S32$_Z$ (FIG. 10 and Table 2). The subsequent removal of the carboxylbenzyl (Cbz) protecting groups on the lysine residues of SNAPPs yielded water-soluble stars S16 and S32 with pendent primary amine functionalities along the star arms (FIG. 1; see FIGS. 8b and 9b for $^1$H NMR spectroscopic analysis), which would remain protonated at physiological pH (pKa=10.5). The molecular weight characteristics of SNAPPs were estimated by aqueous gel permeation chromatography (GPC) (number-average molecular weight ($M_n$)=43.8 kDa for S16 and 74.8 kDa for S32) (Table 2). The solvated dimensions of SNAPPs S16 and S32 were studied via dynamic light scattering (DLS) analysis in minimal essential medium (MEM), which revealed monomodal particle size distributions and hydrodynamic diameters ($D_H$) of 7.7 and 13.5 nm, respectively (FIGS. 11 and 12). The sizes of SNAPPs were further substantiated by transmission electron microscopy (TEM) analysis which showed that S16 and S32 have uniform diameters of 7.8±1.2 and 7.5±1.6 nm, respectively (FIG. 13).

$^1$H NMR Spectroscopic Analysis of SNAPPs $^1$H NMR spectroscopic analysis (FIGS. 8 and 9) was employed to confirm successful synthesis of SNAPPs. Proton resonances characteristic of valine (i.e., $\delta_H$ 0.8 ppm corresponding to the methyl groups on the valine side chain) and lysine (i.e., $\delta_H$ 1.2-1.8 ppm corresponding to the methylene protons on the lysine side chain) residues were observed. Integration and comparison of these resonances (FIG. 10) provided lysine-to-valine ratios of approximately 2:1, which is consistent with the ratio of lysine and valine NCA monomers used in the synthesis (Table 2). Resonances resulting from the G2 and G3 PAMAM cores were difficult to observe upon star formation as they overlap with the broad peptide polymer peaks. It is also likely that the intensities of the core resonances are much smaller relative to those resulting from the star arms as the contribution of the PAMAM core to the overall molecular weight of the star is relatively small.

Synthesis and Characterization of SNAPPs

To demonstrate the potential of this new class of antimicrobial nanomaterial, SNAPPs in the form of 16- and 32-arm star peptide polymer nanoparticles S16 and S32, respectively, were synthesized via NCA-ROP (number-average molecular weight, $M_n$=43.8 kDa (S16), 74.8 kDa (S32); hydrodynamic diameter, $D_H$=7.7 nm (S16), 13.5 nm (S32); see FIG. 1, the 'Synthesis and Characterization of SNAPPs' section in the Examples, FIGS. 6-13, Table 2). Lysine and valine were selected as cationic and hydrophobic amino acids, respectively. Their monomeric NCA derivatives were randomly polymerized from a PAMAM dendritic core to form the star arms with a theoretical lysine-to-valine ratio of 2:1, which was selected to promote water solubility, and an average degree of polymerization (DP) of 30 residues per star arm at complete monomer conversion.

Example 3

In Vitro Antimicrobial Properties of SNAPPs.

We evaluated the antibacterial efficacy of SNAPPs by determining their minimum bactericidal concentrations (MBCs) against a range of Gram-positive (*S. mutans* and *S. aureus*) and Gram-negative (*E. coli, P. aeruginosa, K. pneumoniae,* and *A. baumannii*) bacteria. The MBC is defined as the minimum drug concentration that causes quantitative cell death (see 'Methods' section in Examples, FIG. 14, Table 3 for further clarification). The antimicrobial susceptibility assays were initially conducted in Mueller-Hinton broth (MHB), a nutrient-rich bacterial growth medium. Our initial studies which focused on the two Gram-positive bacteria (*S. aureus* and *S. mutans*) and two Gram negative bacteria (*E. coli* and *P. aeruginosa*) showed that S16 and S32 had preferential activity towards the Gram-negative species (MBC<1.4 µM) (Table 1) over the Gram-positive strains (MBC>1.8 µM) (Table 4). It is worthwhile noting that homolysine star-shaped peptide polymer nanoparticles, i.e. those that do not contain valine residues, exhibited a higher MBC value (>3-fold increase in MBC against *E. coli*), thus demonstrating the need for an amphipathic structure to effect antimicrobial activity.

In further studies using Gram-negative bacteria, S16 and S32 were also found to be effective against *K. pneumoniae* and *A. baumannii*, with S16 registering MBC values of 1.54 and 0.85 µM, respectively, and S32 showing similar MBC values of 0.83 and 0.79 µM. Further, both S16 and S32 were found to be equally effective against CMDR clinical isolates of *P. aeruginosa* (FADDI-PA067) and *A. baumannii* (FADDI-AB156) (Tables 5-6) as to drug-sensitive strains, yielding MBC values that range from 0.85 to 1.61 µM (Table 1). We observed that the MBC values of SNAPPs against all bacteria tested were within a similar order of magnitude, which implied that the antimicrobial efficacies of S16 and S32 might not be species-specific for Gram-negative bacteria. This was surprising as *P. aeruginosa* and *K. pneumoniae* possess low antibiotic susceptibility as a result of their thick extracellular capsules, which contribute to reduced cell permeability and is a resistance mechanism against antibiotics and AMPs. Noteworthy, the probability of the PAMAM dendrimer centres contributing to the antimicrobial efficacies of S16 and S32 in this study was discounted, as the PAMAM cores were found to be non-active against the range of bacterial species tested above (Table 7).

Figure 15:
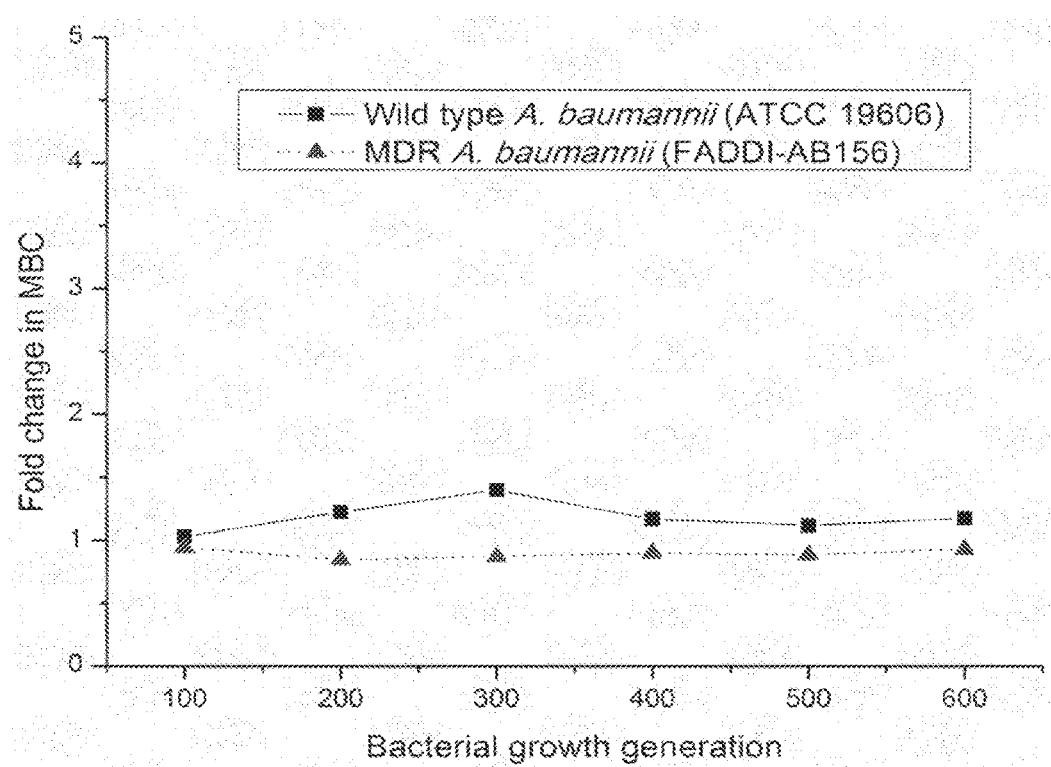
FIG. 15. Resistance acquisition in the presence of sub-MBC levels of star S16. Wild type (ATCC 19606) and colistin-resistant MDR (FADDI-AB156) *A. baumannii* were serially passaged in MHB containing sub-MBC levels of star peptide polymer S16. The change in the MBC of star peptide polymer S16 against both strains of *A. baumannii* is shown on the y axis over 600 generations of growth. Note that MBC determination was conducted in triplicates completed in two independent experiments.

Further, we conducted an antimicrobial resistance study to evaluate if resistance against SNAPPs could be generated easily. Following serial passaging of bacterial cells in the presence of sub-MBC levels of S16, we did not obtain de novo resistant mutants of wild type and CMDR *A. baumannii* to S16 even after 600 generations of growth (over a period of 24 days) (FIG. 15). The MBC values of S16 against these bacterial strains remained relatively constant throughout the experiment, despite the fact that the CMDR strain is genetically capable of mutation and rapid resistance acquisition. This result suggests that resistance to SNAPPs is not acquired easily.

Figure 16:
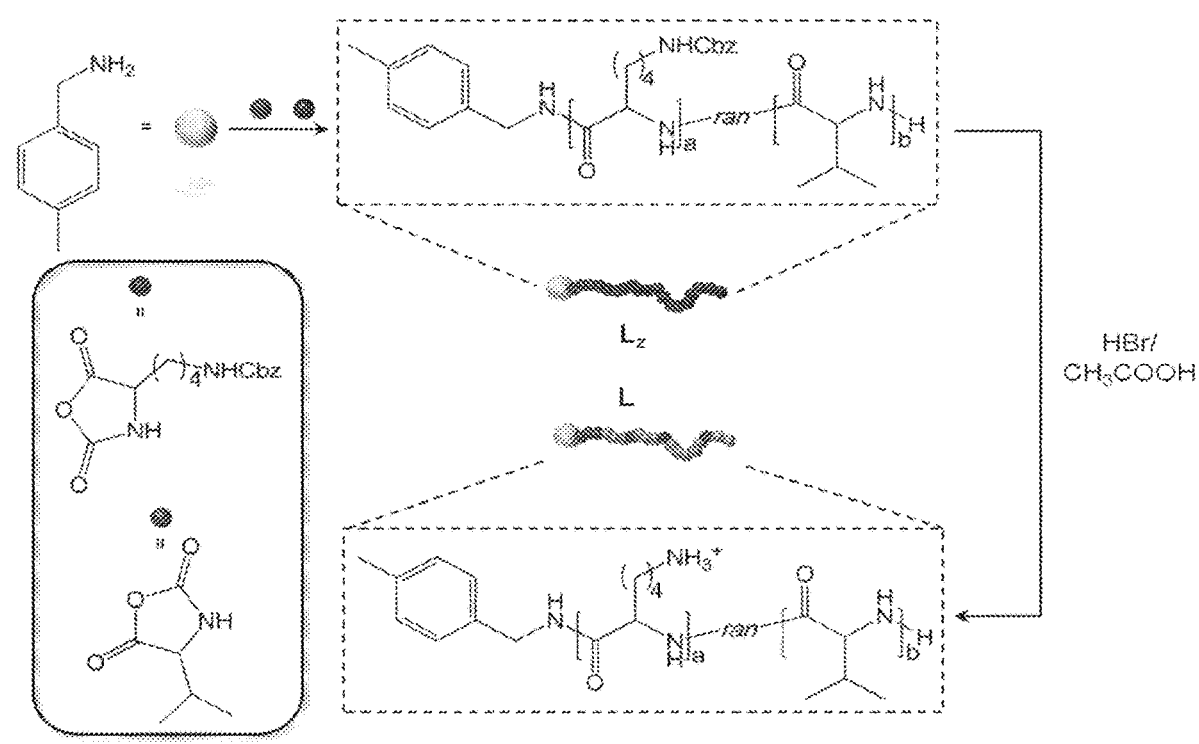
FIG. 16. Synthesis of linear peptide polymer $L_Z$. The ROP of lysine NCA and valine NCA initiated by 4-methylbenzylamine, followed by deprotection of the carboxybenzyl groups on the lysine residues with HBr and subsequent dialysis in RO water to afford water-soluble linear peptide polymer L. The number of repeating units for lysine and valine are a and b, respectively. The lysine-to-valine ratio, a:b, is provided in Table 8.
Figure 17:
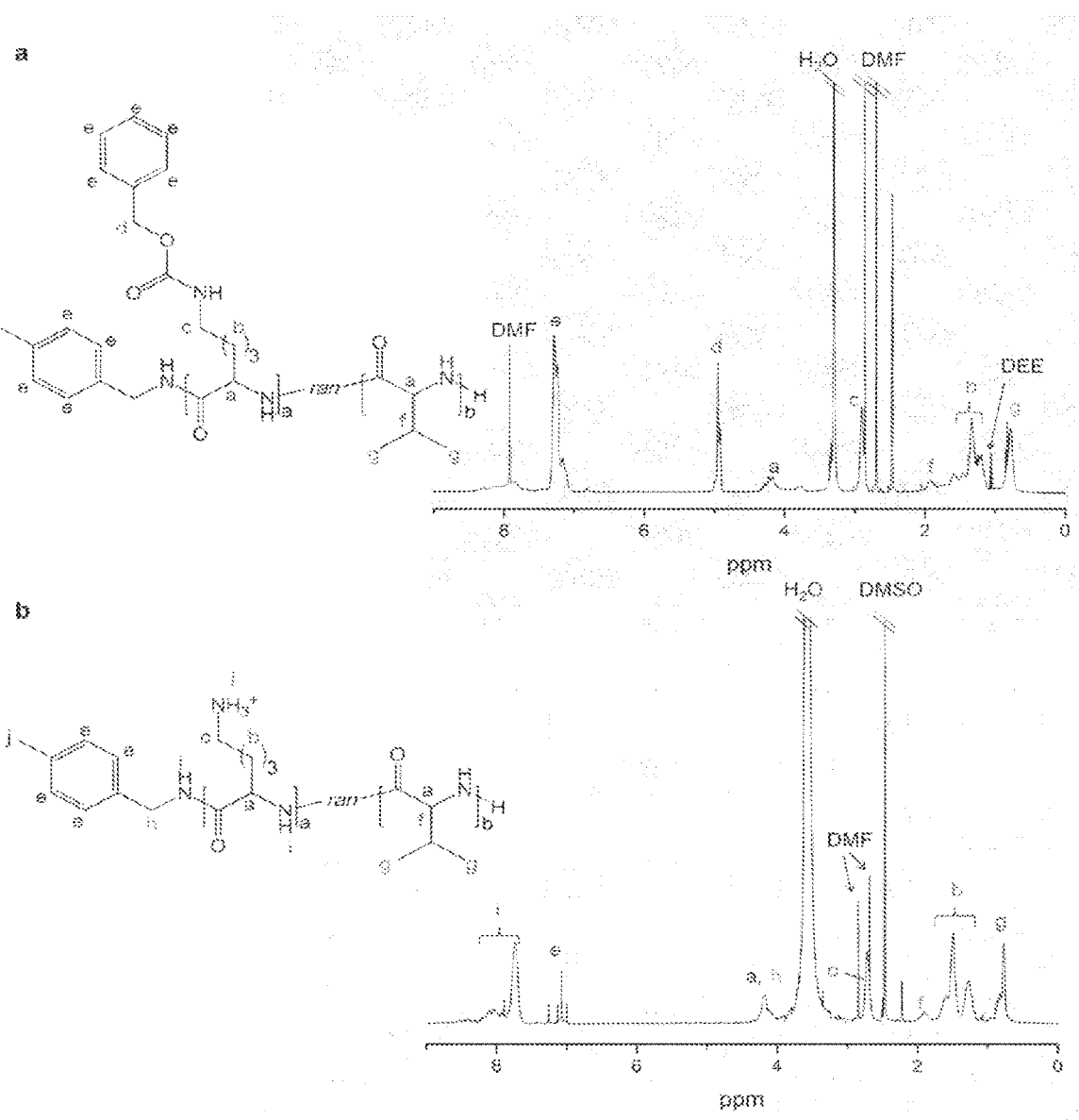
FIG. 17. a-b, $^1$H NMR spectra ($d_6$-DMSO) of linear Cbz-protected peptide polymer $L_Z$ (a) and deprotected peptide polymer L (b). The spectra are representative of three independent experiments. For linear random co-peptide polymer L, the peaks associated with the 4-methylbenzylamine initiator could be observed, which enabled the number-averaged degree of peptide polymerisation ($DP_n$) to be determined. The $DP_n$ value for L was found to be 36 repeat units, which is close to the targeted value of 30.
Figure 18:
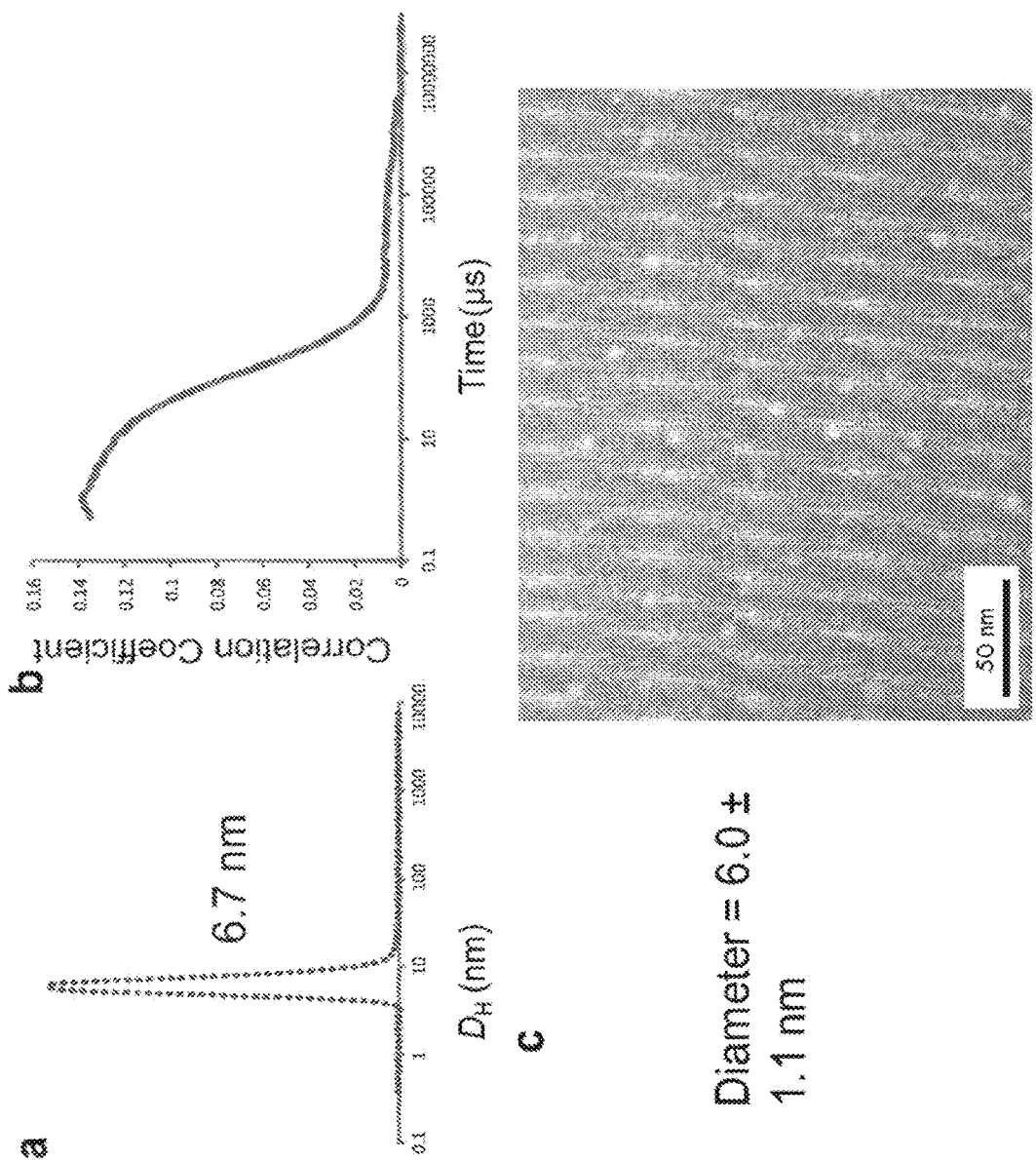
FIG. 18. DLS and TEM analysis of the linear random co-peptide polymer L. a-b, DLS normalized mass % of the linear random co-peptide polymer L in minimal essential medium (MEM) (a) as a function of hydrodynamic diameter ($D_H$), where the average $D_H$ was determined as an average of 3 sets of 15 measurements per set. The intensity autocorrelation curve corresponding to the DLS trace is shown in (b). c, TEM analysis of L (negative-staining, air dried, sample concentration of 0.5 μg/mL). The data in a and b and the image in c are representative of three independent experiments.

As a comparator, we synthesized the linear analog L to represent one arm of S16 and S32 (FIGS. 16-18, Table 8). Interestingly, compared to SNAPPs, the linear analog was poorly active against *E. coli* and *S. aureus*, with MBCs that are at least 40-fold higher than those of SNAPPs (Table 9). We hypothesize that the star architecture has a significant effect on enhancing the antimicrobial action of random co-peptide polymers against bacteria. Similar to that observed by Yang and co-workers, we theorize that the improvement in activity is a result of the increased local concentration of charges provided by the nanostructure, thereby leading to greater ionic interactions with the bacterial membranes. Additionally, bacterial membrane-induced peptide aggregation has been postulated to be a key factor of AMP efficacy, as it enables AMPs to achieve the high threshold concentrations needed for membrane disruption. Extending from this concept, we hypothesize that the star architecture affords a high local concentration of peptide mass even in solution before contacting bacterial cells, which may contribute to the enhanced efficacy of SNAPPs.

The antimicrobial activities of S16 and S32 were compared with several peptide-based antimicrobial agents known to be effective against Gram-negative pathogens, including magainin II, ovispirin and melittin (Table 1). The antimicrobial efficacies of these AMPs against certain Gram-negative pathogens have been well-documented; however, they (as with most AMPs) tend to demonstrate selective activity towards certain bacterial strains, even within the Gram-negative family (Table 1). This is in direct contrast to SNAPPs which displayed effective equipotent activity against all of the Gram-negative species tested. Furthermore, SNAPPs were orders of magnitude more effective than these AMPs (Table 1).

Figure 19:
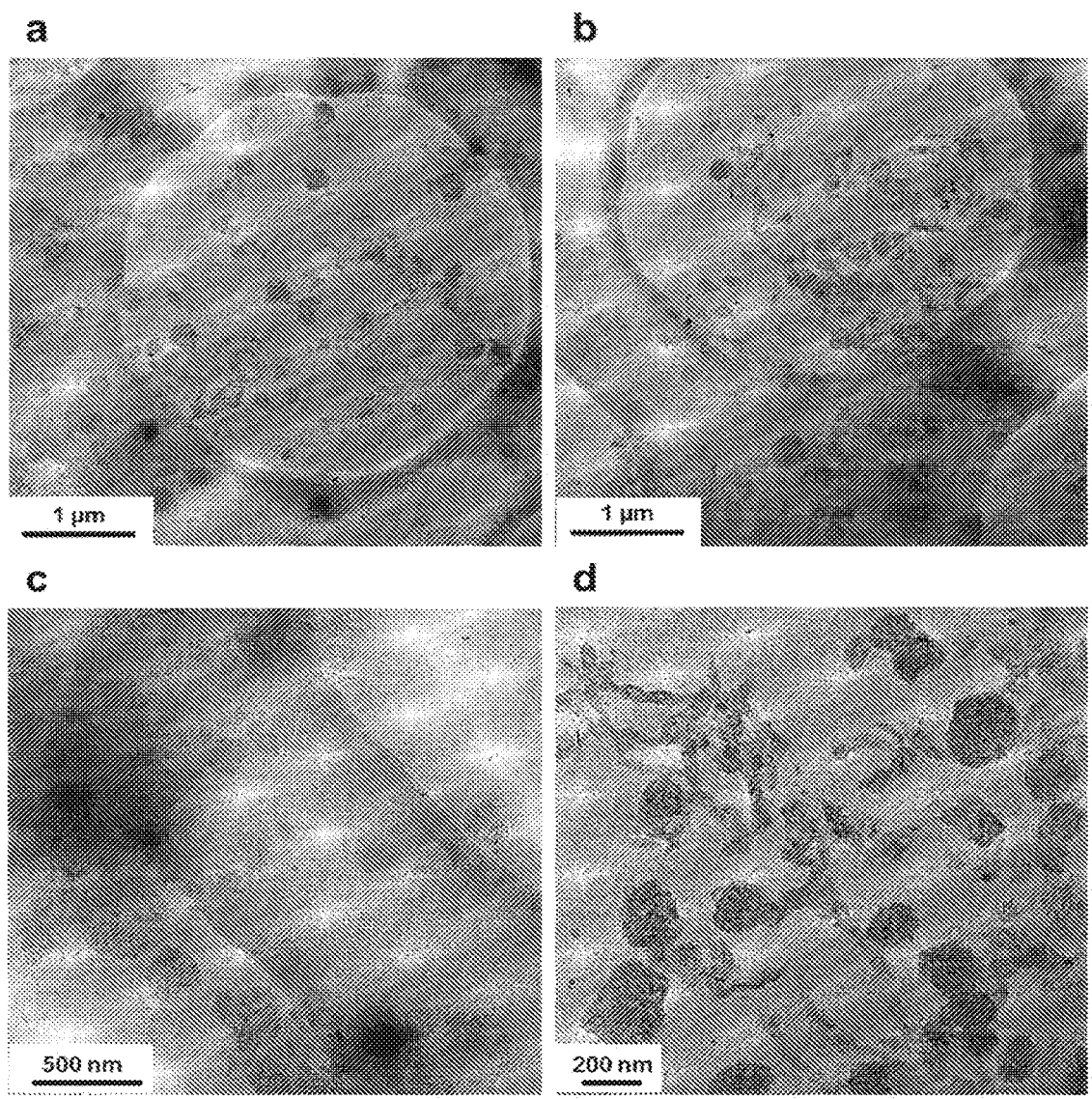
FIG. 19. Visualization of SNAPP in MHB using cryo-TEM. a-d, Cryo-TEM images of S16 in MHB at 35 μg/mL (0.8 μM). All images are representative of three independent experiments.
Figure 20:
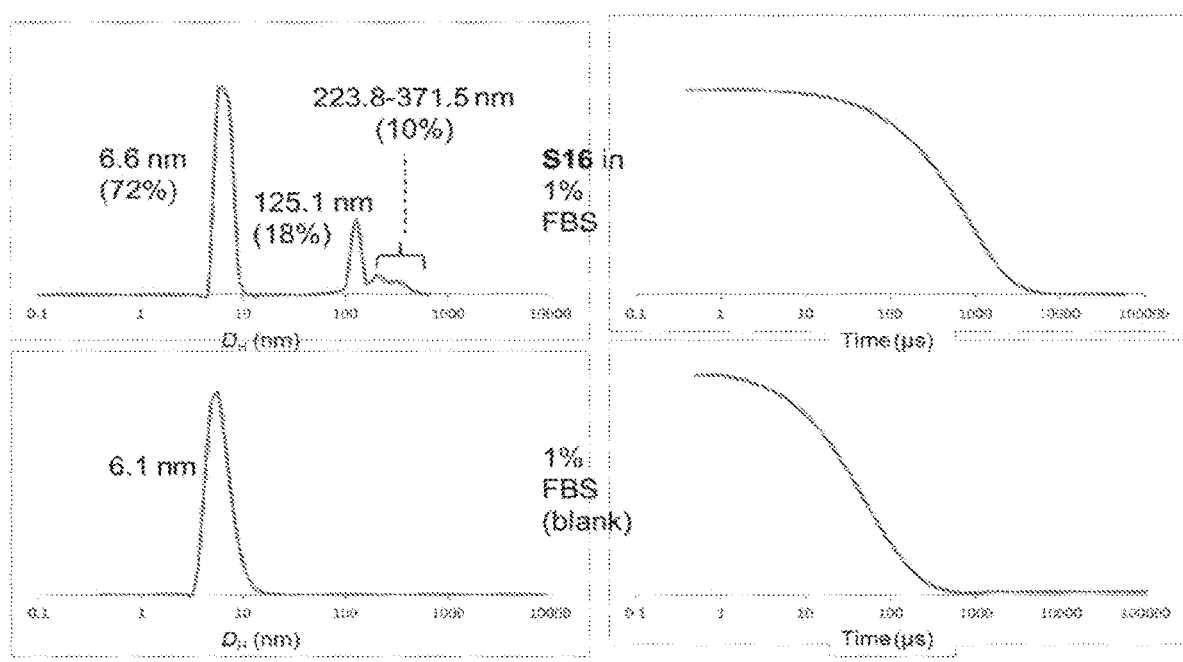
FIG. 20. DLS analysis of SNAPP S16 in 1% fetal bovine serum (FBS). DLS normalized mass % of 1% FBS with or without SNAPP S16 as a function of hydrodynamic diameter ($D_H$) was determined as an average of 3 sets of 15 measurements per set. The intensity autocorrelation curves corresponding to the DLS traces are shown. The numbers on the DLS distributions show the average $D_H$ of each peak. For the sample containing S16 in 1% FBS, a multimodal distribution was obtained and the % mass contributing to each peak was listed in parentheses. The addition of S16 to 1% FBS resulted in the detection of larger sized populations not present in pure 1% FBS. These populations are attributed to the formation of protein-S16 aggregates, with the majority possessing an average $D_H$ of 125.1 nm. The peak at 6.6 nm is likely contributed by proteins found in FBS and possibly non-aggregated S16 particles.

To explore the antimicrobial efficacy of SNAPPs in different media and to evaluate their toxicity against mammalian cells, we repeated the assays using minimal essential medium (MEM), which is a defined medium for mammalian cells. Both S16 and S32 exhibited at least four times lower MBC values (<0.19 µM) against all bacterial species tested in MEM compared with MHB. In MHB, SNAPPs were found to aggregate to form particles with average $D_H$ values of ~224.2 nm or greater, which is significantly larger in size compared to SNAPPs in MEM ($D_H$=7.7 and 13.5 nm for S16 and S32, respectively) (FIGS. 11-12). Cryo-TEM images of S16 in MHB further confirmed that the star formed large aggregates (~200-500 nm in diameter) (FIG. 19). The formation of aggregates is consistent with previous studies that have reported that nutrient/ion-rich media often contain anionic peptide and protein fragments, which might bind non-specifically to cationic antimicrobials, thereby causing aggregation and the formation of larger-sized particles in MHB as observed herein. This postulation was validated as we observed a similar phenomenon where aggregates of S16, predominantly sized at 125 nm, were formed in 1% fetal bovine serum, another protein-rich medium (FIG. 20). The aggregation of SNAPPs with the medium contents could possibly shield the active components of SNAPPs, thereby reducing their potency. Nevertheless, both S16 and S32 still possessed high efficacies in MHB, especially compared to the lead AMPs.

Example 4

Biocompatibility of SNAPPs.

Figure 21:
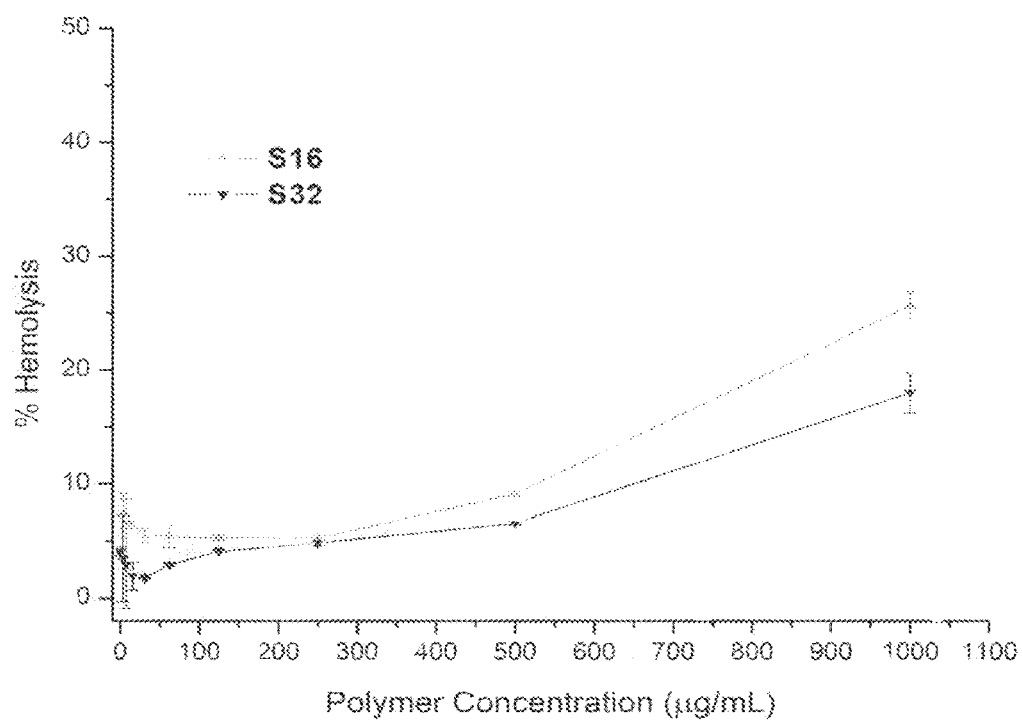
FIG. 21. Percent hemolysis as a function of SNAPP concentration. Error bars represent the standard deviation from the mean (n=4).

As a test of biocompatibility, the hemolytic activities of SNAPPs were investigated by incubating them with red blood cells at different nanoparticle concentrations. Both S16 and S32 (as well as the control homolysine star) had negligible hemolytic activity (>45 µM, Table 10). Even at a very high concentration of >100×MBC, the extent of hemolysis was well below 30% (FIG. 21). Subsequently, the viability of two types of mammalian cells, human embryonic kidney (HEK293T) cells and rat hepatoma (H4IIE) cells, in response to SNAPPs was investigated. The therapeutic indices (TI) of SNAPPs ranged from 52 to 171 (Table 11), generally higher than the TI of colistin which is now being used as the last therapeutic option for MDR Gram-negative pathogens.

Example 5

In Vivo Efficacy of SNAPPs.

Figure 2:
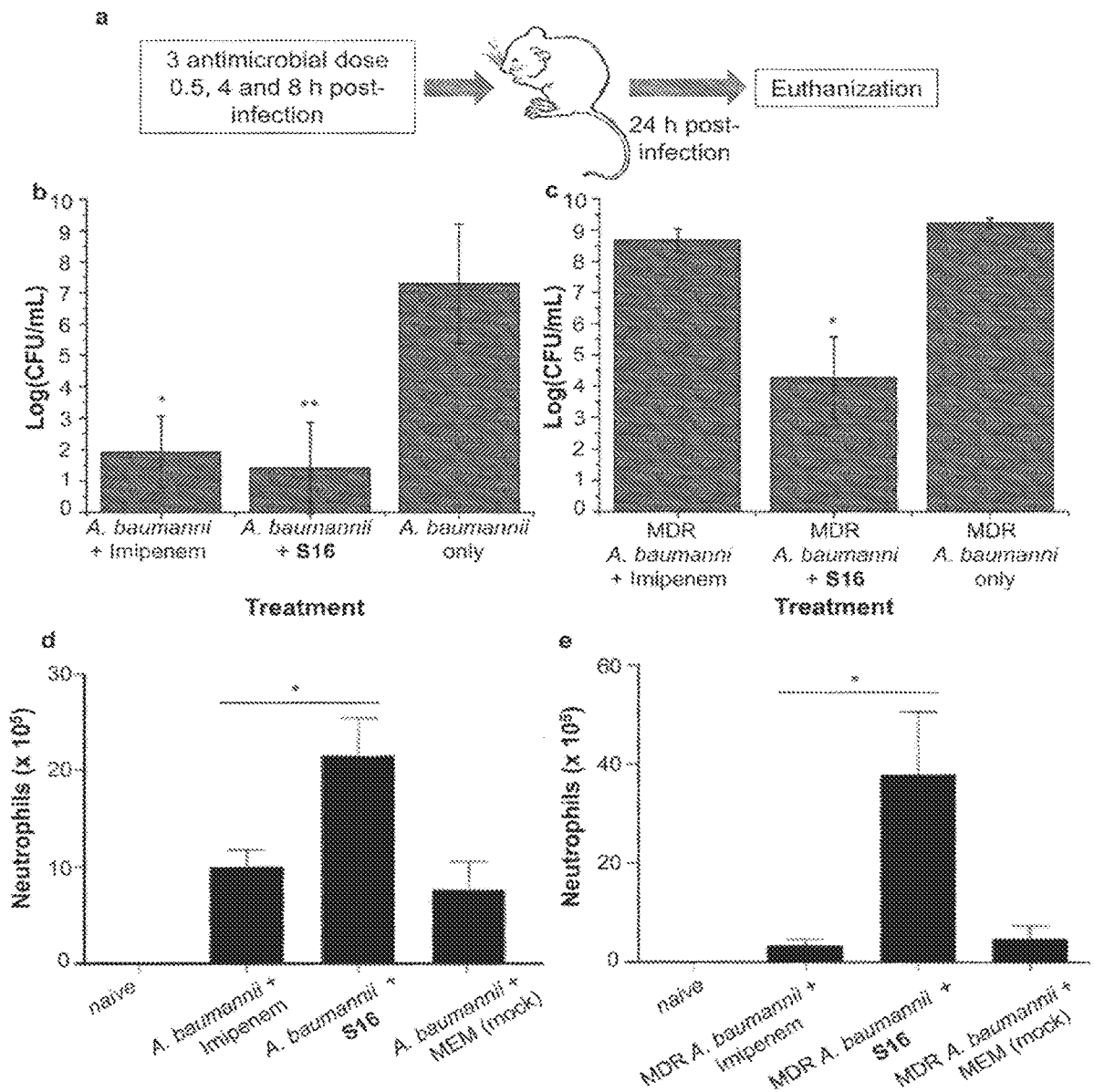
FIG. 2. In vivo efficacy of SNAPP S16 in a mouse peritonitis model. a, Schematic of the experimental protocol for the mouse peritonitis model. b-c, Colony forming units (CFU) of *A. baumannii* (ATCC 19606) (b) and CMDR *A. baumannii* (FADDI-AB156) (c) found in the peritoneal wash of infected mice 24 h after mock (MEM) treatment or treatment with imipenem (40 mg/kg) or S16 (8.3 mg/kg). d-e, Numbers of peritoneal neutrophils in the mild peritonitis model with mice 24 h after infection with *A. baumannii* (ATCC 19606) (d) and MDR *A. baumannii* (FADDI-AB156) (e) and either mock, imipenem (40 mg/kg) or S16 (8.3 mg/kg) treatments. All data are expressed as mean±standard deviation as indicated by the error bars, based on values obtained from at least four biological replicates (n=5 for (b) and n=5 for (c)). *$P<0.01$, **$P<0.001$, Student's t test, significant difference from the mock (MEM) control group (b, c) and the imipenem-treated group (d, e).

The effectiveness of S16 in vivo was evaluated in a mouse peritonitis model, where the intraperitoneal (i.p.) dose of *A. baumannii* ($2 \times 10^8$ cells in MEM) resulted in the establishment of wide-spread bacterial infection by 24 h (FIG. 2a). At 0.5, 4 and 8 h post-infection, mice were treated with either MEM (control), the antibiotic imipenem (40 mg/kg), or S16 (8.3 mg/kg). Similar to the imipenem-treated mice, treatment with S16 resulted in >5-log reduction in bacterial cell counts in the peritoneal cavity (FIG. 2b), quantitative (>99%) eradication of bacterial cells in blood (FIG. 22a), and >3-log CFU reduction in the spleen (FIG. 22b). Additionally, all mice treated with either imipenem or S16 survived with no signs of animal distress, whereas only 20% of the control/mock-treated mice survived after 24 h. A number of studies have found that antimicrobial agents enhance host cell innate immunity to bacteria in vivo; in this study S16-treated group enhanced neutrophil infiltrate in the peritoneal cavity, while the imipenem-treated group did not show any significant difference from the mock-treated group (FIG. 2d).

As S16 was effective in vitro against CMDR bacteria, we extended the peritonitis model by including the CMDR *A. baumannii*. Mice treated with S16 had significantly less bacteria in the peritoneal cavity (FIG. 2c), blood (FIG. 23a) and spleen (FIG. 23b), and higher numbers of neutrophils in the peritoneal cavity (FIG. 2e) compared with the imipenem- and mock-treated groups. Imipenem treatment had no effect on reducing bacteria levels in all tissues examined and this was comparable to the mock-treated group (FIG. 2c, FIG. 23). While all mice treated with S16 survived with no signs of animal distress, only 50% of the mock- or imipenem-treated mice survived the 24 h infection. The mechanism by which host defense peptides (HDPs) effect bacterial clearance in vivo is by neutrophil recruitment; however, unlike SNAPPs, HDPs often have poor direct antimicrobial activity. S16 has both direct (bacterial) and indirect (via neutrophil recruitment) antimicrobial activities in vivo. While the CMDR *A. baumannii* isolate used herein has been found to acquire resistance against the last-resort drug, colistin, these results demonstrated that S16 is capable of treating CMDR *A. baumannii* and potentially other CMDR Gram-negative infections in vivo. To the best of our knowledge, this is the first report of a synthetic antimicrobial polymer having in vivo efficacy against a CMDR Gram-negative bacterial infection.

Example 6

Preliminary Mechanistic Studies

Figure 3:
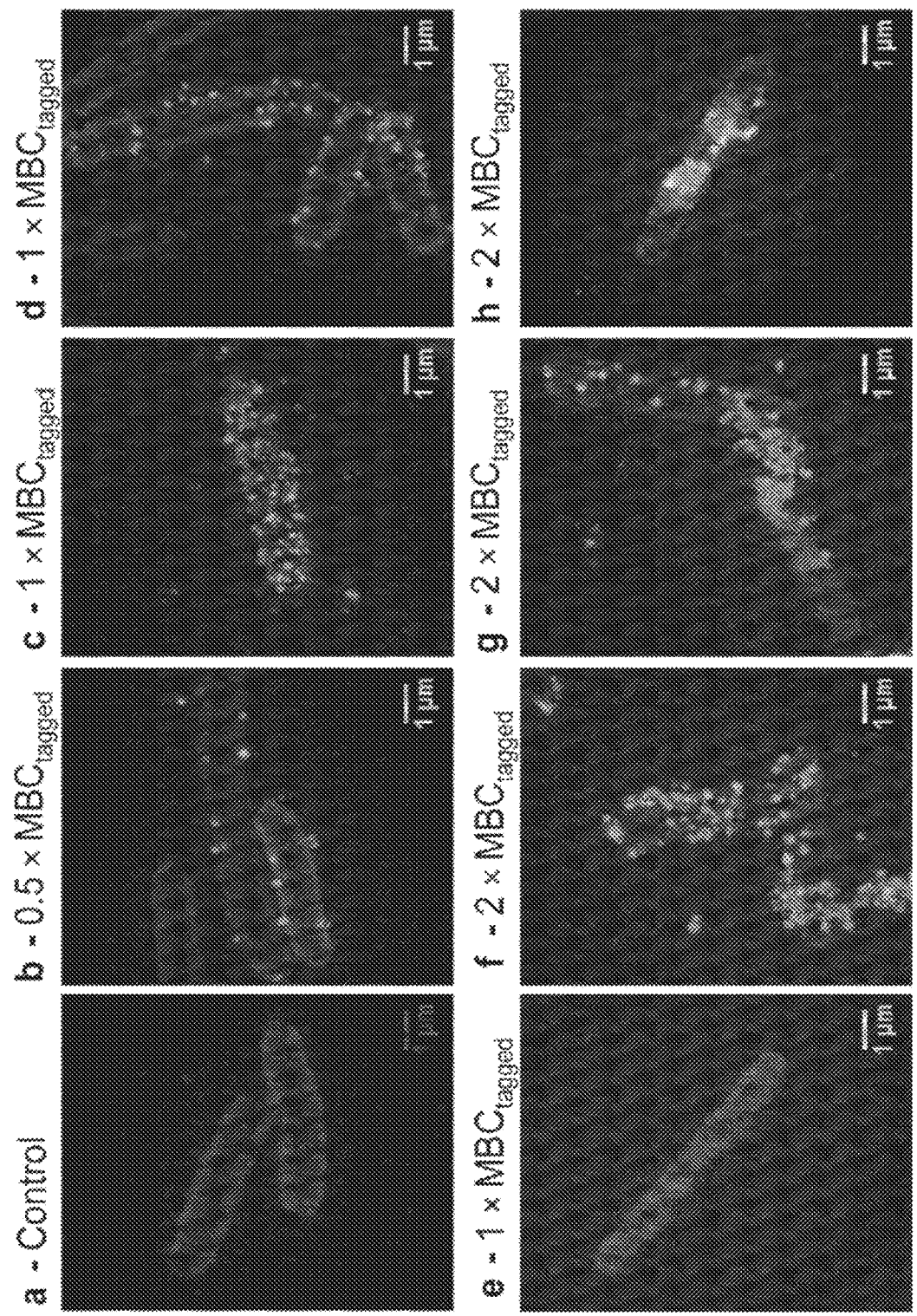
FIG. 3. OMX 3D-SIM images of *E. coli* before and after treatment with AF488-tagged SNAPP S16 in Mueller-Hinton broth (MHB). a-d, Z-projection images of *E. coli* before (a) and after incubation with AF488-S16 at $0.5 \times MBC_{tagged}$ (b), $1 \times MBC_{tagged}$ (c-e), and $2 \times MBC_{tagged}$ (f-h). Scale bars, 1 µm. The *E. coli* cell membrane was stained with FM4-64FX (red) and S16 with AF488 (green) in all images. Note that the MBC used refers to the MBC of the fluorescently tagged SNAPP (Table 12). All images are representative of three independent experiments.
Figure 26:
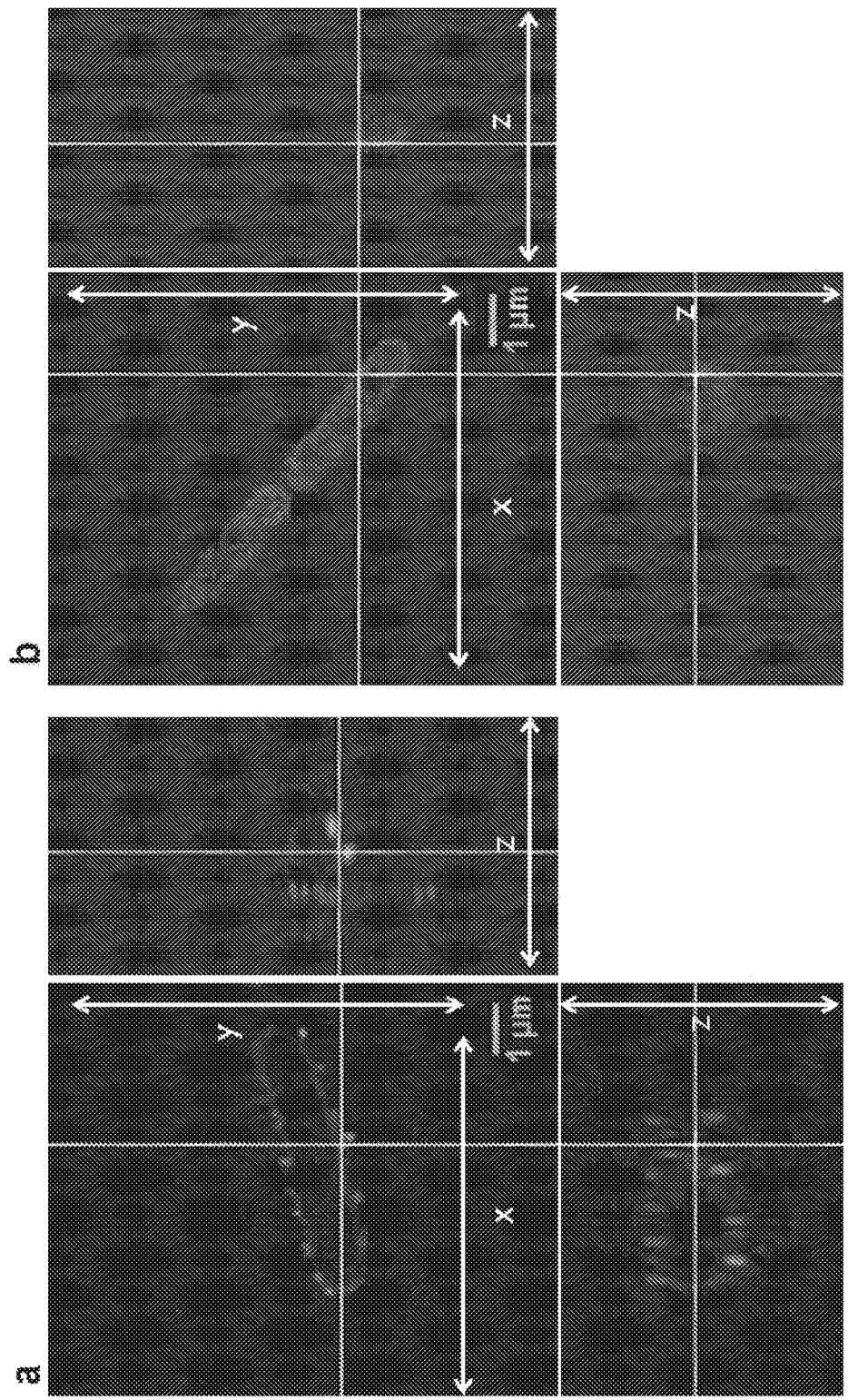
FIG. 26. OMX 3D-SIM images of *E. coli* after treatment with AF488-tagged SNAPP S16 at 1×$MBC_{tagged}$ in MHB. a-b, Examples of the orthogonal projections of FIG. 3*c* (a) and FIG. 3*e* (b) on the xy-, xz- and yz-planes. The *E. coli* cell membrane was stained with FM4-64FX (red) and S16 with AF488 (green) in all images. All images are representative of three independent experiments.
Figure 27:
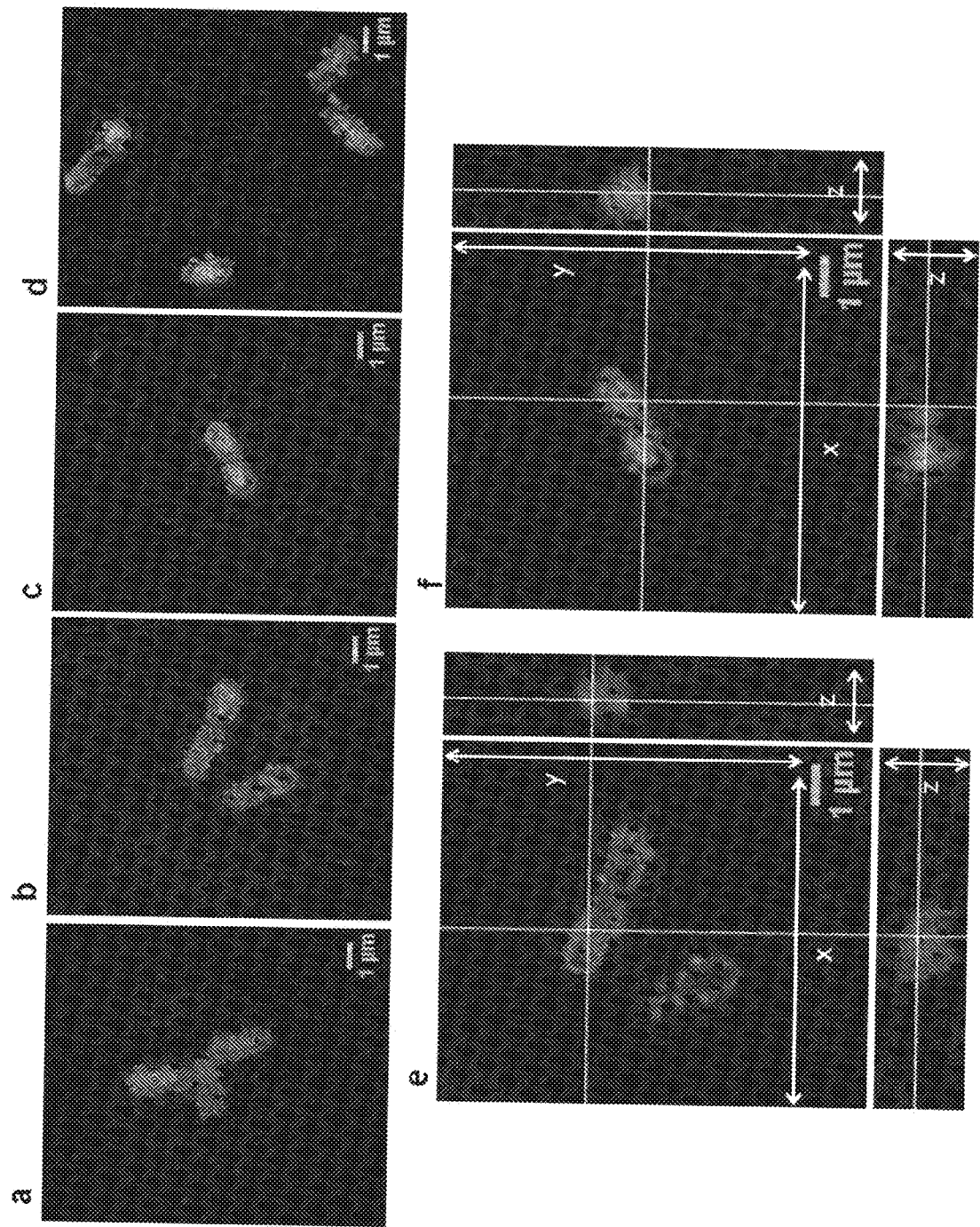
FIG. 27. OMX 3D-SIM images of *E. coli* after treatment with AF488-tagged SNAPP S16 at approximately 2×$MBC_{tagged}$ in MEM. a-d, Z-projection images. e, An example of the orthogonal projections of image b on the xy-, xz- and yz-planes. f, An example of the orthogonal projections of image c on the xy-, xz- and yz-planes. The *E. coli* cell membrane was stained with FM4-64FX (red) and S16 with AF488 (green) in all images. All images are representative of three independent experiments.

To directly observe the interactions between an antimicrobial agent and bacterial cells, we conducted super-resolution fluorescence imaging using 3D-Structured Illumination Microscopy (3D-SIM). Sample images of untreated *E. coli* are provided in FIG. 3a and FIG. 25a. FIG. 3 shows the 3D-SIM images of *E. coli* (labelled red with lipid membrane FM4-64FX dye) incubated with the AF488-labelled S16 (FIG. 24, Table 12) in MHB at a dose approximately equivalent to 0.5×, 1× and 2× the MBC of the fluorescently tagged SNAPP ($MBC_{tagged}$). While the action of antimicrobials on bacteria has been imaged using a range of microscopy techniques, this is one of the first instances whereby a clear visualization of the interaction between an antimicrobial agent and bacterial cells at the super-resolution level has been demonstrated. S16 (labelled green) was found to associate at certain sites on and in the bacteria depending on the SNAPP concentration (FIG. 3b-h, FIGS. 25-26). This is different to the membrane interactions of proline-rich AMPs, where the peptides localized uniformly around the *E. coli* membrane as previously reported by us. At $0.5 \times MBC_{tagged}$, SNAPPs associate with the surface of the bacteria (FIG. 3b); however, at $1 \times MBC_{tagged}$, we observed a high density of bacterial cells with either membrane associated or internalized star peptide polymers (FIG. 3c-e). On the other hand, in our previous study on membrane-lytic proline-rich AMPs, we observed complete internalization and uniform localization of peptides throughout the cytosol of the bacterial cells. We attributed this difference to the larger sizes of SNAPPs, which possibly inhibited the quantitative internalization of all membrane-bound SNAPP macromolecules even when the membranes were disrupted. At $2 \times MBC_{tagged}$, there is clearly more membrane-associated or internalized SNAPPs per bacterial cell (FIG. 3f-h, FIG. 25b-e). Orthogonal projections showed that the membrane localized SNAPPs appear to aggregate and span the cell envelope (FIG. 26). Further, bacteria with internalized SNAPPs were observed to have distinct cell envelope perforations (FIG. 3h, FIGS. 25d-e and 26b). When the experiments were conducted in MEM at $2 \times MBC_{tagged}$, the results were similar to that observed in MHB at supra-MBC dosage, albeit with a larger extent of SNAPP internalization into the cells (FIG. 27).

Figure 28:
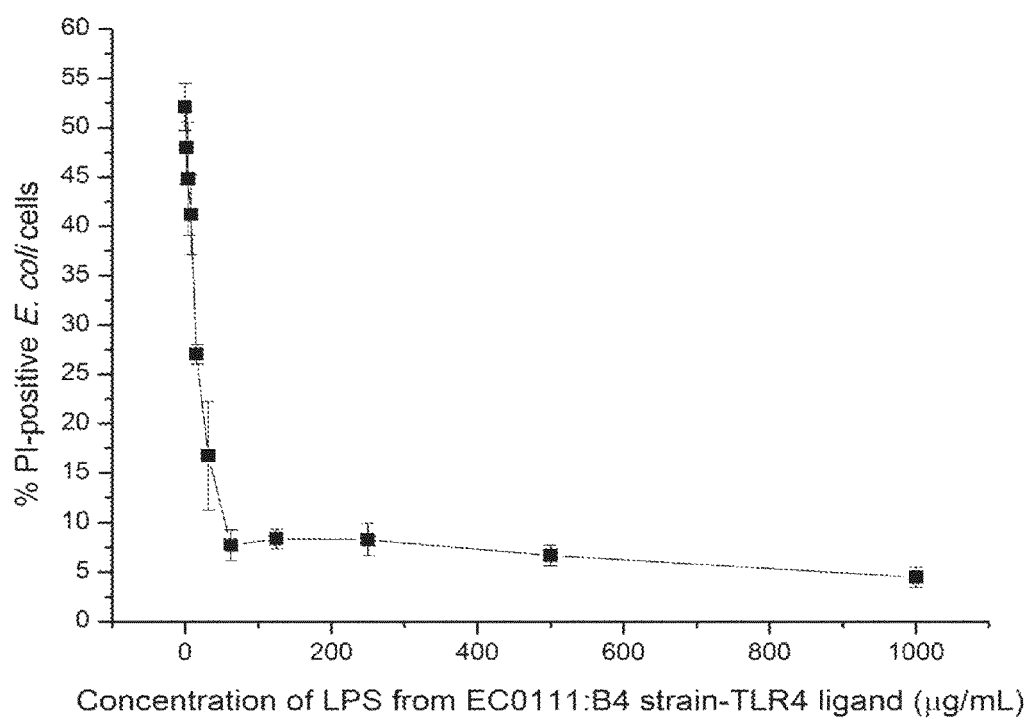
FIG. 28. Percentage of PI-positive (membrane-disrupted) *E. coli* cells as a function of LPS concentration. The concentration of S16 used was fixed at 4 µg/mL (0.09 µM). Error bars represent the standard deviation from the mean (n=4).
Figure 30:
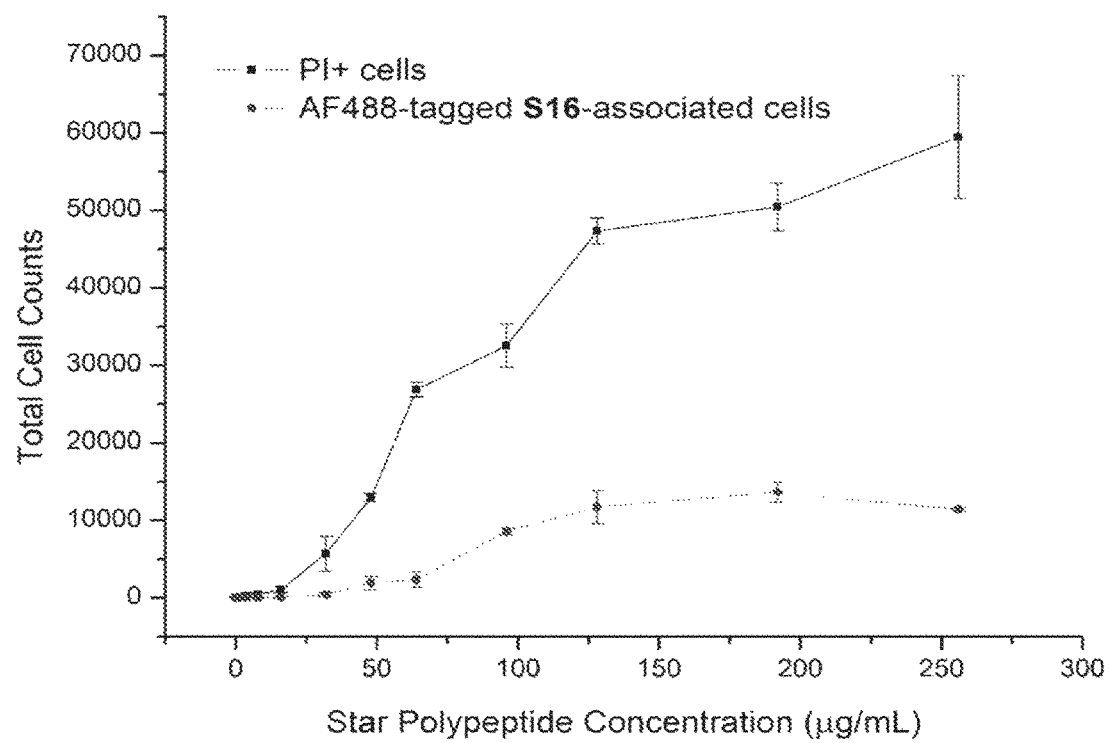
FIG. 30. Total counts of PI+ cells and cells associated with AF488-tagged S16 as a function of S16 concentration. Error bars represent the standard deviation from the mean (n=4).
Figure 31:
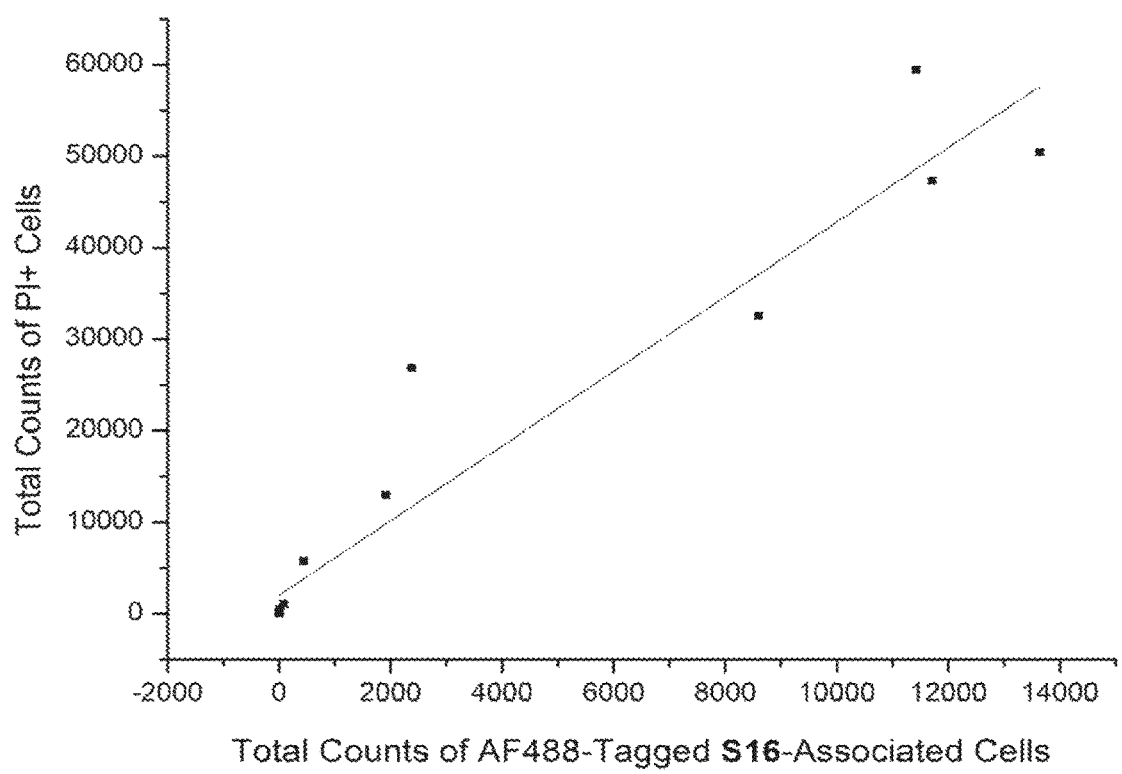
FIG. 31. Total counts of PI+ cells as a function of the total counts of cells associated with AF488-tagged S16. A linear trend line (red) was fitted over the acquired data points (slope=4.078, y-intercept=2010, $R^2$=0.93). All assays were conducted in quadruplicates over two independent runs.
Figure 32:
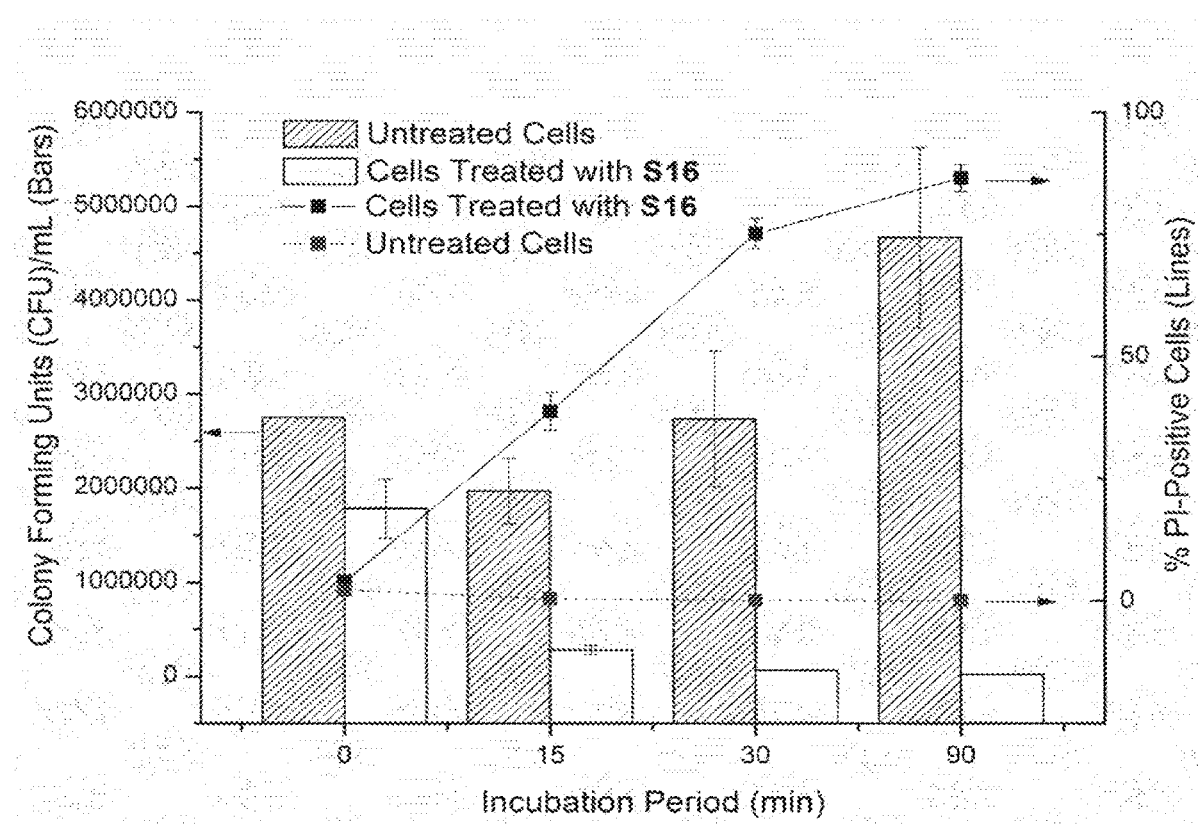
FIG. 32. Effects of SNAPP-bacteria incubation period on antimicrobial activity; measured in terms of CFU/mL and % PI-positive or membrane-disrupted cells. The concentration of SNAPP S16 used was ~1×MBC (i.e., 8 µg/mL). All data are expressed as mean±standard deviation as indicated by the error bars (n=4). *P<0.05, **P<0.001, Student's t test, significant difference from the untreated control at the corresponding time points.

Based upon the fluorescence imaging studies conducted, we hypothesized that SNAPPs initially localize on the bacterial OM as a result of electrostatic interactions. This could cause areas of destabilization/fragmentation leading to SNAPPs possibly translocating to and disrupting the CM, thus leading to cell death. To investigate this hypothesis, we conducted a competitive inhibition assay with LPS. The co-incubation of LPS (from *E. coli*) with S16 was found to inhibit the ability of S16 to disrupt the membrane of *E. coli* cells in a dose-dependent manner (FIGS. 28-29). This suggested that SNAPPs bind to LPS on the OM and could explain the selective antimicrobial activity of SNAPPs towards Gram-negative bacteria. However, as SNAPPs were still moderately active against the Gram-positive species tested, we postulate that the LPS-SNAPP interactions are preferred, due to the strong electrostatic interactions, but not highly specific to the extent where antimicrobial activity would be lost in the absence of LPS. Using flow cytometry, we demonstrated that the association of the AF488-tagged S16 with *E. coli* was linearly correlated with bacterial membrane disruption (FIGS. 30-31). Furthermore, a time-course study showed that the action of S16 was rapid as >90% of an *E. coli* cell population had disrupted membranes within 30 min which correlated with complete population death (FIG. 32).

Figure 33:
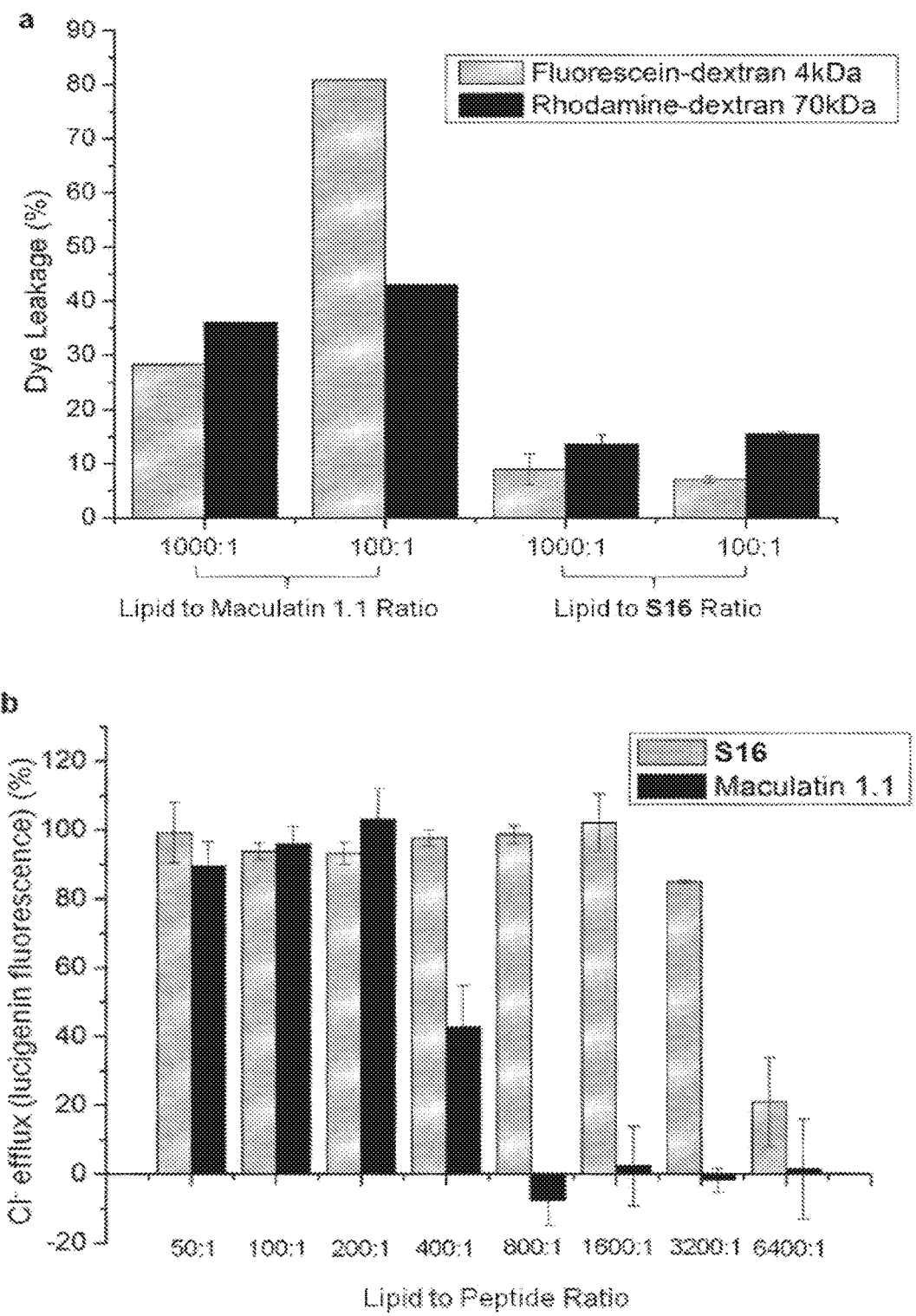
FIG. 33. Large unilamellar vesicle (LUV) studies. (A) Effect of SNAPP S16 and maculatin concentration on the release of rhodamine-dextran 70 kDa (RD-70, black bars) and fluorescein-dextran 4 kDa (FD-4, grey bars) from POPE/POPG LUVs. RD-70 and FD-4 loaded LUVs were incubated with SNAPP S16 or control AMP maculatin 1.1 with a lipid/peptide molar ratio of 1000:1 or 100:1 for 0.5 h at 37° C., after which supernatant was removed from lipid pellets. The excitation wavelengths for RD-70 and FD-4 excitations were 550 and 480 nm, respectively. Emissions were recorded from 560 to 650 nm. (B) Effect of SNAPP S16 (grey bars) and maculatin 1.1 (black bars) concentrations on chloride ion efflux from POPE/POPG LUVs. LUVs were loaded with lucigenin solution containing NaCl (100 mM), and sodium phosphate salt (10 mM, pH 7.3) and incubated with SNAPP S16 or control AMP maculatin 1.1 in $NaNO_3$ (100 mM, pH 7.3) with a lipid/peptide molar ratio of 50:1 to 6400:1 for 18 h at 37° C., after which the lucigenin fluorescence was monitored by excitation at 372 nm, and the emission was recorded at 503 nm. All data are expressed as mean±standard deviation as indicated by the error bars (n=4).
Figure 34:
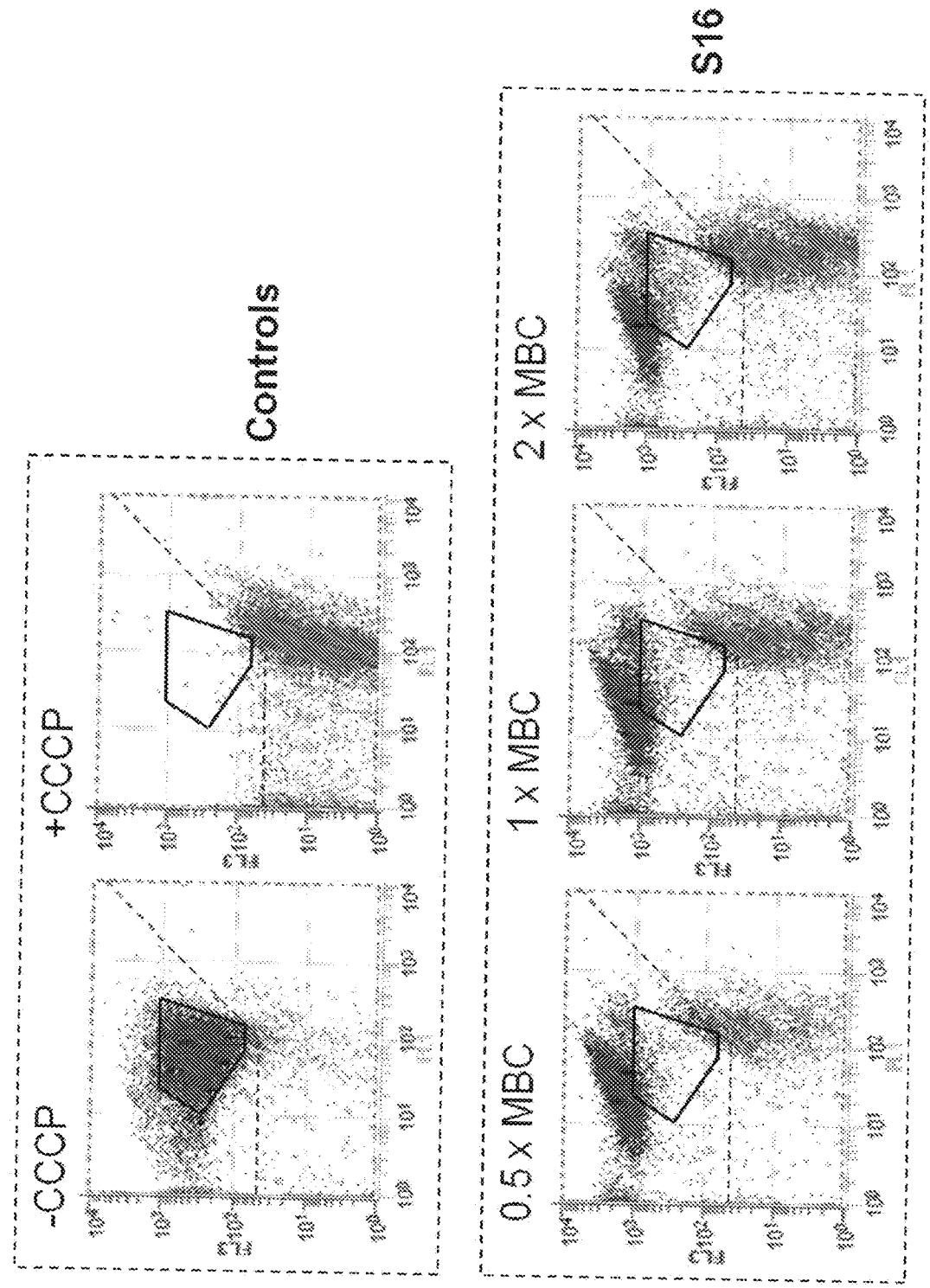
FIG. 34. Membrane potential flow cytometric dot plots obtained after incubating *E. coli* with 30 µM $DiOC_2(3)$ for 1 h in the presence/absence of CCCP (a proton ionophore), and SNAPP 16 at 0.5×, 1×, and 2× its MBC. The controls where CCCP was either absent (–CCCP) or present (+CCCP) represent the normal membrane potential state and fully depolarized state for *E. coli*, respectively. A flow cytometry gate (black polygon) was drawn in each panel to indicate the position of the viable bacteria in the absence of CCCP or SNAPP.
Figure 35:
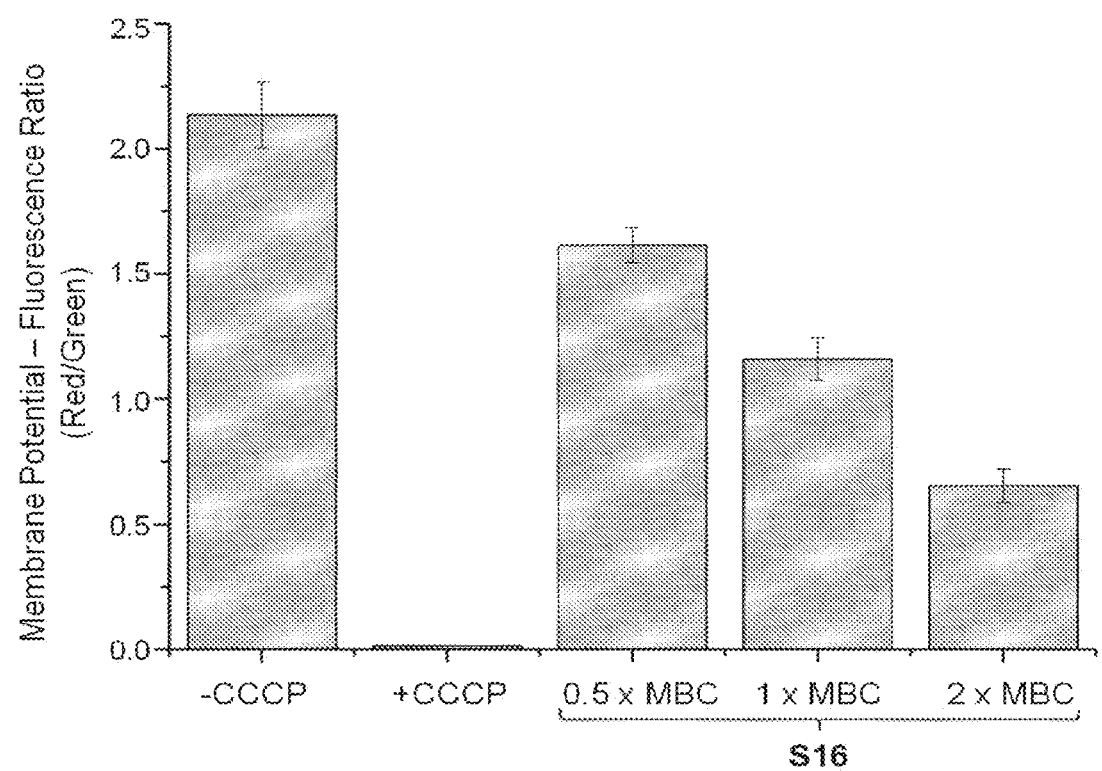
FIG. 35. Membrane potential measurements in *E. coli* with serial SNAPP addition. Bacterial membrane potential was indicated by the ratio of cells that exhibited a red fluorescence (i.e., healthy or hyperpolarized cells as captured on FL-3) to those that displayed a green fluorescence (i.e., depolarized cells as captured on FL-1). *E. coli* bacterial cells were incubated with 30 µM $DiOC_2(3)$ for 1 h in the presence or absence of CCCP, and with 0.5×, 1×, and 2× the MBC of SNAPP S16. All data are expressed as mean±standard deviation as indicated by the error bars (n=4).

To investigate if SNAPP-induced membrane disruption is a result of pore formation like some AMPs, we conducted a dye release assay using dextran-loaded large unilamellar vesicles (LUVs) as a mimic for Gram-negative CM. The results suggested that SNAPPs do not cause membrane disruption via pore formation (FIG. 33a). Another mechanism of membrane disruption is through unregulated ion movement, which we investigated using the LUV chloride ion ($Cl^-$) transport assay. $Cl^-$ ion efflux was found to increase with increasing concentrations of S16 (FIG. 33b). Additionally, we performed membrane potential measurements on bacterial cells to determine the ability of SNAPPs to alter membrane potential. It was observed that the treatment of *E. coli* cells with S16 induced mixed hyperpolarized and depolarized bacterial cell populations, with a shift towards a more depolarized population as concentration increased (FIGS. 34-35). Taken together, these studies suggested that the interaction of SNAPPs with the CM may result in membrane perturbations that led to unregulated ion movement and membrane potential dissipation.

Figure 36:
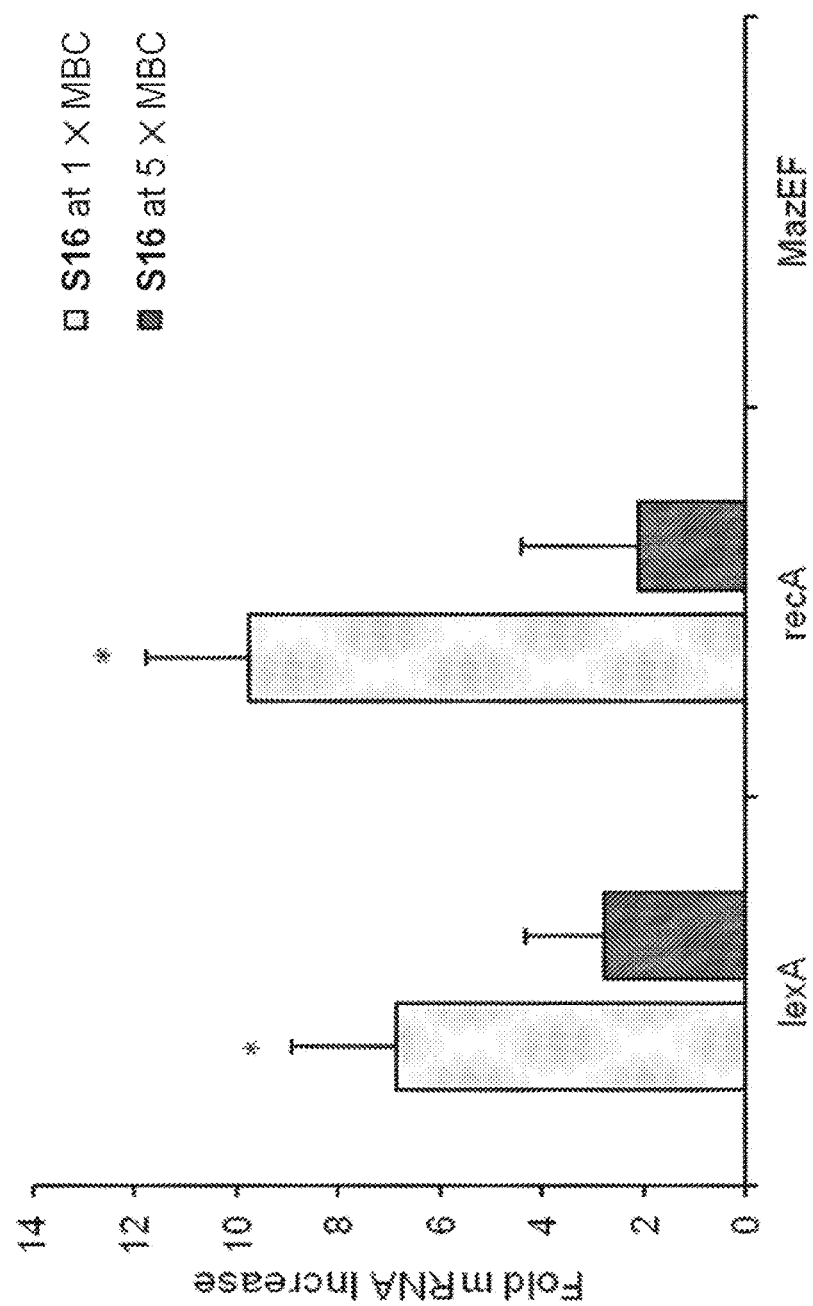
FIG. 36. Programmed cell death PCR studies. SNAPP S16 induced programmed cell death in *E. coli* via the apoptotic-like death (ALD, recA and lexA expression) pathway but not the MazEF pathway. All data were expressed as mean±standard deviation as indicated by the error bars (n=4) of the fold increase in RNA levels as determined by real-time PCR from untreated cells. *$P<0.05$, Student's t test, significant difference from the untreated control.

A number of recent studies have shown that bacteria, like eukaryotic cells, have mechanisms of programmed cell death (PCD) that could be triggered under stressful conditions, such as membrane disruption. Two major PCD pathways have been described in bacteria: (i) the ALD pathway mediated by recA and lexA genes, and (ii) the mazEF pathway. Based on gene expression studies, S16 at 1×MBC induced a 10- and 7-fold increase in recA and lexA but no change in mazEF levels (FIG. 36). These results, when observed under cell death conditions, suggested that S16 induced ALD responses in *E. coli*. Further, we observed the production of reactive oxygen species (ROS) following S16 treatment (FIG. 37), which has been reported to be a characteristic of ALD. The induction of ALD in bacteria has been reported in previous studies to lead to cell lysis. We also found that when ALD was inhibited by pre-treating *E. coli* with a translation inhibitor (doxycycline), the antimicrobial activity of S16 remained comparable to that when ALD was not inhibited (FIG. 38). This suggested that the induction of the ALD pathway is not a prerequisite for SNAPP activity, but likely to be either an event that coincides with early membrane disruption or a supplementary (but not essential) bactericidal mechanism. At 5×MBC, S16 induced significantly less recA and lexA mRNA than that at 1×MBC concentration (FIG. 36). We speculate that at supra-MBC dosage other killing mechanisms would dominate, thus leading to insufficient time for the expression of ALD pathway components. This agreed with our previous postulation that there might be multiple mechanisms involved in the antimicrobial action of SNAPPs.

Figure 4:
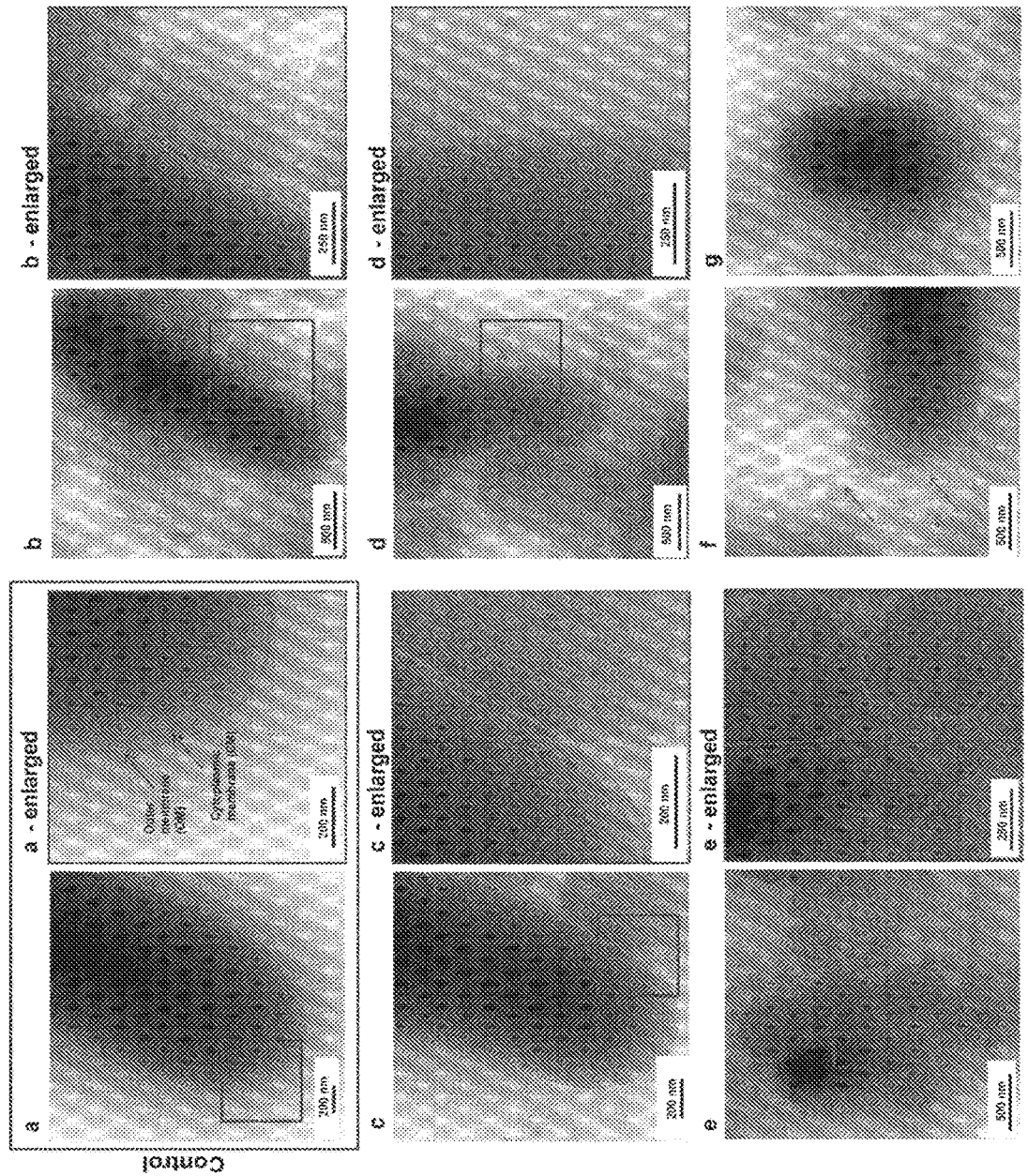
FIG. 4. Morphological studies of *E. coli* before and after treatment with S16 in Mueller-Hinton broth (MHB). a-g, Cryo-TEM images of *E. coli* before (a) and after incubation with S16 for 90 min at a lethal dose of 35 μg/mL (i.e., 1×MBC of the unlabelled S16 in MHB) (b-g). Large aggregates (possibly aggregates of S16 with medium contents) were observed around the rod-shaped *E. coli* cells (b-g). Binding of the aggregates to *E. coli* was observed and the cell membrane appeared disrupted (b). Hole formation (c), OM fragmentation (d), stripping of cell walls and membranes (e), ripping of cell ends (f), and isolated cell fragments (g) were observed. Enlarged images of a-e are provided and the sections enlarged are boxed in red. Scale bars, 200 nm, 250 nm, or 500 nm as indicated. Regions of interest are highlighted by red arrows. All images are representative of three independent experiments.
Figure 39:
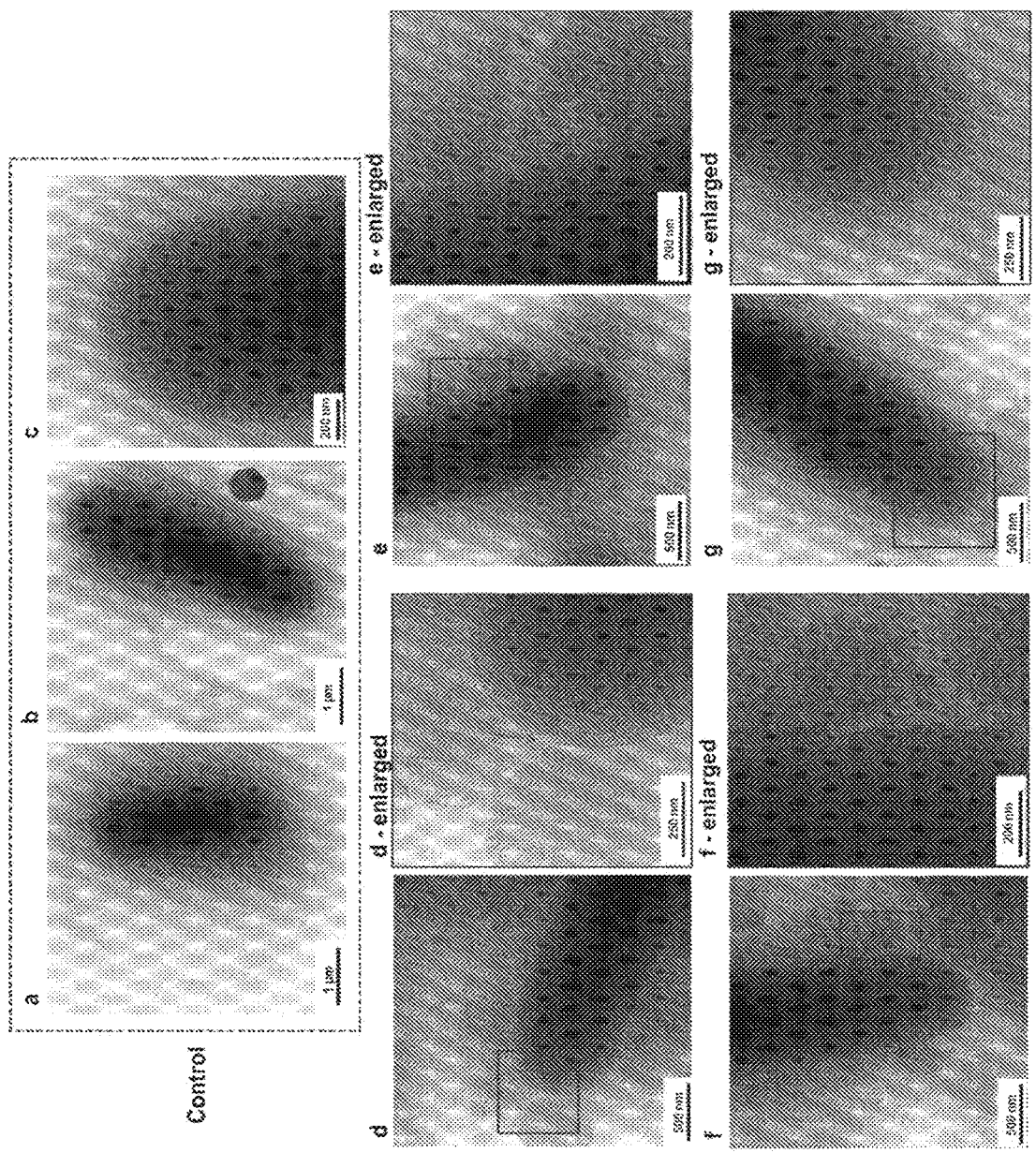
FIG. 39. Morphological studies of *E. coli* before and after treatment with S16 in MHB. Cryo-TEM images of *E. coli* before (a-c) and after incubation with S16 for 90 min at a lethal dose of 35 µg/mL (i.e., 1×MBC of the unlabelled star in MHB) (d-g). Large aggregates (possibly aggregates of S16 with lysed cell contents) were observed around the rod-shaped *E. coli* cells (d-g). Hole formation (d), outer membrane fragmentation (e, f), and isolated cell fragments (g) were observed. Enlarged images of d-g are provided and the sections enlarged are boxed in red. Regions of interest are highlighted by red arrows. All images are representative of three independent experiments.
Figure 40:
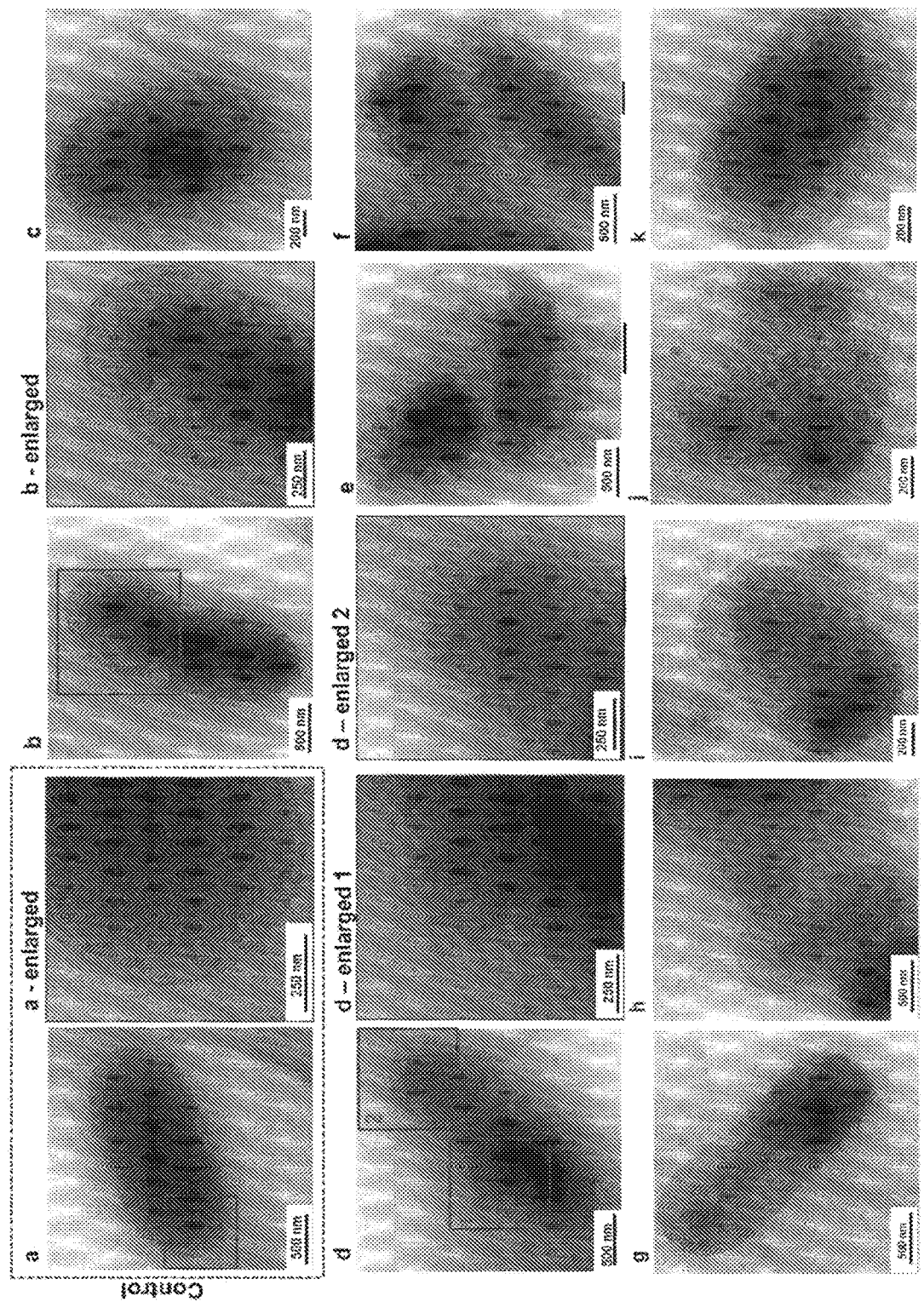
FIG. 40. Morphological studies of *E. coli* before and after treatment with S16 in MEM. Cryo-TEM images of *E. coli* before (a) and after incubation with S16 for 90 min at approximately 2×MBC (i.e., 15 µg/mL) (b-d) and 5×MBC of the unlabelled star in MEM (i.e., 35 µg/mL) (e-k). Damaged cells showed intracellular electron dense patches which were irregular in shape (b-k). Leakage of cellular contents and ruptured membranes (d-f, j) were observed. Enlarged images of a, b, and d are provided and the sections enlarged are boxed in red. All images are representative of three independent experiments.

Next, we used cryo-TEM to visualize the effect of SNAPP treatment on *E. coli* cell morphology. Prior to treatment, all cells showed intact OMs and CMs (FIG. 4a, FIG. 39a-c). After treatment with S16 in MHB at its MBC, large aggregates—probably formed by aggregation between S16 and media contents (vide supra)—were observed around the cells (FIG. 4b-g, FIG. 39d-g). The cell membranes of bacteria incubated with S16 appeared disrupted (FIG. 4b) and had pores that transversed the OM, PG layer, and CM (FIG. 4c, FIG. 39d). Most bacterial cells had fragmented or perforated OMs (FIG. 4d-e, FIG. 39e-f), and some cells appeared to be broken into isolated fragments (FIG. 4g, FIG. 39g). These observations were in agreement with the flow cytometry data which indicated that SNAPP association leads to membrane disruption. Cryo-TEM experiments conducted in MEM at supra-MBC dosage resulted in observations similar to when MHB was used at similar dosages; however, more drastic cell lysis was noted in the case of MEM (FIG. 40).

Figure 5:
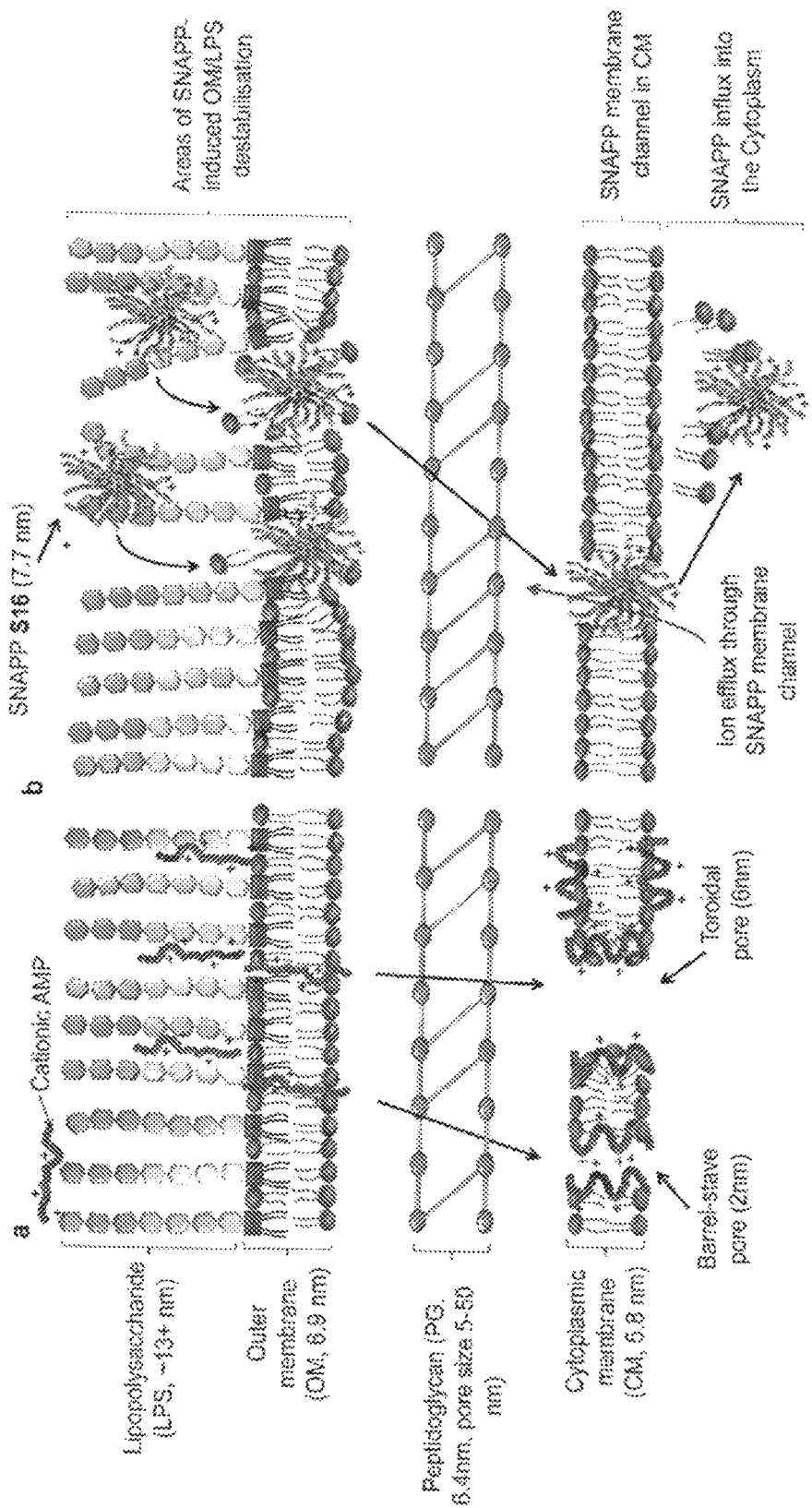
FIG. 5. A comparison between the antimicrobial mechanism(s) of typical membrane-disrupting cationic AMPs and the possible mechanism of SNAPPs against Gram-negative bacteria. (a) Cationic AMPs bind to the OM of Gram-negative bacteria via electrostatic interactions, transit across the OM through membrane destabilization, and disrupt the physical integrity of the CM by the 'barrel-stave', 'toroidal-pore' or 'carpet' pore (not shown in figure) mechanisms. (b) SNAPPs, whether in its aggregated or unaggregated state, interact with the OM, PG and CM layers of Gram-negative bacteria via electrostatic attractions and kill the cell by fragmenting/destabilizing its OM and possibly disrupting the CM such that unregulated ion movement is resulted, but also by the induction of the apoptotic-like death pathway (not shown in figure), thereby lysing the cell.
Figure 41:
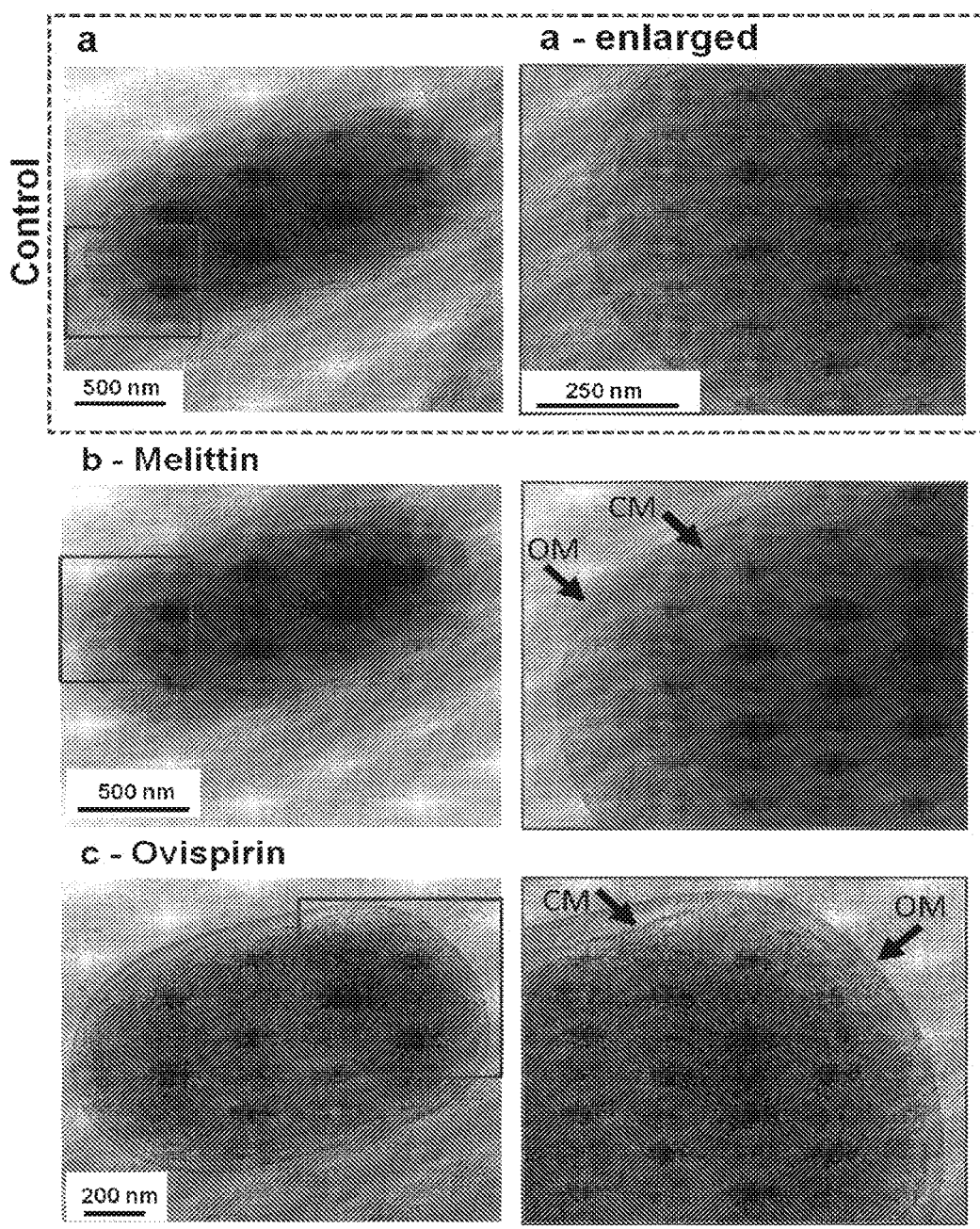
FIG. 41. Morphological studies of *E. coli* before and after treatment with melittin or ovispirin in MHB. Cryo-TEM images of *E. coli* before (a) and after incubation with melittin (b) or ovispirin (c) for 90 min at 1×MBC. Damaged cells showed damaged cytoplasmic membranes with the outer membranes intact. Enlarged images are provided and the sections enlarged are boxed in red. All images are representative of three independent experiments.

Taken together, we postulate that SNAPPs have a multimodal mechanism of inducing bacterial cell death. Initially, SNAPPs bind via electrostatic interactions with LPS and the OM, leading to destabilized/fragmented areas. They then assemble and traverse the cell envelope driven by the transmembrane electrical potential (interior/cytosol being negative), most likely causing membrane perturbations that result in unregulated transmembrane ion movement in the CM. These membrane disruption events induce ALD at low SNAPP concentrations, thus leading to cell lysis. At high concentrations, SNAPPs rapidly cause cell lysis by direct disruption of the OM and CM. Collectively, fluorescence imaging, flow cytometry and cryo-TEM assays provided evidence for membrane association, membrane disruption, OM fragmentation/destabilization and cell lysis. Although the exact sequence of events is subjected to further investigations, we can conclude that the succession of antimicrobial events, as depicted in FIG. 5, is substantially different from the action of a monomeric cationic AMP. A typical monomeric AMP is commonly thought to traverse the OM of a Gram-negative bacterial cell via self-promoted uptake, binds to and inserts itself into the anionic surface of the CM, then kills the bacteria by either membrane disruption (pore formation) or translocation across the CM and acting on internal targets. In the case whereby cell death is caused by membrane disruption, loss of CM integrity was commonly thought to be the lethal event. Cryo-TEM analysis of *E. coli* after incubation with melittin or ovispirin (which are well-characterized AMPs) confirmed that the AMPs disrupted the CM while leaving the OM intact (FIG. 41). On the other hand, as demonstrated here, it is likely that S16 effects its antimicrobial action in a cascade manner and by first disrupting the physical integrity of the OM upon binding with LPS.

AMPs as a whole class of compounds kill bacteria by multiple mechanisms but each specific AMP tends to kill bacteria by one major mechanism. The multi-faceted interactions shown here between SNAPPs and bacteria (in combination with indirect antimicrobial activity via neutrophil recruitment in vivo) are truly unique and this, to the best of our knowledge, has not been shown previously in a definitive manner for any one single AMP. The equipotency of SNAPPs against all of the Gram-negative bacteria tested suggested that the multi-modal mechanism of action is non-specific and we postulate that this is why bacteria did not acquire resistance to star S16 even after 600 generations of growth in the presence of the agent. The successful demonstration of the antimicrobial efficacy of SNAPPs against CMDR *A. baumannii* in vivo as well as their biocompatibility distinguishes SNAPPs as a new class of antimicrobial agents, capable of addressing the dearth of suitable drug candidates to combat Gram-negative pathogens resistant to conventional antibiotics.

Correlation of Antibacterial Activity with the Cellular Uptake of S16

Flow cytometric analysis was used to correlate the cellular uptake of SNAPP with the resulting bacterial membrane lysis. As a proof of concept, the same amount of the model gram-negative bacteria, *E. coli*, was treated with Alexa Fluor 488-tagged SNAPP S16 of varying concentrations using MHB as the medium and the mixtures were then subjected to analysis using the Cell Lab Quanta SC MPL system. The propidium iodide (PI) nucleic acid stain was added to the *E. coli*-S16 mixture to quantify cells with compromised membranes. Utilizing the ability of flow cytometers to provide accurate quantification of cell numbers, the counts of AF488- and PI-positive cells were measured for each S16 concentration (FIG. 30).

Based on FIG. 30, as the concentration of AF488-tagged S16 increases, the number of cells with compromised membranes (PI-positive cells) increases as expected and plateaus at about 128 µg/mL (2.92 µM). Similarly, the number of AF488-positive cells follows the same trend. As the cells were not tagged with AF488, the presence of AF488-positive cells correlates with cells which are associated with the AF488-tagged S16. It is noteworthy that the gating of the flow cytometer was done so as to exclude populations such as free S16 with significantly smaller sizes than bacterial cells. Hence, this indicates that S16 association with the cells increases with S16 concentration and plateaus at high concentrations in a similar fashion as the lysis of bacterial cells. Based on the similar trends exhibited for the cellular association of peptide polymer AF488-tagged S16 and bacterial membrane lysis as S16 concentration increases, a direct correlation between these two parameters is indicated. By plotting one parameter against the other (FIG. 31), we then conclude that the uptake of AF488-tagged S16 is proportional to the membrane disruption of *E. coli*.

SNAPP S16 Induces Reactive Oxygen Species (ROS) Production

Figure 37:
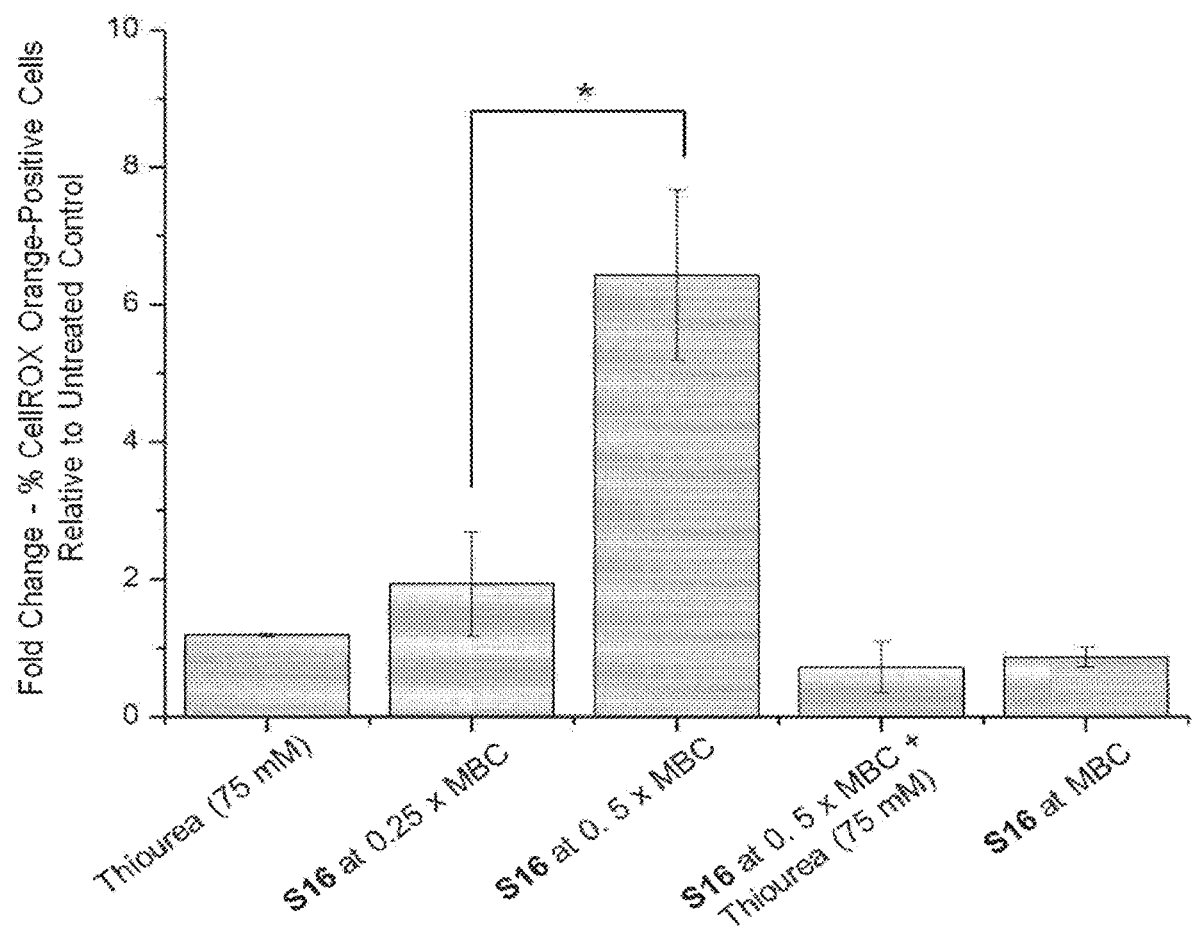
FIG. 37. Fold change in percentage of *E. coli* cells stained with CellROX® Orange relative to the untreated control. All data are expressed as mean±standard deviation as indicated by the error bars (n=4). *$P<0.05$, Student's t test, significant difference from the untreated control.
Figure 38:
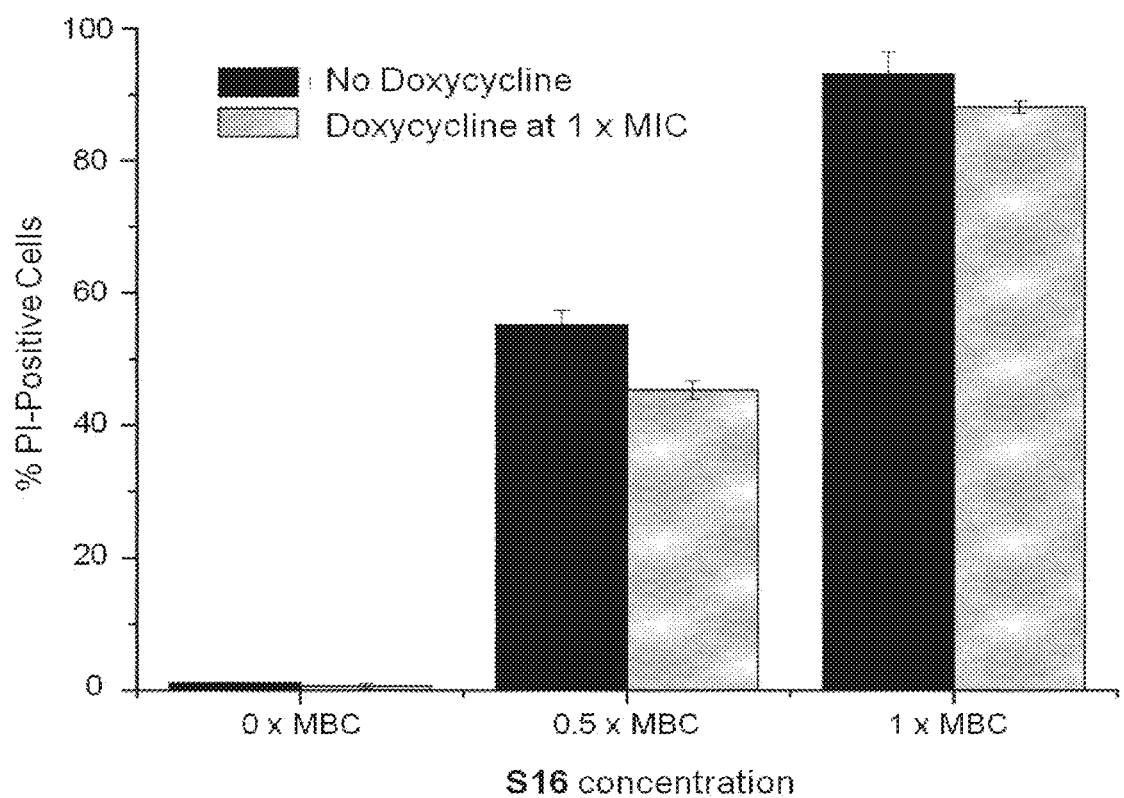
FIG. 38. Percentage of PI-positive (membrane-disrupted) *E. coli* cells following treatment with various concentrations of SNAPP S16 at 0×, 0.5× and 1×MBC for 90 min. The bacterial cells were either used without prior treatment or pre-treated with a translation inhibitor, doxycycline, at 1×its MIC (where MIC=0.5 µg/mL). Error bars represent the standard deviation from the mean (n=4).

We measured the production of ROS in untreated *E. coli* cells and in cells treated with S16 (at 0.25×, 0.5×, and 1×its MBC), thiourea (75 mM) or a combination of S16 (0.5× MBC) and thiourea (75 mM) for 90 min using the CellROX® Orange Reagent (FIG. 37). The reagent is non-fluorescent in a reduced state and exhibits bright orange fluorescence (ca. 545/565 nm) when oxidized by ROS. Hence, the cells were analysed via flow cytometry to determine the percentage of ROS-producing cells as indicated by the amount of cells stained with the reagent (i.e., CellROX® Orange-positive cells). A slight increase (i.e., 2-fold relative to the untreated control) in cells stained with CellROX® Orange was observed when the cells were treated with S16 at 0.25×MBC. When the S16 concentration was increased to 0.5×MBC, more than a 6-fold increase in the percentage of cells stained with CellROX® Orange was observed compared to the untreated control, indicating increased ROS production. The addition of thiourea, a ROS scavenger, inhibited ROS production by S16 at 0.5×MBC as indicated by a reduction in the percentage of cells stained with the reagent (i.e., less than a 1-fold increase compared to the untreated control). We observed that the treatment of *E. coli* with S16 at its MBC resulted in a negligible increase in ROS production. This could be due to significant and rapid cell lysis and fragmentation upon treatment with S16 at its lethal dose that occur well within the 90 min incubation period, resulting in the inability to sample the cells at the stage where ROS is being produced prior to cell lysis. In support of the postulation, we noted a significant reduction in the number of bacterial cell population (>3-log reduction compared to the untreated control) and a high percentage (>90%) of membrane-disrupted cells after 90 min treatment with S16 at its MBC (FIG. 38).

Inhibition of Protein Synthesis does not Affect SNAPP-Induce Membrane Disruption.

In initial experiments, using flow cytometry to enumerate the number of viable bacterial cells, the bacterial cell counts for *E. coli* incubated with doxycycline (1× its MIC) for 4 h remained the same as the starting inoculum. This was as expected as doxycycline is bacteriostatic against *E. coli*. Membrane disruption as measured by propidium iodide inclusion was not affected when *E. coli* was incubated with doxycycline (FIG. 38). SNAPP S16 was found to induce membrane disruption at the same level in *E. coli* in the presence or absence of doxycycline, indicating that DNA translation and novel protein synthesis are not a requirement for SNAPP induced membrane disruption leading to cell death.

Example 7

Effects of Polymer Structure on the Antimicrobial Activity and Biocompatibility of Star-Shaped Polypeptides The following experiments investigate the relationship between polymer structure and function, i.e., (1) the effect of star arm(co)polymer structure (block copolymer or homopolymer versus random copolymer) on bacterial membrane disruption ability, antimicrobial activity and biocompatibility, and (2) the reason(s) as to why the 'one arm' linear polypeptide equivalent of SNAPPs was inferior in efficacy.

To test these, a library consisting of 16- and 32-arm star polypeptides and linear polypeptides with varying polymer structure (block and random copolymers as well as homopolymers) was prepared.

The antimicrobial properties against Gram-positive and Gram-negative bacteria, and mammalian cell toxicity effects were assessed using standard antimicrobial susceptibility, hemolysis and apoptosis assays.

Also demonstrated herein is the use of a high-throughput approach based upon flow cytometry and nucleic acid staining of bacterial cells to enable the rapid screening of the membrane disrupting ability of the polypeptides.

To elucidate the effect of the star architecture and the possible contribution of secondary structure on antimicrobial activity, circular dichroism (CD) spectroscopy was conducted to compare the secondary structures of the star and linear polymers under conditions that mimicked interaction with the bacterial membrane.

Experimental Details

Materials

H-Lys(Z)—OH (>99%, Fluke), DL-Valine (>99%, Acros Organics), sodium chloride (NaCl, Chem-Supply), potassium chloride (KCl, Chem-Supply), sodium phosphate dibasic (Na2HPO4, Chem-Supply), potassium phosphate monobasic (KH2PO4, 99%, Aldrich), D-(+)-glucose solution (100 g/L, Aldrich), diethyl ether (Chem-Supply), acetonitrile (Univar), generation 2.0 poly(amido amine) dendrimer (G2 PAMAM, 8.95% w/w in water, Dendritech), generation 3.0 poly(amido amine) dendrimer (G3 PAMAM, 8.84% w/w in water, Dendritech), 4-methylbenzylamine (97%, Aldrich), bis(trichloromethyl)carbonate (triphosgene, 99%, Aldrich), trifluoroacetic acid (TFA) (99%, Aldrich), hydrobromic acid (33% in acetic acid) (Aldrich), pentane (anhyd., >99%, Aldrich), dimethyl sulfoxide (DMSO, Aldrich), N,N-dimethylformamide (DMF, anhyd., Acros Organics), Spectra/Por® molecular porous membrane tubing 8000 MWCO (Spectrum Laboratories, Inc.), and penicillin-streptomycin (Aldrich) were used as received. THF (99%, Lab Scan) was distilled from sodium benzophenone ketal under argon. Dimetylsulfoxide-d6 (DMSO-d6) (99.9%) was purchased from Cambridge Laboratory Isotopes and used as received. RPMI-1640 medium without L-glutamine (GIBCO Cat. No. 21870), Dulbecco's Modified Eagle Medium (DMEM, GIBCO Cat. No. 11995), fetal bovine serum (FBS, GIBCO Cat. No. 10099), GlutaMAX™ supplement (100×, GIBCO Cat. No. 35050), antibiotic-antimycotic (100×, GIBCO Cat. No. 15240), MEM non-essential amino acids (100×, GIBCO Cat. No. 11140), Dulbecco's Phosphate Buffered Saline (DPBS, GIBCO 14190), 0.05% trypsin-EDTA (1×, GIBCO Cat. No. 25300), SYTO® 9 green fluorescent nucleic acid stain, and propidium iodide (PI) were purchased from Invitrogen and used as received. Defibrinated horse and sheep blood were obtained from Commonwealth Serum Laboratories (CSL) Melbourne. Mueller-Hinton Broth (CM0405), Blood Agar Base No. 2 (CM0271), and Yeast Extract (LP0021) were purchased from Oxoid. Bacto™ Tryptone, and Bacto™ Agar were purchased from BD Biosciences. Vybrant® Apoptosis Assay Kit #4 (YO-PRO®-1/PI, Invitrogen) was used to perform the apoptosis/necrosis assay. 96-well cell culture plates and T175 cell culture flasks (Corning) were used for cell culture.

Synthesis of L-lysine(Z)-NCA (Lys NCA)

H-Lys(Z)—OH (1.24 g, 4.42 mmol) was added to anhydrous THF (15 mL) in an oven-dried two-neck round bottom flask under argon. Triphosgene (525 mg, 1.77 mmol) was dissolved in anhydrous THF (2 mL) and added to the H-Lys(Z)—OH suspension. The mixture was heated at 50° C. for 30 min with continuous stirring.

The clear solution was allowed to cool to room temperature and added to anhydrous pentane (100 mL). The resulting precipitate was isolated via centrifugation and washed with anhydrous pentane (30 mL×2). The resulting white solid was dried at ambient temperature in vacuo to afford Lys NCA, 1.097 g (81%).

$^1$H NMR (400 MHz, d6-DMSO) δH 1.23-1.37 (m, γ-CH$_2$, 2H), 1.37-1.45 (m, δ-CH$_2$, 2H), 1.60-1.80 (m, β-CH$_2$, 2H), 2.94-3.02 (m, ε-CH$_2$, 2H), 4.40-4.43 (m, α-CH, 1H), 5.00 (dd, C$_6$H$_5$CH$_2$—, 2H), 6.90 (s, cyclic NH, 1H), 7.30-7.39 (m, C$_6$H$_5$—, 5H).

Synthesis of DL-valine-NCA (Val NCA)

DL-valine (1.24 g, 10.58 mmol) was dissolved in anhydrous THF (20 mL) in an oven-dried two-neck round bottom flask under argon. Triphosgene (1.26 g, 4.23 mmol) was dissolved in anhydrous THF (5 mL) and added to the DL-Val-THF suspension. The mixture was heated at 50° C. for 30 min with continuous stirring. The clear solution was allowed to cool to room temperature and precipitated with anhydrous pentane (100 mL), followed by washing with more anhydrous pentane (30 mL×2). The resulting residue was dried at ambient temperature in vacuo to afford Val NCA, 1.29 g (85%).

$^1$H NMR (400 MHz, d6-DMSO) 1H NMR (400 MHz, d6-DMSO) δH 0.91 (dd, CH$_3$, 6H), 2.00-2.12 (m, CH, 1H), 4.32 (dd, cyclic CH, 1H), 9.06 (s, cyclic NH, 1H).

Synthesis of poly(DL-valine-b-Z-L-lysine)$_{arm}$PAMAM-(NH$_2$)$_{16,core}$ Star Polymers SB$_{16,Z}$ Lys NCA (1.3 g, 4.19 mmol) was dissolved in anhydrous DMF (13 mL) and added via syringe to PAMAM-(NH$_2$)$_{16}$ (dried, 43 mg, 13.1 µmol) dissolved in anhydrous DMF (1 mL). After stirring for 24 h under argon, Val NCA (0.3 g, 2.1 mmol) dissolved in anhydrous DMF (3 mL) was added to the reaction mixture. The reaction mixture was stirred for a further 24 h under argon, after which n-butyl alcohol (1 mL) was added and the mixture was stirred for a further 1 h. Precipitation of the concentrated polymer solution into diethyl ether (3×40 mL), followed by isolation via centrifugation and drying (0.1 mbar), afforded (PVal-b-PZLL)$_{arm}$-PAMAM-(NH$_2$)$_{16,core}$ star polymer SB$_{16,Z}$ as an off-white solid, 1.2 g (89%).

Synthesis of poly(DL-valine-b-Z-L-lysine)$_{arm}$PAMAM-(NH$_2$)$_{32,core}$ Star Polymers SB$_{32,Z}$ Lys NCA (1.3 g, 4.19 mmol) was dissolved in anhydrous DMF (13 mL) and added via syringe to PAMAM-(NH$_2$)$_{32}$ (dried, 45 mg, 6.5 µmol) dissolved in anhydrous DMF (1 mL). After stirring for 24 h under argon, Val NCA (0.3 g, 2.1 mmol) dissolved in anhydrous DMF (3 mL) was added to the reaction mixture. The reaction mixture was stirred for a further 24 h under argon, after which n-butyl alcohol (1 mL) was added and the mixture was stirred for a further 1 h. Precipitation of the concentrated polymer solution into diethyl ether (3×40 mL), followed by isolation via centrifugation and drying (0.1 mbar), afforded (PVal-b-PZLL)$_{arm}$-PAMAM-(NH$_2$)$_{32,core}$ star polymer SB$_{32,Z}$ as an off-white solid, 1.17 g (87%).

Synthesis of poly(Z-L-lysine-r-DL-valine)$_{arm}$PAMAM-(NH$_2$)$_{16,core}$ Star Polymers SR$_{16,Z}$ Lys NCA (1.3 g, 4.19 mmol) and Val NCA (0.3 g, 2.1 mmol) were dissolved in anhydrous DMF (16 mL) and added via syringe to PAMAM-(NH$_2$)$_{16}$ (dried, 43 mg, 13.1 µmol) dissolved in anhydrous DMF (1 mL). After stirring for 24 h under argon, n-butyl alcohol (1 mL) was added and the mixture was stirred for a further 1 h. Precipitation of the concentrated polymer solution into diethyl ether (3×40 mL), followed by isolation via centrifugation and drying (0.1 mbar), afforded (PZLL-r-PVal)$_{arm}$PAMAM-(NH$_2$)$_{16,core}$ star polymer SR$_{16,Z}$ as an off-white solid, 1.21 g (90%).

$^1$H NMR (400 MHz, d$_6$-DMSO) δH 0.67-0.89 (b, CH$_3$, 6H), 1.11-1.77 (b, γ-CH$_2$+δ-CH$_2$+β-CH$_2$, 6H), 1.84-2.00 (b, CH, 1H), 2.78-3.00 (b, ε-CH$_2$, 2H), 4.06-4.40 (b, α-CH, 1H), 4.90-5.00 (b, C$_6$H$_5$CH$_2$—, 2H), 7.00-7.44 (b, C$_6$H$_5$—, 5H), 7.60-8.30 (b, NH, 1H).

Synthesis of poly(Z-L-lysine-r-DL-valine)$_{arm}$PAMAM-(NH$_2$)$_{32,core}$ Star Polymers SR$_{32,Z}$ Lys NCA (1.3 g, 4.19 mmol) and Val NCA (0.3 g, 2.1 mmol) were dissolved in anhydrous DMF (16 mL) and added via syringe to PAMAM-(NH$_2$)$_{32}$ (dried, 43 mg, 13.1 µmol) dissolved in anhydrous DMF (1 mL). After stirring for 24 h under argon, n-butyl alcohol (1 mL) was added and the mixture was stirred for a further 1 h. Precipitation of the concentrated polymer solution into diethyl ether (3×40 mL), followed by isolation via centrifugation and drying (0.1 mbar), afforded (PZLL-r-PVal)$_{arm}$PAMAM-(NH$_2$)$_{32}$,core star polymer SR$_{32,Z}$ as an off-white solid, 1.15 g (85%).

$^1$H NMR (400 MHz, d6-DMSO) δH 0.67-0.89 (b, CH$_3$, 6H), 1.11-1.77 (b, γ-CH$_2$+δ-CH$_2$+β-CH$_2$, 6H), 1.84-2.00 (b, CH, 1H), 2.78-3.00 (b, ε-CH$_2$, 2H), 4.06-4.40 (b, α-CH, 1H), 4.90-5.00 (b, C$_6$H$_5$CH$_2$—, 2H), 7.00-7.44 (b, C$_6$H$_5$—, 5H), 7.60-8.30 (b, NH, 1H).

Synthesis of poly(Z-L-lysine)$_{arm}$PAMAM-(NH$_2$)$_{16,core}$ Star Polymer SH$_{16,Z}$ Lys NCA (1 g, 3.26 mmol) was dissolved in anhydrous DMF (9 mL) and added via syringe to PAMAM-(NH$_2$)$_{16}$ (dried, 33 mg, 10.2 µmol) dissolved in anhydrous DMF (1 mL). After stirring for 24 h under argon, n-butyl alcohol (1 mL) was added and the mixture was stirred for a further 1 h. Precipitation of the concentrated polymer solution into diethyl ether (3×40 mL), followed by isolation via centrifugation and drying (0.1 mbar), afforded PZLL$_{arm}$PAMAM-(NH$_2$)$_{16,core}$ star polymer SH$_{16,Z}$ as an off-white solid, 770 mg (87%).

Synthesis of poly(Z-L-lysine)$_{arm}$PAMAM-(NH$_2$)$_{32,core}$ Star Polymer SH$_{32,Z}$ Lys NCA (1 g, 3.26 mmol) was dissolved in anhydrous DMF (9 mL) and added via syringe to PAMAM-(NH$_2$)$_{32}$ (dried, 35 mg, 5.1 µmol) dissolved in anhydrous DMF (1 mL). After stirring for 24 h under argon, n-butyl alcohol (1 mL) was added and the mixture was stirred for a further 1 h. Precipitation of the concentrated polymer solution into diethyl ether (3×40 mL), followed by isolation via centrifugation and drying (0.1 mbar), afforded PZLL$_{arm}$PAMAM-(NH$_2$)$_{32,core}$ star polymer SH$_{32,Z}$ as an off-white solid, 780 mg (87%).

Synthesis of Linear poly(Z-L-lysine) Polymer LH$_Z$

Lys NCA (0.5 g, 1.63 mmol) was dissolved in anhydrous DMF (5 mL) and added via syringe to 4-methylbenzylamine (6.9 µL, 54.4 µmol). After stirring for 24 h under argon, n-butyl alcohol (1 mL) was added and the mixture was stirred for a further 1 h. Precipitation of the concentrated polymer solution into diethyl ether (3×40 mL), followed by isolation via centrifugation and drying (0.1 mbar), afforded linear PZLL polymer LH$_Z$ as an off-white solid, 411 mg (95%).

Synthesis of Linear poly(Z-L-lysine-r-DL-valine) Polymer LR$_Z$

Lys NCA (0.5 g, 1.63 mmol) and Val NCA (117 mg, 0.82 mmol) were dissolved in anhydrous DMF (6 mL) and added via syringe to benzylamine (10.3 µL, 81.6 µmol). After stirring for 24 h under argon, n-butyl alcohol (1 mL) was added and the mixture was stirred for a further 1 h. Precipitation of the concentrated polymer solution into diethyl ether (3×40 mL), followed by isolation via centrifugation and drying (0.1 mbar), afforded linear PZLL-r-PVal polymer LR$_Z$ as an off-white solid, 420 mg (81%).

$^1$H NMR (400 MHz, d6-DMSO) δH 0.67-0.89 (b, CH$_3$, 6H), 1.11-1.77 (b, γ-CH$_2$+δ-CH$_2$+β-CH$_2$, 6H), 1.84-2.00 (b, CH, 1H), 2.78-3.00 (b, ε-CH$_2$, 2H), 4.06-4.40 (b, α-CH, 1H), 4.90-5.00 (b, C$_6$H$_5$CH$_2$—, 2H), 7.00-7.44 (b, C$_6$H$_4$—, 4H), 7.60-8.30 (b, NH, 1H).

NMR Spectroscopic Analysis $^1$H NMR spectroscopy was performed at room temperature using a Varian Unity 400 (400 MHz) spectrometer with the deuterated solvent as reference and a sample concentration of ca. 10 mg/mL.

Gel Permeation Chromatography (GPC)

GPC analysis was performed on a Shimadzu liquid chromatography system equipped with a Shimadzu RID-10 refractometer (λ=633 nm), using three Waters Ultrahydrogel columns in series ((i) 250 Å porosity, 6 µm diameter bead size; (ii) and (iii) linear, 10 µm diameter bead size), operating at 60° C. and a flowrate of 0.5 mL/min. The eluent was Milli-Q water containing 20% v/v acetonitrile and 0.1% w/v TFA). The molecular weight characteristics of the analytes were determined with reference to a conventional column calibration with narrow molecular weight poly(ethylene glycol) standards. All samples for GPC analysis were prepared at a concentration of 10 mg/mL and were filtered through 0.45 µm nylon filters prior to injection.

Dynamic Light Scattering (DLS)

DLS measurements were performed on a Malvern Zetasizer Nano ZS with a 4.0 mW He—Ne laser (633 nm) at an angle of 173° and a temperature of 25±0.1° C. Initial sample concentrations of 1 mg/mL in water (purified by reverse osmosis) were used and serial dilutions were performed until stable spectra were obtained. All sample solutions were filtered using 0.45 µm syringe filters.

Measurement of Minimum Disruptive Concentrations (MDC)

The detailed protocols for bacterial cell culture are provided herein. A dilution series of each polypeptide was made by diluting polypeptide stock in sterilized Mueller-Hinton broth (MHB) for *Escherichia coli*, Luria broth (LB) for *Staphylococcus aureus* or Todd Hewitt broth for *Streptococcus mutans* to a desired concentration range with a final volume of 100 µL in each well of a 96-well plate. Bacterial cells (which gave an optical density reading of ca. 0.7 at 650 nm for *E. coli* and *S. aureus* and ca. 1.8 at 650 nm for *S. mutans*) were diluted to 2.5×106 cells/mL and 100 µL of the bacteria solution was added to each well. The 96-well plate was then incubated at 37° C. for 90 min. A 50 µL aliquot was taken from each well, transferred to a second 96-well plate and 100 µL of saline and dye mixture (i.e., saline with 0.1% of SYTO® 9 and 0.1% of PI) was added. Each well in the second 96-well plate was analyzed with a Cell Lab Quanta SC MPL flow cytometer to determine the % of cells with intact membranes and cells with compromised membranes for each polymer at each concentration. Positive controls containing cells alone were incorporated. Percentage of cells with intact membranes was plotted against polymer concentration and linear regression analysis was used to determine the lowest concentration (MDC) at which all of the cells had their membranes disrupted. Two independent runs of the assay were conducted and two replicates were used in each run for each bacteria, polymer, and concentration.

Measurement of Minimum Bactericidal Concentrations (MBC)

Identical to the preparative steps taken for the measurement of MDC, a dilution series of each polypeptide was prepared and incubated with bacterial cells at 37° C. for 90 min. For each well, microbial solution was diluted with saline using an appropriate dilution factor and placed on an agar plate (identical to that used for bacteria culture). For *E. coli* and *S. aureus*, the agar plates were incubated overnight at room temperature and then at 37° C. with aeration for 2 h. For *S. mutans*, the agar plates were incubated at 37° C. in an anaerobic chamber for 48 h. The number of colony-forming units (CFU) was counted and expressed as CFU/mL. Positive controls consisting of cells without any treatment were used. CFU/mL was plotted against polymer concentration and linear regression analysis was used to determine the lowest concentration (MBC) at which the CFU/mL becomes zero. Two independent runs of the assay were conducted and two replicates were used in each run for each bacteria, polymer, and concentration.

To evaluate TIs, MBC measurements were also performed in minimal essential medium (MEM, 136.9 mM NaCl, 10.1 mM Na$_2$HPO$_4$, 2.7 mM KCl, 1.8 mM KH2PO4, 0.2% w/v D-(+)-glucose) for SR16 and SR32.

Measurement of Minimum Inhibitory Concentrations (MIC)

The MICs of the polypeptides were determined using a broth microdilution method. After the preparation of a dilution series of each polypeptide and the addition of bacterial cells (Note: steps identical to that taken for the measurement of MDC), the optical density readings of each well at 630 nm were measured as a function of time using a microplate reader (Multiskan Ascent, Pathtech Pty. Ltd.). Positive controls containing cells alone were incorporated. Optical density was plotted against polymer concentration and linear regression analysis was used to determine the lowest concentration (MIC) at which the optical density reading becomes zero. Two independent runs of the assay were conducted and two replicates were used in each run for each bacteria, polymer, and concentration.

Circular Dichroism (CD)

CD spectra were recorded at 25° C. on an Aviv Biomedical CD Spectrometer Model 410 with stopped flow unit add-on. A glass cuvette with a path length of 1 mm was used. Spectra were generated from 195 to 250 nm wavelengths at 0.5 nm intervals, 4 s averaging time, 0.333 s settling time, and 1 nm bandwidth. Polymers were dissolved to a final concentration of 0.2 mg/mL in RO water with 0%, 20%, 50%, and 80% TFE. The spectra were plotted as mean residue ellipticity, [θ], against wavelength.

Hemolysis Assay

Fresh sheep red blood cells (RBCs) were diluted 1 in 20 in PBS (pH 7.4), pelleted by centrifugation, and washed three times in PBS (1000 g, 10 min). The RBCs were counted using a cell counter (Coulter Particle Counter Z series, Beckman Coulter) and diluted to a final concentration of 2×107 cells/mL. 100 µL aliquots of the RBC solution were seeded into a V-bottomed 96-well plate containing 100 µL of polypeptide solution of varying concentrations (4-256 µg/mL) and incubated in a humidified atmosphere containing 5% CO$_2$ at 37° C. for 2 h. Following incubation, the 96-well plate was centrifuged (1000 g, 10 min) and aliquots (100 µL) of supernatant were transferred to a flat-bottomed 96-well plate. Hemoglobin release upon lysis of the RBCs was monitored at 405 nm using a microplate reader (PerkinElmer 1420 Multilabel Counter VICTOR3). Positive and negative controls for hemolysis were taken as RBC lysed with 0.5% Triton X-100 (1:1 v/v) and RBC suspension in PBS, respectively. The percentage of hemolysis was calculated using the following formula:

$$\% \text{ Hemolysis} = \left( \frac{A_{405} \text{ test sample} - A_{405} \text{ negative control}}{A_{405} \text{ positive control} - A_{405} \text{ negative control}} \right) \times 100$$

The percentage hemolysis was plotted against polypeptide concentration and linear regression analysis was used to determine the hemolytic concentration needed to lyse 50% (HC$_{50}$) of RBCs. Two independent runs of the assay were conducted and two replicates were used in each run for each polypeptide and concentration.

Apoptosis/Necrosis Assay

Adherent HEK293T or H4IIE cells were grown to 80% confluence and trypsinized prior to assays. Cells were diluted 1:2 with 'complete' medium (RPMI-1640 for HEK293T cells or DMEM for H4IIE cells) and seeded in a 24-well plate (1 mL per well). The cells were incubated at 37° C. in 5% CO2 for 24 h until ca. 95% confluence. The medium was removed. Varying concentrations of polypeptides (4 to 128 µg/mL) were prepared and 200 µL aliquots of each were added to the cells, after which the cells were incubated at 37° C. in 5% CO2 for 90 min. The cells were then harvested and all well contents were transferred to round-bottomed polypropylene tubes (5 mL). The cells were washed with cold DPBS, then stained with YO-PRO®-1 and PI (0.2 mL from a stock solution, whereby both dyes were diluted 1:1000 in cold DPBS, per well), and incubated on ice for 20 to 30 min. The cells were analyzed by flow cytometry (Cytomics FC 500 MPL System). Standard compensation was performed using single-colour stained cells. Negative controls using untreated cells were included. Two independent runs of the assay were conducted and two replicates were used in each run for each polypeptide and concentration.

Flow cytometry. Bacterial cell sample analysis was performed using a Cell Lab Quanta SC MPL flow cytometer (Beckman Coulter) equipped with a 100 W stabilized mercury arc lamp with wavelengths of 365, 404, and 435 nm, and a 488 nm diode laser. The fluorescence from SYTO® 9 was measured through a 525-nm band-pass filter (Fluorescent Channel 1, FL-1), and the red emission of PI was measured with a 670-nm long pass filter (Fluorescent Channel 3, FL-3). The multiparametric data were analyzed using the Cell Lab Quanta SC software. Cell samples from the apoptosis/necrosis assay were analyzed using a Cytomics FC 500 MPL flow cytometer (Beckman Coulter) equipped with a 20 mW argon ion laser operating at 488 nm and a solid-state 25 mW red diode laser operating at 635 nm. The green fluorescence from YO-PRO®-1 was measured with a 525 nm filter (FL-1) and PI was measured through a 575 nm filter (FL-2). For each run, a total of 50 000 cells were acquired and cell debris was gated out using forward and side scatter properties.

Results and Discussion

Star Polypeptide Design and Synthesis

Figure 42:
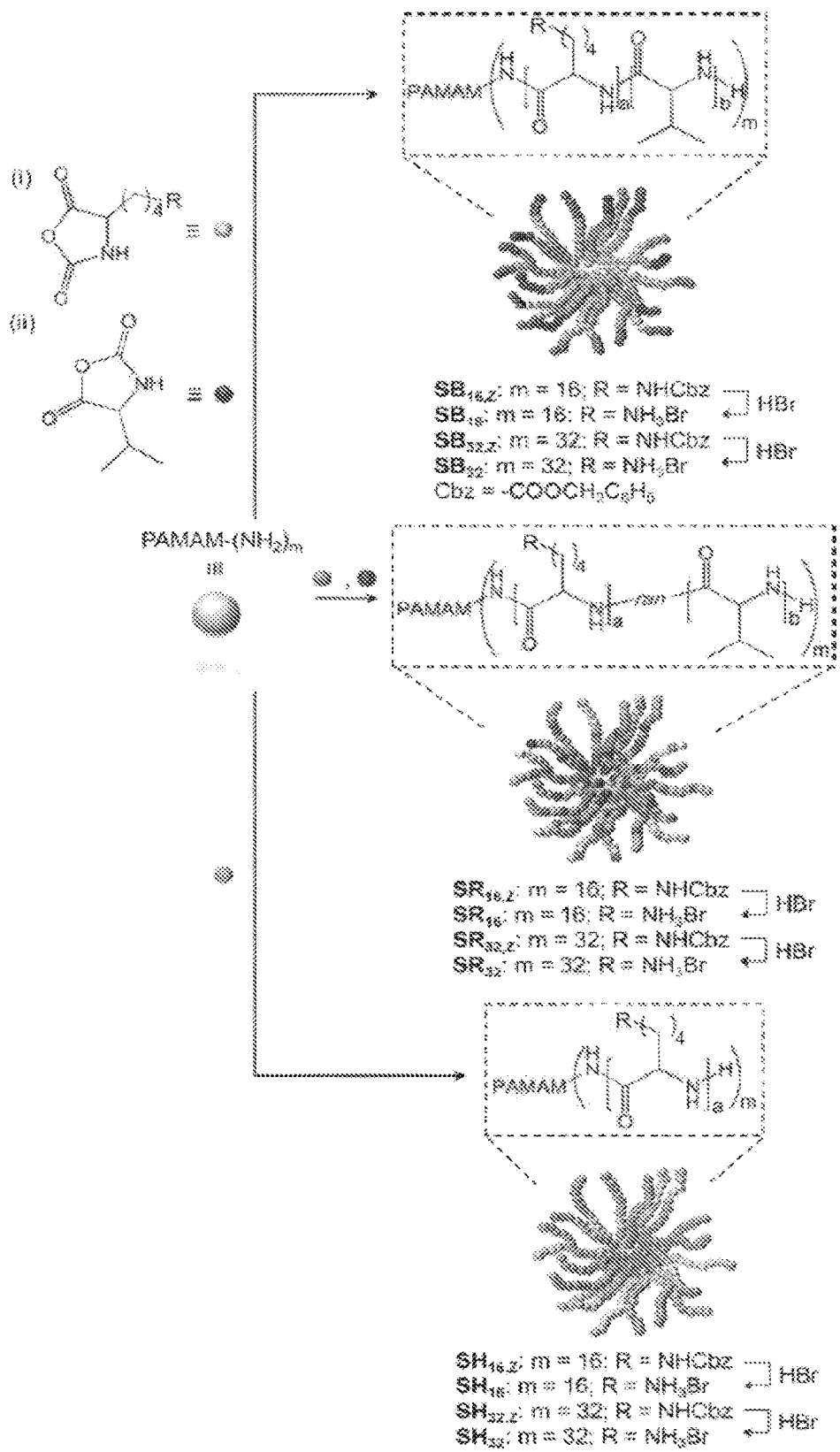
FIG. 42: Synthesis of star polypeptides. Synthesis of the star polypeptides via ROP of lysine NCA only (SH16,Z, SH16, SH32,Z, and SH32) or both lysine NCA and valine NCA (SB16,Z, SB16, SB32,Z, SB32, SR16,Z, SR16, SR32, Z, and SR32) was initiated from the terminal amines of PAMAM dendrimers.
Figure 43:
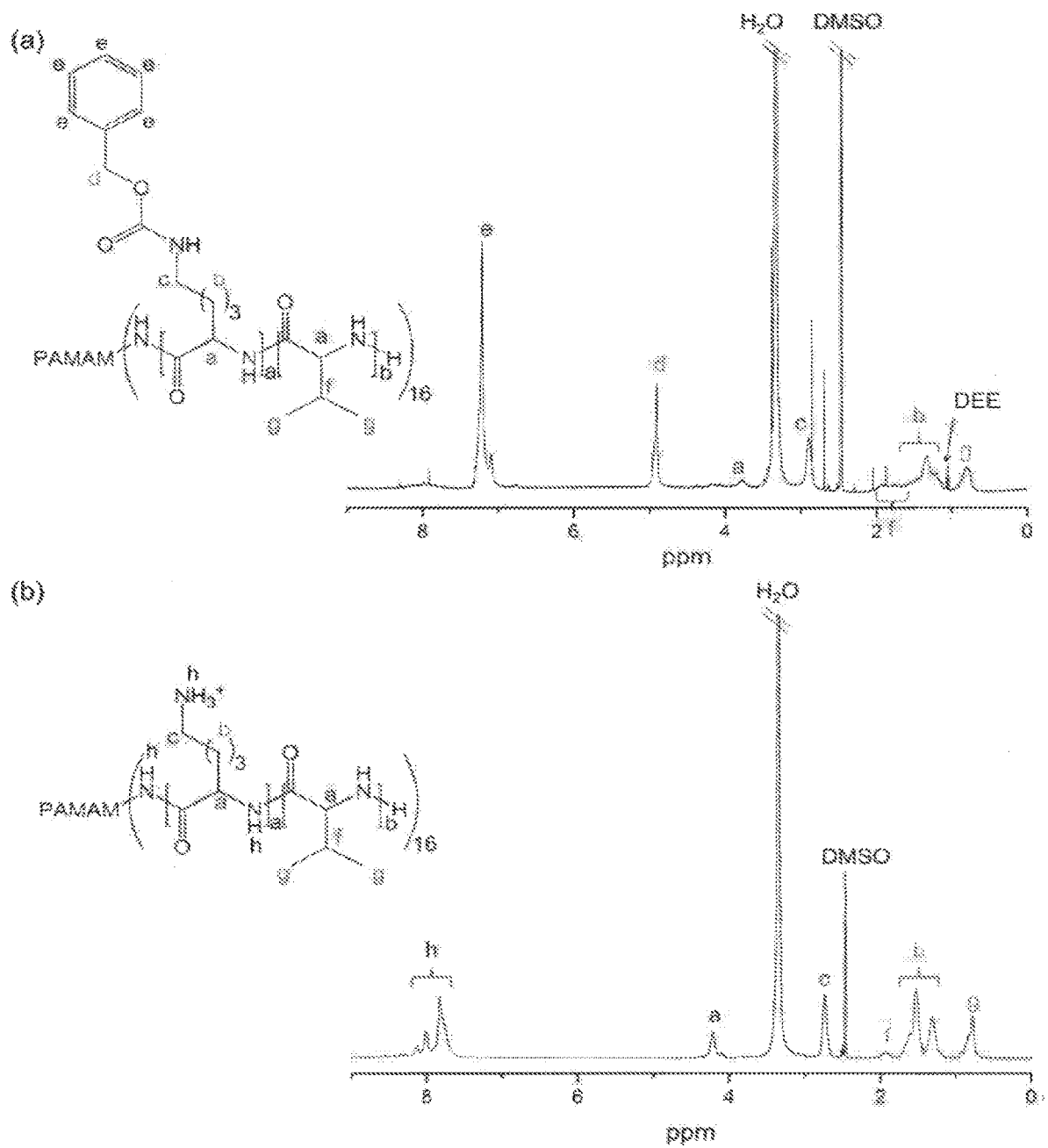
FIG. 43: 1H NMR spectra (d6-DMSO) of (a) 16-arm Cbz-protected star polymer SB16,Z and (b) deprotected star polymer SB16.
Figure 44:
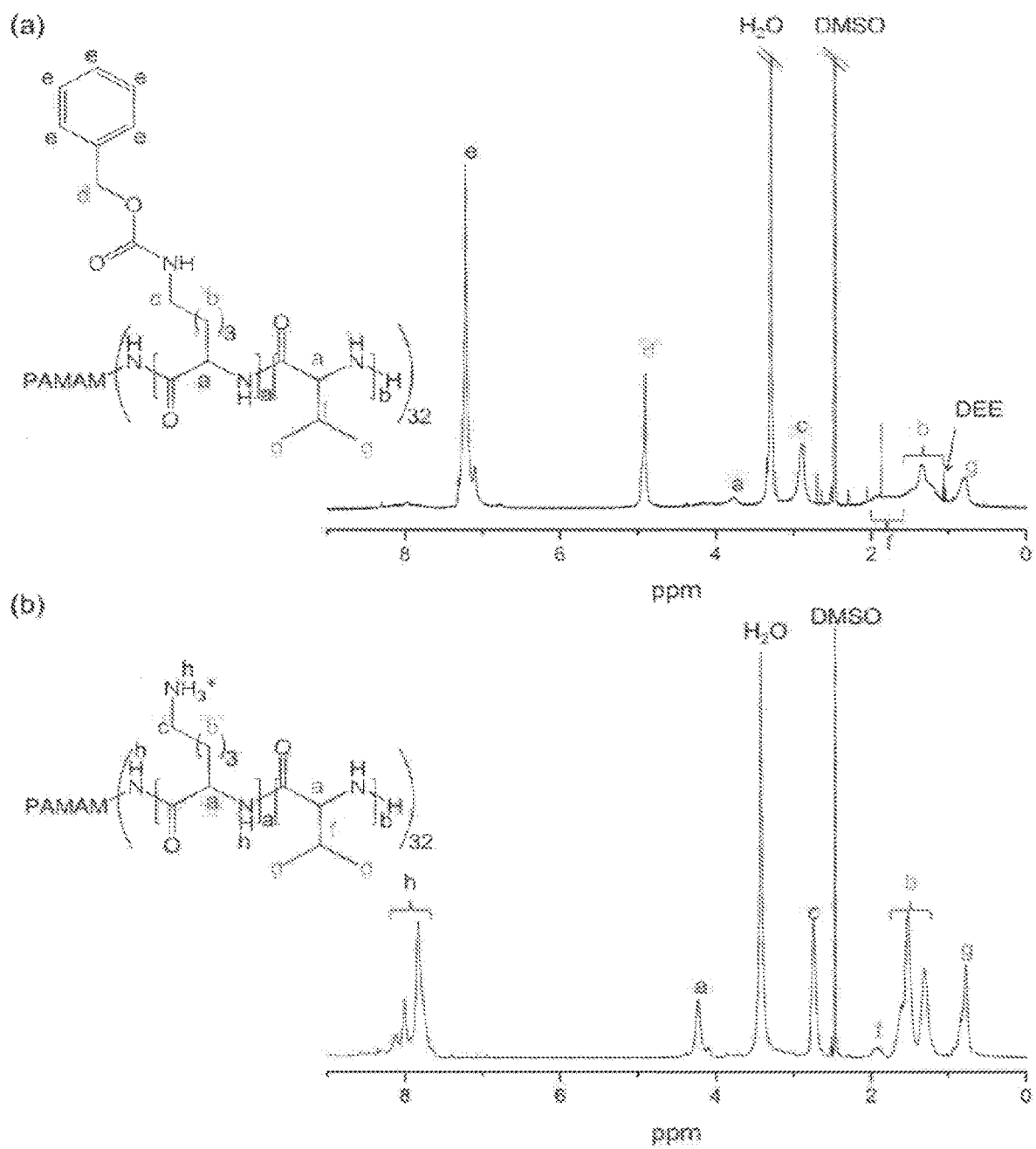
FIG. 44: 1H NMR spectra (d6-DMSO) of (a) 32-arm Cbz-protected star polymer SB32,Z and (b) deprotected star polymer SB32.
Figure 45:
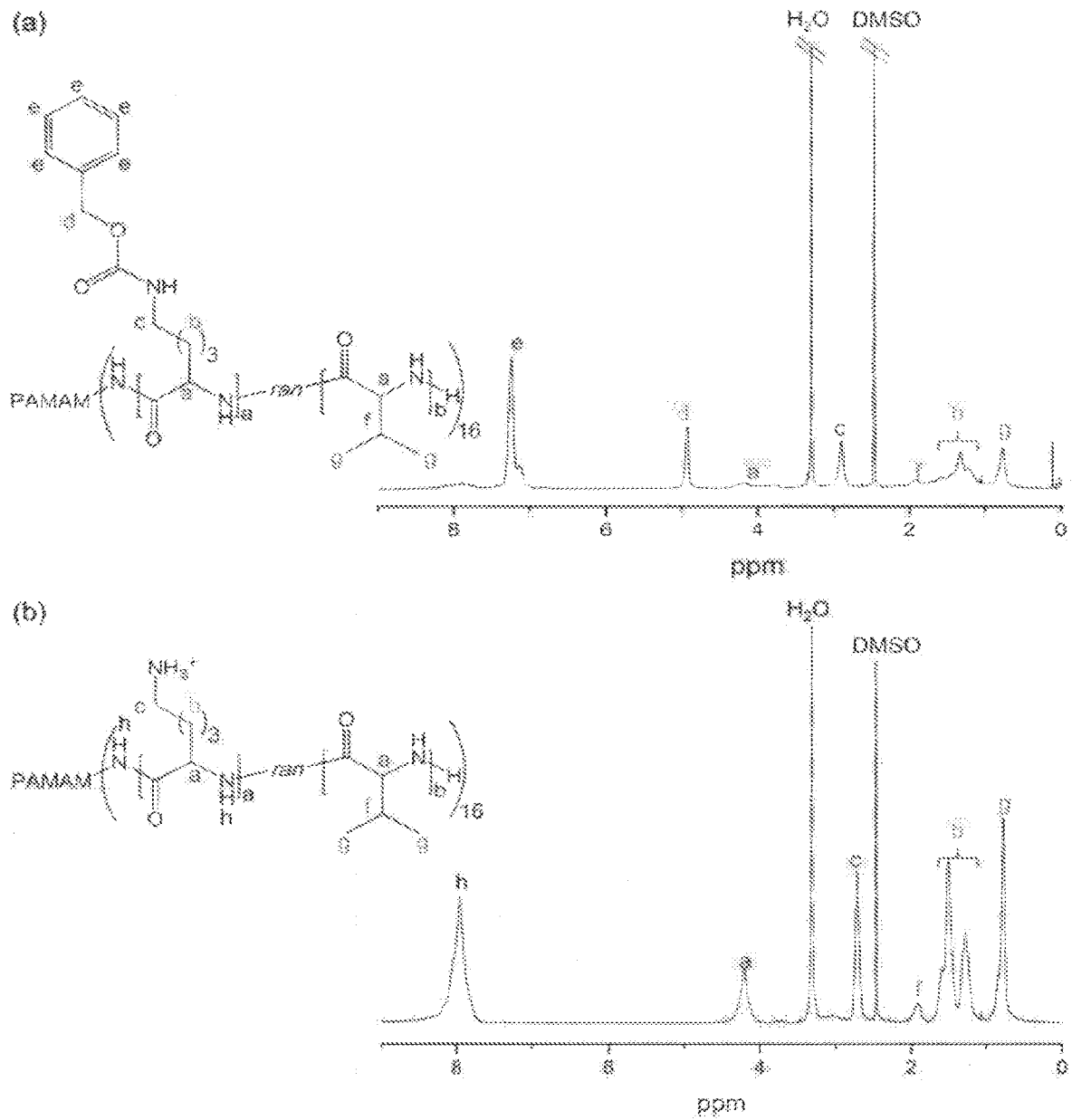
FIG. 45: 1H NMR spectra (d6-DMSO) of (a) 16-arm Cbz-protected star polymer SR16,Z and (b) deprotected star polymer SR16.
Figure 46:
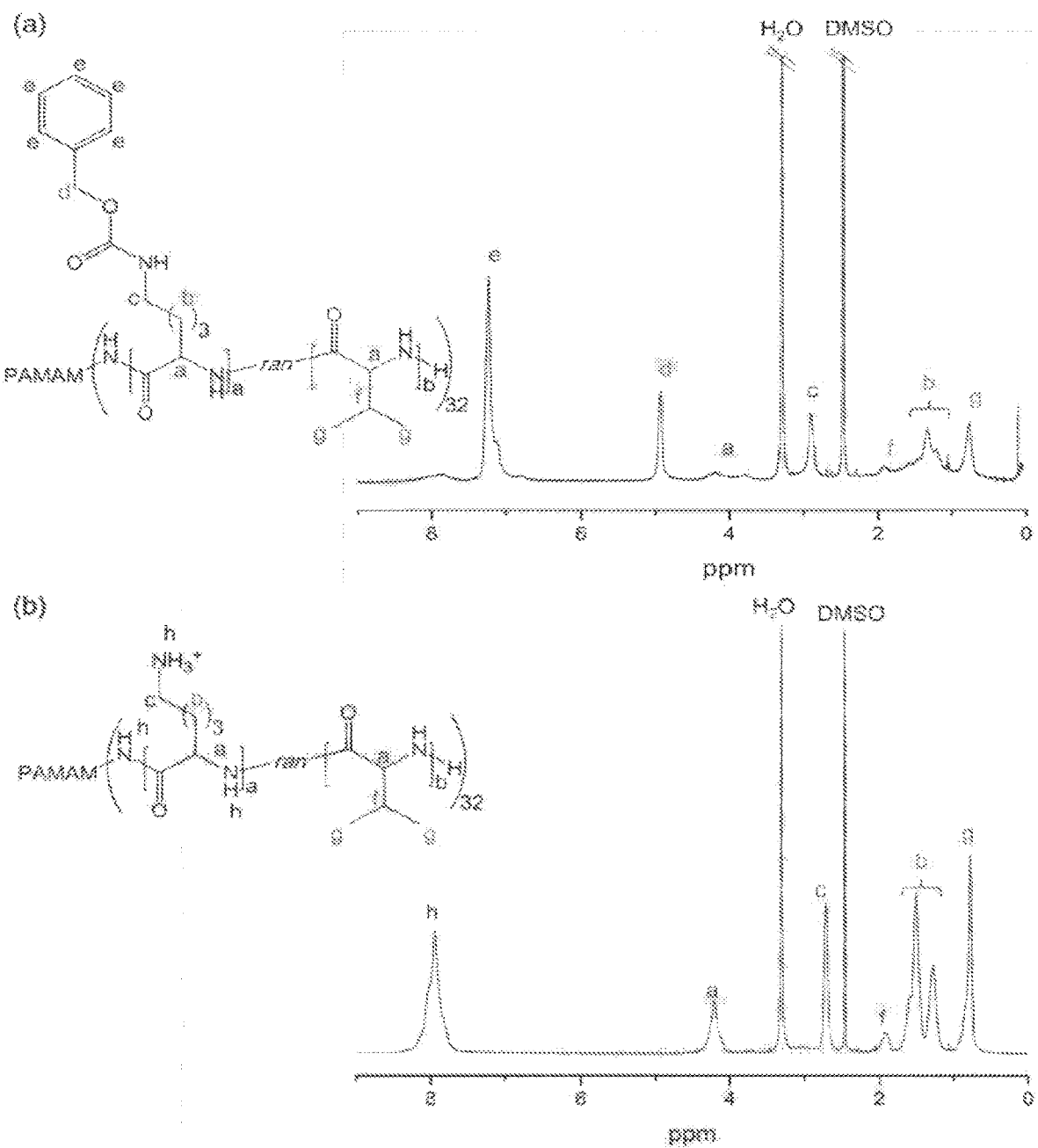
FIG. 46: 1H NMR spectra (d6-DMSO) of (a) 32-arm Cbz-protected star polymer SR32,Z and (b) deprotected star polymer SR32.
Figure 47:
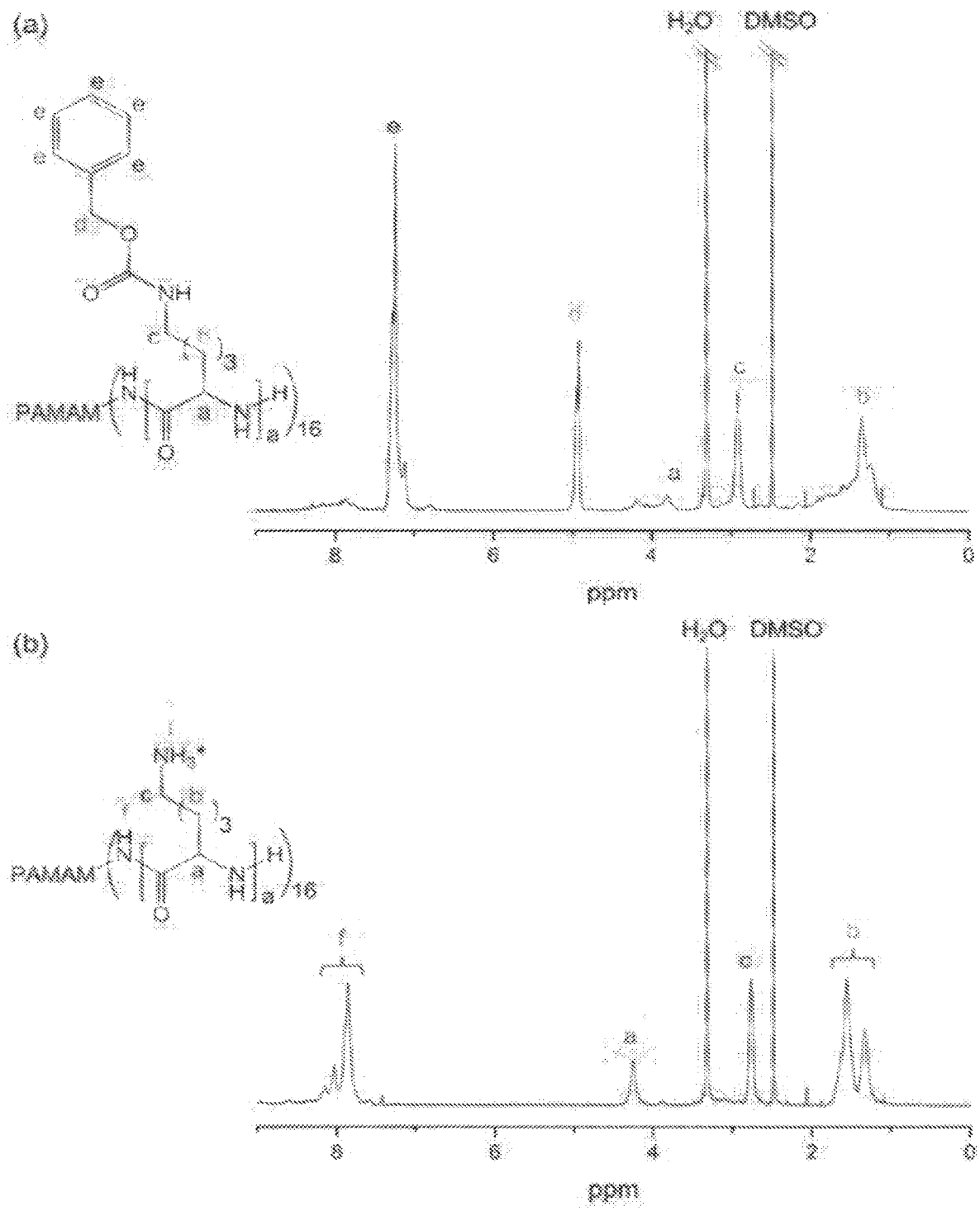
FIG. 47: 1H NMR spectra (d6-DMSO) of (a) 16-arm Cbz-protected star polymer SH16,Z and (b) deprotected star polymer SH16.
Figure 48:
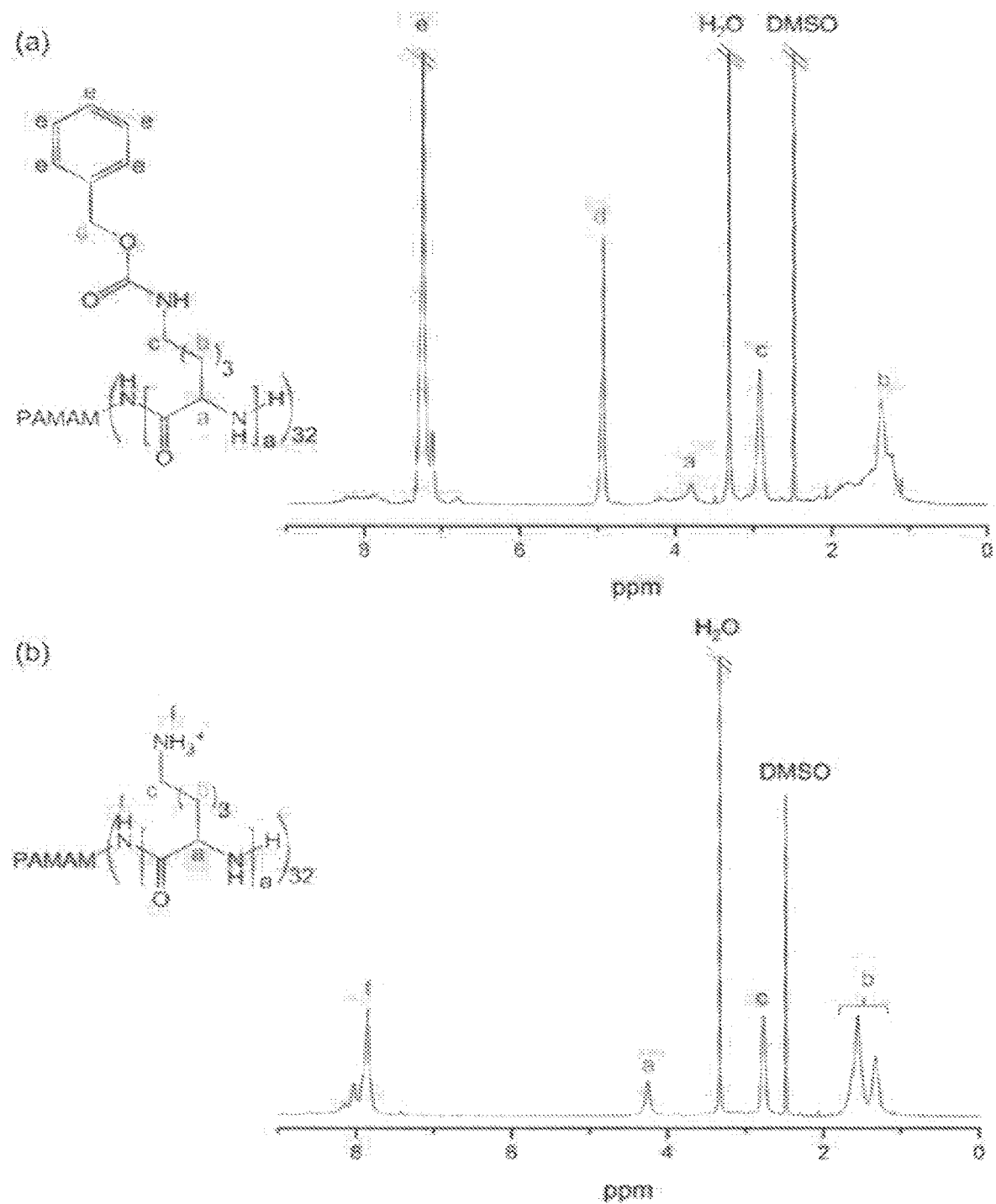
FIG. 48: 1H NMR spectra (d6-DMSO) of (a) 32-arm Cbz-protected star polymer SH32,Z and (b) deprotected star polymer SH32.

A polymer library consisting of six star polypeptides was synthesized via ROP of amino acid NCA monomers using the primary amines of multifunctional dendrimers as initiators (FIG. 42). Lysine and valine were selected as cationic and hydrophobic amino acids, respectively. Second (G2) and third (G3) generation PAMAM dendrimers with 16 and 32 peripheral primary amines were used as initiators to prepare 16- and 32-arm star polymers, respectively. The stoichiometric ratio of the NCA monomers to the initiators was controlled to target a theoretical degree of polymerization (DP) of 30 per star arm at complete monomer conversion. For star polymers comprising of both lysine and valine, the mole ratio of lysine to valine was kept at around 2:1, which was determined to be the optimum ratio for water solubility while resembling the typical cationic-to-hydrophobic ratio of membrane-active AMPs. The number of repeat units for lysine and valine are a and b, respectively. For copolymers of lysine and valine, the lysine-to-valine ratios (i.e., a:b) are provided Table 13 below.

The arrangement of lysine and valine repeat units along the polymer chains was also systematically varied. 16- and 32-arm star polymers SB16,Z and SB32,Z, respectively, possess block copolypeptide arms consisting of poly(DL-valine) (PVal) at the corona and poly(ε-Z-L-lysine) (PZLL; carboxybenzyl (Cbz or Z) protected) nearer to the core. For 16- and 32-arm star polymers SR16,Z and SR32,Z, respectively, lysine and valine NCAs were randomly polymerized to form random copolypeptide arms. Stars SH16,Z and SH32,Z, on the other hand, are 16- and 32-arm star polymers, respectively, with PZLL homopeptide arms.

Successful synthesis of the star polypeptides was confirmed by 1H NMR spectroscopic analysis (FIG. 43(a)-48(a)). For the star polypeptides comprised of lysine and valine (SB16,Z, SB32,Z, SR16,Z and SR32,Z), proton resonances characteristic of valine (i.e., δH 0.8 ppm corresponding to the methyl groups on the valine side chain) and lysine (i.e., δH 1.2-1.8 ppm corresponding to the methylene protons on the lysine NCA side chain) residues were observed. Integration and comparison of these resonances provided lysine-to-valine ratios of approximately 2-3:1, which is consistent with the ratio of lysine and valine NCA monomers used in the synthesis shown in Table 14 below.

Resonances resulting from the G2 and G3 PAMAM cores were difficult to observe upon star formation as they overlap with the broad polypeptide peaks. It is also likely that the intensities of the core resonances were much smaller relative to those resulting from the polypeptide arms, as the contribution of the PAMAM core to the overall molecular weight of the star is relatively small. The subsequent removal of the carboxylbenzyl (Cbz or Z) protecting groups on the lysine residues along the arms of the star polypeptides using HBr yielded water-soluble stars (SB16, SB32, SR16, SR32, H16, and SH32) with pendent protonated amine functionalities along the arms. At physiological pH, the pendent amine groups (pKa=10.5) would remain protonated. 1H NMR spectroscopic analysis revealed quantitative deprotection (i.e., >99% removal of the Cbz protecting groups) for all of the polymers (FIG. 43(b)-48(b)). The lysine-to-valine ratios of the star polypeptides remained unchanged after deprotection (ca. 2-3:1), indicating that the polymeric structures were not altered by the deprotection process.

Figure 49:
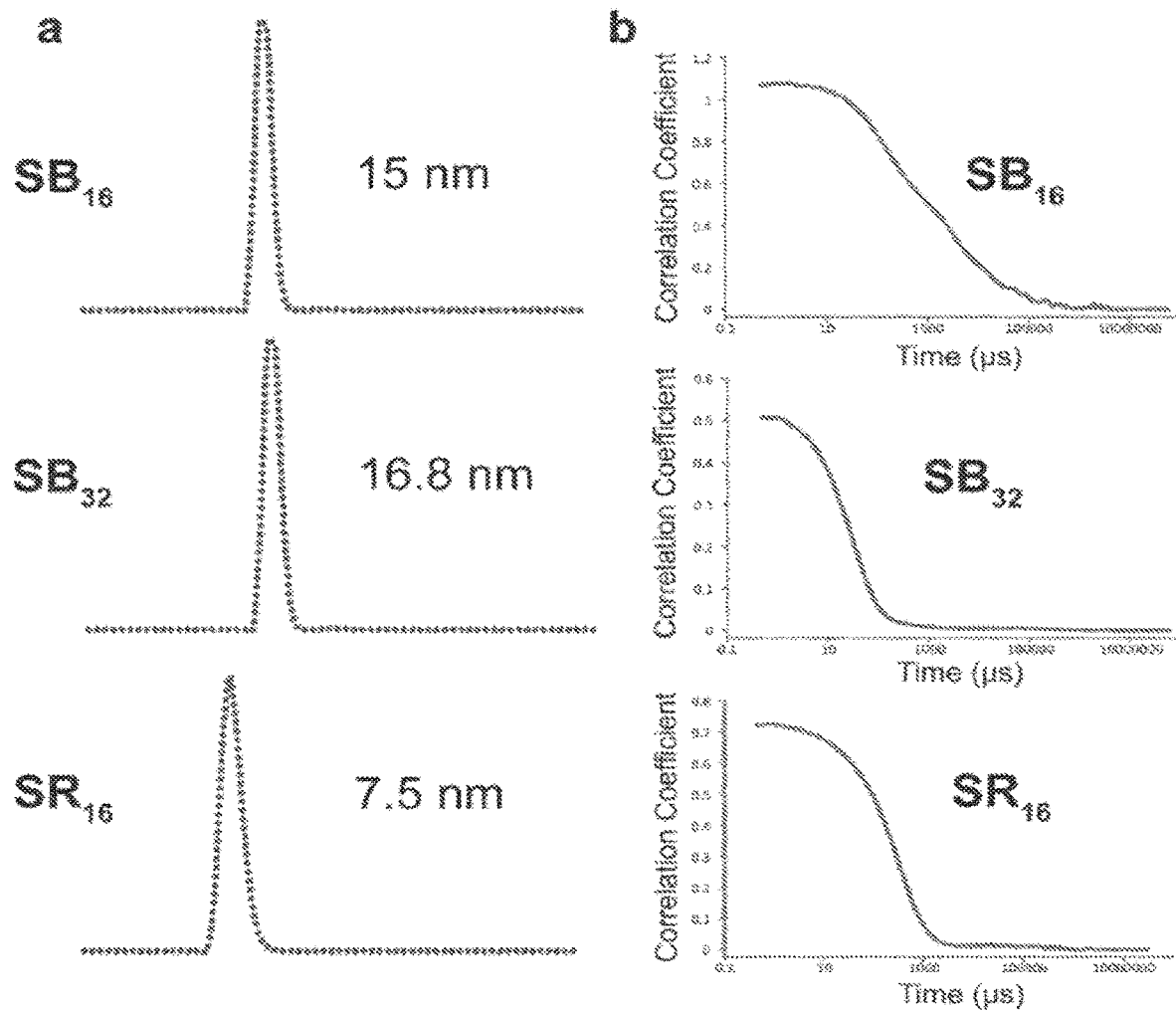
FIG. 49: DLS analysis of the star polypeptides. (a) DLS normalized mass % of the star polypeptides as a function of hydrodynamic diameter (DH). The numbers on the DLS distributions show the average DH of the polymers in water, each determined as an average of 30 measurements. (b) The intensity autocorrelation curve corresponding to each DLS trace is shown.
Figure 49:
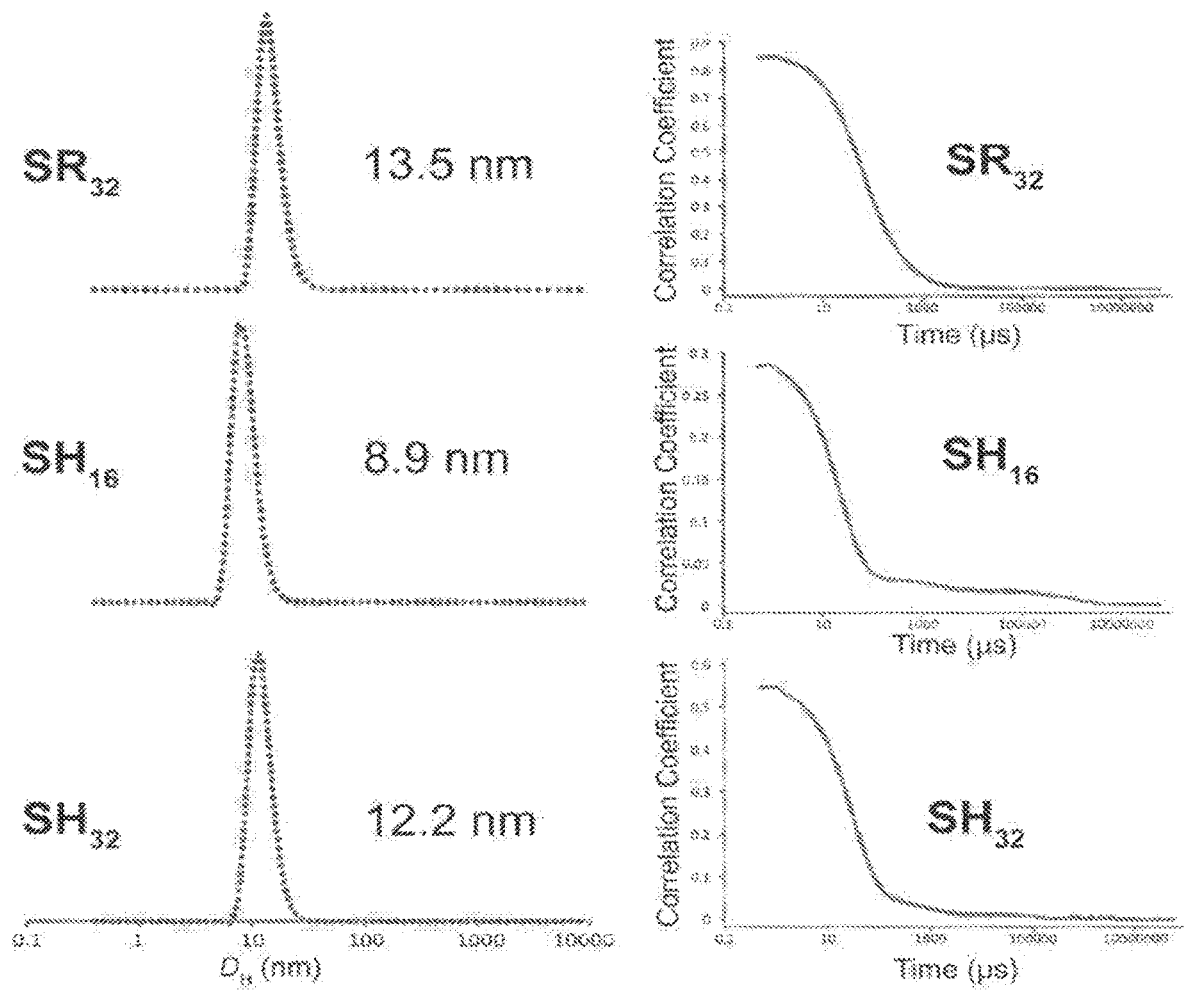
Figure 50:
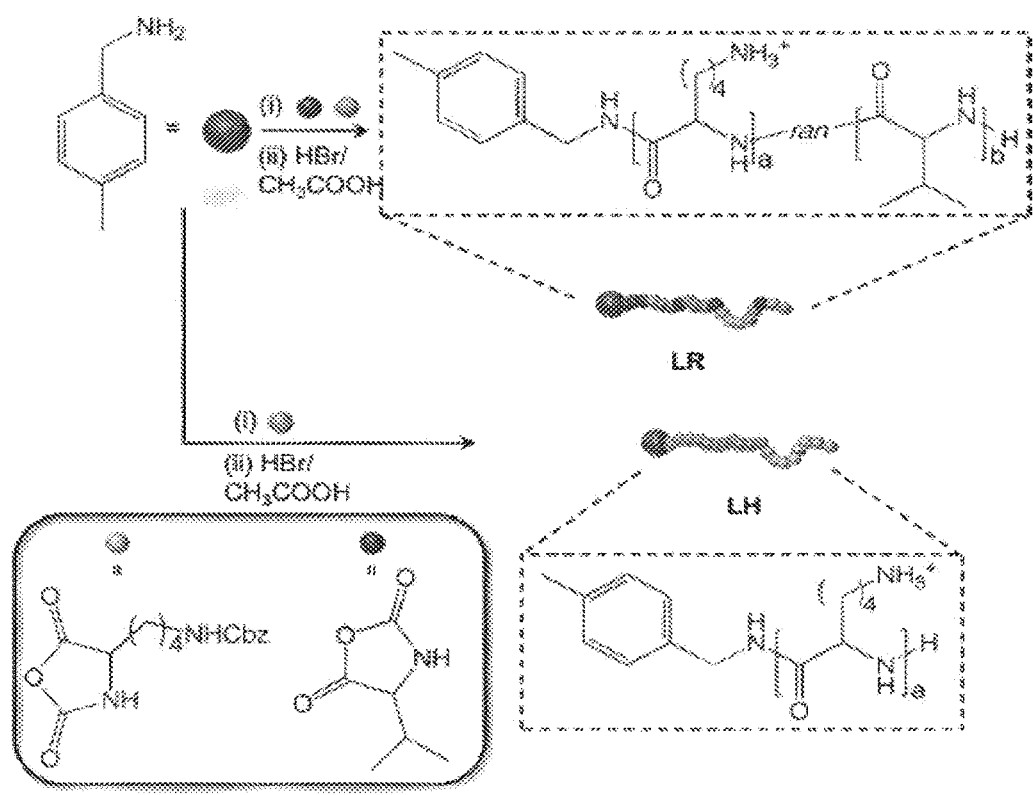
FIG. 50: Synthesis of linear polypeptides via the ROP of lysine NCA only or mixtures of lysine NCA and valine NCA initiated by 4-methylbenzylamine, followed by deprotection of the carboxybenzyl groups on the lysine residues with HBr and subsequent dialysis in RO water to afford water-soluble linear polypeptides LH and LR, respectively.
Figure 51:
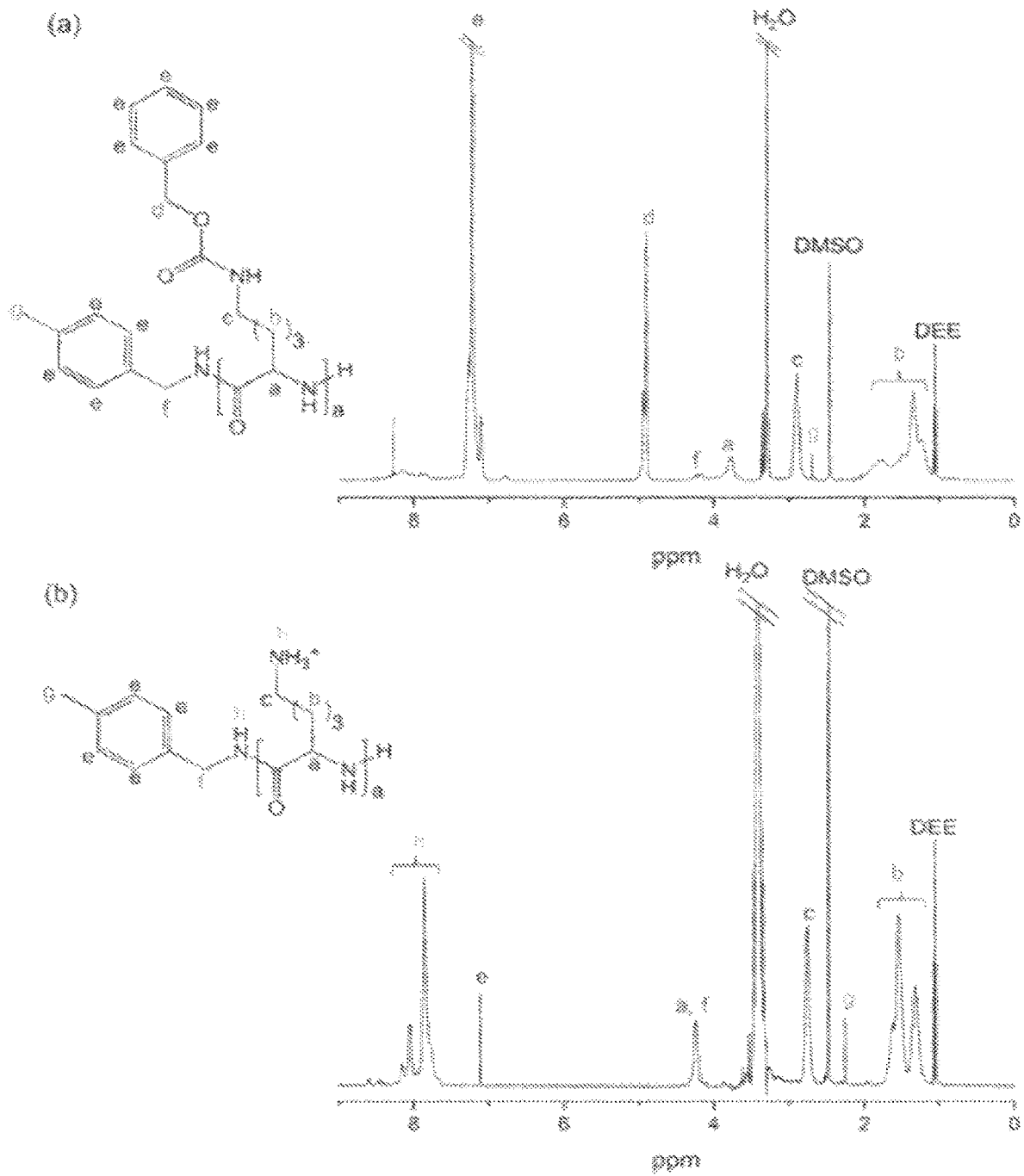
FIG. 51: 1H NMR spectra (d6-DMSO) of (a) linear Cbz-protected polymer LHZ and (b) deprotected polymer LH.
Figure 53:
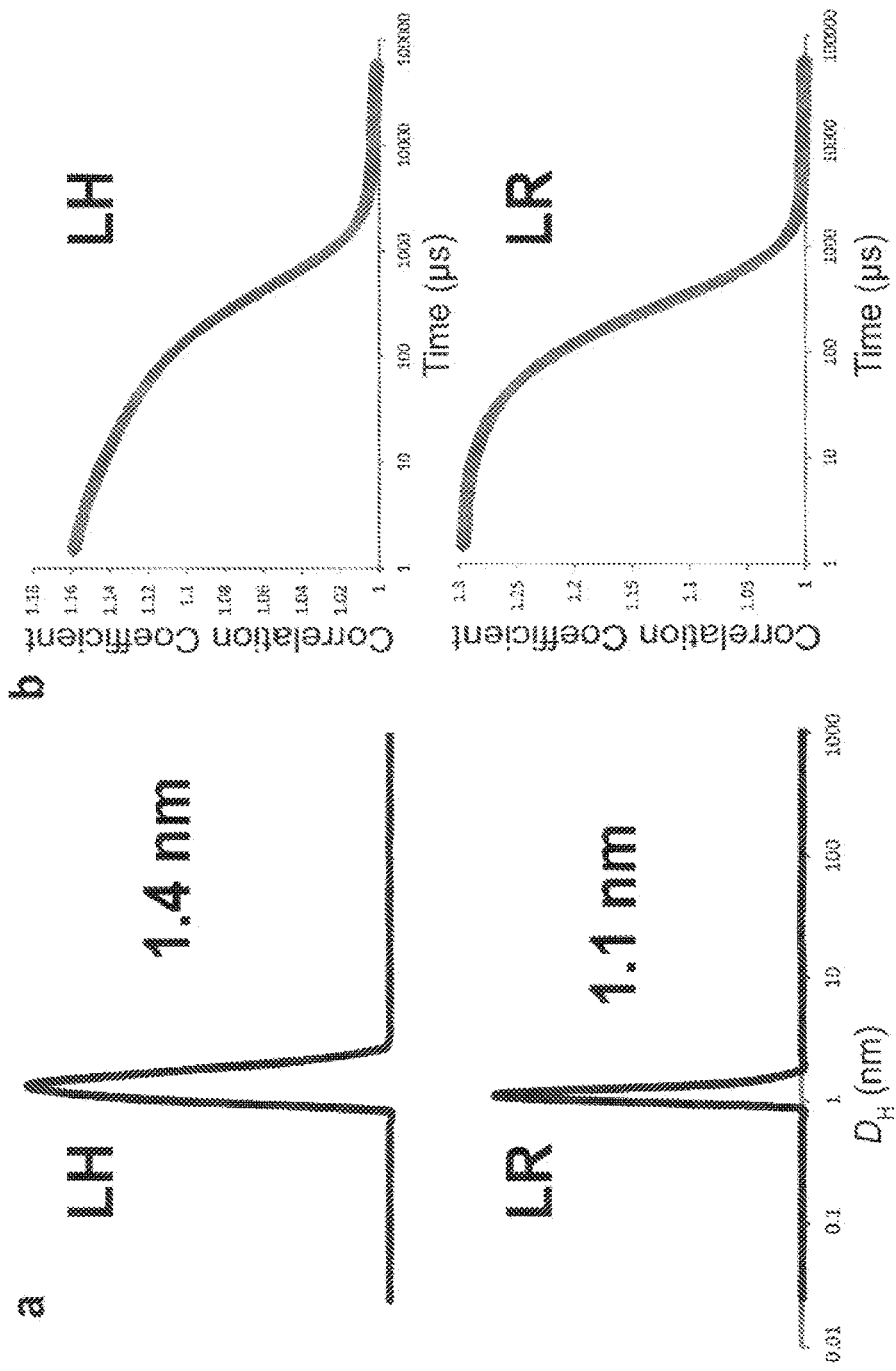
FIG. 53: DLS analysis of the linear polypeptides

In order to characterize the solvated dimensions of the star polypeptides, dynamic light scattering (DLS) analysis was conducted in water. The particle size distribution of each polymer was monomodal with hydrodynamic diameters (DH) that range from 7.5 to 16.8 nm (FIG. 49). Using aqueous gel permeation chromatography, the molecular weight characteristics of all deprotected star polypeptides were determined relative to poly(ethylene glycol) (PEG) standards (Table 14).

Antimicrobial Properties of Star Polypeptides

The antibacterial efficacy of the star polypeptides against *Escherichia coli* and *Staphylococccus aureus*—commonly used model Gram-negative and positive bacteria, respectively—is presented in Table 15. The antimicrobial activities were assessed in nutrient-rich media (i.e., undiluted Mueller-Hinton broth, MHB, for *E. coli* and Luria broth, LB, for *S. aureus*) to ensure optimum bacterial growth. Firstly, as we have previously demonstrated that the bactericidal action of SNAPPs involved membrane disruption, the ability of the star polypeptides synthesized herein to disrupt bacterial membranes was evaluated via determination of their minimum membrane disruptive concentrations (MDCs). The MDC is defined as the minimum drug (in this case, polypeptide) concentration that causes membrane disruption in all cells, and was determined using a combination of nucleic acid staining and a high throughput flow cytometric analytical protocol as previously reported by us (O'Brien-Simpson et al. PLoS ONE 2016, 11, e0151694). The MDC assay is a rapid and quantitative method that enables the assessment of antimicrobial activities by measuring peptide-bacteria interactions and lysed cell numbers. Compared to growth-based minimum bactericidal concentration (MBC) and minimum inhibitory concentration (MIC) assays that require at least an overnight incubation, the use of flow cytometry enables MDC determination to be completed within 90 min.

Star polypeptide SR16 with random copolypeptide arms was the most effective at causing membrane disruption, with MDCs of 0.8 and 1.0 μM against *E. coli* and *S. aureus*, respectively. By comparing these values to those of several common AMPs, such as ovispirin, magainin II, alamethicin, and caerin 1.1, SR16 was found to possess higher membrane disrupting abilities by at least one order of magnitude. On the other hand, star polymer SB16 with block copolypeptide arms registered the highest MDC (i.e., lowest membrane disrupting ability) against *E. coli* compared to the star polymers with random copolypeptide arms and homopeptide PLL arms. Furthermore, within the concentration range tested (≤100 μM), the star polypeptide SB16 did not show any significant disruptive activity towards the membranes of *S. aureus*. This might be expected as the cationic PLL block necessary for interaction with the anionic bacterial cell membrane was shielded by the neutral, outer poly(DL-valine) (PVal) block. Homopeptide star SH16 with cationic arms was more effective than block copolypeptide star SB16 in disrupting the membranes of *E. coli* and *S. aureus*, but was inferior to the random copolypeptide star SR16. Similar trends were also observed for the 32-arm star polypeptides (Table 15). These results elucidate the importance of both peptide composition and sequence in dictating the membrane lysis abilities of these macromolecular antimicrobials. Specifically, the presence of both (i) unshielded cationic segments and (ii) hydrophobic segments is necessary for microbial membrane disruption. While it is postulated that stars having block copolypeptide arms with PLL on the corona and PVal nearer to the core might display membrane lytic properties comparable to or even better than those of stars SR16 and SR32, precipitation of the PVal star (due to aggregation as a result of β-sheet formation) prior to addition of the second block rendered the synthesis of these block copolypeptide stars challenging.

The MDCs of the star polypeptides were compared to their MBCs and MICs (Table 15), which were measured via standard antimicrobial susceptibility testing methods, to provide more comprehensive insights on the effect(s) of the polypeptides on *E. coli* and *S. aureus*. When tested against *E. coli*, the MBCs and MICs of stars SB16, SB32, SR32 and SH16 were in agreement with their respective MDCs. This indicated that membrane disruption (as indicated by the MDC) and cell death (as indicated by the MBC and suggested by the MIC) occurred simultaneously for the aforementioned polypeptides. From the antibacterial tests against *S. aureus*, star polymers SB16 and SB32 displayed no MBCs or MICs, which was consistent with their inability to disrupt the membrane of *S. aureus*.

The star polypeptide SH32 was found to be bactericidal against *E. coli*; interestingly its MDC of 2.0 μM was much higher than its MBC of 0.9 μM and MIC of 0.8 μM. These differences indicate that membrane disruption was not the primary mechanism involved in the killing of *E. coli* by polymer SH32. As previously reported by us, the production of reactive oxygen species (ROS) and the induction of apoptotic-like death (ALD) responses were supplementary bactericidal mechanisms of SR16, aside from its primary mode of action—membrane disruption. In the case of star SH32, it is postulated that the supplementary mechanisms could dominate, resulting in the ability of the star to effect cell death even before quantitative membrane disruption. Further, the existence of other antibacterial mechanisms is also possible, such as the inhibition of cellular processes through interactions with other intracellular enzyme or nucleic acid targets. Interestingly, homopeptide stars SH16 and SH32, which were able to quantitatively disrupt the membrane of *S. aureus*, did not register any MBC or MIC against *S. aureus* within the range of concentrations tested. Furthermore, polymer SR16, which was the most effective star polymer in terms of membrane disruption, had an MBC against *S. aureus* that was higher than its MDC. A possible explanation is that while these polymers were capable of disrupting bacterial membranes, membrane disruption itself was not sufficient to induce quantitative death in *S. aureus*. In fact, it is likely that the membrane pores induced by these polymers had low overall stability and half-lives, thereby allowing the fluid lipid bilayers of the bacterial membrane to reorganize and recover from the initial disruptive effects of the polymers. Hence, in the case of SR16, a polymer concentration higher than its MDC (i.e., MBC 4.6 μM) was needed for complete cell death of *S. aureus*. Taken together, these results indicated the complex nature of the antibacterial mechanism of the star polypeptides studied due to the multiple targets involved, which highlighted the importance of performing in-depth mechanistic studies (such as evaluating polymer-membrane interactions through MDC determination as shown) to better understand the structure-activity relationships of antimicrobial polymers in general.

The poor correlation noted between the MICs of several polymers and their respective MBCs and/or MDCs implied that MIC measurements might not be a reliable technique for this class of polymers, possibly due to the interactions between the polymers and medium contents.

It was noted that the MICs of several star polymers are higher than their MDCs and MBCs, such as star SR16 against *E. coli* and star SR32 against *S. aureus*. Typically, MIC values should be at least equal to the MBC values, if not lower, as cell death correlates to the inhibition of growth. The discrepancies observed herein could possibly be attributed to the fact that for the MIC assays, the polymers were incubated with bacterial cells in nutrient broth for an extended duration (i.e., overnight as compared to 90 min for MDC and MBC measurements). Hence, the precision of the MIC measurements could be affected by polymer aggregation as a result of interactions with the nutrient broth components (e.g., proteins). The formation of aggregates with medium contents has been previously observed for SR16, as well as reported in literature for several cationic antimicrobials. The aggregated polymers could scatter spectrophotometer light and interfere with the optical density (OD) measurements, thereby explaining why substantial OD is still present when most cells have been killed in the aforementioned cases.

Further, MBC and MDC assays, which measure bacterial cell death/lysis, are able to provide more conclusive insights on the antibacterial activities of the polypeptides compared to the MIC assay, which evaluates bacterial growth inhibition. Based upon the MDCs and MBCs, it can be concluded that the star polymers with random copolypeptide arms (SR16 and SR32) were superior to other star polymers in the library, displaying excellent activity against *E. coli* and satisfactory potency against *S. aureus*.

Overall, all star variants were also found to be more effective against *E. coli* than *S. aureus*.

Effect of the Star Architecture on the Antimicrobial Efficacy of Polypeptides

To investigate the effect of the star architecture on antibacterial activity, linear homo (LH) and random (LR) polypeptide analogues were prepared for comparison. While polypeptide LH was synthesized to represent one arm of stars SH16 and SH32, the polypeptide LR is the linear analogue (one arm equivalent) of stars SR16 and SR32. It should be noted that linear counterparts of star polypeptides SB16 and SB32 were not synthesized as the linear amphiphilic block copolymers could possibly self-assemble or aggregate in solution, making them unreliable for any systematic comparison. Further, the preparation of linear, amphiphilic polypeptides with similar molecular weights as the stars (>500 repeat units needed) was not possible synthetically, which highlighted the advantage of the star polymer platform in synthesizing high molecular weight, stable and covalently-linked peptides that are hard to access via other methods. Details characterization the linear polypeptides are shown in FIG. 50-53, and in Table 16 which provides the lysine-to-valine ratio.

The antibacterial properties of the linear polypeptides are provided in Table 15. The amphiphilic star polypeptides SR16 and SR32 possessed efficacy against both *E. coli* and *S. aureus*, while their linear analogue LR was poorly active with an MBC that was 40-fold higher. In this study, by evaluating the MDCs and MICs, we validated that LR displayed weak antibacterial action, both in terms of bacterial membrane disruption and growth inhibition, with an MDC that was 14-fold higher than those of the stars and no MIC recorded within the range of concentrations tested (≤100 µM). In the case of the purely cationic PLL polymers, the star polymers SH16 and SH32 were found to exhibit enhanced antimicrobial activity compared to the linear analogue LH, albeit to a lesser extent (5 to 15-fold in terms of the MBCs) compared to the random copolypeptides.

To investigate whether this observation applies to other bacteria, antimicrobial testing was conducted on another bacterial species, *Streptococcus mutans*. As expected, the amphiphilic star polypeptides SR16 and SR32 displayed good bactericidal activity (MBC 1.8-3.6 µM), while LR was ineffective as shown in Table 17.

These results strongly suggested that the star architecture had a significant effect on enhancing the antimicrobial effect of polypeptides, especially random copolypeptides, against a range of Gram-positive and Gram-negative bacteria.

Figure 54:
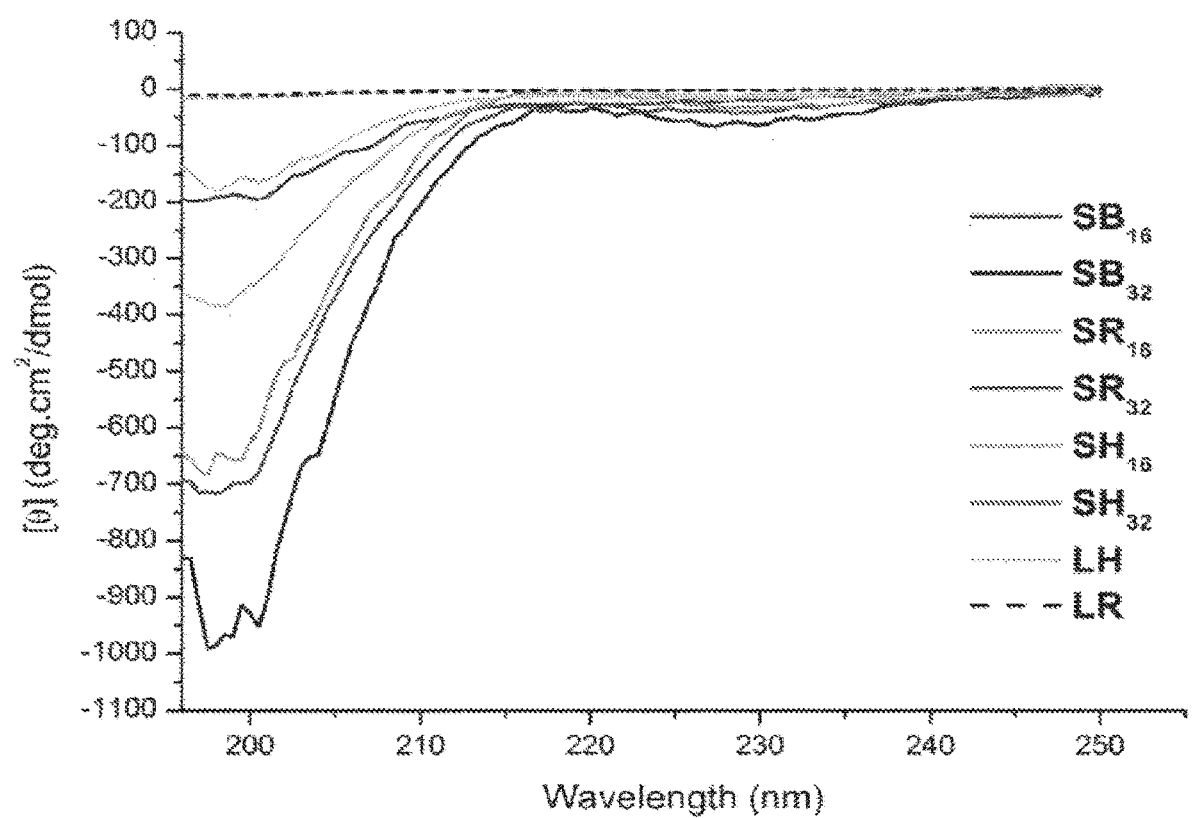
FIG. 54: CD spectra of the star and linear polypeptides (at a concentration of 0.2 mg/mL) in RO water.
Figure 55:
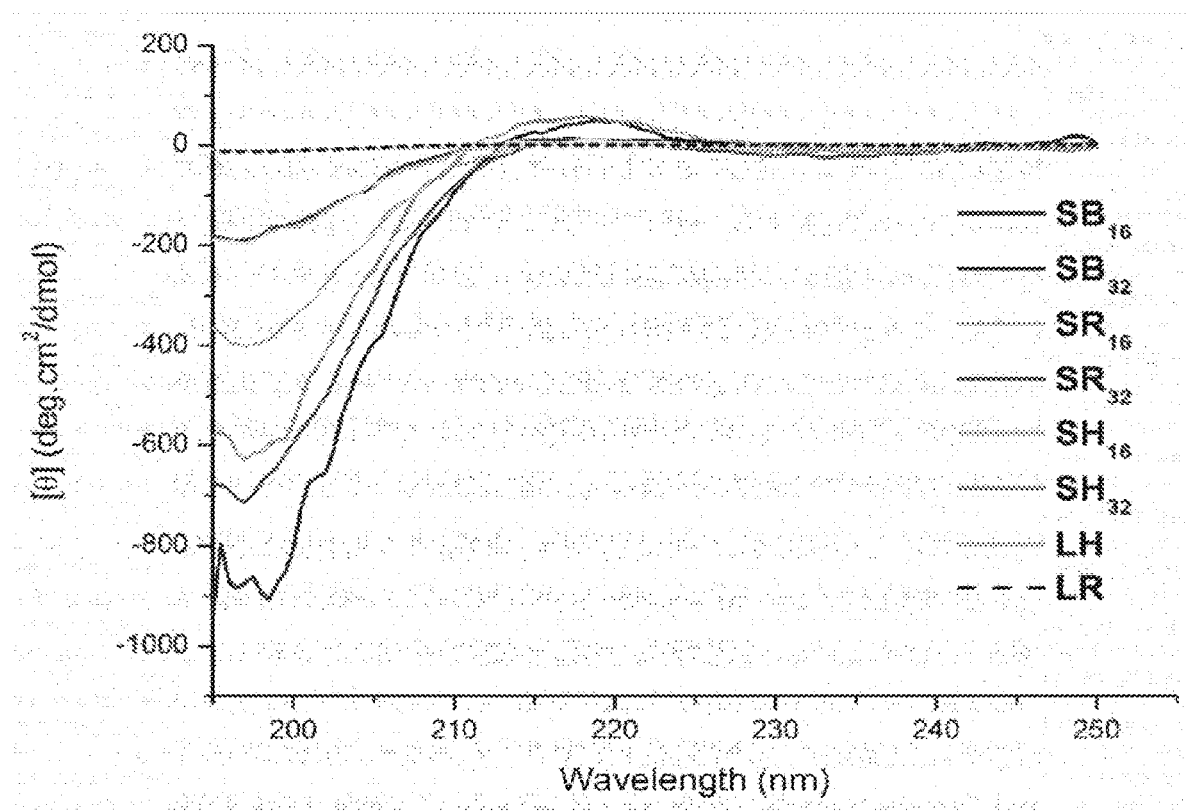
FIG. 55: CD spectra of the star and linear polypeptides (at a concentration of 0.2 mg/mL) in RO water with 20% v/v TFE.
Figure 56:
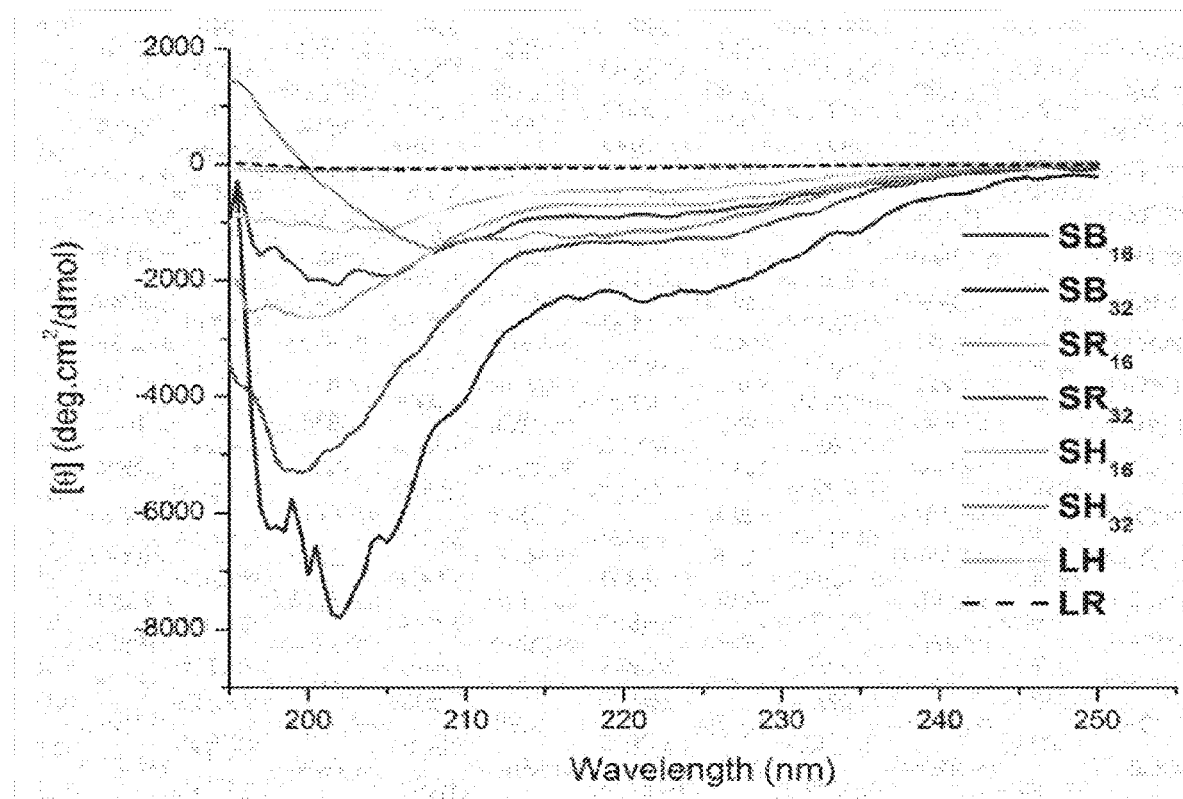
FIG. 56: CD spectra of the star and linear polypeptides (at a concentration of 0.2 mg/mL) in RO water with 50% v/v TFE.
Figure 57:
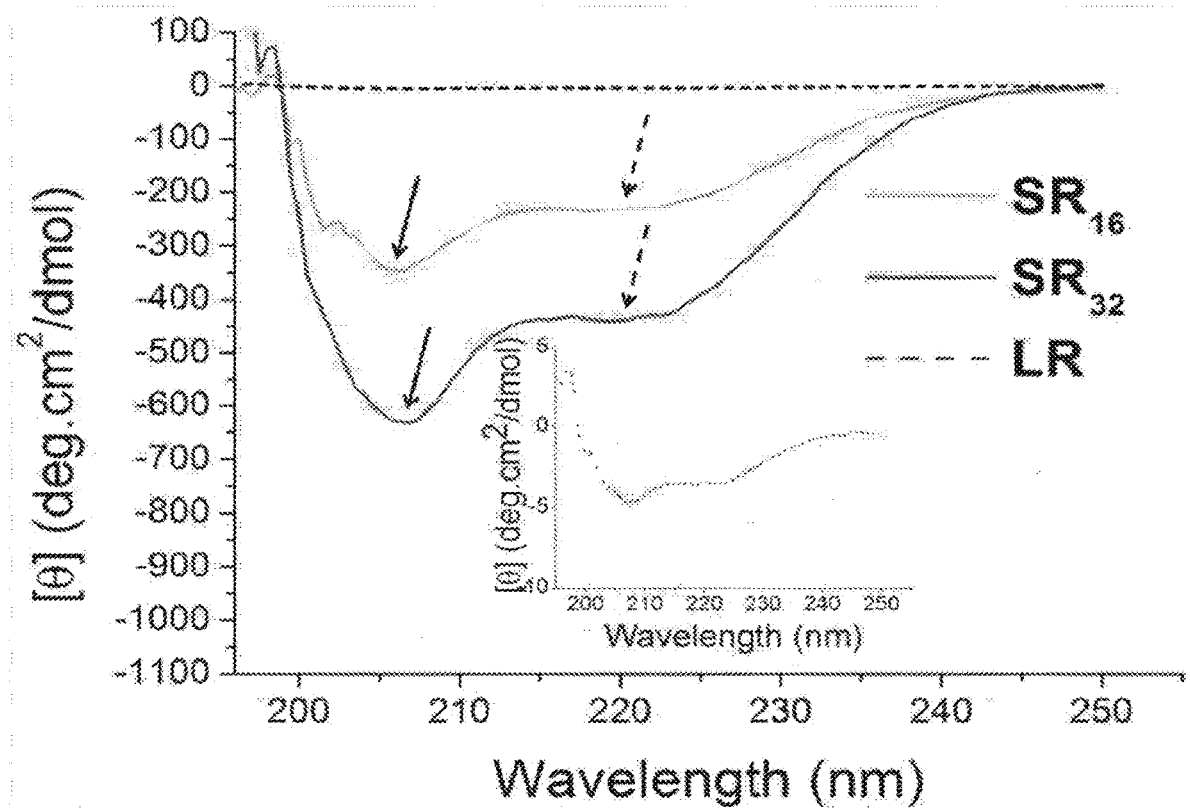
FIG. 57: CD spectra of SR16, SR32 and LR (at a concentration of 0.2 mg/mL) in RO water with 80% v/v TFE. The arrows point towards the troughs on the spectra for SR16 and SR32, which are characteristic of α-helices. Arrows with solid line: Characteristic troughs between 205 and 210 nm. Arrows with dotted line: Characteristic troughs at 220 nm. Inset: Expanded view of the CD spectra of LR.
Figure 58:
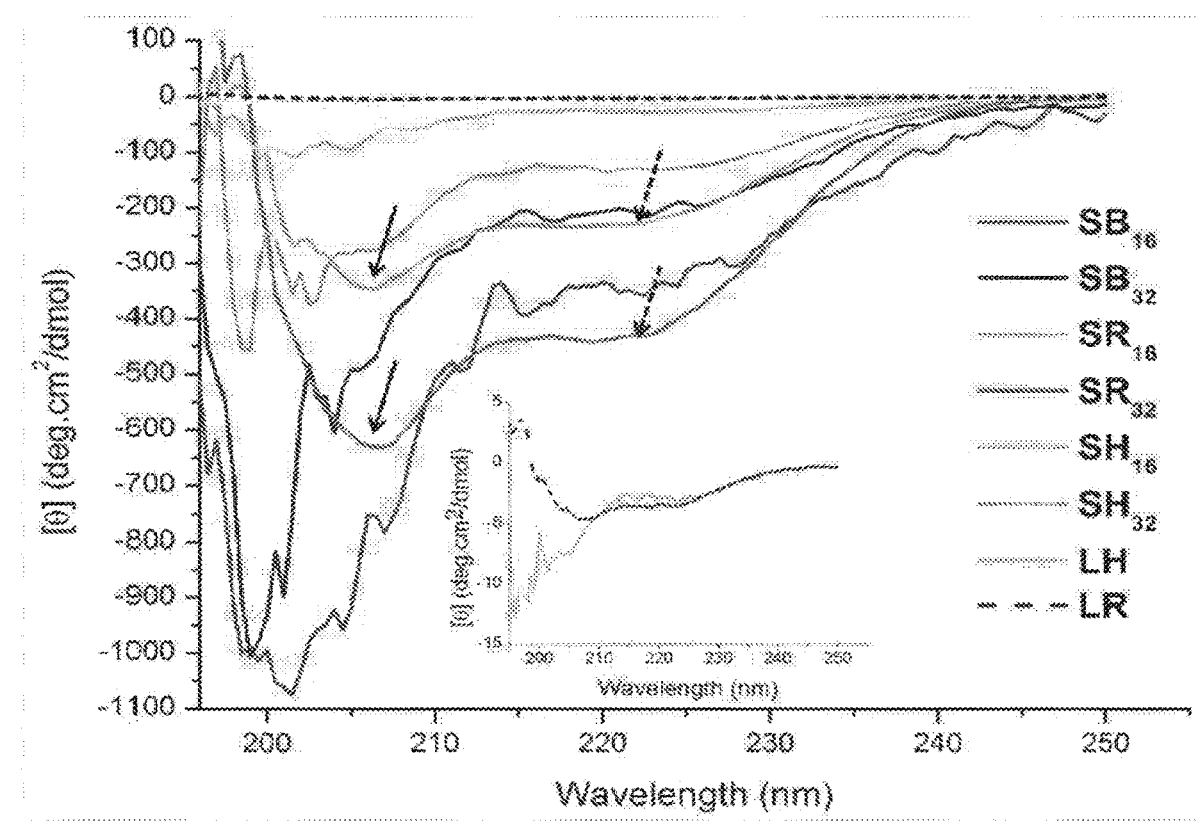
FIG. 58: CD spectra of the star and linear polypeptides (at a concentration of 0.2 mg/mL) in RO water with 80% v/v TFE. The arrows point towards the troughs on the spectra for SR16 and SR32, which are characteristic of α-helices. Arrows with solid line: Characteristic troughs between 205 and 210 nm. Arrows with dotted line: Characteristic troughs at 220 nm. Inset: Expanded view of the CD spectra of LH and LR.

To further investigate the rationale behind this observation, CD spectroscopy was used to assess the secondary structure of the star and linear polypeptides in water with incremental additions of trifluoroethanol (TFE). TFE, which is a well-known secondary structure inducer, is commonly used to mimic the hydrophobic cell membrane environment. By progressively increasing the amount of TFE in an aqueous environment, we investigated the propensity of the polypeptides to form distinct secondary structure. At 0, 20 and 50% v/v TFE, none of the polypeptides exhibited any distinct secondary structures (FIGS. 54-56). Interestingly, when the amount of TFE was increased to 80% v/v, SR16 and SR32 displayed distinct spectra characteristic of α-helices (FIG. 57). The linear analogue of these star polypeptides (i.e., LR), on the other hand, displayed only a very weak (almost negligible) α-helical character as indicated by the low intensity of the spectrum relative to those of SR16 and SR32 (FIG. 57). No distinct secondary structure was observed for any of the other polypeptides (FIG. 58). The CD spectroscopy results demonstrated that the star polypeptides SR16 and SR32 had the propensity to adopt α-helical structures in a hydrophobic environment (mimicked by the 80% v/v TFE solution), and indicated a strong correlation between α-helicity and the excellent antibacterial activities of the polymers against *E. coli, S. aureus*, and *S. mutans*. It was therefore hypothesized that the star architecture amplified the α-helical character of the random copolypeptides when in contact with bacterial membranes, which possibly contributed to the excellent potency of SR16 and SR32 against bacteria compared to their linear analogue. It is known that the most abundant class of AMPs adopts an α-helical conformation in hydrophobic environments and helicity has been demonstrated in some studies to be crucial for the antimicrobial activity of these peptides. However, it is important to note that while the potency of star polypeptides SR16 and SR32 may be correlated to α-helicity in this study, α-helicity is not a prerequisite for the antimicrobial activity of all peptides, as α-helicity has previously been disregarded as imperative for the antimicrobial efficacy of certain peptides.

While the star architecture (from a peptide valency of 1 to 16) was found to enhance antimicrobial activity, our results suggested that increasing the number of star arms from 16 to 32 did not result in any substantial improvement in antimicrobial efficacy, and no obvious trends in MDCs, MBCs and MICs could be detected.

Polypeptide Biocompatibility

As an initial test of biocompatibility, the hemolytic activities were assessed of all polypeptides (which are their abilities to lyse red blood cells (RBCs)) by incubating them with RBCs at different polypeptide concentrations. While the star architecture and peptide (co)polymer structure were shown to influence antimicrobial activity significantly, these factors did not seem to have an effect on the hemocompatibility of the polypeptides. Minimal hemolysis was demonstrated for all the polypeptides used in this study and even at a high concentration of 1 mg/mL, the extent of hemolysis was well below 50% (see FIG. 59, see also Table 18 and Table 19 below). This is in contrast to other synthetic polymers that reported good antimicrobial efficacy but also possess high hemolytic activity. By comparing their MBCs against *E. coli* to their hemolytic activities (based on extrapolated $HC_{50}$, i.e., the 50% hemolytic concentration), the polypeptides displayed favourable TIs (determined as $HC_{50}/MBC_{50}$), with the highest indices shown by SR16, SR32, SH32, and LH (i.e., 126-223) (Table 18 and Table 19). When compared to the TIs of several AMPs known to be effective against Gram-negative bacteria, including magainin II, ovispirin and melittin (TIs 0.2-15, Table 19), the polypeptides developed in this study demonstrated higher selective toxicity against bacteria. The low hemolytic activities of the polypeptides, despite having strong antibacterial properties, could be attributed to the fact that the RBC membranes comprise neutral outer leaflets and slightly negatively charged inner leaflets at physiological pH, while bacterial membranes are highly negatively charged. Consequently, the electrostatic interaction between the cationic polypeptides and the RBC membranes was not as strong as that between the polypeptides and the bacterial membranes.

Figure 60:
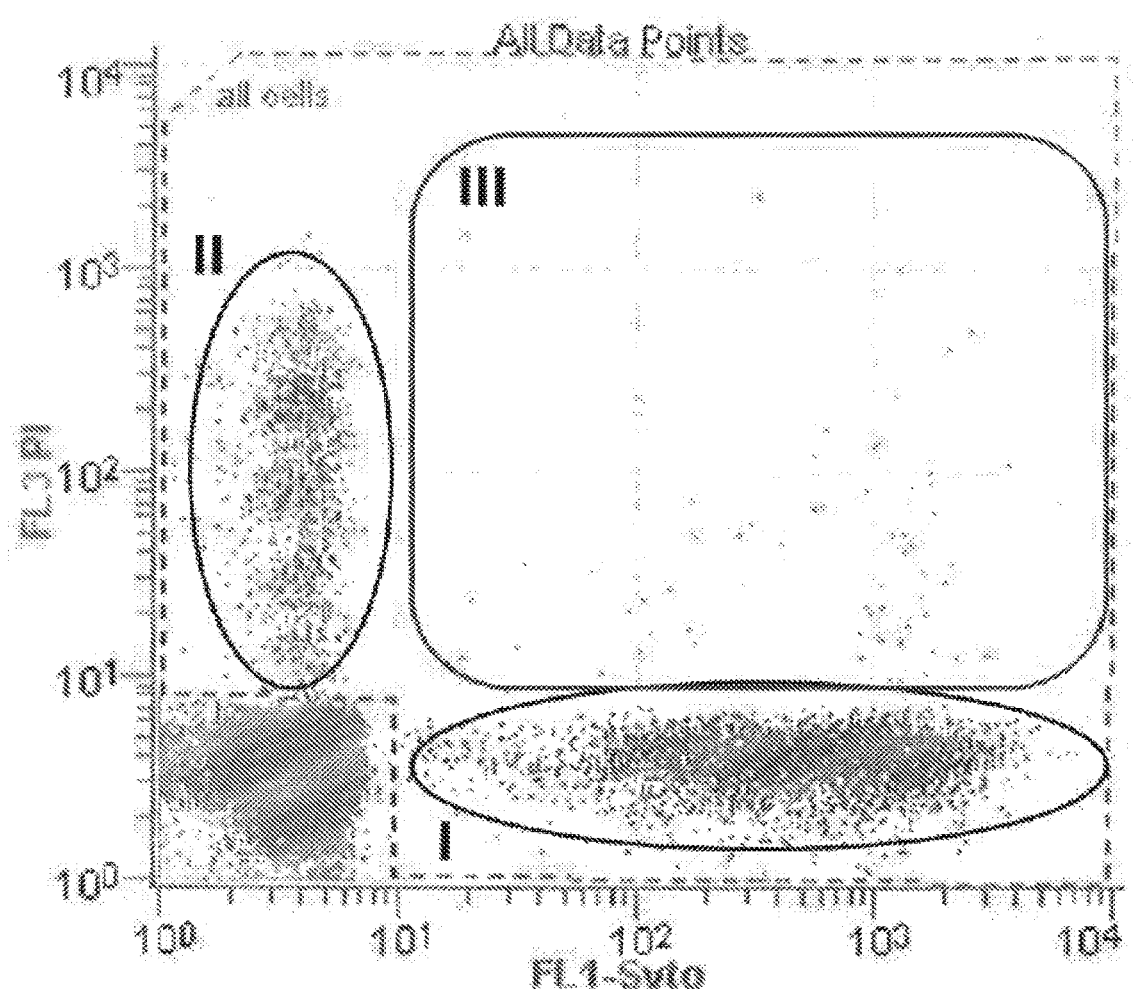
FIG. 60: Diagram explaining the interpretation of data obtained from Cytomics FC 500 flow cytometer. A two-parameter dot plot is obtained whereby cell counts are shown by dot density. The x-axis represents fluorescent channel 1 (FL-1) which measures the fluorescent emission by YO-PRO-1. The y-axis represents fluorescent channel 2 (FL-2) which measures the fluorescent emission by PI. M2: YO-PRO-1-positive, PI-positive cells i.e., the population of necrotic cells in the sample. M3: YO-PRO-1- and PI-negative cells i.e., the population of viable cells in the sample. M4: YO-PRO-1-positive, PI-negative cells i.e., the population of early apoptotic cells in the sample. By evaluating the percentage of cells in M2, M3 and M4, the percentage of viable, necrotic, and early apoptotic cells, respectively, can be obtained.
Figure 61:
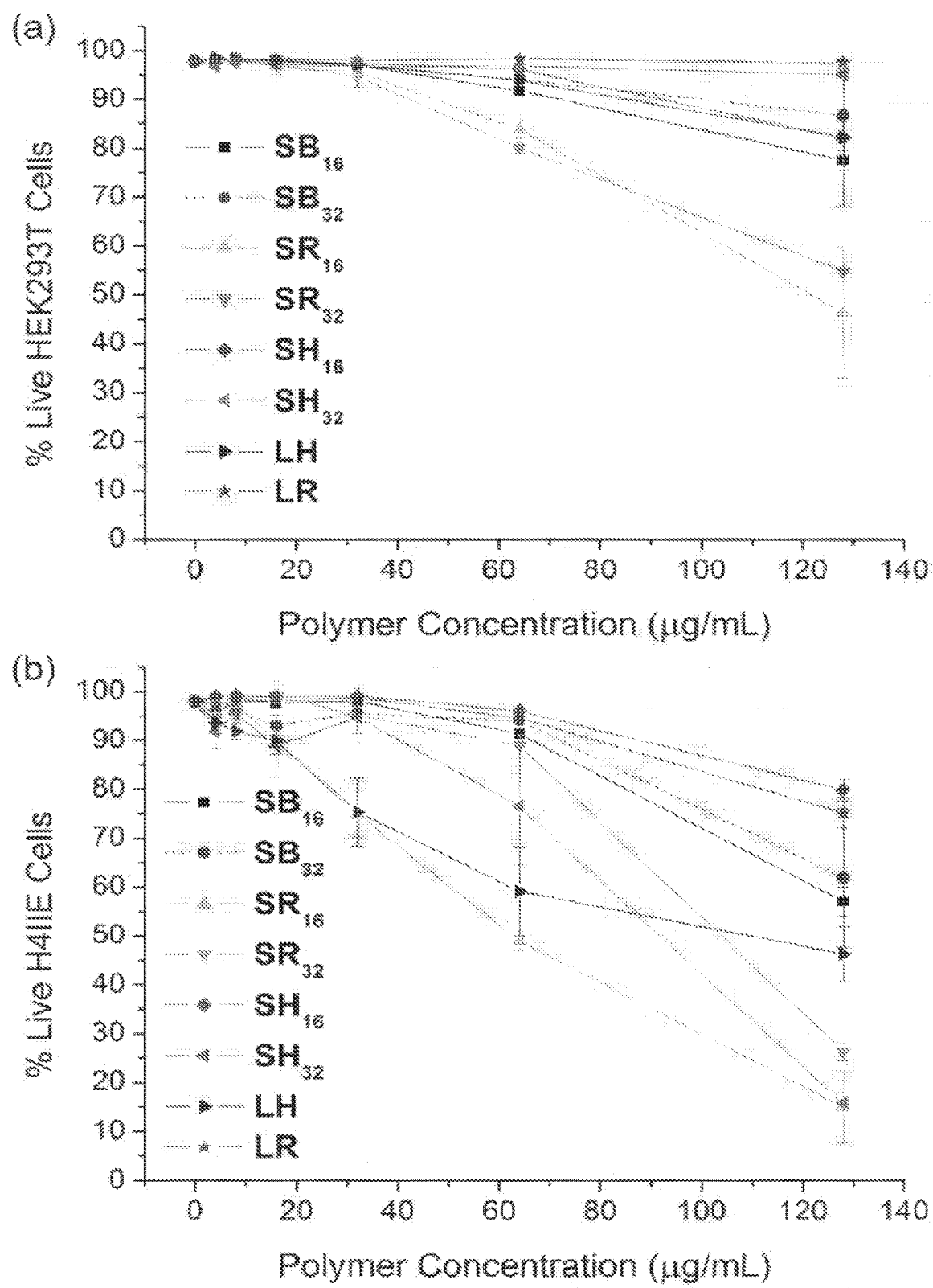
FIG. 61: Percent viable (a) HEK293T and (b) H4IIE cells as a function of polypeptide concentration. Viable cells are defined as cells which were PI- and YO-PRO-1-negative. Error bars represent the standard deviation from the mean (n=4).
Figure 63:
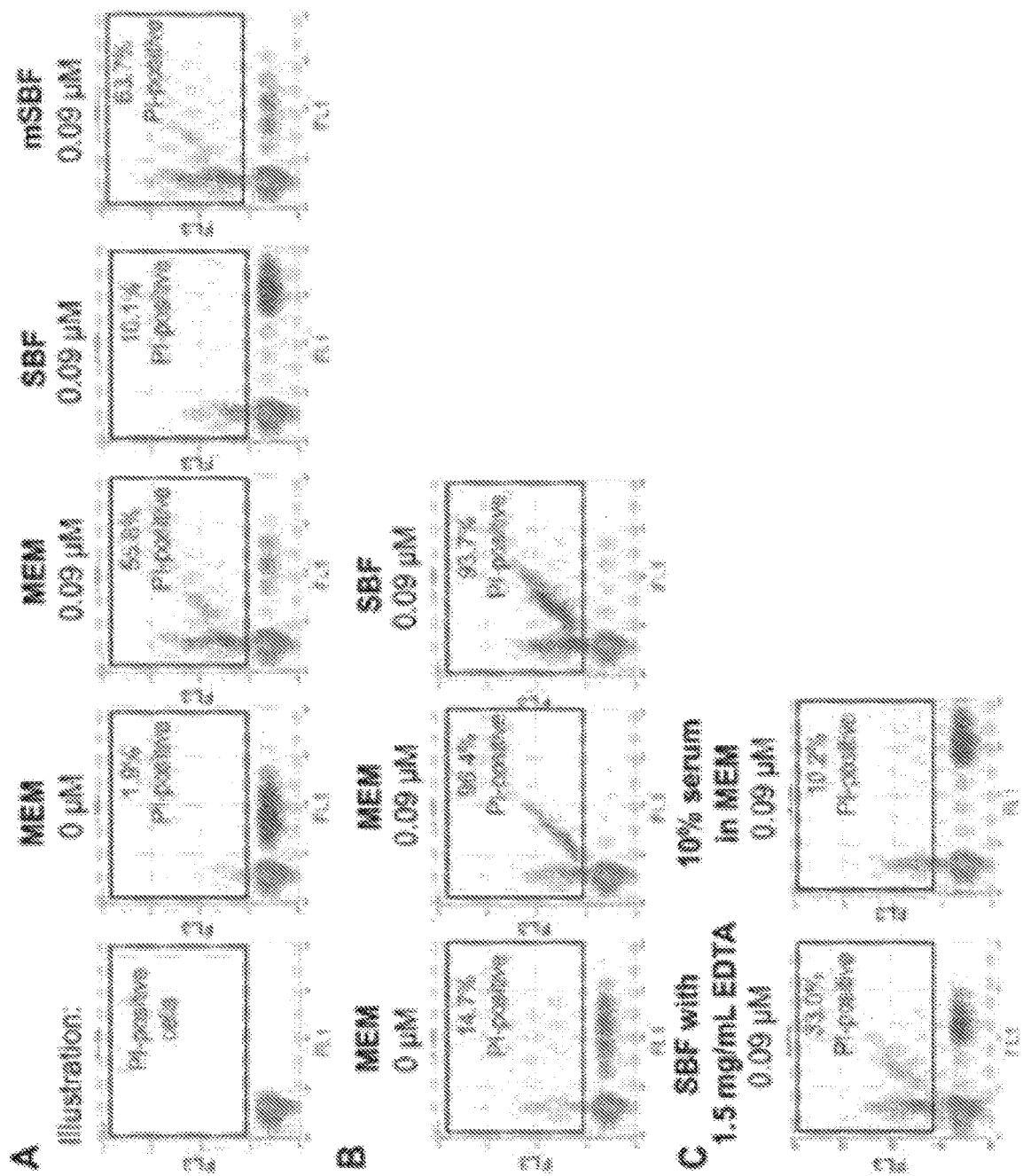
FIG. 63: Uptake of propidium iodide (PI) by $E.$ $coli$ and $A.$ $baumannii$ cells before and after treatment with SNAPP S16. $E.$ $coli$ (A, C) or $A.$ $baumannii$ (B) cells were incubated with S16 for 90 min at a sub-MIC of 0.09 µM. After incubation the cells were stained with SYTO® 9 and PI nucleic acid dyes prior to analysis. On the two-parameter dot plots obtained by flow cytometry, the x-axis represents fluorescent channel 1 (FL1), which measures the fluorescent emission of SYTO® 9. The y-axis represents fluorescent channel 3 (FL3), which measures the fluorescent emission of PI. Cells were determined to be 'PI-positive' if fluorescence emitted is captured by FL3. Controls whereby no S16 was added (0 µM) were included. For $E.$ $coli$, the assays were conducted in MEM (A), SBF (A), mSBF (A), 10% serum in MEM (C), or SBF with 1.5 mg/mL EDTA (C). For $A.$ $baumannii$, assays were conducted in either MEM or SBF (B).

Subsequently, the viability of two types of mammalian cells, human embryonic kidney (HEK293T) cells and rat hepatoma (H4IIE) cells, in response to the polypeptides was investigated. The adhered cells were incubated with the polypeptides for 90 minutes, stained with YO-PRO-1 and PI dyes, and analyzed by flow cytometry. Using YO-PRO-1 as an indicator of early apoptosis and PI as a measure of necrosis or cell death, viable cells were determined as cells that were negative for both YO-PRO-1 and PI (FIG. 60). The polypeptides were found to induce both apoptosis and necrosis, but to varying extents. When tested against HEK293T cells, star polypeptides SR16 and SR32 were found to have $IC_{50}$ values (i.e., peptide concentrations that result in 50% cell death) of 121.8 µg/mL (2.8 µM) and 128 µg/mL (1.7 µM), respectively (Table 18). However, for the other polypeptides, cell viability remained relatively high (i.e., at least 80%) even at the highest concentration tested (i.e., 128 µg/mL) (FIG. 63a). Against H4IIE cells, the polypeptides are slightly more cytotoxic, with SR16, SR32, SH32, and LH found to reduce the cell viability by more than 50% at 128 µg/mL (see FIG. 61, Table 18, and Table 20)

The cell line-dependent cytotoxic effects shown here were not unexpected, as similar observations have been reported for other polymeric nanoparticles and were attributed to the differences in resistance between different cell lines. It is interesting to note that while star polypeptides SR16 and SR32 were found to have excellent antibacterial efficacies compared to the other polypeptides, they displayed toxicity towards mammalian cells that was higher than most of the other polypeptides as well. In spite of this, against certain bacterial species such as *E. coli*, these star polypeptides were bactericidal at concentrations which were a few times (i.e., 4 to 8 times) lower than those needed to kill mammalian cells. However, it should be noted that different environmental conditions were used in determining the $IC_{50}$ and MBC$_{50}$ values, where the media used for the antimicrobial susceptibility tests had higher protein contents than that used in determining IC$_{50}$. As shown in our previous study, an increase in antimicrobial efficacy was observed when the antimicrobial assays were conducted in minimal essential medium (MEM) used for mammalian cell growth. Hence, by comparing the MBC$_{50}$ values determined in MEM to the IC$_{50}$ values, SR16 and SR32 were found to possess TIs (IC$_{50}$/MBC$_{50}$) that ranged from 16 to 57 (see Table 21). These indices are more favourable compared to a range of commercial pharmaceutical drugs, such as digoxin (cardiac drug, TI 2-3), fluconazole (antifungal drug, TI ca. 10 against certain fungal strains), amphotericin (antifungal drug, TI ca. 16 against certain fungal strains), gentamicin, and polymyxin B (antibiotics, TI<10 against certain bacterial strains).

In this study, we have successfully synthesized and characterized a library of polypeptides, consisting of 16- and 32-arm star polymers with different peptide arrangements along the arms, as well as their linear analogues. Combining advanced flow cytometery techniques with traditional antimicrobial susceptibility assays, the antimicrobial properties of the polypeptides were determined. Among the star polypeptides, stars with random copolypeptide arms of lysine and valine were found to efficiently disrupt the membranes and kill model Gram-positive and Gram-negative bacteria, with superior performance compared to the block copolypeptide and homolysine stars. Based on secondary structure analysis, the enhancement in antimicrobial efficacy observed by the star polypeptides with random copolypeptide arms was possibly attribute to their ability to adopt α-helical conformations in the presence of hydrophobic environments. Importantly, no significant hemolytic activity was observed for the polypeptides over a wide range of concentrations, regardless of polypeptide composition and copolymer structure. Although the random copolypeptide star polymers induced greater toxicity towards mammalian cells compared to the other polypeptides studied, their therapeutic indices were still found to be favourable as a result of their excellent antimicrobial activity. This study highlights the potential of the star architecture with random copolypeptide arms as a new design motif to develop highly potent but safe antimicrobial polypeptides that could potentially kill a wide range of multi-drug resistant and clinically significant bacteria.

Example 8

In this study we investigated the bio-nano interactions between SNAPPs and biological molecules, and the effects of such interactions on the antibacterial efficacy and mechanism of SNAPPs. To the best of our knowledge, such studies are rare in the field of antimicrobial research and no study has been reported on polymer-based macromolecular antimicrobials, as the few investigations that have been conducted in this area were mostly focused on antibiotics and linear AMPs. Our study was achieved by assessing the antimicrobial efficacy of SNAPPs in media that mimic the ionic and protein composition in vivo. Specifically, we tested SNAPPs against four different Gram-negative bacterial species in simulated body fluid (SBF)—a solution with an ion concentration similar to that in blood plasma—and animal serum, which contains physiologically relevant salt and protein concentrations. The effects of polymer-medium interactions on the bactericidal action of SNAPPs were further probed by using OM and IM permeability assays based on fluorometric assessment and flow cytometry. Based on our observations, we suggest and demonstrate a strategy to improve the effectiveness of SNAPPs against bacteria under physiological conditions.

Materials

Sodium chloride (NaCl, Chem-Supply), potassium chloride (KCl, Chem-Supply), sodium phosphate dibasic (Na2HPO4, Chem-Supply), potassium phosphate monobasic (KH2PO4, 99%, Aldrich), sodium bicarbonate (NaHCO3, ≥99.5%, Aldrich), potassium phosphate dibasic trihydrate (K2HPO4·3H2O, ≥99.0%, Aldrich), magnesium chloride hexahydrate (MgCl2·6H2O, 99.0-102.0%, Aldrich), hydrochloric acid (HCl, Chem-Supply), calcium chloride (CaCl2, ≥99.9%, Aldrich), sodium sulphate (Na2SO4, ≥99.0%, Aldrich), Tris base (NH2C(CH2OH)3, Aldrich), ethylenediaminetetraacetic acid disodium salt dihydrate (EDTA, 99.0-101.0%, Aldrich), N-phenyl-1-naphthylamine (NPN, 98%, Aldrich), D-(+)-glucose solution (100 g/L, Aldrich), HEPES (1 M, GIBCO Cat. No. 15630, Life Technologies), MEM non-essential amino acids (100, GIBCO Cat. No. 11140, Life Technologies), fetal bovine serum (FBS, GIBCO Cat. No. 10099, Life Technologies), SYTO® 9 green fluorescent nucleic acid stain (Cat. No. S-34854, Life Technologies), propidium iodide (PI, 1.0 mg/mL solution in water, Cat. No. P3566, Life Technologies), bovine serum albumin (BSA, Bovogen Biologicals), Blood Agar Base No. 2 (CM0271, Oxoid, Mueller-Hinton broth (CM0405, Oxoid), yeast extract (LP0021, Oxoid), tryptone (LP0042, Oxoid), Bacto™ Agar (BD Biosciences), and fresh defibrinated horse blood (Commonwealth Serum Laboratories, Melbourne) were used as received. 96-well cell culture plates (Greiner Bio-One) were used for cell culture.

SNAPPs were synthesized and characterized based on the materials and methods as described herein.

Instrumentation.

Bacterial cell sample analysis was performed using a Cell Lab Quanta SC MPL flow cytometer (Beckman Coulter) equipped with a 100 W stabilized mercury arc lamp with wavelengths of 365, 404, and 435 nm, and a 488 nm diode laser. The fluorescence from SYTO® 9 was measured through a 525-nm band-pass filter (Fluorescent Channel 1, FL-1), and the red emission of PI was measured with a 670-nm long pass filter (Fluorescent Channel 3, FL-3). The multiparametric data were analyzed using the Cell Lab Quanta SC software.

Bacterial Strain, Culture Media and Growth Conditions.

Freeze-dried cultures of *Escherichia coli* (*E. coli*, ATCC 25922), *Klebsiella pneumoniae* (*K. pneumoniae*, ATCC 13883), *Acinetobacter baumannii* (*A. baumannii*, ATCC 19606), and *Pseudomonas aeruginosa* (*P. aeruginosa*, ATCC 47085) were grown aerobically and maintained by passage at ambient temperature on horse blood agar (10% v/v defibrinated horse blood, 4.4% w/v Oxoid Blood Agar Base No. 2). Overnight cultures were made from transferring a colony from the agar plates to culture tubes containing sterilized Luria-Bertani broth (LB, 1% w/v tryptone, 1% w/v NaCl, 0.5% w/v Oxoid Yeast Extract) (20 mL). Bacterial cultures were incubated overnight at 37° C. with aeration and without agitation. On the next day, for *E. coli*, *K. pneumoniae*, and *P. aeruginosa*, small aliquots (i.e., 0.5-2 mL) were taken from the culture tubes, further diluted with LB (20 mL), and incubated for 3-4 h at 37° C. with aeration before use. All bacterial cultures were cultured without agitation, with the exception of *P. aeruginosa* which was cultured with shaking at 150 rpm. For *A. baumannii*, an aliquot of 0.5 mL was taken from the overnight culture tube, further diluted with LB (200 mL), and incubated overnight at 37° C. with aeration before use.

Bacterial Cell Counting.

Prior to use in assays, the bacterial cells were pelleted (3000 g, 10 min, 25° C.), washed and resuspended in the relevant medium (20 mL). A Cell Lab Quanta SC 28 MPL flow cytometer was used to count the number of bacterial cells. Cells were diluted with saline using an appropriate dilution factor and incubated with SYTO® 9 and PI (i.e., 1 mL cell solution to 1 μL of each dye). SYTO® 9 stains the nucleic acids in all cells, while PI stains the nucleic acids in cells with damaged membranes. Using the Cell Lab Quanta SC software, the number of viable cells/mL (SYTO® 9-positive, PI-negative) was obtained.

Measurement of Minimum Inhibitory Concentrations (MIC).

The MICs of SNAPPs S16 and S32 were determined using a broth microdilution method. Nine types of media were used for the assay: minimal essential medium (MEM; 1×phosphate-buffered saline with 1×MEM non-essential amino acids and 2 g/L D-(+)-glucose), simulated body fluid (SBF; prepared according to the protocol reported by Kokubo et al. 44 and supplemented with 1×MEM non-essential amino acids and 2 g/L D-(+)-glucose), modified SBF (mSBF; prepared in a similar manner to SBF but without the addition of $CaCl_2$ and $MgCl_2.6H_2O$), SBF without $CaCl_2$ (prepared in a similar manner to SBF but without the addition of $CaCl_2$), SBF without $MgCl_2.6H_2O$ (prepared in a similar manner to SBF but without the addition of $MgCl_2.6H_2O$), 10% serum (10% v/v FBS in MEM), 50% serum (50% v/v FBS in MEM), 0.22 mg/mL BSA in MEM, and 1.1 mg/mL BSA in MEM.

A dilution series of each peptide polymer was made by diluting SNAPP stock solutions in medium to a desired range of concentrations and a final volume of 100 μL in each well of a 96-well plate. Bacterial cells (which gave an optical density reading of ca. 0.7 at 650 nm for *E. coli*, *K. pneumoniae*, and *P. aeruginosa*, and ca. 0.5 at 650 nm for *A. baumannii*) were diluted to 2.5×106 cells/mL in medium and 100 μL of the bacteria solution was added to each well. The 96-well plate was then incubated at 37° C. for 90 min, after which Mueller-Hinton broth (MHB, 50 μL, 2.1% w/v Oxoid Mueller-Hinton Broth) was added. The optical density readings of each well at 630 nm were then measured as a function of time over a period of 24 h at 37° C. using a microplate reader (Multiskan Ascent, Pathtech Pty. Ltd.). Positive controls containing cells alone were incorporated. Optical density was plotted against SNAPP concentration and linear regression analysis was used to determine the lowest concentration (MIC) at which the optical density reading becomes zero. A minimum of two independent experiments (biological replicates) of the assay were conducted and two technical replicates were used in each experiment for each bacterial species, peptide polymer, and concentration. Data is expressed as mean±standard deviation (SD) of the biological replicates.

Note that the antimicrobial action of SNAPPs have been shown herein to be fully effected within 90 min. The addition of MHB after the 90 min incubation period was to allow for optimal growth of any remaining viable bacterial cells in the microplate reader.

NPN Uptake (Outer Membrane, OM, Permeability) Assays.

The assays were conducted in either mSBF or SBF. A dilution series of SNAPP S16 was made by diluting S16 stock in medium to concentrations of 0.2 to 11.7 μM and a final volume of 50 μL in each well of a 96-well plate. A 5 mM NPN stock solution in acetone was prepared which was then diluted to 40 μM in the medium of interest before use. S16 (50 μL), NPN (40 μM, 50 μL), and medium (50 μL) were pipetted into the 96-well plates in advance, and either *E. coli* or *A. baumannii* cell suspension (50 μL, 5×106 cells/mL in medium) was added to each well immediately before fluorescence measurement using a microplate reader (PerkinElmer 1420 Multilabel Counter VICTOR3). The fluorescence values were recorded after 5 min and until a plateau was reached. Control wells which included (i) medium alone (200 μL), (ii) medium (150 μL) and bacterial cell suspension (50 μL), (iii) medium (150 μL) and NPN (40 μM, 50 μL), and (iv) medium (100 μL), NPN (40 μM, 50 μL) and bacterial cell suspension (50 μL) were incorporated. For *E. coli*, an additional set was conducted in SBF with EDTA (final concentration of 1.5 mg/mL EDTA) as an additive. The results are expressed in relative fluorescence units (RFUs) where the fluorescence value of cell suspension and NPN (control iv) was subtracted from that of the test well RFUs. A minimum of two independent experiments (biological replicates) of the assay were conducted and two technical replicates were used in each experiment for each bacterial species and S16 concentration. Data is expressed as mean±standard deviation (SD) of the biological replicates.

Inner Membrane (IM) Disruption Assays Using Flow Cytometry.

Briefly, the IM disruption assay was conducted as previously described (O'Brien-Simpson et al. PLoS One 2016, 11, e0151694). Bacterial cells (100 μL, final concentration of 2.5×106 cells/mL) were added to SNAPP S16 (100 μL, final concentration of 0.09 μM) in the relevant medium in a 96-well plate. The plate was then incubated at 37° C. for 90 min. A 50 μL aliquot was taken from each well, transferred to a second 96-well plate and 100 μL of saline and dye mixture (i.e., saline with 0.1% of SYTO® 9 and 0.1% of PI) was added. Each well in the second 96-well plate was analyzed with a Cell Lab Quanta SC MPL flow cytometer to determine the % of cells with intact membranes (PI-negative) and cells with compromised membranes (PI-positive). Positive controls containing cells alone were incorporated. Two independent runs of the assay were conducted and two replicates were used in each run for each bacteria.

Investigating the Effect of EDTA on the MIC of SNAPP S16.

The assays were conducted using the broth microdilution method described above, except that different concentrations of EDTA disodium salt (0.5 to 2 mg/mL) were added to the S16 solution prior to the addition of bacterial cells.

Results and Discussion 16- and 32-arm SNAPPs S16 and S32, respectively, were synthesized via ring-opening polymerization (ROP) of α-amino acid (i.e., lysine and valine)N-carboxyanhydride (NCA) monomers as previously reported (see FIG. 1 for chemical structure). SNAPPs S16 and S32 were found to have hydrodynamic diameters (DH) of 7.7 and 13.5 nm, respectively, in phosphate-buffered saline (PBS, pH 7.4), and number-average molecular weights (Mn) of 43.8 and 74.8 kDa, respectively. We evaluated the minimum inhibitory concentrations (MICs) of SNAPPs against a range of Gram-negative bacteria that include *Escherichia coli*, *Pseudomonas aeruginosa*, *Klebsiella pneumoniae* and *Acinetobacter baumannii*. *P. aeruginosa*, *K. pneumoniae* and *A. baumannii* are referred to as the 'ESKAPE' pathogens, which are responsible for a substantial percentage of hospital-acquired infections and are capable of acquiring antibiotic resistance rapidly. The MICs were firstly determined in MEM, which is a chemically-defined minimal medium supplemented with minimum non-essential amino acids and glucose (Table 22). The MICs of S16 and S32 were found to approximate their minimum bactericidal concentrations (MBCs) (Table 22), indicating that SNAPPs were bactericidal. It is noteworthy that the antimicrobial activities of both S16 and S32 were not species-specific for the range of bacteria tested, as their MICs against different bacterial species were within a similar order of magnitude.

Antimicrobial Studies in Simulated Body Fluid (SBF).

Although MEM is able to sustain bacterial viability for antimicrobial susceptibility testing purposes, its ionic composition does not reflect the type and concentration of salts in vivo. For example, divalent cations such as magnesium ($Mg^{2+}$) and calcium ($Ca^{2+}$) ions, which are present in the blood, are absent in MEM. Therefore, to better reflect the therapeutic efficacy of SNAPPs in vivo, the MICs of the peptide polymers were evaluated in SBF supplemented with amino acids and glucose (see 'Materials and Methods' for composition). The ionic composition of SBF mimics that of human blood plasma, containing $Mg^{2+}$ and $Ca^{2+}$ ions at physiological concentrations. Interestingly, we observed significant reductions ($P<0.05$) in inhibitory activity (as indicated by the increase in MIC values) by at least 9 times from nM to low μM MICs for both S16 and S32 against *E. coli*, *P. aeruginosa* and *K. pneumoniae* when SBF was used as the medium, instead of MEM (Table 22). The antimicrobial activity of S32 against *E. coli* was the most severely antagonized compared to the other polymer-bacteria combinations, as the MIC of S32 against *E. coli* increased more than 30 times from 0.05 μM in MEM to 1.68 μM in SBF.

We hypothesized that the reductions in activity observed were a result of the antagonistic effects exhibited by one or more of the salts in SBF towards SNAPPs. To validate this hypothesis, modified versions of SBF were prepared in the same way as SBF but with certain salts (such as magnesium and/or calcium salts) removed. SNAPP S16 was chosen as the model compound for subsequent studies, and its antimicrobial activity was evaluated in the modified media. The MICs of S16 against *E. coli* were found to be 1.62±0.17 μM in the absence of a magnesium salt ($MgCl_2.6H_2O$) and 0.39±0.01 μM in the absence of a calcium salt ($CaCl_2$), which in both cases were lower than its MIC in SBF. The removal of $Ca^{2+}$ ions resulted in a more substantial recovery in inhibitory activity, although the resulting MIC was still more than double of that in MEM. In modified SBF without both $MgCl_2.6H_2O$ and $CaCl_2$ (hereby denoted as 'mSBF'), the MIC of S16 dropped to 0.22±0.03 μM, which was comparable to its activity in MEM (i.e., 0.17 μM). Similarly, the MIC of S16 against *P. aeruginosa* was reduced by almost 12-fold from 1.64 μM in SBF to 0.14±0.06 μM in mSBF, close to its MIC in MEM.

These observations implied an antagonistic effect of both $Mg^{2+}$ and $Ca^{2+}$ divalent cations on the antimicrobial activity of SNAPPs. Interestingly, in our study, the antagonistic effect displayed by $Mg^{2+}$ and $Ca^{2+}$ seemed to be species-dependent. While the antimicrobial activity of S16 and S32 against *E. coli*, *K. pneumoniae* and *P. aeruginosa* were affected, their activity against *A. baumannii* remained unchanged regardless of the salt composition of the medium used.

Figure 62:
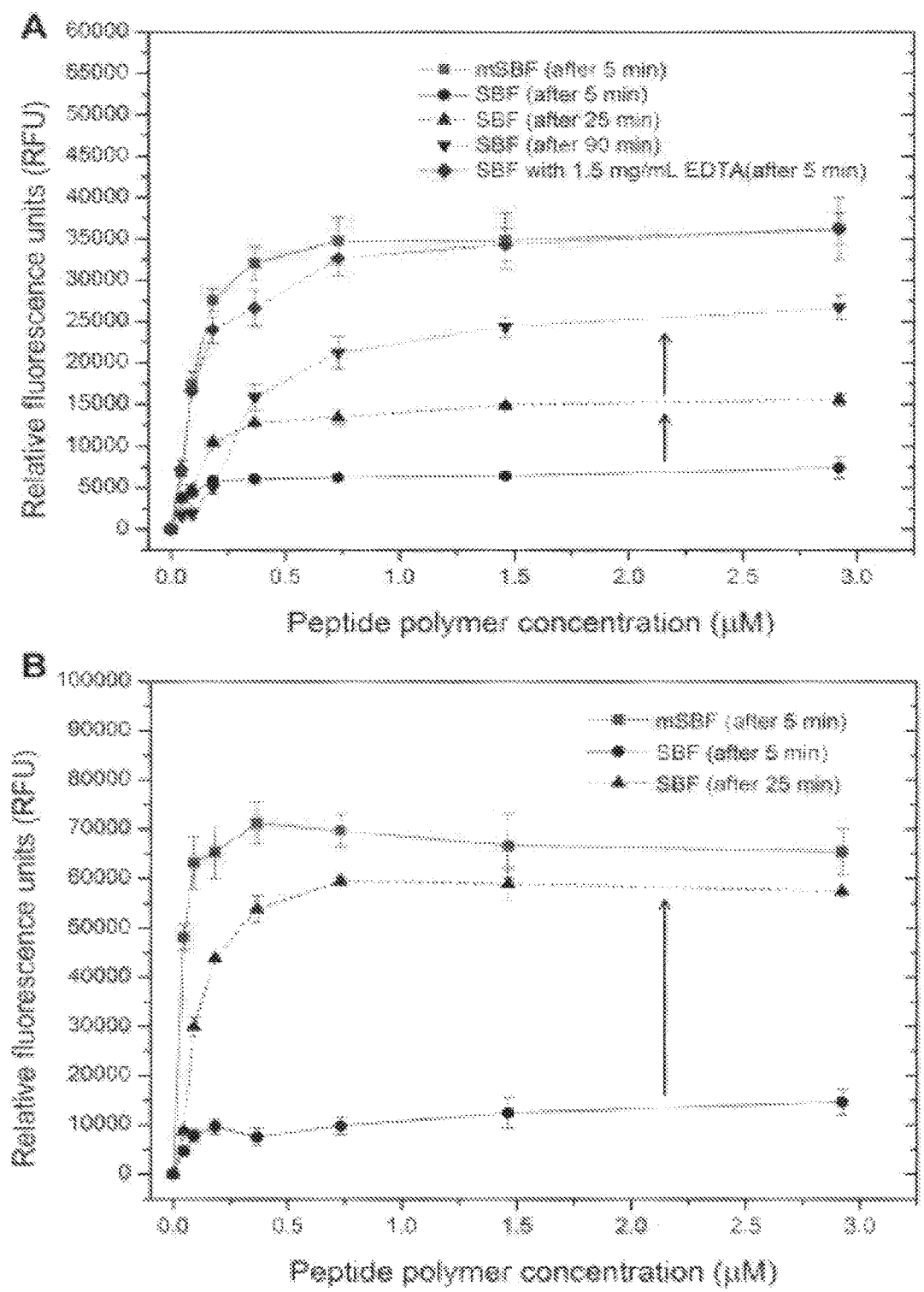
FIG. 62: 1-N-phenylnaphthylamine (NPN) uptake of $E.$ $coli$ and $A.$ $baumannii$ induced by SNAPP S16. $E.$ $coli$ (A) and $A.$ $baumannii$ (B) cells were added to NPN in the presence of increasing concentrations of S16 (0.05-2.92 µM), and NPN fluorescence was monitored starting at t=5 min after the addition of bacterial cells and continued until a maximum is reached (if not at t=5 min). NPN fluorescence was expressed in terms of relative fluorescence units (RFU). Controls whereby no S16 was added (0 µM) were included. The assays were conducted in either SBF (black) or mSBF (red). For $E.$ $coli$, an additional assay was performed in SBF with 1.5 mg/mL of EDTA (blue).

To explore the effect of divalent cations on the antimicrobial mechanism of SNAPPs, we conducted an OM permeability assay using a hydrophobic 1-N-phenylnaphthylamine (NPN) fluorescent probe. NPN emits weak fluorescence in an aqueous environment and only fluoresces strongly in a hydrophobic environment such as in the bacterial membrane. 38 As NPN, like most hydrophobic substances, is normally excluded by intact OMs, an increase in fluorescence intensity when incubated with Gram-negative bacterial cells would indicate disruption to the OM. Bacterial cells (either *E. coli* or *A. baumannii*) were added to varying concentrations of SNAPP S16 in the presence of NPN, and the fluorescence intensity (expressed in terms of relative fluorescence units, RFU) was measured as a function of time (FIG. 62). The medium used was either SBF or mSBF. In all cases, regardless of the bacterial species and the type of medium used, the increase in NPN fluorescence intensity was found to reach a maximum for all polymer concentrations within 90 min.

When *E. coli* cells were treated with S16 in mSBF, NPN was taken up in a dose-dependent manner and the RFU recorded at each concentration reached its maximum 5 min after the addition of bacterial cells (FIG. 62A). The increase in RFU with S16 concentration reached a plateau at about 35000 RFU at a concentration of 0.73 μM (FIG. 62A). As the MIC of S16 in mSBF was found to be 0.22 μM, we postulated that the extent of OM damage induced at this concentration (correlating to an RFU of ca. 27500) is the OM disruption threshold needed to result in bacterial growth inhibition.

In SBF, only a slight increase in NPN uptake with S16 concentration was observed (RFU≤5000) 5 min after the addition of *E. coli* cells (FIG. 62A). The RFUs across all S16 concentrations continued to increase with time until 90 min post-cell addition. However, it was noted that at 0.22 μM (MIC of S16 in mSBF), the RFU recorded in SBF was still very low (ca. 5000) even after 90 min, which indicated that the extent of OM disruption at this concentration was unlikely to be significant in the complete medium. A relatively high RFU of 25000 (close to the membrane disruption threshold of 27500) was only achieved at the highest concentration tested of 2.92 μM after 90 min, which closely correlated with the MIC (Table 22).

Similar to the observations made for *E. coli*, the NPN uptake of *A. baumannii* proceeded in a dose-dependent fashion (FIG. 62B). When mSBF was used as the medium, prominent NPN uptake was observed within a short time (i.e., 5 min), even at a low dosage of 0.05 μM (corresponding to an RFU of ca. 48000). On the other hand, in SBF, NPN uptake across all SNAPP concentrations was low initially, but increased with time and became constant at 25 min. At 25 min, the RFUs recorded using SBF as the medium were close to those measured in mSBF at the corresponding concentrations, albeit slightly lower. It is worthwhile noting that at concentrations that corresponded to the MICs of S16 in mSBF (0.13 μM) and SBF (0.17 μM), RFUs that were above 40000 were achieved. Collectively, these results, together with those obtained when tested against *E. coli*, suggested that an OM disruption threshold needs to be reached for SNAPPs to induce bacterial cell death.

Subsequently, in order to better understand the effects of different media on polymer-OM interactions, we compared the initial increase in RFU as a function of S16 concentration (slope of curve before a plateau was reached) across the different media and time points (Table 23). Against *E. coli*, it was noted that the slopes obtained at 5 min when either mSBF or a combination of SBF and EDTA (1.5 mg/mL) was used were comparable (ca. 3000 RFU·mL/μg). However, when the NPN assay was conducted in SBF, the slope was smaller and remained relatively constant (991-1301 RFU·mL/μg) even when the incubation time was increased from 5 to 90 min. In the case of *A. baumannii*, while the slope obtained after a 5-min incubation in SBF was significantly (ca. 8 times) lower than that in mSBF, it increased by close to 4-fold when the incubation time was extended to 25 min.

Based on these results (FIG. 62A and Table 23), we theorized that the divalent cations (from the MgCl2.6H2O and CaCl2 salts in SBF) drastically reduced the interaction between SNAPP S16 and the OM of *E. coli*. The decrease in interaction was independent of the polymer-bacteria incubation time. The extent of OM disruption was consequently antagonized, as a higher concentration of S16 was needed to cause microbial growth inhibition. We further hypothesized that this postulation could be applied to account for the reduction in activity of SNAPPs observed against *P. aeruginosa* and *K. pneumoniae* in SBF. On the other hand, when tested against *A. baumannii*, we postulated that the presence of divalent cations resulted in an initial lag time where the polymer-bacteria interaction was prevented. When incubation was prolonged beyond the lag time, OM permeabilization was initiated to effect sufficient damage to the OM, resulting in an MIC that was similar to that when the divalent cations were absent. We also observed that the slopes obtained when tested against *A. baumannii* were substantially higher (e.g., 4.5 times higher in mSBF) than those obtained against *E. coli* regardless of the medium used. This indicated the enhanced ability of SNAPPs to disrupt the OMs of *A. baumannii* compared to those of other bacterial species.

*A. baumannii* is an opportunistic pathogen that is responsible for a significant number of hospital-acquired infections and has become extensively resistant to numerous antibiotics. SNAPP S16 has been demonstrated to possess excellent in vivo efficacy against wild-type and colistin-multidrug-resistant (CMDR) *A. baumannii* species. The results herein substantiated the potential of SNAPPs as effective antimicrobial agents against *A. baumannii* infections as their potency against this species was retained at physiologically relevant salt concentrations. Despite the reduction in efficacy against the other bacterial species tested (i.e., *E. coli, K. pneumoniae* and *P. aeruginosa*), SNAPPs were still able to maintain good MIC values within the range of 0.59 to 4.68 µM, which are superior (e.g., >20 times more effective against *E. coli*) to the MICs of several AMPs, such as LL-37, indolicidin, defensin, and magainin I.

Next, we conducted an inner membrane (IM) disruption assay to validate the species-dependent effects of divalent cations on the antimicrobial activity of SNAPPs. Based on earlier observations (FIG. 62), the SNAPP-cell interactions occurred within 90 min of incubation, regardless of the medium used. For the IM disruption assay, SNAPP S16 was incubated with either *E. coli* or *A. baumannii* cells for 90 min, and then a mixture of SYTO® 9 green fluorescent nucleic acid stain and propidium iodide (PI), a red fluorescent nucleic acid stain, was added. The SYTO® 9 dye is membrane-permeable and stains the nucleic acid of all bacterial cells, while the membrane-impermeant PI only labels bacteria with damaged IMs. In our case, as all bacterial species investigated are Gram-negative, a bacterial cell that is 'PI-positive' would possess damaged OM and IM (see FIG. 63A—illustration). The untreated *E. coli* and *A. baumannii* cells were found to have 1.9% and 14.7% of PI-positive cells, respectively (FIGS. 63A and B). The cells were then incubated with S16 at 0.09 µM (a sub-inhibitory concentration that approximates one-half of the MIC of S16 in MEM) for 90 min in different media (either MEM, SBF or mSBF) and the resulting percentage of PI-positive cells was compared (FIGS. 63A and B). A sub-inhibitory concentration was used, instead of the lethal concentration, to prevent the occurrence of cell fragmentation or lysis which would reduce the size of the bacterial cell population detectable by the flow cytometer. When tested against *E. coli* in SBF, only 10.1% of cells were PI-positive compared to 55.8% in MEM. However, in mSBF which has no Mg2+ and Ca2+ ions, the proportion of membrane-disrupted cells increased to 63.7% (comparable to that in MEM). On the other hand, against *A. baumannii*, the percentage of PI-positive cells in MEM and SBF were similar (96.4% and 93.7%, respectively). The results validated the postulation that the presence of Mg2+ and Ca2+ ions at biologically-relevant concentrations attenuated the extent of membrane disruption in *E. coli* caused by S16, whereas against *A. baumannii* the membrane disrupting ability of SNAPP S16 was not affected.

Effect of Chelating Agent Addition.

Figure 64:
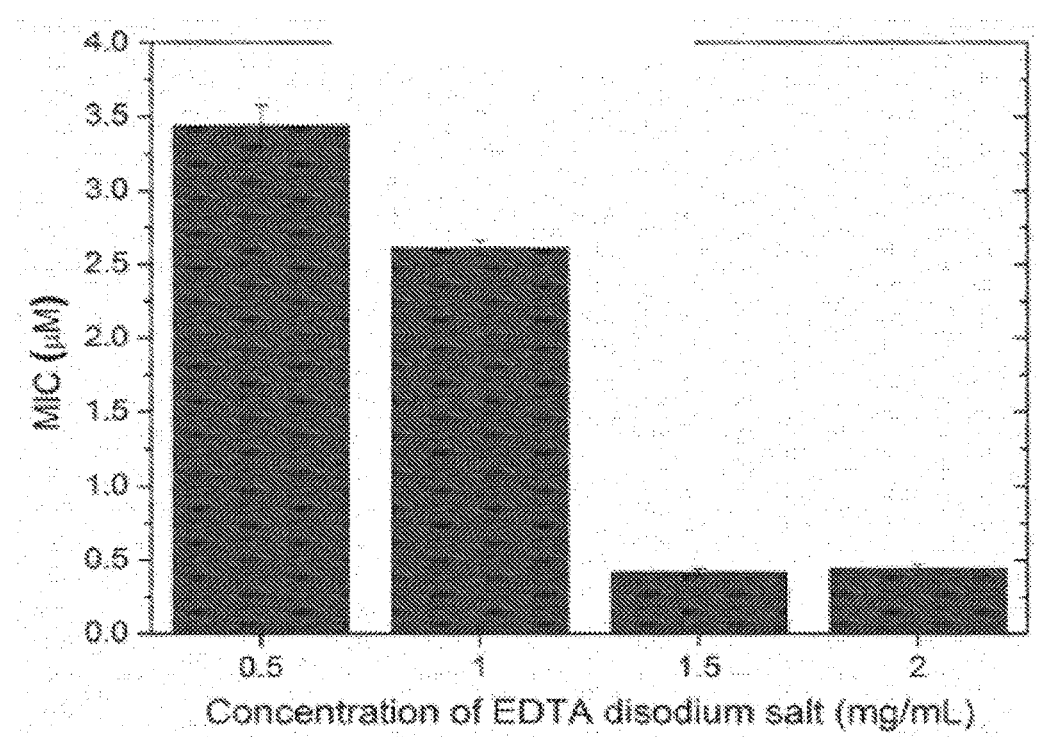
FIG. 64: Effect of EDTA on antimicrobial activity of SNAPP S16 against $E.$ $coli$. $E.$ $coli$ cells were treated with varying concentrations of S16 (0.05-4 µM) and EDTA disodium salt (0.5-2 mg/mL), and the MICs of S16 were evaluated. All data are expressed as mean±standard deviation as indicated by the error bars (n=4).

We postulated that the addition of a chelating agent such as ethylenediaminetetraacetic acid (EDTA) disodium salt which chelates Ca2+ and Mg2+ ions could attenuate the antagonistic effect of the divalent cations on antimicrobial activity. To validate this, we treated *E. coli* cells with S16 and varying concentrations of EDTA disodium salt, and observed a reduction in MIC of S16 as the concentration of EDTA disodium salt was increased (FIG. 64). The lowest MIC of S16 achieved was 0.42±0.02 µM at an EDTA disodium salt concentration of 1.5 mg/mL. The chelating agent was found to restore the OM disrupting ability of SNAPP S16 to the same rate and extent as in the modified SBF without any divalent cations (i.e., mSBF) (FIG. 62A). The IM permeabilization ability of S16 was also restored (FIG. 63C). Further increase in EDTA disodium salt concentration did not lead to further reduction in MIC. It should be noted that the addition of EDTA at all concentrations tested did not affect the bacterial cell viability. Although there are some safety concerns regarding the use of EDTA for in vivo applications, strategies such as the use of more biocompatible chelators (e.g., citric acid), tethering of the chelator to the SNAPP through chemical conjugation, on-demand release of the chelator at the infection site, or any combination thereof, could possibly improve the therapeutic utility of such SNAPP-chelator drug combination. Further, this study demonstrates that challenges posed by inhibitory substances present in vivo such as divalent cations can be circumvented.

Antimicrobial Studies in Serum.

To facilitate the evaluation of SNAPPs S16 and S32 for possible therapeutic utility, we developed an ex vivo assay to assess their antimicrobial efficacies in animal serum (i.e., fetal bovine serum (FBS); diluted to 10% and 50% in MEM). Serum is a cell-free biomatrix isolated from the coagulation of blood and plasma components, with associated activation of proteases and other factors. Besides salts which have been shown to have an inhibitory effect on antimicrobial activity, blood serum contains serum albumin and a range of other proteins such as transferrin and lactoferrin which could collectively form a protein corona around antimicrobials and decrease their therapeutic activity by reducing the free fraction of drug or nanoparticle available for bacteria association and/or killing.

When 10% FBS in MEM was used, the MICs of SNAPPs S16 and S32 increased significantly by ca. 3 to 17 times depending on the peptide polymer and bacterial species tested against (Table 22). The activity of SNAPP S32 against *K. pneumoniae* was reduced by almost 10 times, while S16 became non-active against *K. pneumoniae* within the range of concentrations tested (≤6 µM). When tested against *A. baumannii*, a relatively weaker effect (ca. 3 to 5-fold reduction in activity) was observed for both S16 and S32. These observations substantiated the potential of SNAPPs as effective antimicrobials against *A. baumannii* even under physiologically-relevant conditions. The reduction in activity (albeit to different extents depending on serum concentration and bacterial species tested against) may be attributed to weaker membrane disruption activities in the presence of serum. The extent of membrane disruption caused by SNAPP S16 against *E. coli*, as indicated by flow cytometry, dropped from 55.8% in MEM to 10.2% in 10% serum (FIG. 63C). The inhibitory activities of SNAPPs (against *E. coli* and *P. aeruginosa*, as shown in Table 22) were further antagonized when the serum concentration was increased to 50%.

While the activity of the SNAPPs were lowered in serum they still exhibited significant anti-bacterial effects and highlights their utility in treating bacterial infections.

Example 9

Synthesis of SNAPPs

This example reports an alternative method for producing SNAPPs. In the examples discussed above, the SNAPPs were prepared through random ring opening polymerisation (ROP) of the cationic capable (S-carboxybenzyl, CBz,Z protected) L-lysine and hydrophobic racemic D,L-valine amino acid N-carboxyanhydride (NCA) monomers. Polymerisation was performed through a core-first approach, initiated by the terminal primary amines of a PAMAM dendrimer core, and conducted at room temperature. However, the inventors have now found that reducing the reaction temperature during polymerisation, to as low as 0° C., can slow down and reduce side reactions in primary amine initiated NCA ROP, resulting in greater "livingness" of the polymers and lead to improved control of polymerisation.

Figure 65:
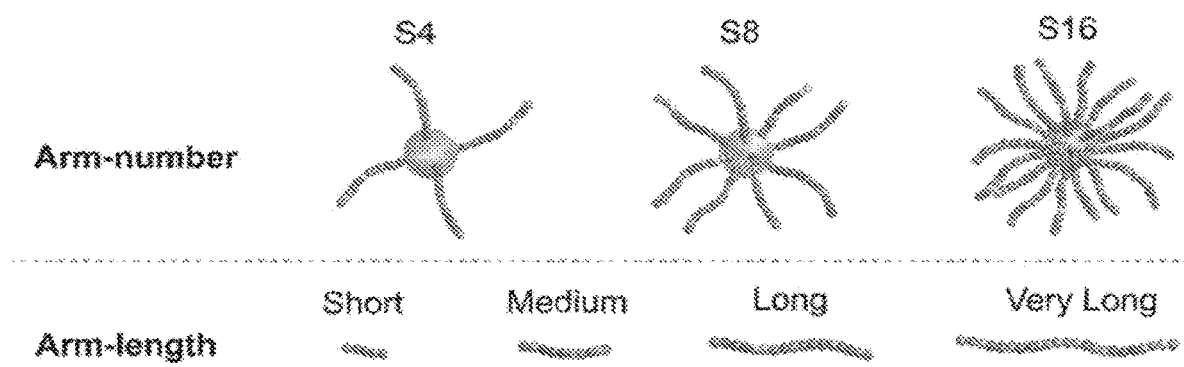
FIG. 65: Scheme illustrating arm number and arm length of star-shaped SNAPPs of Examples 9 and 10.

FIG. 65 provides an illustration of SNAPPs that were prepared using this alternative method in the form of 4-arm (S4), 8-arm (S8) and 16-arm (S16) stars. Stars of varying arm length were also prepared. Using the core-first approach, NCA monomers were polymerised randomly by primary amine initiation from a PAMAM core under ice (4° C.). The resulting CBz/Z-protected lysine residues were then deprotected with hydrobromic acid (HBr), generating fully water soluble polymers.

Figure 66:
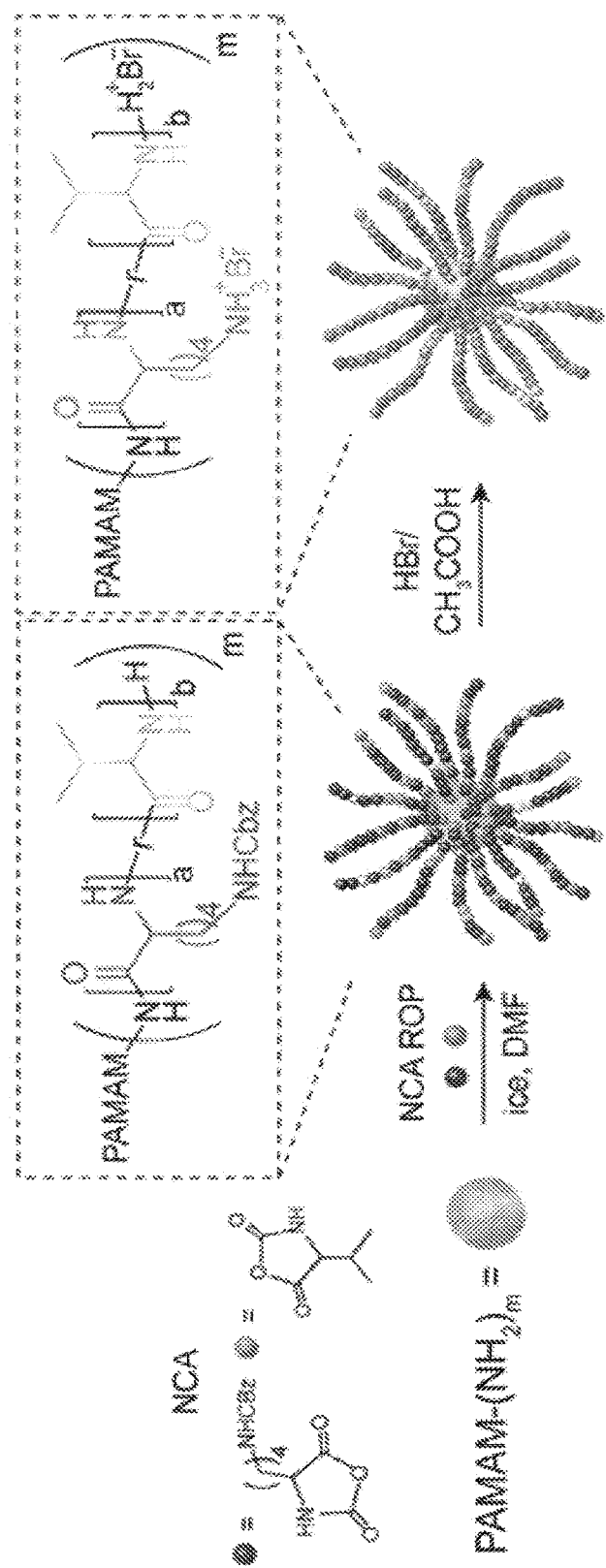
FIG. 66: Scheme illustrating synthesis of SNAPPs of Example 9.

FIG. 66 illustrates the general reaction scheme for the synthesis of lysine and valine SNAPPs in ice through ROP of lysine and valine N-carboxyanhydride (NCAs) monomers by initiation from the terminal amines of poly(amido amine) (PAMAM) dendrimers. First, second and third generation PAMAM dendrimers with 4, 8 and 16 peripheral primary amines respectively were used to prepare S4 (m=4), S8 (m=8) and S16 (m=16) star shaped SNAPPs. Deprotection of lysine CBz group with H Br yielded fully water soluble star SNAPPs.

The methods used to synthesise the NCAs and the SNAPPs, and the method for the subsequent deprotection of the SNAPPs is outlined below.

Synthesis of D,L-Valine and (Z)-L-Lysine N-Carboxyanhydrides (NCAs)

ε-(Z)-L-Lysine and D,L-Valine NCAs were synthesized as per the previous examples, with the inclusion of an additional purification step to remove hydrochloride impurities from the reaction. Dried H-Lys(Z)—OH (2 g, 7.14 mmol) or D,L-Valine (2 g, 17.0 mmol)) were suspended in anhydrous THF (50 mL) in a three-necked round bottomed flask under argon. Triphosgene (lys: 0.85 g, 2.86 mmol, 1.2 equiv. phosgene; val: 2.0 g, 6.74 mmol, 1.2 equiv. phosgene) was then added and the mixture was refluxed at 65° C. for 2 h with continuous stirring. After cooling to room temperature, the reaction mixture was sparged with argon for 45 mins into a sat. NaOH solution, then solvent removed completely in vacuo to a white solid. The solid was then suspected in EtOAc (anhydrous), chilled and placed into a separator funnel where the crude NCA solution was gently washed with chilled saturated brine solution (50 mL), and 0.5% w/v $NaHCO_3$ solution (50 mL). The organic phase was then dried with MgSO4, filtered and concentrated to an oil under low heat, and re-crystalized (×2) from EtOAc (anhydrous) and n-pentane (anhydrous). The resulting crystals were then filtered and washed with n-pentane (dry), then re-precipitated and washed (×2) with dry n-pentane to afford white powder solids (Yields: ~80%)$^1$H NMR ($CDCl_3$): (Z)-L-Lysine NCA $^1$H NMR (400 MHz, CDCl3): $δ_H$ 1.40-1.60 (m, 4H, NH—$CH_2$—$CH_2$—$CH_2$—$CH_2$—), 1.81-1.94 (m, 2H, NH—$CH_2$—$CH_2$—$CH_2$—$CH_2$—), 3.18 (m, 2H, NH—$CH_2$—$CH_2$—$CH_2$—$CH_2$—), 4.25 (t, 1H, CHN), 4.97 (s, 1H, side chain NH), 5.09 (s, 2H, $CH_2$—ArH), 7.04 (s, 1H, ring NH), 7.3-7.4 (m, 5H, ArH). D,L-Valine NCA $^1$H NMR (400 MHz, $CDCl_3$): $δ_H$ 1.02 (d, 3H, J=7.0 Hz, $CH_3$), 1.08 (d, 3H, J=7.0 Hz, $CH_3$), 2.25 (m, 1H, $CH(CH_3)_2$), 4.22 (d, 1H, J=4.4 Hz, CH—NH), 6.95 (s, 1H, CO—NH).

General Procedure for Synthesis of $(PZLL-r-PVal)_{arm}$ $PAMAM-(NH_2)_{m,core}$.

In line with the previous examples, a theoretical lysine-to-valine ratio of approximately 2.5:1 was targeted. To account for different observed reactivity rates of the two monomers, Lys NCA and Val NCA in approximately 2:1 molar ratio were both dissolved in anhydrous DMF ($[NCA]_{total}$=~55 mg/mL) and added via syringe to a test tube containing $PAMAM-(NH_2)_m$ (dried) dissolved completely in anhydrous DMSO (volume corresponding to 10% v/v of final reaction volume) under $N_2$. The test tube was then immersed in an ice chest and stirred for 24 h in ice under constant nitrogen flow and with a bleed for $CO_2$ removal (Note: $S8_{VL}$ was stirred for total 50 h). n-butanol (0.86 μL/mg of $NCA_{total}$ added to reaction) was then added to quench remaining NCA monomer and the mixture stirred for a further 1 h. The reaction mixture was then concentrated under vacuum and transferred into diethyl ether to precipitate. The precipitate was then washed thoroughly with ether and dried in vacuo to afford an off-white solid. Average yield ~60%

General Deprotection of $(PLL-r-PVal)_{arm}$ $PAMAM-(NH_2)_{m,core}$.

Protected star polymer was first fully dissolved in TFA (5 mL/g polymer). 33% HBr in acetic acid was then added (10 mL/g polymer), the reaction mixture stoppered and stirred at room temperature with precipitate forming soon after. After stirring for a total of 2 h at room temperature, the solution was added directly into diethyl ether, washed further in ether (×2) and dried under vacuum. The dried solid was then dissolved up in minimal DI water, transferred to 3.5 kDa dialysis tubing and dialysed against a large volume of DI water (~180 times volume of original dialysis content)(×3) for 24 h. The dialysed solutions were then lyophilised to obtain the deprotected SNAPP as a dried white solid. $^1$H NMR ($D_2O$): $δ_H$ 0.9 (s, $2(CH_3)_3$), 1.3-1.9 (m, NH—$CH_2$—$CH_2$—$CH_2$—$CH_2$—), 2.0 (br s, CH—NH valine), 3.0 (s, NH—$CH_2$—$CH_2$—$CH_2$—$CH_2$—), 4.0-4.15 (s, CH—NH backbone valine), 4.2-4.4 (s, CH—NH backbone lysine).

Characterisation of SNAPPs.

$^1$H NMR analysis was performed using a Varian unity Plus 400 MHz NMR spectrometer using the deuterated solvent as reference. Size exclusion chromatography (SEC) analysis was performed on an aqueous gel permeation chromatography (GPC) units using an eluent of Milli-Q water containing 0.1% v/v trifluoroacetic acid (TFA). The system was operated at a flow rate of 1 mL min$^{-1}$ at 25° C. A Shimadzu Liquid Chromatography system was utilized, equipped with a Shimadzu RID-10 refractometer ($\lambda$=633 nm) and Wyatt 3-angle light scattering detector, with three Waters Ultrahydrogel columns in series ((i) 250 Å porosity, 6 μm diameter bead size; (ii) and (iii) linear, 10 μm diameter bead size) for separation. The dn/dc value of the S4$_M$, S8$_M$, and S16$_M$ SNAPPs were calculated to be 0.187, 0.183, 0.188 respectively at 25° C. using a batch injection protocol and Wyatt ASTRA SEC/LS software. Molecular weight and polydispersity values were calculated on the Wyatt ASTRA SEC/LS software package using Debye modelling with a fit of 2. All GPC samples prepared at a concentration of 5 mg/mL and were filtered through 0.45 μm nylon filters prior to injection. DLS measurements were performed on a Malvern Zetasizer Nano ZS with 4.0 mW HeNe laser operating at 632.8 nm. Analysis was performed at an angle of 173° at a constant temperature of 25±0.01° C. Samples were made to an initial concentration of 1 mg/mL in DMEM (the same media conducted for antibacterial studies) serial dilutions performed until stable spectra was obtained. Measurements were performed in triplicate. All samples filtered through 0.45 μm nylon filters to measurement.

Results

Figure 67:
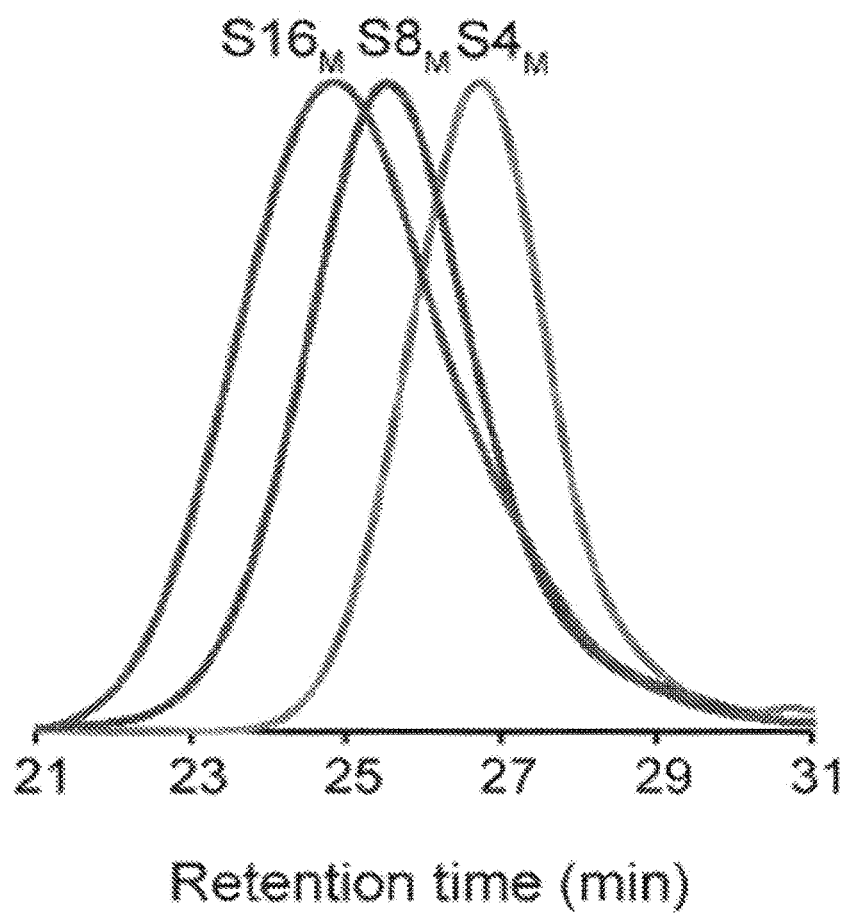
FIG. 67: Size exclusion chromatography (SEC) refractive index (RI) chromatograms of $S4_M$, $S8_M$, $S16_M$ star SNAPPs.
Figure 68:
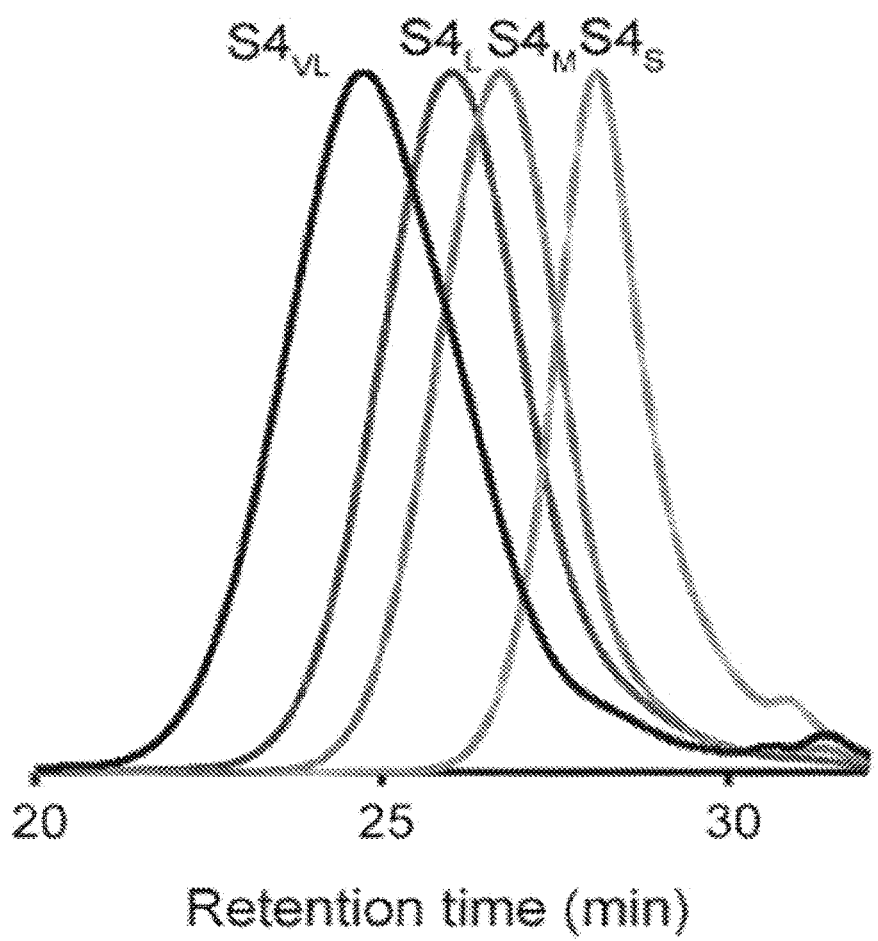
FIG. 68: SEC refractive index (RI) chromatograms of $S4_S$, $S4_M$, $S4_L$, $S4_{VL}$ star SNAPPs.
Figure 69:
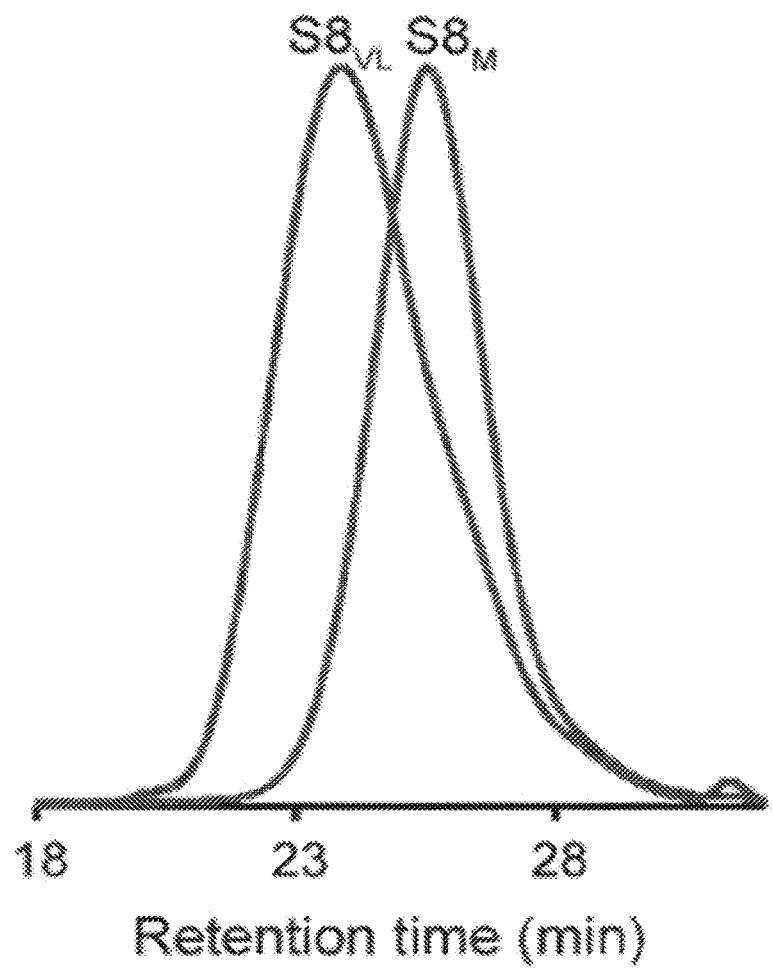
FIG. 69: SEC refractive index (RI) chromatograms of $S8_M$, $S8_{VL}$.

The star-shaped SNAPPs and their corresponding characterisation data is shown in Table 24. All stars contained similar lysine to valine ratios and close to the theoretical ratio of 2.5:1 as determined through $^1$H NMR analysis. Absolute molecular weight (MW) of the stars was calculated through size exclusion chromatography (SEC) using light scattering measurements, which in conjunction with NMR studies, lead to highly accurate determination of star arm length (arm DP) and arm composition. SEC profiles of all SNAPPs displayed typical mono-modal profiles (see FIG. 67, FIG. 68, and FIG. 69).

The polydispersities of these stars (≤1.8) were considerably lower than that report in the earlier examples. It must be noted that the PDIs of these particular star-shaped polypeptides are expected to be intrinsically higher than other polypeptide star systems due to the use of valine, an amino acid well known to produce insoluble β-sheet structures in situ, and therefore likely to have an impact on polymerisation control.

To investigate the effect of arm number, S4, S8 and S16 star shaped SNAPPs were prepared, each with a similar medium (M) range in arm length of ~14 repeat units per arm (S4$_M$, S8$_M$, S16$_M$ respectively). This arm length was targeted as it was similar to the calculated arm length of the S16 SNAPP we reported previously. As expected, SEC analysis showed an increase in star MW with increasing arm number. (Table 24, FIG. 67) Due to the increase in PAMAM core size with generation/arm number the hydrodynamic diameter of the stars was expected to slightly increase in size with arm number and this was observed (Table 24).

Three additional S4 SNAPPs were synthesised with different arm lengths; short (S) with ~DP of 5, long (L) with ~DP of 18, and very long (VL) with ~DP of 27. SEC analysis confirmed the increasing MW of these species (FIG. 68) and as expected, increased hydrodynamic diameters were observed following increases in star arm length (Table 24). An S8 SNAPP containing significantly longer arms than S8$_M$, with an arm DP of 29 (S8$_{VL}$) was also prepared (Table 24, FIG. 69).

Example 10

This example reports in vitro tests using a selection of the SNAPPs synthesised in Example 9.

Materials and Methods

Materials.

Mueller-Hinton broth (MHB), Dulbecco's modified eagle medium (DMEM) and phosphate-buffered saline (PBS) were purchased from Sigma-Aldrich. BacLight® viability kit was purchased from Thermo Fisher Scientific.

Bacterial Strains.

*Escherichia coli* (ATCC® 25922), *Acinetobacter baumannii* (ATCC® 19606), *Pseudomonas aeruginosa* (ATCC® 47085), *Klebsiella pneumoniae* (ATCC® 13883), *Staphylococcus aureus* (ATCC® 29213), methicillin resistant *Staphylococcus aureus* (MRSA, ATCC® 43300), *Enterococcus faecalis* (ATCC® 29212).

Instrumentation.

MIC values were calculated using a Multiskan Ascent (Labsystems) microplate reader. MDC values were calculated by flow cytometry using a Quanta SC MPL (Beckman Coulter Pty, Ltd) equipped with a 100-W stabilised mercury arc lamp with wavelengths of 365, 404, and 435 nm, and a 488-nm diode laser.

Antimicrobial Assays—General Sample Preparation

150 μL of serial 2-fold dilutions of SNAPPs (200-3.12 mg·mL$^{-1}$) in DMEM were added to a 96-well microplate. A bacterial inoculum in MHB was incubated at 37° C. with orbital shaking (200 rpm) for 2 h to reach exponential growth. After this time, the culture was diluted with DMEM to give final concentration of 2.5·10$^6$ cells·mL$^{-1}$, and 150 μL of this stock of bacteria were mixed with the SNAPP dilutions in the microplate, to give a final mixture of bacteria and SNAPP (100-1.56 mg·mL$^{-1}$) of 300 μL. A sample of bacteria without SNAPP was prepared likewise as negative antimicrobial control by replacing the SNAPP solution with neat DMEM. This microplate was incubated at 37° C. standing still for 90 min. After this time, the MIC, MDC and MBC experiments described below were performed. The results from all antimicrobial assays described herein were collected from two independent experiments (i.e. biological replicates), and each sample was analysed as five (MIC and MDC) or three (MBC) technical replicates.

Minimum Inhibitory Concentration (MIC).

After 90 min of incubation (see "Antimicrobial assays—General sample preparation" above), 100 μL of the SNAPP and bacteria mixtures were diluted with the same volume of MHB in a new microplate. This microplate was incubated at 37° C. with orbital shaking (180 rpm) in a microplate reader, and the optical density at 630 nm (OD$_{630}$) of the samples was read every 20 min over 20 h. The OD$_{630}$ of the samples at the time point were the control without SNAPP finished exponential growth were normalised to the OD$_{630}$ of this control (100% relative growth), plotted against SNAPP concentration and fitted to an exponential regression (FIG. 70). The MIC was defined as the lowest concentration of SNAPP that inhibited 99.9% of bacterial growth, and was determined as the concentration that corresponded to 0.1% relative growth in the exponential regression of the data (FIG. 70).

Minimum Disruptive Concentration (MDC).

Figure 71:
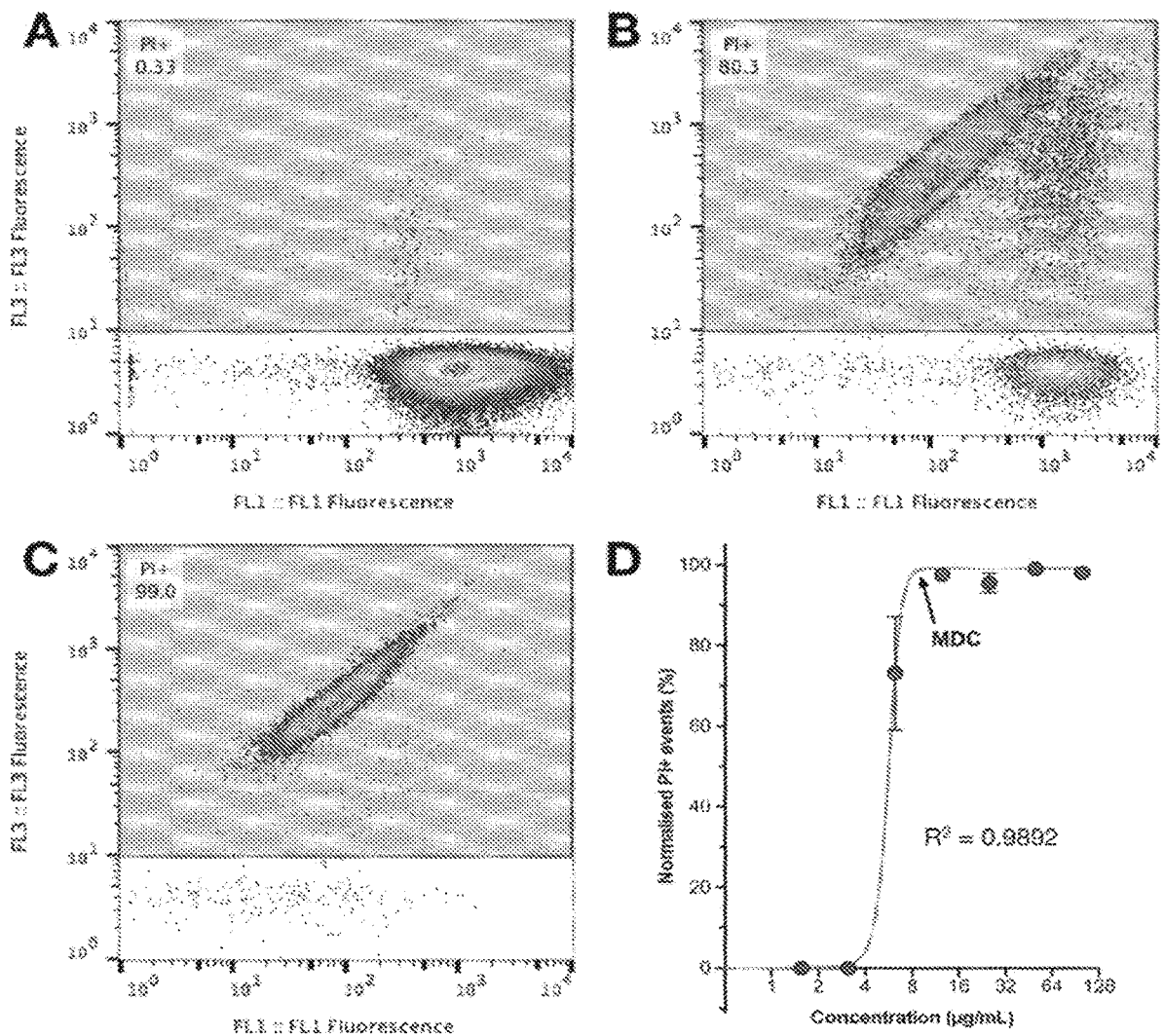
FIG. 71: Flow cytometry plots of green Syto® 9 (FL1) versus red propidium iodide (FL3) emission from $E.$ $coli$ cultures in the absence (A) and presence of 6.25 µg/mL $S4_{VL}$ (B), and treated with 70% v/v/ethanol (C), showing red gates for PI+ events (%, inset). PI+ events in samples with SNAPPs were normalised to the values of PI- (0%, A) and PI+(100%, C) controls, then plotted against SNAPP concentration and fitted to an exponential function, whose X value at Y=99.9% was established as the MDC (D). n=10; Data points represent the mean value±one standard deviation.

After 90 min of incubation (see "Antimicrobial assays— General sample preparation" above), 100 µL of the SNAPP and bacteria mixtures were diluted with 100 µL of PBS containing 0.1% v/v of BacLight® dyes: Syto® 9 (3.34 mM stock solution) and propidium iodide (50 µg·mL$^{-1}$ stock solution). These samples were incubated for 10 min in the dark at room temperature, to be then analysed by flow cytometry measuring Syto® 9 emission at 525 nm (fluorescence channel 1, FL-1) and propidium iodide emission at 670 nm (fluorescence channel 3, FL-3). A sample of bacteria treated for 30 min with 70% v/v ethanol in water, centrifuged and resuspended in DMEM, was analysed likewise as positive control for membrane damage. The MDC was defined as the lowest concentration of SNAPP that caused membrane damage in 99.9% of the bacterial cells, and was determined as the concentration that corresponded to a normalised 99.9% propidium iodide-positive (PI+) cells (FIG. 71).

Minimum Bactericidal Concentration (MBC).

Figure 72:
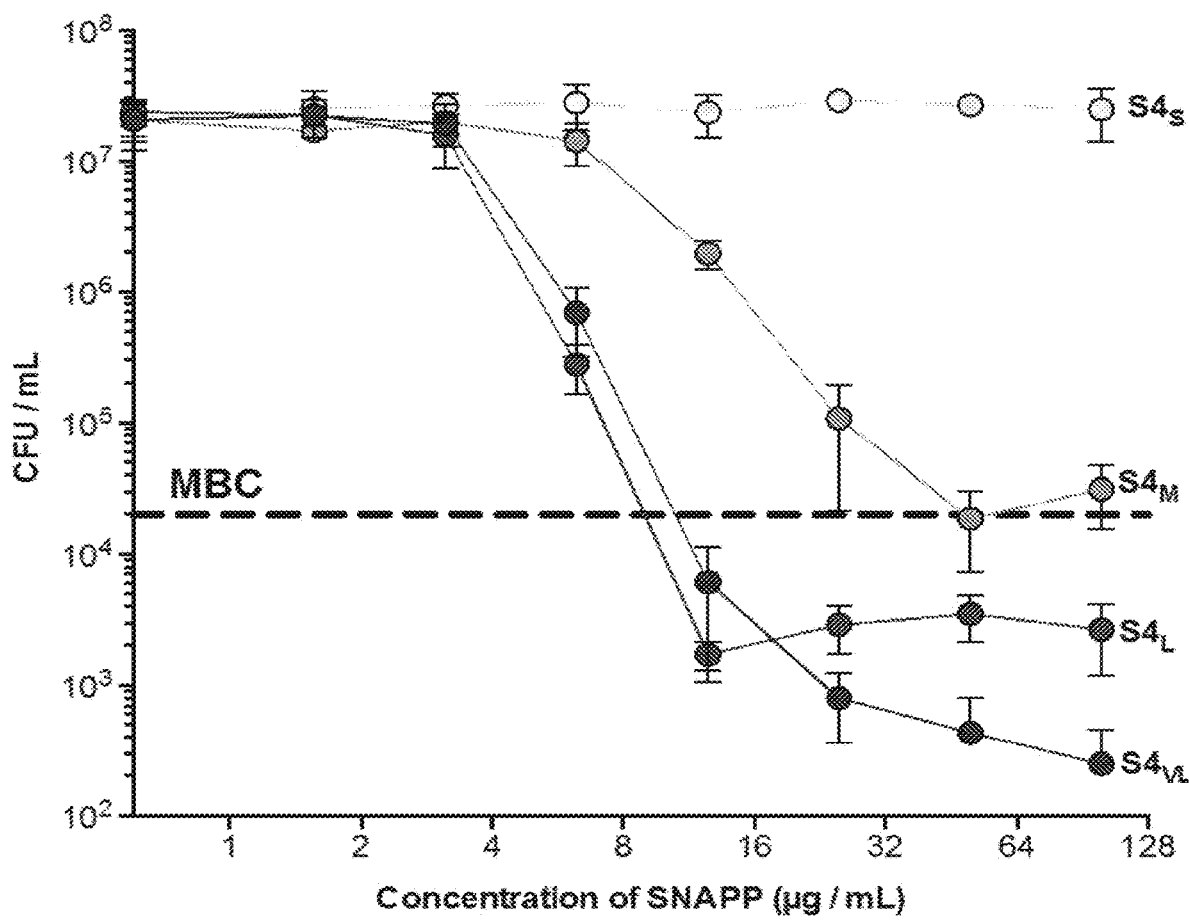
FIG. 72: Concentration of bacterial colonies (CFUs) found in samples of $E.$ $coli$ incubated with different concentrations of SNAPPs. The line 'MBC' indicates a $10^3$-fold decrease from the initial CFU/mL value of the controls without SNAPP. The lowest concentration of SNAPP tested experimentally that falls on/below the 'MBC line' was established as the MBC: e.g. 12.5 µg/mL for $S4_{VL}$ and $S4_L$, 50 mg/mL for $S4_M$, whereas $S4_S$ was inactive. n=6; Data points represent the mean value±one standard deviation.

After 90 min of incubation (see "Antimicrobial assays— General sample preparation" above), the SNAPP and bacteria mixtures were serially diluted 10-fold four times. 10 µL of each dilution were spotted on MHB agar plates and incubated at room temperature and/or 37° C. until individual colonies were visible. Bacterial colonies, or colony forming units (CFUs), were counted at the dilution that allowed to count the most individual colonies without significant overlap between them. The MBC was defined as the lowest concentration of SNAPP that caused a decrease of 99.9% in viable bacterial cells (i.e. CFU·mL$^{-1}$) as compared to a control sample in the absence of SNAPP (FIG. 72).

MIC Calculation.

The optical density at 630 nm ($OD_{630}$) of bacterial cultures with different concentrations of SNAPPs was recorded every 20 min, and the $OD_{630}$ values at the time point were the control sample with 0 µg·mL$^{-1}$ of SNAPP finished exponential growth (e.g. '3 h' in FIG. 70(A)) were normalised to the $OD_{630}$ of this control (e.g. '100%' in FIG. 70(A)). These normalised $OD_{630}$, which correlate to the relative bacterial growth at this time point, were plotted against SNAPP concentration and fitted to an exponential function, whose X value for Y=0.1% was established as the MIC (FIG. 70(B)). The sample described here is an example of the method that was applied to all SNAPPs for the calculation of their MIC values.

MDC Calculation.

The emission of bacteria in the FL-1 and FL-3 channels (see 'Minimum Disruptive Concentration (MDC)' above) was measured by flow cytometry, setting a gate for bacteria with damaged membranes as propidium iodide positive (PI+) events above a FL-3 threshold (FIG. 71(A)-(C)). The percentage of PI+ events in the samples was normalised to that of a control without SNAPP (0%, FIG. 2A) and a control treated with 70% v/v ethanol in water (100%, FIG. 71C), and the control-normalised PI+ values were plotted against SNAPP concentration and fitted to an exponential function (FIG. 71(D)): The X value for this exponential fit at Y=99.9% was established as the MDC. The sample described here is an example of the method that was applied to all SNAPPs for the calculation of their MDC values.

MBC Calculation.

The number of colony forming units (CFUs) found in bacterial samples spotted on agar plates (see 'Minimum Bactericidal Concentration (MBC)' above) was corrected for dilution and plotted as CFU/mL against SNAPP concentration (FIG. 72). The MBC was calculated as the lowest concentration of SNAPP that displayed a value of CFU/mL below a 10$^3$-fold drop from the value found in the control samples without SNAPP (i.e. FIG. 72, values on the Y-axis).

Results

FIG. 70 Growth curves of E. coli in the presence and absence of different S4$_{VL}$ concentrations (A). Relative $OD_{630}$ at 3 h of these samples compared to the control (0 µg/mL, '100%') fitted to an exponential function, whose X value at Y=0.1% was established as the MIC (B). n=10; Data points represent the mean value±one standard deviation.

FIG. 71 Flow cytometry plots of green Syto® 9 (FL1) versus red propidium iodide (FL3) emission from E. coli cultures in the absence (A) and presence of 6.25 µg/mL S4$_{VL}$ (B), and treated with 70% v/v/ethanol (C), showing red gates for PI+ events (%, inset). PI+ events in samples with SNAPPs were normalised to the values of PI– (0%, A) and PI+(100%, C) controls, then plotted against SNAPP concentration and fitted to an exponential function, whose X value at Y=99.9% was established as the MDC (D). n=10; Data points represent the mean value±one standard deviation.

FIG. 72 Concentration of bacterial colonies (CFUs) found in samples of E. coli incubated with different concentrations of SNAPPs. The line 'MBC' indicates a 10$^3$-fold decrease from the initial CFU/mL value of the controls without SNAPP. The lowest concentration of SNAPP tested experimentally that falls on/below the 'MBC line' was established as the MBC: e.g. 12.5 µg/mL for S4$_{VL}$ and S4$_L$, 50 mg/mL for S4$_M$, whereas S4$_S$ was inactive. n=6; Data points represent the mean value±one standard deviation.

FIG. 73 Antimicrobial concentrations (MIC/MDC/MBC) of different SNAPPs against E. coli. Numerical values can be found in Table 25.

Figure 74:
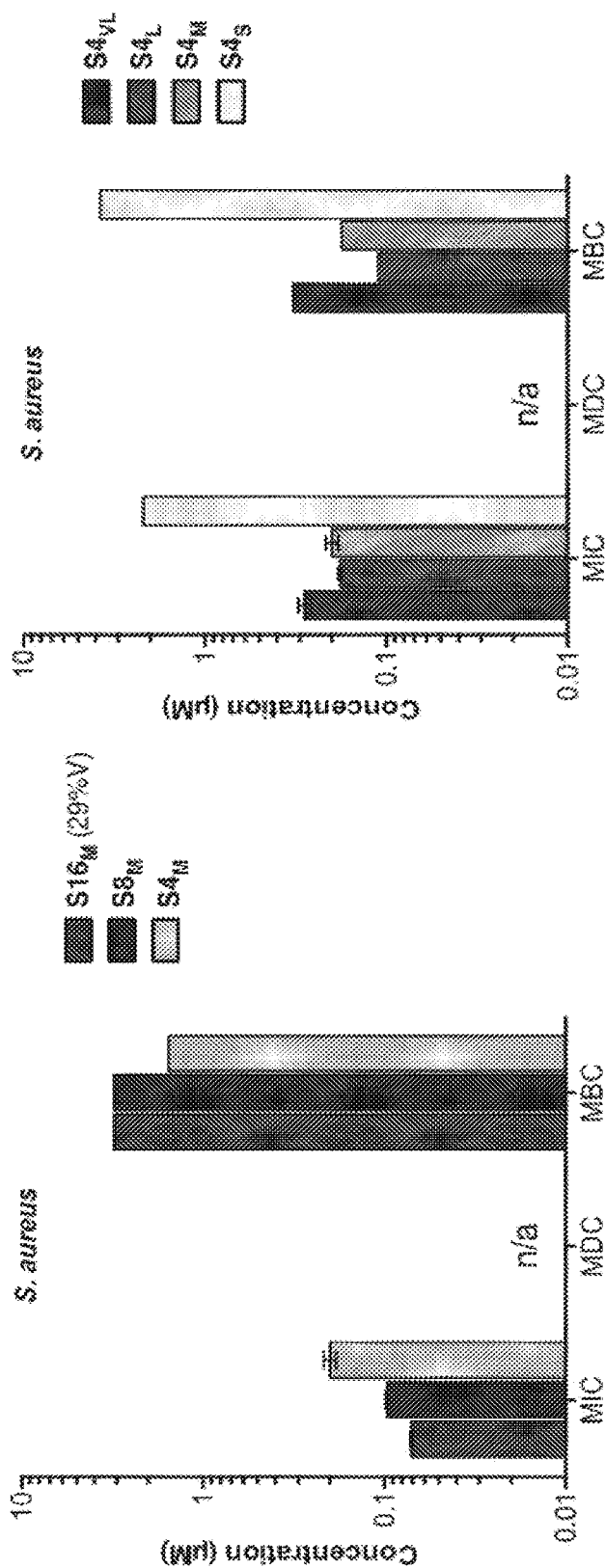
FIG. 74: Antimicrobial concentrations (MIC/MDC/MBC) of different SNAPPs against $S.$ $aureus$.

FIG. 74 Antimicrobial concentrations (MIC/MDC/MBC) of different SNAPPs against S. aureus. Numerical values can be found in Table 26.

Figure 75:
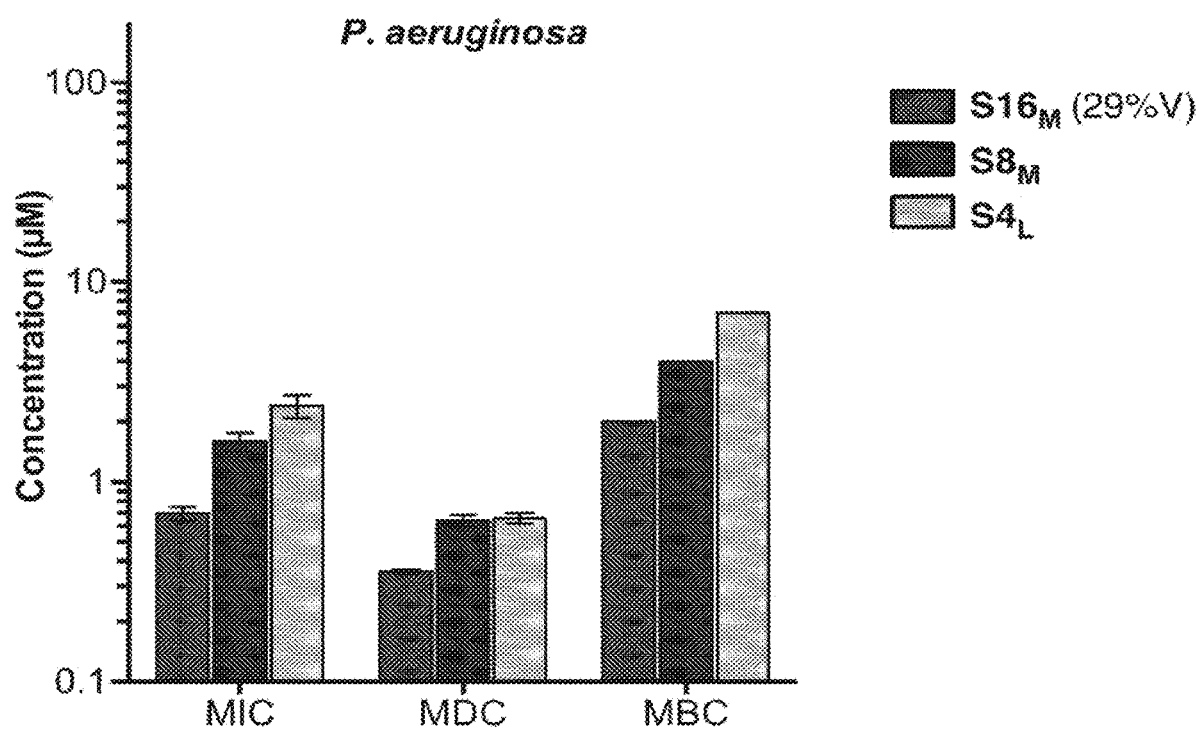
FIG. 75: Antimicrobial concentrations (MIC/MDC/MBC) of different SNAPPs against $P.$ $aeruginosa$.

FIG. 75 Antimicrobial concentrations (MIC/MDC/MBC) of different SNAPPs against P. aeruginosa. Numerical values can be found in Table 27.

Figure 76:
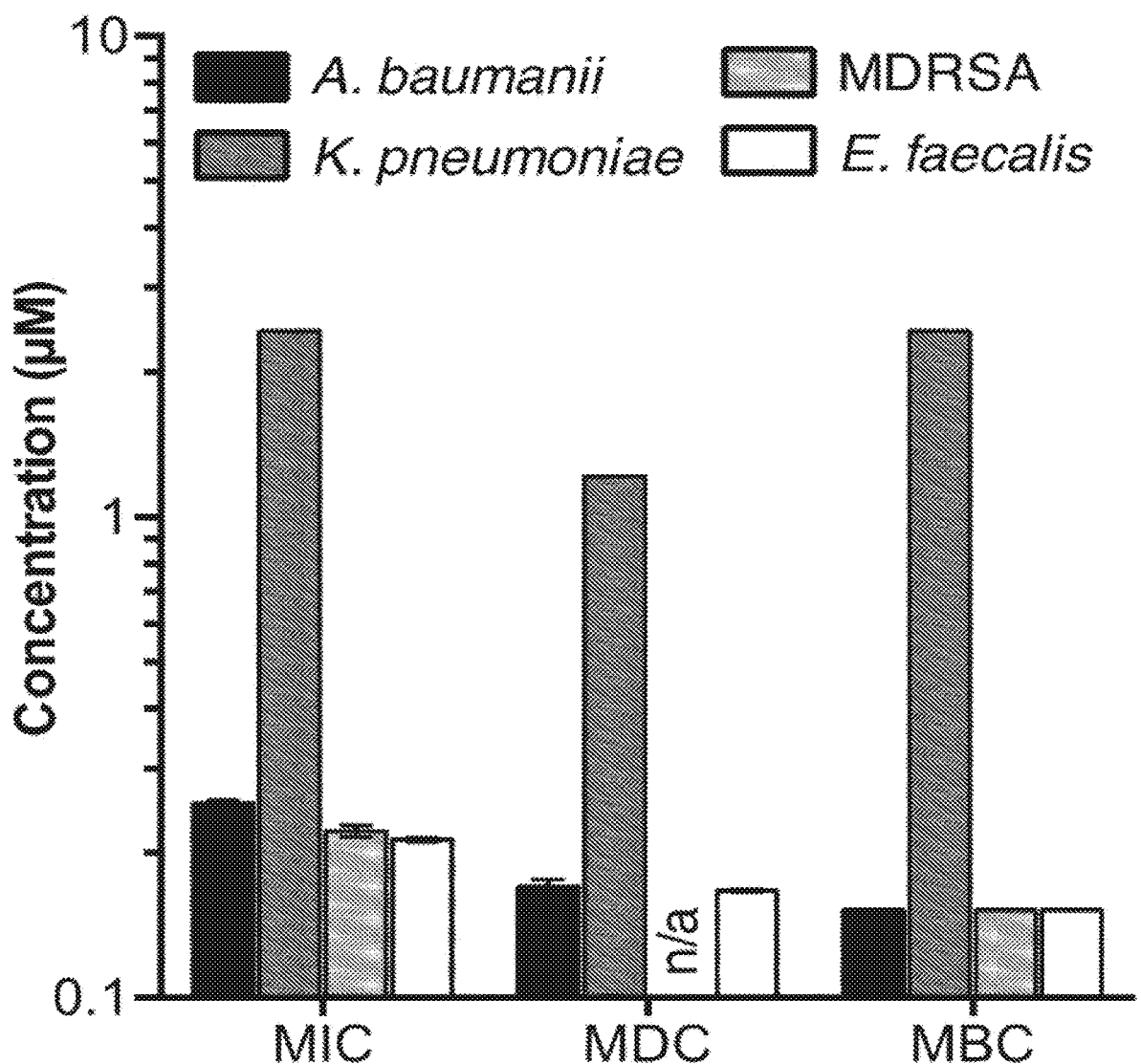
FIG. 76: Antimicrobial concentrations (MIC/MDC/MBC) of $S16_M$ (29% V) against other Gram-negative ($A.$ $baumanii$ and $K.$ $pneumoniae$) and Gram-positive (methicillin resistant $S.$ $aureus$ MRSA, and $E.$ $faecalis$).

FIG. 76 Antimicrobial concentrations (MIC/MDC/MBC) of S16$_M$ (29%) against other Gram-negative (A. baumanii and K. pneumoniae) and Gram-positive (methicillin resistant S. aureus, MRSA, and E. faecalis). Numerical values can be found in Table 28.

Figure 77:
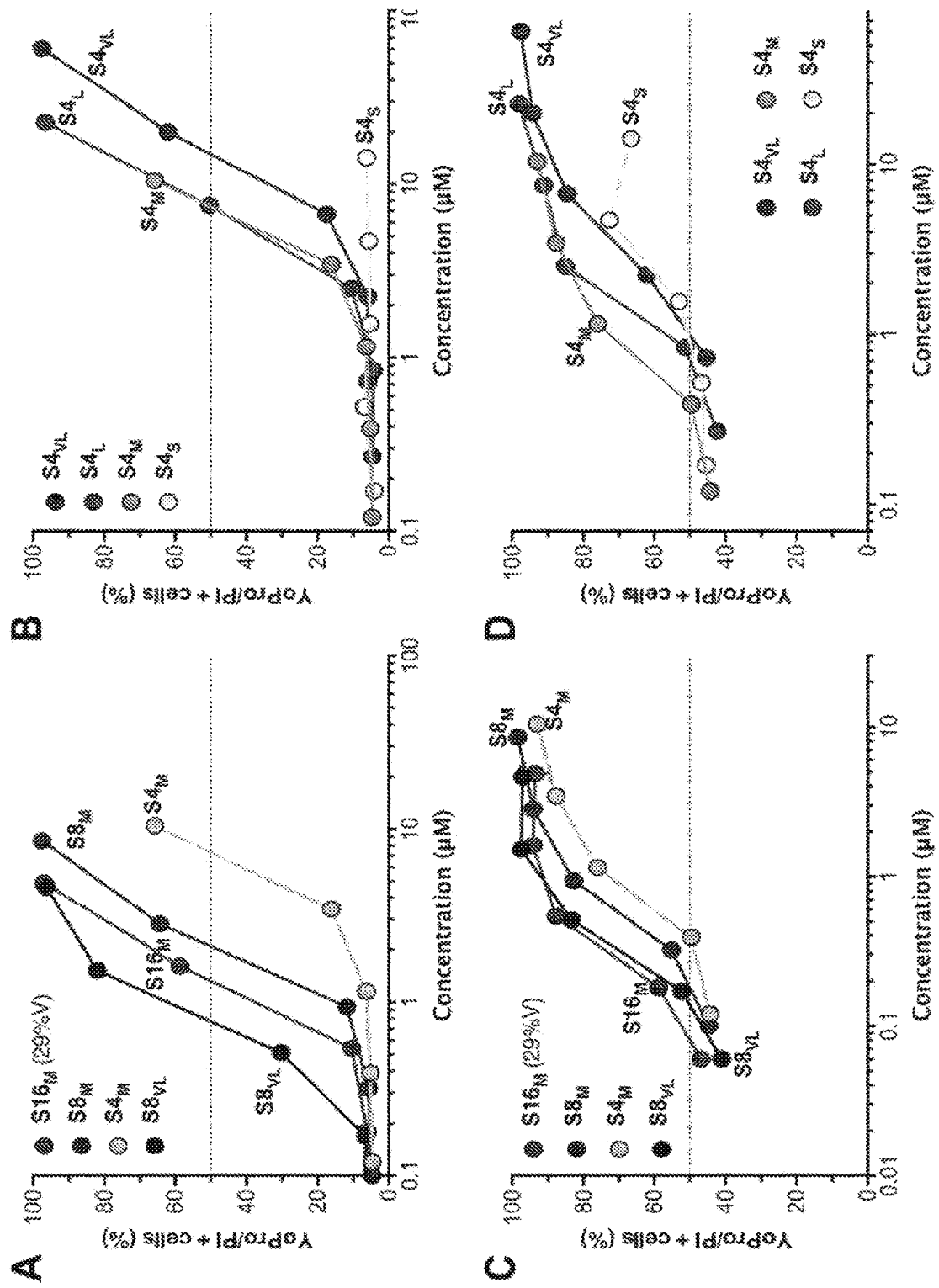
FIG. 77: Cytotoxicity of SNAPPs against H4IIE (A-B) and HEK (C-D) cells.

FIG. 77 Cytotoxicity of SNAPPs against H4IIE (A-B) and HEK (C-D) cells. The star shaped polymers only exhibited some cytotoxicity at high concentrations indicating a large therapeutic index.

From FIGS. 70, 71, 72, and 73 it can clearly be seen that the S16$_M$ with a 29% content of valine to lysine in the SNAPP has the greatest activity (MIC, MBC and MDC) against E. coli compared to the S8$_M$ and S4$_M$ and the S16$_M$ containing lower or greater amounts of valine in the SNAPPs. Furthermore, it is evident the activity of poor performing S4 can be improve by increasing the length of the peptides arms from the S4$_M$ to the S4$_L$ and S4$_{VL}$ (FIG. 73).

FIG. 74 shows that S16$_M$ and S8$_M$ have activity against the Gram positive bacteria S. aureus which was significantly better that S4$_M$. The length of the arms of the SNAPPs contributes to the increase in activity against S. aureus with the S4L having greater activity compared to S4$_M$, S4$_{VL}$ and $S4_S$. The number of arms of the $S16_M$ was found to be important in killing *P. aeruginosa*, with $S16_M$ having greater activity than $S8_M$ and S4L (FIG. 75). Importantly, the $S16_M$ was found to have significant ability to kill Gram-positive bacteria including MRSA at a similar level of activity compared to the Gram negative bacteria *A. baumannii* but greater than the ability to kill *K. pneumonia* (FIG. 76). FIG. 77 shows that the mammalian cell cytotoxicity of the S4, S8 and S16 variations have similar levels of cytotoxicity as in Table 11, indicating that these new variants have the same level of therapeutic indices and will thus be good candidates for clinical trial development as the level of cytotoxicity is low compared to the bactericidal activity.

Tables

TABLE 1

Antimicrobial Activity of SNAPPs and Other Peptides against a Range of Gram-Negative Pathogens.

| Antimicrobial type | Code/Name | Media | $MBC^a$, AM | | | | | |
|---|---|---|---|---|---|---|---|---|
| | | | *E. coli* | *P. aeruginosa* | *K. pneumoniae* | *A. baumannii* | MDR *P. aerugmosa* | MDR *A. baumannii* |
| SNAPP | S16 | MHB | 0.72 ± 0.06 | 1.42 ± 0.08 | 1.54 ± 0.08 | 0.85 ± 0.05 | 1.38 ± 0.03 | 1.61 ± 0.23 |
| | | MEM | 0.17 ± 0.01 | 0.07 ± 0.04 | 0.19 ± 0.05 | $0.05^b$ | $0.08^b$ | 0.05 ± 0.01 |
| | S32 | MHB | 0.72 ± 0.54 | 0.97 ± 0.05 | 0.83 ± 0.14 | 0.79 ± 0.02 | 1.00 | 0.85 ± 0.03 |
| | | MEM | 0.05 ± 0.01 | 0.02 | 0.08 ± 0.02 | $0.02^b$ | 0.03 ± 0.01 | 0.03 ± 0.01 |
| | Ovispirin$^c$ | MHB | 8.39 ± 0.44 | 95.49 ± 9.73 | 11.49 ± 4.86 | 2.21 ± 0.88 | Not Tested | Not Tested |
| | Magainin II$^c$ | MHB | 47.85 ± 6.08 | 55.96 ± 2.84 | 154.59 ± 9.32 | 19.87 ± 3.24 | Not Tested | Not Tested |
| | Melittin$^c$ | MHB | 33.71 ± 5.18 | 29.37 ± 8.24 | 109.25 ± 20.43 | 0.91 ± 0.09 | Not Tested | Not Tested |

$^a$MBC is defined as the minimum drug concentration that causes quantitative bacterial cell death (refer to 'Materials and Methods' section, and FIG. 14 and Table 3 for further clarification). All data are expressed as mean and standard deviations of four replicates (n = 4) completed in two independent experiments.
$^b$The MBC values obtained were identical across all replicates.
$^c$The amino acid sequences of ovispirin, magainin II and melittin are KNLRRIIRKIIHIIKKYG-COOH, GIGKFLHSAKKFGKAFVGEIMNS-CONH$_2$, and GIGAVLKVLTTGLPAL-ISWIKRKRQQ-COOH, respectively. Ovispirin and magainin II were synthesized using standard solid-phase peptide synthesis protocols for Fmoc (9-fluorenylmethoxy carbonyl) chemistry and their antimicrobial activities were evaluated as per SNAPPs.

TABLE 2

Composition, Molecular Weight and Dispersity of the Star Peptide Polymers

| | Peptide Polymer | Arm Number | Lysine:Valine, a:b$^a$ | $M_n$ (kDa)$^b$ | $M_w$ (kDa)$^b$ | Đ$^b$ |
|---|---|---|---|---|---|---|
| Before deprotection | $S16_z$ | 16 | 1.83:1 | | | |
| | $S32_z$ | 32 | 1.97:1 | | | |
| After deprotection | S16 | 16 | 1.83:1 | 43.8 | 127.9 | 2.9 |
| | S32 | 32 | 1.97:1 | 74.8 | 141.1 | 1.9 |

$^a$Determined by $_1$H NMR spectroscopic analysis.
$^b$The number-average ($M_n$) and weight-average ($M_w$) molecular weights and the dispersity (Đ) values were determined by aqueous GPC using a conventional calibration with PEG standards for the peptide polymers in the deprotected form. The dispersity (Đ) values of SNAPPs as indicated by GPC analysis (Table 2) are not necessarily a true reflection of the uniformity of SNAPPs due to potential interactions between the amphiphilic stars with the GPC columns causing tailing. Hence in this case, GPC analysis is not considered as the primary analytical tool but simply served as a routine inspection for SNAPPs. TEM and DLS analysis (FIGS. 11-13) represent most accurately the uniformity of SNAPPs as they provide direct visualization of the nanoparticles in their native form and thus should be used primarily in judging the size distribution of the nanoparticles.

TABLE 3

Killing Levels of SNAPPs

| | Bacteria | Media | MBC (μM)$^a$ | % reduction$^b$ |
|---|---|---|---|---|
| S16 | *E. coli* | MHB | 0.72 ± 0.06 | 94.1 |
| | | MEM | 0.17 ± 0.01 | 98.7 |
| | *P. aeruginosa* | MHB | 1.42 ± 0.08 | 91.3 |
| | | MEM | 0.07 ± 0.04 | 99.8 |
| | *K. pneumoniae* | MHB | 1.54 ± 0.08 | 95.1 |
| | | MEM | 0.19 ± 0.05 | 96.7 |
| | *A. baumannii* | MHB | 0.85 ± 0.05 | 92.9 |
| | | MEM | 0.05 | 98.1 |
| | MDR *P. aeruginosa* | MHB | 1.38 ± 0.03 | 96.8 |
| | | MEM | 0.08 | 97.9 |
| | MDR *A. baumannii* | MHB | 1.61 ± 0.23 | 95.7 |
| | | MEM | 0.05 ± 0.01 | 99.5 |
| S32 | *E. coli* | MHB | 0.72 ± 0.54 | 94.9 ± 0.1 |
| | | MEM | 0.05 ± 0.01 | 99.7 |
| | *P. aeruginosa* | MHB | 0.97 ± 0.05 | 95.8 ± 0.1 |
| | | MEM | 0.02 | 98.5 |
| | *K. pneumoniae* | MHB | 0.83 ± 0.14 | 99.2 |
| | | MEM | 0.08 ± 0.02 | 99.4 |
| | *A. baumannii* | MHB | 0.79 ± 0.02 | 99.9 |
| | | MEM | 0.02 | 99.2 |
| | MDR *P. aeruginosa* | MHB | 1.00 | 95.9 |
| | | MEM | 0.03 ± 0.01 | 96.9 |
| | MDR *A. baumannii* | MHB | 0.85 ± 0.03 | 96.4 |
| | | MEM | 0.03 ± 0.01 | 98.3 |

$^a$The MBC listed in this column was determined over two independent experiments with two replicates for each variation in each experiment.
$^b$The '% reduction' was calculated by comparing the CFU/mL at x concentration to the CFU/mL of the untreated control at the end of a 90 min incubation.

TABLE 4

MBCs of SNAPPs against Gram-Positive Pathogens

| | $MBC^a$ (μM) | |
|---|---|---|
| SNAPP | *S. aureus* | *S. mutans* |
| S16 | 4.58 ± 1.13 | 3.55 ± 1.20 |
| S32 | 2.23 ± 0.62 | 1.80 ± 0.14 |

$^a$All data are expressed as mean and standard deviations of four replicates (n = 4) completed in two independent experiments.

TABLE 5

Antibiogram of MDR P. aeruginosa (FADDI-PA067)

| Antibiotic | Susceptibility[a] |
|---|---|
| Aztreonam | Resistant |
| Ceftazidime | Resistant |
| Ciprofloxacin | Sensitive |
| Gentamicin | Resistant |
| Piperacillin | Resistant |
| Ticarcillin | Resistant |
| Tobramycin | Resistant |
| Colistin Sulfate | Resistant (>110.8 μM) |

[a]Susceptibility of the bacteria species towards a particular antibiotic is interpreted based on resistant breakpoints provided by the Clinical and Laboratory Standards Institute.

TABLE 6.

Antibiogram of MDR A. baumannii (FADDI-AB156)

| Antibiotic | MIC (μM) | Susceptibility[a] |
|---|---|---|
| Amikacin | ≥109.3 | Resistant |
| Ampicillin | ≥91.6 | Resistant |
| Amoxicillin/Clavulanic Acid | ≥87.6 | Resistant |
| Cefazolin | ≥140.8 | Resistant |
| Cefepime | ≥133.2 | Resistant |
| Cefoxitin | ≥149.7 | Resistant |
| Ceftazidime | ≥117.1 | Resistant |
| Ceftriaxone | ≥115.4 | Resistant |
| Ciprofloxacin | ≥12.1 | Resistant |
| Gentamicin | ≥33.5 | Resistant |
| Meropenem | ≥41.7 | Resistant |
| Nalidixic Acid | ≥137.8 | Resistant |
| Nitrofurantoin | ≥2149.8 | Resistant |
| Norfloxacin | ≥50.1 | Resistant |
| Piperacillin/Tazobactam | ≥247.3 | Resistant |
| Ticarcillin/Clavulanic Aid | ≥333.0 | Resistant |
| Tobramycin | ≥34.2 | Resistant |
| Trimethoprim | ≥55.1 | Resistant |
| Trimethoprim/Sulfamethoxazole | ≥1102.2 | Resistant |
| Imipenem | ≥213.8 | Resistant |
| Colistin Sulfate[b] | 13.8 | Resistant |

[a]Susceptibility of the bacteria species towards a particular antibiotic is interpreted based on resistant breakpoints provided by the Clinical and Laboratory Standards Institute.

TABLE 7

MICs of PAMAM G2 and G3 dendrimers

| | MIC[a] (μM) | | | |
|---|---|---|---|---|
| PAMAM | E. coli | P. aeruginosa | K. pneumoniae | A. baumannii |
| G2 | 157.2 | 78.6 | >314.5 | >314.5 |
| G3 | >148.2 | 148.2 | >148.2 | >148.2 |

[a]MIC is defined as the minimum concentration of an antimicrobial agent at which no visible microbial growth is observed. Identical MIC values were obtained across four replicates completed in two independent experiments.

TABLE 8

Composition, Molecular Weight, and Dispersity of the Linear Random Co-peptide Polymer L

| Peptide Polymer | Lysine:Valine, a:b[a] | $M_n$ (kDa)[b] | $M_n$ (kDa)[c] | $M_w$ (kDa)[b] | Đ[b] |
|---|---|---|---|---|---|
| L | 1.89:1 | 4.9 | 7.7 | 12.7 | 1.7 |

[a]Determined from $^1$H NMR spectroscopic analysis of peptide polymer L. Ratio was the same as before deprotection.
[b]Determined from $DP_n$ and the lysine:valine ratio obtained via $^1$HNMR spectroscopic analysis of peptide polymer L.
[c]Determined by aqueous GPC using PEG standards. As mentioned above, the dispersity (Đ) values of the peptide polymer L as indicated by GPC analysis (Table 8) are not necessarily a true reflection of the uniformity of L due to potential interactions between the amphiphilic peptide polymer L with the GPC columns causing tailing. Hence in this case, GPC analysis is not considered as the primary analytical tool but simply served as a routine inspection for L. TEM and DLS analysis (FIG. 18) represent most accurately the uniformity of L as they provide direct visualization of the nanoparticles in their native form and thus should be used primarily in judging the size distribution of the nanoparticles.

TABLE 9

MBCs of Linear Random Co-peptide Polymer L against a Range of Bacteria (in Nutrient-Rich Medium)

| Bacteria | MBC (μM) |
|---|---|
| E. coli | 29.50 |
| S. aureus | 213.37 |

TABLE 10

Hemolytic Activity of SNAPPs

| Antimicrobial type | Code/Name | Media | $HC_{50}$[a], μM |
|---|---|---|---|
| SNAPP | S16 | MHB | 58.3 |
| | | MEM | |
| | S32 | MHB | 45.3 |
| | | MEM | |
| Linear analog | L | MHB | 674.5 |
| AMP | Ovispirin | MHB | 61.8 |
| | Magainin II | MHB | 81.1 |
| | Melittin | MHB | 2.8 |

[a]$HC_{50}$ is the peptide concentration that results in 50% hemolysis.

TABLE 11

Biocompatibility of SNAPPs (as Determined by YO-PRO-1/P1 Apoptosis Assay)

| | HEK293T | | | H4IIE | | |
|---|---|---|---|---|---|---|
| SNAPP | IC50[a] (μM) | $MBC_{50}$[b] (μM) | Therapeutic index, $IC_{50}/MBC_{50}$ | IC50[a] (μM) | $MBC_{50}$[b] (μM) | Therapeutic index, $IC_{50}/MBC_{50}$ |
| S16 | 2.78 | 0.027 | 102 | 1.43 | 0.027 | 52 |
| S32 | 1.71[c] | 0.010 | 171 | 1.39 | 0.010 | 139 |

[a]$IC_{50}$ is the SNAPP concentration that results in death in 50% of the cell population.
[b]$MBC_{50}$ refers to the SNAPP concentration that results in death in 50% of the bacterial cell population. The $MBC_{50}$ values here (rounded to the nearest two significant figures) were against CMDR A. baumannii.
[c]The % live cells at the highest concentration tested (i.e., 128 μg/mL or 1.71 μM) is 54.9 ± 0.3%. All experiments were conducted in minimal essential medium (MEM). The adhered cells were incubated with SNAPPs for 90 minutes, stained with YO-PRO-1 and PI dyes, and analyzed by flow cytometry. Using YO-PRO-1 as an indicator of early apoptosis and PI as a measure of necrosis or cell death, viable cells were determined as cells that are negative for both YO-PRO-1 and PI.

TABLE 12

MBCs of SNAPP S16 before and after fluorescent labelling against *E. coli*

| Peptide Polymer | MBC[a] (μM) MHB | MEM |
|---|---|---|
| S16 | 0.72 ± 0.06 | 0.17 ± 0.01 |
| AF488-S16 | 2.50 ± 0.03 | 0.39[b] |

[a]All data are expressed as mean and standard deviations of four replicates (n = 4) completed in two independent experiments.
[b]Identical results were obtained across all replicates. Although the conjugation of AF488 to SNAPP S16 was found to slightly decrease its potency (3.5 and 2.2 times less effective against *E. coli* in MHB and MEM, respectively), the interaction mechanism of the fluorescently tagged SNAPP with bacteria was expected to be similar to that before fluorescent tagging.

TABLE 13

Composition, Molecular Weight and Dispersity of the Star Peptide Polymers

| | Peptide Polymer | Arm Number | Lysine:Valine, a:b[a] | $M_n$ (kDa)[b] | $M_w$ (kDa)[b] | Đ[b] |
|---|---|---|---|---|---|---|
| Before deprotection | $S16_z$ | 16 | 1.83:1 | | | |
| | $S32_z$ | 32 | 1.97:1 | | | |
| After deprotection | S16 | 16 | 1.83:1 | 43.8 | 127.9 | 2.9 |
| | S32 | 32 | 1.97:1 | 74.8 | 141.1 | 1.9 |

[a]Determined by $^1$H NMR spectroscopic analysis.
[b]The number-average (Mn) and weight-average (Mw) molecular weights and the dispersity (Đ) values were determined by aqueous GPC using a conventional calibration with PEG standards for the peptide polymers in the deprotected form.
Note:
The dispersity (Đ) values of SNAPPs as indicated by GPC analysis (in Table 13 above) are not necessarily a true reflection of the uniformity of SNAPPs due to potential interactions between the amphiphilic stars with the GPC columns causing tailing. Hence in this case, GPC analysis is not considered as the primary analytical tool but simply served as a routine inspection for SNAPPs.

TABLE 14

Composition, Molecular Weight and Dispersity of the Star Polypeptides

| | Star Polypiptide | Arm Number | Lysine:Valine, a:b[a] | $M_n$ (kDa)[b] | $M_w$ (kDa)[b] | Đ[b] |
|---|---|---|---|---|---|---|
| Before deprotection | $SB_{16,Z}$ | 16 | 2.45:1 | — | — | — |
| | $SB_{32,Z}$ | 32 | 2.87:1 | — | — | — |
| | $SR_{16,Z}$ | 16 | 1.83:1 | — | — | — |
| | $SR_{32,Z}$ | 32 | 1.97:1 | — | — | — |
| | $SH_{16,Z}$ | 16 | — | — | — | — |
| | $SH_{32,Z}$ | 32 | — | — | — | — |
| After deprotection | $SH_{16}$ | 16 | 2.45:1 | 11.0 | 32.1 | 2.9 |
| | $SH_{32}$ | 32 | 2.87:1 | 15.2 | 44.8 | 2.9 |
| | $SR_{16}$ | 16 | 1.83:1 | 43.8 | 127.9 | 2.9 |
| | $SR_-$ | 32 | 1.97:1 | 74.8 | 141.1 | 1.9 |
| | $SH_{16}$ | 16 | — | 27.6 | 40.7 | 1.5 |
| | $SH_-$ | 32 | — | 56.3 | 88.7 | 1.6 |

[a]Determined by 1H NMR
[b]Determined by aqueous GPC using a conventional calibration with narrow molecular weight PEG standards for the deprotected star polypeptides.

TABLE 15

MDCs and MBCs of the Star and Linear Polypeptides against *E. coli* and *S. aureus*

| | | Polypeptide | E. coil MDC[a] (μM) | E. coil MBC[b] (μM) | E. coil MIC[c] (μM) | S. aureus MDC (μM) | S. aureus MBC (μM) | S. aureus MIC (μM) |
|---|---|---|---|---|---|---|---|---|
| Star | Block | $SB_{16}$ | 173.3 ± 1.3 | 10.5 ± 4.7 | 10.5 ± 5.1 | >100 | >100 | >100 |
| | | $SB_{32}$ | 6.2 ± 0.1 | 6.1 ± 1.3 | 4.9 ± 0.1 | >100 | >100 | >100 |
| | Random | $SR_{16}$ | 0.8 ± 0.1 | 0.7 ± 0.1 | 3.2 ± 0.1 | 1.0 ± 0.1 | 4.6 ± 1.1 | 3.9 ± 0.7 |
| | | $SR_{32}$ | 0.5 ± 0.1 | 0.7 ± 0.3 | 1.1 ± 0.1 | 1.7 ± 0.3 | 2.2 ± 0.6 | >100 |
| | Homo | $SH_{16}$ | 3.0 ± 1.0 | 2.9 ± 0.1 | 2.4 ± 0.2 | 5.7 ± 1.6 | >100 | >100 |
| | | $SH_{32}$ | 2.0 ± 0.1 | 0.9 ± 0.4 | 0.8 ± 0.1 | 2.9 ± 0.2 | >100 | >100 |
| Linear | Random | LR | 11.4 ± 2.9 | 29.5 ± 0.1 | >100 | 92.8 ± 0.1 | >100 | 11.0 ± 0.9 |
| | Homo | LH | 27.5 ± 0.6 | 13.4 ± 1.6 | 18.6 ± 0.1 | 28.5 ± 4.2 | 44.1 ± 8.5 | 9.9 ± 0.1 |

[a]MDC is defined as the minimum polymer concentration that causes membrane disruption in all cells.
[b]MBC is defined as the minimum polymer concentration that causes 100% bacterial cell death.
[c]MIC is defined as the minimum polymer concentration that causes microbial growth inhibition.

TABLE 16

Composition, Molecular Weight, and Dispersity of the Linear Polypeptides

| Polymer | Lysine:Valine, a:b[a] | $M_n$ (kDa)[b] | $M_n$ (kDa)[c] | $M_w$ (kDa)[c] | Đ[c] |
|---|---|---|---|---|---|
| LH | NA | 1.6 | 6.2 | 8.8 | 1.4 |
| LR | 1.89:1 | 4.9 | 7.7 | 12.7 | 1.6 |

[a]Determined by 1H NMR for polymers after deprotection. Ratios were the same as before deprotection.
[b]Determined based upon DPn obtained via 1H NMR for polymers after deprotection.
[c]Determined by aqueous GPC using PEG standards for polymers in the deprotected form.

TABLE 17

MDCs, MBCs, and MICs of the Polypeptides against *S. mutans*

| Bacteria | Polypeptide | MDC (μM) | MBC (μM) | MIC (μM) |
|---|---|---|---|---|
| *S. mutans* | $SR_{16}$ | 0.4 ± 0.1 | 3.6 ± 1.2 | 3.2 ± 0.3 |
| | $SR_{32}$ | 0.3 ± 0.1 | 1.8 ± 0.1 | >100 |
| | LR | >100 | >100 | >100 |

TABLE 18

Biocompatibility of SR16 and SR32 (Determined by Hemolysis ($HC_{50}$) and YO-PRO-1/PI Apoptosis ($IC_{50}$) Assays)

| Polypeptide | $HC_{50}$[a], μg/mL (μM) | $HC_{50}/MBC_{50}$[b] (*E. coli*) | $IC_{50}$[c], μg/mL (μM) | |
|---|---|---|---|---|
| | | | HEK293T | H4IIE |
| $SR_{16}$ | 2550 (58.3) | 161[d] | 121.8 (2.8) | 62.8 (1.4) |
| $SR_{32}$ | 3390 (45.3) | 126[d] | 128.0 (1.7) | 103.9 (1.4) |

[a]$HC_{50}$ is the peptide concentration which results in 50% hemolysis. Since the hemolytic activites of SR16 and SR32 at the highest concentration tested (1 mg/mL) were below 50%, their $HC_{50}$ values were extrapolated from FIG. 59.
[b]$MBC_{50}$ is the peptide concentration which results in 50% bacterial cell death.
[c]$IC_{50}$ is the peptide concentration which results in 50% mammalian cell death.

TABLE 19

$HC_{10}$, $HC_{50}$ and $HC_{50}/MBC_{50}$ of Polypeptides Synthesized.

| | Polypeptide | | $HC_{10}$, μg/mL (μM) | $HC_{50}$[a], μg/mL (μM) | $HC_{50}$[a]/ $MBC_{50}$ (*E. coli*) |
|---|---|---|---|---|---|
| Star | Block | $SB_{16}$ | 11.1 (1.0) | 6110 (555.5) | 105 |
| | | $SB_{32}$ | 33.3 (2.2) | 1850 (121.7) | 40 |
| | Random | $SR_{16}$ | 25.4 (0.6) | 2550 (58.3) | 161 |
| | | $SR_{32}$ | 17.6 (0.2) | 3390 (45.3) | 126 |
| | Homo | $SH_{16}$ | 18.3 (0.7) | 3300 (119.6) | 82 |
| | | $SH_{32}$ | 16.9 (0.3) | 5330 (94.7) | 223 |
| Linear | Random | LH | 22.6 (6.3) | 3070 (852.8) | 127 |
| | Homo | LR | 27.2 (5.6) | 5190 (1059.2) | 72 |
| Antimicrobial | Ovispirin[b] | | — | 27 (61.8) | 15 |
| Peptide | Magainin II[b] | | — | 33 (81.1) | 3 |
| M | elitiin[b] | | — | 1.0 (2.8) | 0.2 |

Figure 59:
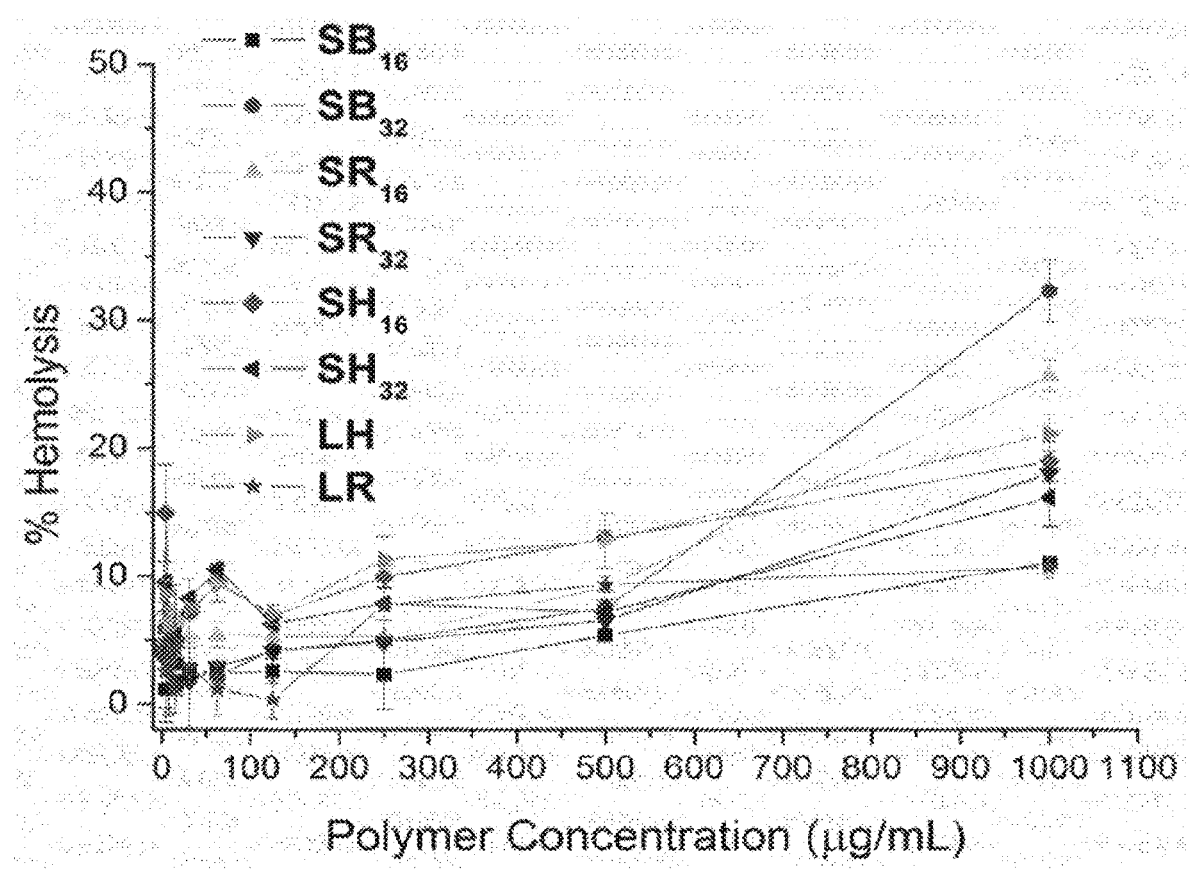
FIG. 59: Percent hemolysis as a function of polypeptide concentration. Error bars represent the standard deviation from the mean (n=4).

[a]Based upon extrapolation from FIG. 59.
[b]The amino acid sequences of ovispirin, magainin

TABLE 20

$IC_{50}$ of Polypeptides using H4IIE Cells (Determined by the YO-PRO-1/PI Apoptosis Assay).

| Polypeptide | $IC_{50}$, μg/mL, (μM) |
|---|---|
| $SH_{32}$ | 92.0 ( 1.6) |
| LH | 109.6 (30.4) |

TABLE 21

Therapeutic indices of SR16 and SR32 (where MBC and MBC$_{50}$ were determined against *E. coli* in minimal medium)

| Polypeptide | MBC$_{MEM}$ (μM) | MBC$_{50,MEM}$ (μM) | Therapeutic index, IC$_{50}$/MBC$_{50,MEM}$ HEK293T | H4IIE |
|---|---|---|---|---|
| SR$_{16}$ | 0.17 | 0.09 | 31 | 16 |
| SR$_{32}$ | 0.05 | 0.03 | 57 | 46 |

TABLE 22

Antimicrobial Activity of SNAPPs against a Range of Gram-Negative Pathogens Tested in Different Media

| Bacteria | SNAPP | MIC$^a$ (μM) MEM | SBF | 10% serum | 50% serum | MBC$^b$ (μM) MEM |
|---|---|---|---|---|---|---|
| *E. coli* | S16 | 0.17 ± 0.01 | 3.43 ± 0.05 | 2.89 ± 0.42 | 4.09 ± 0.28 | 0.17 ± 0.01 |
|  | S32 | 0.05 ± 0.00 | 1.68 ± 0.07 | 0.49 ± 0.01 | 2.24 ± 0.15 | 0.05 ± 0.01 |
| *P. aeruginosa* | S16 | 0.08 ± 0.05 | 1.64 ± 0.13 | 1.10 ± 0.41 | 2.89 ± 0.02 | 0.07 ± 0.04 |
|  | S32 | 0.04 ± 0.01 | 0.59 ± 0.18 | 0.48 ± 0.03 | 0.95 ± 0.20 | 0.02 ± 0.00 |
| *K. pneumomine* | S16 | 0.30 ± 0.10 | 4.68 ± 0.34 | >6.00 | Not tested | 0.19 ± 0.05 |
|  | S32 | 0.21 ± 0.01 | 1.92 ± 0.14 | 1.95 ± 0.54 | Not tested | 0.08 ± 0.02 |
| *A. baumannii* | S16 | 0.13 ± 0.05 | 0.17 ± 0.01 | 0.66 ± 0.05 | Not tested | 0.05 ± 0.00 |
|  | S32 | 0.08 ± 0.02 | 0.10 ± 0.00 | 0.21 ± 0.00 | Not tested | 0.02 ± 0.00 |

$^a$MIC is defined as the minimum drug concentration that causes quantitative bacterial growth inhibition.
$^b$MBC is defined as the minimum drug concentration that causes quantitative bacterial cell death. All MIC and MBC data are expressed as mean and standard deviations of four replicates (n = 4) completed in two independent experiments.

TABLE 23

Initial Increase in RFU as a Function of S16 Concentration (Slope of Curve Before Plateau)

| Medium | Incubation time (min) | Slope (RFU · mL/μg) *E. coli* | *A. baaumannii* |
|---|---|---|---|
| mSBF | 5 | 3443 | 15794 |
| SBF | 5 | 1104 | 1955 |
|  | 25 | 1302 | 7487 |
|  | 90 | 991 | — |
| SBF + 1.5 mg/mL EDTA | 5 | 3000 | — |

TABLE 24

Characterisation of SNAPPs synthesised in Example 9.

| SNAPP code | Arm number | Lys/Val$^a$ | M$_n$ (kDa)$^b$ | Đ$^b$ | Arm DP | D$_h$ (nm)$^c$ |
|---|---|---|---|---|---|---|
| S4$_S$ | 4 | 2.1 | 3.3 | 1.3 | 5 | 1.0 ± 0.4 |
| S4$_M$ | 4 | 2.3 | 8.8 | 1.3 | 12 | 4.4 ± 0.7 |
| S4$_L$ | 4 | 2.5 | 14.1 | 1.5 | 18 | 5.6 ± 0.7 |
| S4$_{VL}$ | 4 | 2.8 | 19.2 | 1.7 | 26 | 6.6 ± 0.5 |
| S8$_M$ | 8 | 2.4 | 23.4 | 1.5 | 15 | 7.9 ± 1.2 |
| S8$_{vL}$ | 8 | 2.6 | 43.4 | 1.8 | 29 | 12.2 ± 0.6 |
| S16$_M$ | 16 | 2.5 | 41.1 | 1.7 | 14 | 9.4 ± 0.5 |

Subscript values represent star arm length (S = small, M = medium, L = long, VL = very long).
$^a$Determined through $^1$H NMR
$^b$Absolute number-average molecular weight (M$_n$) and dispersity index (PDI) determined through SEC light scattering using measured dn/dc values.
$^c$Hydrodynamic diameters and standard deviations of SNAPPs determined by DLS. Values represent number distributions in DMEM at concentrations < 1 mg/ml. Values represent an average of 3 sets containing 15 measurements per set.

TABLE 25

Antimicrobial activities of SNAPPs against *E. coli*.

| SNAPP | MIC μg · mL$^{-1}$ | MIC μM | MDC μg · mL$^{-1}$ | MDC μM | MBC μg · mL$^{-1}$ | MBC μM |
|---|---|---|---|---|---|---|
| S16$_M$ (29% V) | 6.207 ± 0.041 | 0.151 ± 0.001 | 5.745 ± 0.030 | 0.140 ± 0.001 | 6.25 | 0.152 |
| S8$_M$ | 8.534 ± 0.052 | 0.365 ± 0.002 | 7.699 ± 0.058 | 0.329 ± 0.002 | 12.5 | 0.534 |
| S4$_M$ | 28.22 ± 0.168 | 3.207 ± 0.019 | 27.62 ± 0.094 | 3.139 ± 0.011 | 50 | 5.682 |
| S4$_{VL}$ | 8.737 ± 0.036 | 0.455 ± 0.002 | 10.71 ± 0.082 | 0.558 ± 0.004 | 12.5 | 0.651 |
| S4$_L$ | 8.896 ± 0.034 | 0.631 ± 0.002 | 8.211 ± 0.111 | 0.582 ± 0.008 | 12.5 | 0.887 |
| S4$_S$ | >100 | >30 | >100 | >30 | >100 | >30 |
| S8$_{VL}$ | 5.505 ± 0.038 | 0.127 ± 0.001 | 5.557 ± 0.030 | 0.128 ± 0.001 | 6.25 | 0.144 |
| S16$_M$ (43% V) | 8.869 ± 0.808 | 0.240 ± 0.022 | 7.704 ± 0.098 | 0.209 ± 0.003 | 12.5 | 0.339 |

TABLE 25-continued

Antimicrobial activities of SNAPPs against *E. coli*.

| SNAPP | MIC µg · mL$^{-1}$ | MIC µM | MDC µg · mL$^{-1}$ | MDC µM | MBC µg · mL$^{-1}$ | MBC µM |
|---|---|---|---|---|---|---|
| S16$_M$ (36% V) | 5.331 ± 0.327 | 0.135 ± 0.008 | 4.260 ± 0.049 | 0.108 ± 0.001 | 6.25 | 0.158 |
| S16$_M$ (24% V) | 6.083 ± 0.037 | 0.153 ± 0.001 | 4.885 ± 0.031 | 0.123 ± 0.001 | 12.5 | 0.314 |

NB: the % V in this table and elsewhere herein relates to the % of total amino acid present in each S16$_M$ molecule that is valine.

TABLE 26

Antimicrobial activities of SNAPPs against *S. aureus*.

| SNAPP | MIC µg · mL$^{-1}$ | MIC µM | MDC µg · mL$^{-1}$ | MDC µM | MBC µg · mL$^{-1}$ | MBC µM |
|---|---|---|---|---|---|---|
| S16$_M$ (29% V) | 2.937 ± 0.039 | 0.071 ± 0.001 | n/a | n/a | 3.12 | 0.076 |
| S8$_M$ | 2.269 ± 0.047 | 0.097 ± 0.002 | n/a | n/a | 3.12 | 0.133 |
| S4$_M$ | 1.756 ± 0.145 | 0.200 ± 0.016 | n/a | n/a | 1.56 | 0.177 |
| S4$_{VL}$ | 5.428 ± 0.452 | 0.283 ± 0.024 | n/a | n/a | 6.25 | 0.326 |
| S4$_L$ | 2.535 ± 0.052 | 0.180 ± 0.004 | n/a | n/a | 1.56 | 0.111 |
| S4$_S$ | 7.216 ± 0.130 | 2.187 ± 0.039 | n/a | n/a | 12.5 | 3.788 |

TABLE 27

Antimicrobial activities of SNAPPs against *P. aeruginosa*.

| SNAPP | MIC µg · mL$^{-1}$ | MIC µM | MDC µg · mL$^{-1}$ | MDC µM | MBC µg · mL$^{-1}$ | MBC µM |
|---|---|---|---|---|---|---|
| S16$_M$ (29% V) | 28.53 ± 2.319 | 0.694 ± 0.056 | 14.62 ± 0.316 | 0.356 ± 0.008 | >100 | >2 |
| S8$_M$ | 37.22 ± 3.839 | 1.591 ± 0.164 | 15.00 ± 0.949 | 0.641 ± 0.041 | >100 | >4 |
| S4$_L$ | 33.79 ± 4.435 | 2.396 ± 0.315 | 9.246 ± 0.583 | 0.656 ± 0.041 | >100 | >7 |

TABLE 28

Antimicrobial activities of S16$_M$ (29% V) against other Gram-negative (*A. baumanii* and *K. pneumoniae*) and Gram-positive (methicillin resistant *S. aureus*, or MRSA, and *E. faecalis*).

| SNAPP | MIC µg · mL$^{-1}$ | MIC µM | MDC µg · mL$^{-1}$ | MDC µM | MBC µg · mL$^{-1}$ | MBC µM |
|---|---|---|---|---|---|---|
| *A. baumanii* | 10.4 ± 0.218 | 0.253 ± 0.005 | 6.978 ± 0.248 | 0.170 ± 0.006 | 6.25 | 0.152 |
| *K. pneumoniae* | 100 | 2.433 | 50 | 1.217 | 100 | 2.433 |
| MRSA | 9.123 ± 0.255 | 0.222 ± 0.006 | n/a | n/a | 6.25 | 0.152 |
| *E. faecalis* | 8.746 ± 0.079 | 0.213 ± 0.002 | 6.873 ± 0.056 | 0.167 ± 0.001 | 6.25 | 0.152 |

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A star shaped peptide polymer comprising a multifunctional core with a plurality of linear arms extending therefrom, wherein the linear arms are random peptide copolymers of at least a cationic amino acid residue and a hydrophobic amino acid residue, wherein the cationic amino acid residue and the hydrophobic amino acid residue are arranged as follows:

([Cationic Amino Acid]$_a$-ran-[Hydrophobic Amino Acid]$_b$)$_m$ wherein 'm' represents the number of linear arms and is $2^n$, wherein n is a number including or between 2 and 8, 'a' and 'b' represent the number of repeat units of the amino acids in the peptide copolymer respectively and 'ran' refers to the random copolymerisation of the amino acids, wherein the copolymer has a molar ratio of cationic amino acid residue to hydrophobic amino acid residue of from about 1.5:1 to about 3.5:1, and wherein the copolymer exhibits a degree of polymerisation of at least 5 and up to 50 on each linear arm.

2. A star shaped peptide polymer according to claim 1, wherein the cationic amino acid residue is a lysine residue, and the hydrophobic amino acid residue is a valine residue.

3. A star shaped peptide polymer according to claim 1, wherein the multifunctional core is a dendrimer, the core comprising a dendrimer centre with a plurality of dendron arms extending therefrom, wherein the dendron arms are formed from repeat units,
wherein the repeat unit is an amidoamine.

4. A star shaped peptide polymer according to claim 1, wherein the multifunctional core includes a number of linear arms of from at least 4 and up to 256 linear arms.

5. A star shaped peptide polymer according to claim 1, wherein the degree of copolymerisation is about 5.

6. A star shaped peptide polymer according to claim 1, wherein the star shaped peptide polymer is selected from:

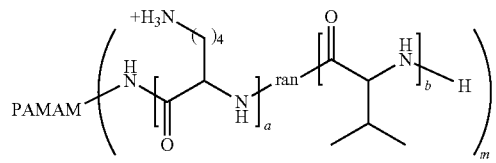

where m is $2^n$ and n is a number between 2 and 8.

7. A pharmaceutical composition comprising
(i) a star shaped peptide polymer, and
(ii) a carrier, diluent or excipient,
wherein the star shaped polymer comprises a multifunctional core with a plurality of linear arms extending therefrom,
wherein the linear arms are random peptide copolymers of at least a cationic amino acid residue and a hydrophobic amino acid residue,
wherein the cationic amino acid residue and the hydrophobic amino acid residue are arranged as follows:

([Cationic Amino Acid]$_a$-ran-[Hydrophobic Amino Acid]$_b$)$_m$ wherein 'm' represents the number of linear arms and is $2^n$, wherein n is a number including or between 2 and 8, 'a' and 'b' represent the number of repeat units of the amino acids in the peptide copolymer respectively and 'ran' refers to the random copolymerisation of the amino acids,
wherein the copolymer has a molar ratio of cationic amino acid residue to hydrophobic amino acid residue of from about 1.5:1 to about 3.5:1, and
wherein the copolymer exhibits a degree of polymerisation of at least 5 and up to 50 on each linear arm.

8. A pharmaceutical composition according to claim 7, wherein the composition further includes a chelating agent.

9. A pharmaceutical composition according to claim 8 wherein the chelating agent is EDTA or citric acid.

10. A pharmaceutical composition according to claim 7, wherein the carrier, diluent or excipient is substantially free of protein.

11. A pharmaceutical composition according to claim 7, wherein the carrier, diluent or excipient is substantially free of divalent ions.

12. A method of treating a bacterial infection in a subject, the method comprising administering to the subject an effective amount of a star shaped peptide polymer, wherein the star shaped peptide polymer comprises a multifunctional core with a plurality of linear arms extending therefrom, wherein the linear arms are random peptide copolymers of at least a cationic amino acid residue and a hydrophobic amino acid residue, wherein the cationic amino acid residue and the hydrophobic amino acid residue are arranged as follows:

([Cationic Amino Acid]$_a$-ran-[Hydrophobic Amino Acid]$_b$)$_m$ wherein 'm' represents the number of linear arms and is $2^n$, wherein n is a number including or between 2 and 8, 'a' and 'b' represent the number of repeat units of the amino acids in the peptide copolymer respectively and 'ran' refers to the random copolymerisation of the amino acids, wherein the copolymer has a molar ratio of cationic amino acid residue to hydrophobic amino acid residue of from about 1.5:1 to about 3.5:1, and wherein the copolymer exhibits a degree of polymerisation of at least 5 and up to 50 on each linear arm;
thereby treating the bacterial infection in the subject.

13. A method of claim 12, wherein the bacterial infection comprises Gram-negative bacteria.

14. A method of claim 12, wherein the bacterial infection comprises Gram-positive bacteria.

15. A method of claim 12, wherein the bacterial infection includes both Gram-negative and Gram-positive bacteria.

16. A method according to claim 12, wherein the bacterial infection comprises an infection with antibiotic resistant bacteria.

17. A method according to claim 2, wherein the bacteria exhibit resistance to any one or more of the following antibiotics:
(1) Macrolides or ketolides;
(2) Beta-lactams;
(3) Quinolones;
(4) Antibacterial sulfonanmides and antibacterial sulphanilamides;
(5) Aminoglycosides;
(6) Tetracyclines;
(7) Rifamycins;
(8) Lincosamides;
(9) Glycopeptides or lipopeptides;
(10) Streptogramins;
(11) Oxazolidinones;
(12) Polymyxin, colistin and colymycin; and
(13) Trimethoprim and bacitracin.

18. A method according to claim 16, wherein the bacterial infection comprises *A. baumannii* that exhibits resistance to treatment of any one or more of Amoxicillin/Clavulanic Acid, Ampicillin, Cefazolin, Cefepime, Cefoxitin, Ceftazidime, Ceftriaxone, Ciprofloxacin, Gentamicin, Meropenem, Nalidixic Acid, Nitrofurantoin, Norfloxacin, Piperacillin/Tazobactam, Ticarcillin/Clavulanic Aid, Tobramycin, Trimethoprim, Trimethoprim/Sulfamethoxazole, Imipenem and Colistin Sulfate.

19. A method according to claim 16, wherein the bacterial infection comprises *P. aeruginosa* that exhibits resistance to treatment of any one or more of Ampicillin, Aztreonam, Ceftazidime, Gentamicin, Piperacillin, Ticarcillin, Tobramycin and Colistin Sulfate.

20. A method according to claim 12, wherein the bacterial infection is an acute infection.

21. A method according to claim 12, wherein the subject had been previously administered an antibiotic with the intention of treating the bacterial infection, however the bacterial infection still persisted.

22. A method according to claim 12 wherein the bacterial infection is a cutaneous or dermal infection.

23. A star shaped peptide polymer according to claim 1, wherein the cationic amino acid residue is an L lysine residue, and the hydrophobic amino acid residue is a D valine, an L valine or DL valine residue.

24. A star shaped peptide polymer according to claim 1, wherein n is 2, 3, 4 or 5 and m is 4, 8, 16, or 32 accordingly.

25. A star shaped peptide polymer according to claim 1, wherein the degree of copolymerisation is at least 12 and up to 50.

26. A method according to claim 17, wherein:
   (1) the macrolides or ketolides are selected from: erythromycin, azithromycin, clarithromycin, and telithromycin;
   (2) the beta-lactams are selected from: penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefinetazole, cefotaxime, ceftizoxime, ceftriaxone, cefoperazone, ceftazidime, cefixime, cefpodoxime, ceftibuten, cefdinir, cefpirome, cefepime, aztreonam, imipenem, meropenem, ertapenem, doripenem, ceftobiprole, and ceftaroline;
   (3) the quinolones are selected from: nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, garenoxacin, gemifloxacin and pazufloxacin;
   (4) the antibacterial sulfonanmides and antibacterial sulphanilamides are selected from: para-aminobenzoic acid, sulfadiazine, sulfisoxazole, sulfamethoxazole and sulfathalidine;
   (5) the aminoglycosides are selected from: streptomycin, neomycin, kanamycin, paromycin, gentamicin, tobramycin, amikacin, netilmicin, spectinomycin, sisomicin, dibekacin and isepamicin;
   (6) the tetracyclines are selected from: tetracycline, chlortetracycline, demeclocycline, minocycline, oxytetracycline, methacycline, tigecycline, doxycycline;
   (7) the rifamycins are selected from: rifampicin, rifapentine, rifabutin, bezoxazinorifamycin and rifaximin;
   (8) the lincosamides are selected from: lincomycin and clindamycin;
   (9) the glycopeptides or lipopeptides are selected from: telavancin, vancomycin, teicoplanin, and daptomycin;
   (10) the streptogramins are selected from: quinupristin and daflopristin; or
   (11) the oxazolidinones are a linezolid.

27. A star shaped peptide polymer according to claim 3, wherein the repeat unit is an amidoamine of the form $R^A$ $[C_2H_4C(=O) NH_2C_2H_4N]R^B R^C$ where $R^A$ is a single covalent bond to either the dendrimer centre, in which case $R^A$ is an $R^1$, or $R^A$ is a bond to a preceding repeat unit that is closer to the dendrimer centre, in which case $R^A$ is an $R^B$ or $R^C$ on the preceding repeat unit; $R^B$ and $R^C$ represent a single bond to a following repeat unit, in which case $R^B$ is an $R^A$ on the following repeat unit, or where there are no following repeat units $R^B$ represents a single bond to the linear arm, and $R^C$ represents a hydrogen atom.

* * * * *

UNITED STATES PATENT AND TRADEMARK OFFICE
CERTIFICATE OF CORRECTION

PATENT NO. : 12,281,205 B2  
APPLICATION NO. : 16/343218  
DATED : April 22, 2025  
INVENTOR(S) : Greg GuangHua Qiao et al.

Page 1 of 1

It is certified that error appears in the above-identified patent and that said Letters Patent is hereby corrected as shown below:

In the Claims

Column 98, Line 31, Claim 17, delete "claim 2," and replace with -- claim 16, --

Column 98, Line 37, Claim 17, delete "sulfonanmides" and replace with -- sulfonamides --

Column 99, Line 19 (approx.), Claim 26, delete "cepalothin," and replace with -- cephalothin, --

Column 99, Line 21 (approx.), Claim 26, delete "cefinetazole" and replace with -- cefmetazole, --

Column 100, Line 1, Claim 26, delete "sulfonanmides" and replace with -- sulfonamides --

Column 100, Line 6, Claim 26, delete "paromycin," and replace with -- paromomycin, --

Column 100, Line 14 (approx.), Claim 26, delete "bezoxazinorifamycin" and replace with -- benzoxazinorifamycin --

Column 100, Line 20, Claim 26, delete "daflopristin;" and replace with -- dalfopristin; --

Column 100, Lines 23-24, Claim 27, delete "$R_A$ [$C_2H_4C(=O)$ $NH_2C_2H_4N$]$R_BR_C$" and replace with -- $R_A$ [$C_2H_4C(=O)NH_2C_2H_4N$]$R_BR_C$ --

Signed and Sealed this  
Fourth Day of November, 2025

John A. Squires  
*Director of the United States Patent and Trademark Office*